United States Patent
Gonzalez, III et al.

(10) Patent No.: US 8,309,543 B2
(45) Date of Patent: *Nov. 13, 2012

(54) COMPOSITIONS USEFUL AS INHIBITORS OF VOLTAGE-GATED SODIUM CHANNELS

(75) Inventors: Jesus E. Gonzalez, III, Carlsbad, CA (US); Andreas P. Termin, Encinitas, CA (US); Esther Martinborough, San Diego, CA (US); Nicole Hilgraf, San Diego, CA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/478,538

(22) Filed: May 23, 2012

(65) Prior Publication Data

US 2012/0238578 A1    Sep. 20, 2012

Related U.S. Application Data

(62) Division of application No. 10/914,988, filed on Aug. 9, 2004, now Pat. No. 8,202,861.

(60) Provisional application No. 60/493,659, filed on Aug. 8, 2003, provisional application No. 60/584,717, filed on Jul. 1, 2004.

(51) Int. Cl.
| | |
|---|---|
| *A61K 31/5415* | (2006.01) |
| *A61K 31/5377* | (2006.01) |
| *A61K 31/522* | (2006.01) |
| *A61K 31/513* | (2006.01) |
| *A61K 31/517* | (2006.01) |

(52) U.S. Cl. .................. 514/225.8; 514/235.5; 514/248; 514/252.14; 514/254.02; 514/256; 514/263.21; 514/266.2; 514/296; 514/369; 514/375; 544/237; 544/269; 544/284; 544/295; 544/310

(58) Field of Classification Search ........................ None
See application file for complete search history.

(56) References Cited

OTHER PUBLICATIONS

Pain, 2012, http://trialx.com/curetalk/2011/01/icagen-pfizer-phase-i-trial-for-pain-sodium-channel-program/.*
PainII, 2012, http://www.dynamicchiropractic.com/mpacms/dc/article.php?id=55917.*
Lamotrigine, 2012, http://en.wikipedia.org/wiki/Lamotrigine.*
Weir et al, 2011, http://www.biomedcentral.com/1741-7015/9/116.*
Matsuki, 2008, http://www.ncbi.nlm.nih.gov/pubmed/18563291.*
Sun et al., 1965, caplus an 1965:93681.*
Arrythmia, 2012, http://en.wikipedia.org/wiki/Sodium_channel_blocker.*
Migraine, 2012, http://headache.emedtv.com/divalproex/divalproex.html.*
Tegretol, 2012, http://epilepsy.emedtv.com/tegretol/tegretol.html.*
Postherpetic, 2012, http://www.mayoclinic.com/health/postherpetic-neuralgia/DS00277/DSECTION=treatments-and-drugs.*
Lyrica, 2012, http://www.ei-resource.org/news/fibromyalgia-news/lyrica-and-fibromyalgia:-dr.-jacob-teitelbaum-offers-his-opinion/.*

* cited by examiner

*Primary Examiner* — Sun Jae Loewe
(74) *Attorney, Agent, or Firm* — Michael J. DiVerdi

(57) ABSTRACT

The present invention relates to compounds useful as inhibitors of voltage-gated sodium channels. The invention also provides pharmaceutically acceptable compositions comprising the compounds of the invention and methods of using the compositions in the treatment of various disorders.

7 Claims, 223 Drawing Sheets

Figure 1-1
| # | Compound |
|---|---|
| 1 | 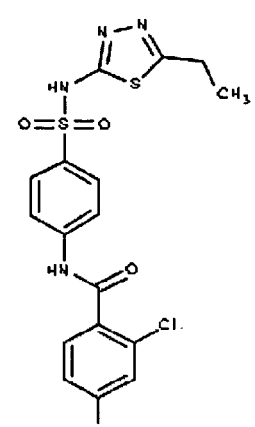 |
| 2 | 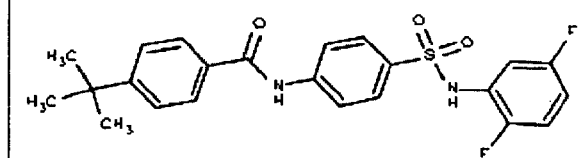 |
| 3 | 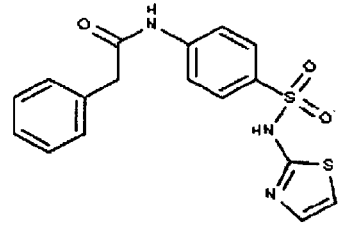 |
| 4 | 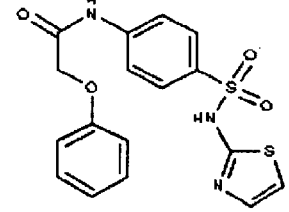 |
| 5 | 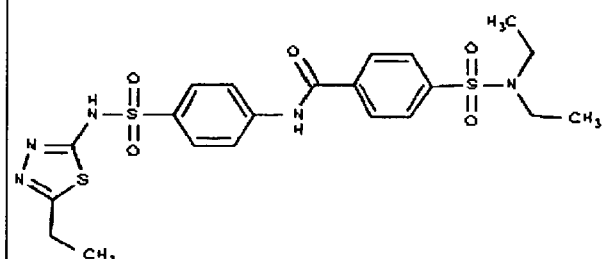 |

Figure 1-2
| # | Compound |
|---|---|
| 6 | 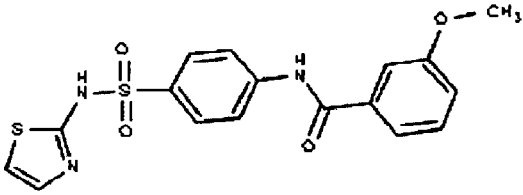 |
| 7 | 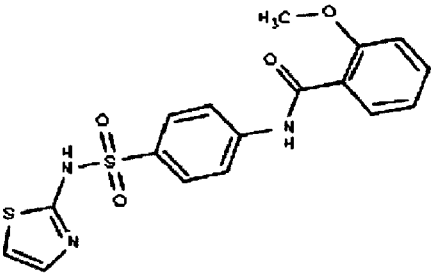 |
| 8 | 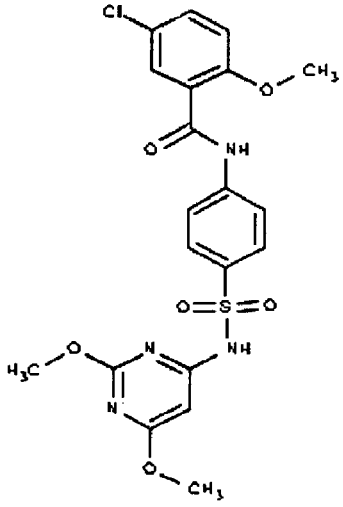 |
| 9 | 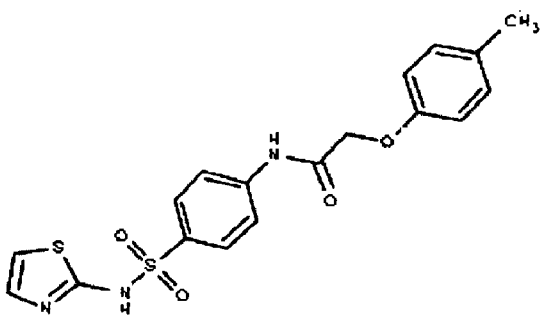 |

Figure 1-3

| # | Compound |
|---|---|
| 10 | (structure) |
| 11 | (structure) |
| 12 | (structure) |
| 13 | (structure) |
| 14 | (structure) |

Figure 1-4

| # | Compound |
|---|---|
| 15 | |
| 16 | |
| 17 | |
| 18 | |
| 19 | |
| 20 | |

| # | Compound |
|---|---|
| 21 |  |
| 22 |  |
| 23 |  |
| 24 |  |
| 25 |  |

Figure 1-6

| # | Compound |
|---|---|
| 26 | |
| 27 | |
| 28 | |
| 29 | |
| 30 | |
| 31 | |

Figure 1-7

| # | Compound |
|---|---|
| 32 | |
| 33 | |
| 34 | |
| 35 | |
| 36 | |

Figure 1-8
| # | Compound |
|---|---|
| 37 | 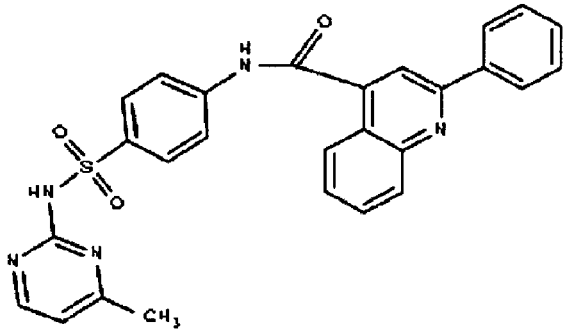 |
| 38 | 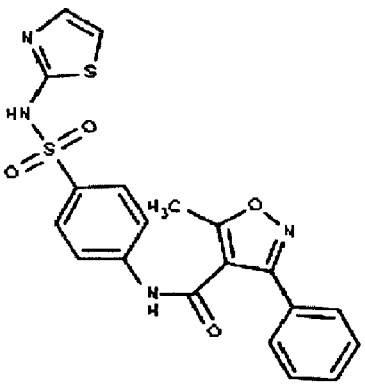 |
| 39 | 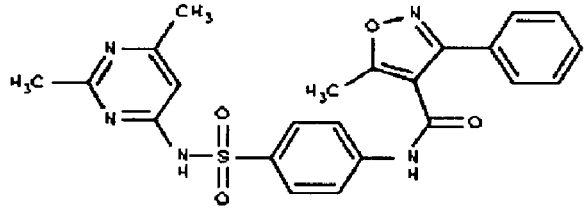 |
| 40 | 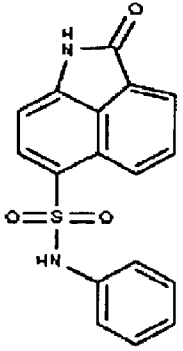 |

Figure 1-9
| # | Compound |
|---|---|
| 41 | 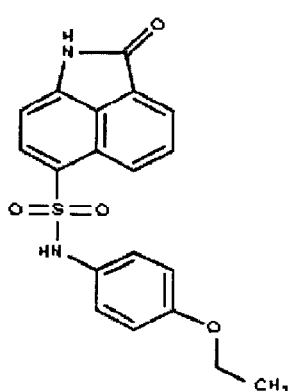 |
| 42 | 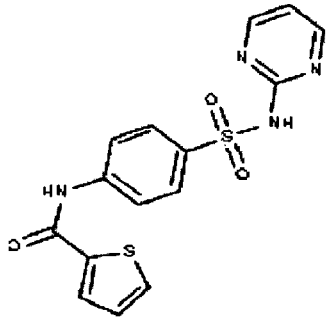 |
| 43 | 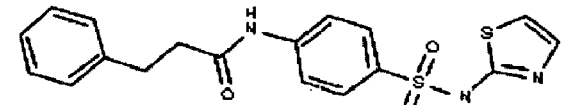 |
| 44 | 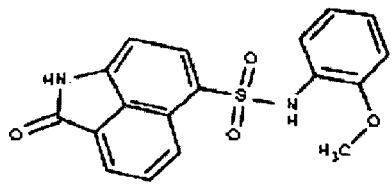 |
| 45 | 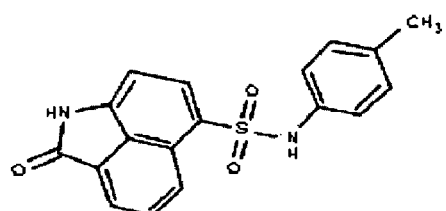 |

Figure 1-10

| # | Compound |
|---|---|
| 46 | |
| 47 | |
| 48 | |
| 49 | |

Figure 1-11
| # | Compound |
|---|---|
| 50 | 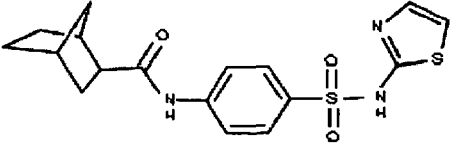 |
| 51 | 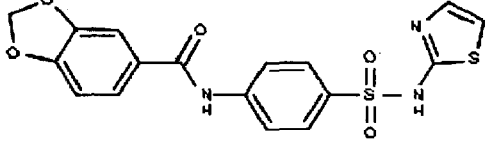 |
| 52 | 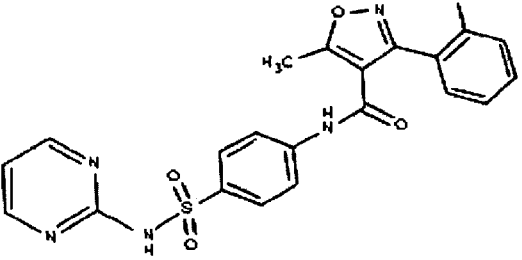 |
| 53 | 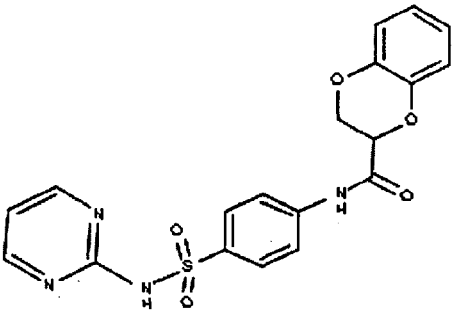 |
| 54 | 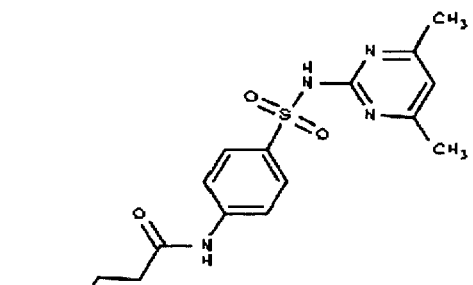 |

Figure 1-12

| # | Compound |
|---|---|
| 55 | |
| 56 | |
| 57 | |
| 58 | |
| 59 | |

Figure 1-13
| # | Compound |
|---|---|
| 60 | 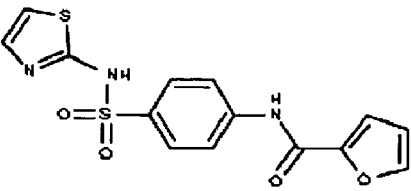 |
| 61 | 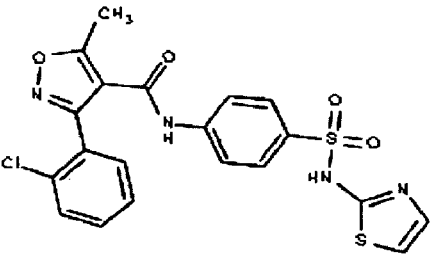 |
| 62 | 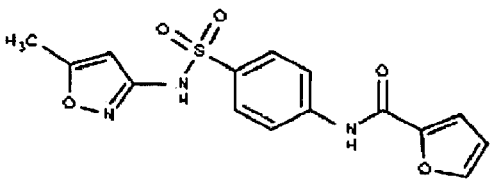 |
| 63 | 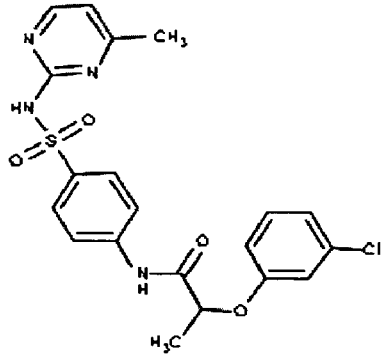 |
| 64 | 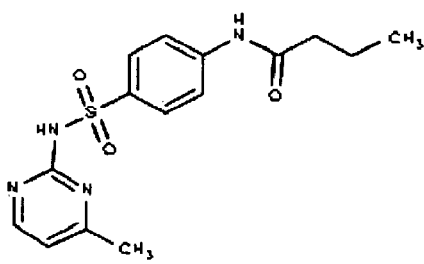 |

Figure 1-14
| # | Compound |
|---|---|
| 65 | 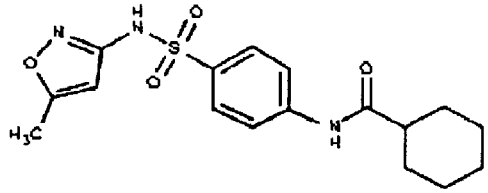 |
| 66 | 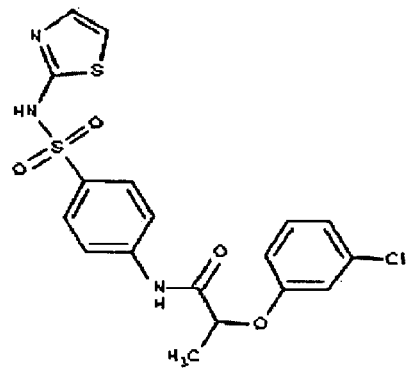 |
| 67 | 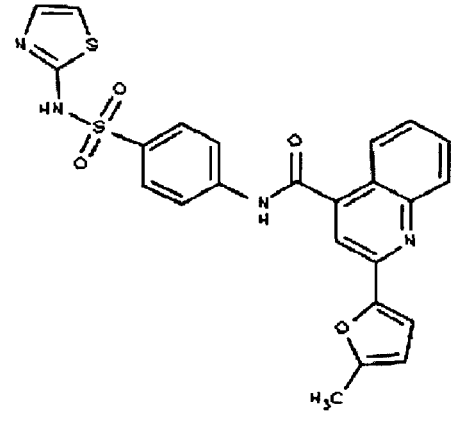 |
| 68 | 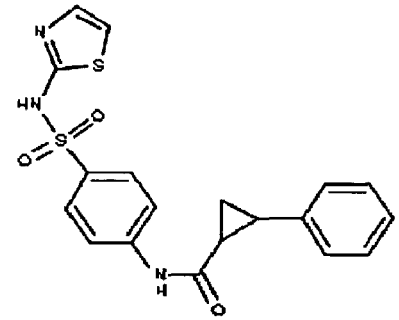 |

Figure 1-15
| # | Compound |
|---|---|
| 69 | 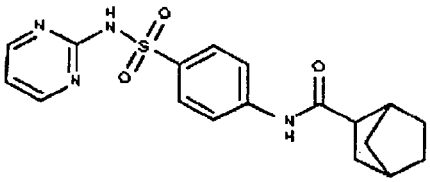 |
| 70 | 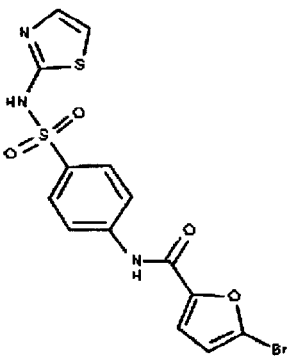 |
| 71 | 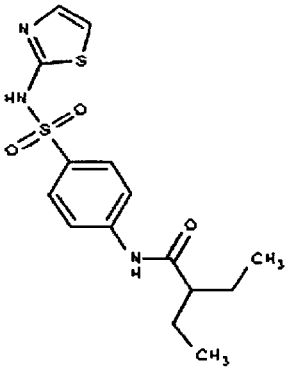 |
| 72 | 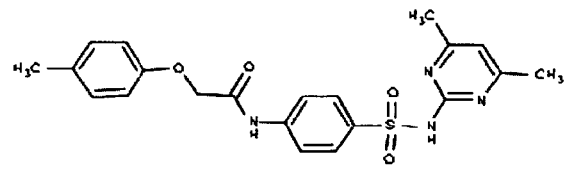 |
| 73 | 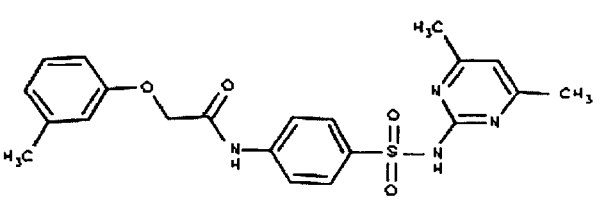 |

Figure 1-16
| # | Compound |
|---|---|
| 74 | 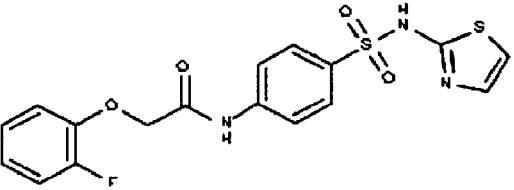 |
| 75 | 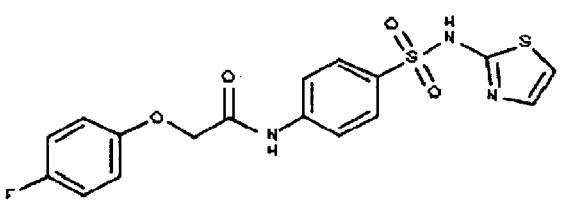 |
| 76 | 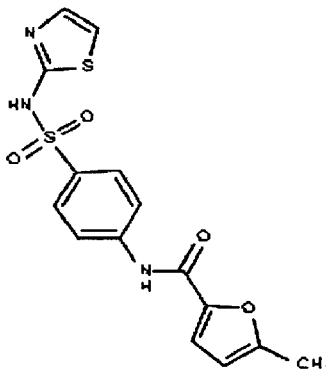 |
| 77 | 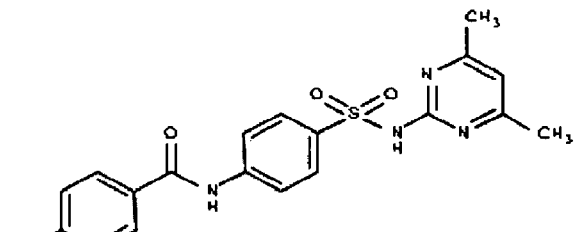 |
| 78 | 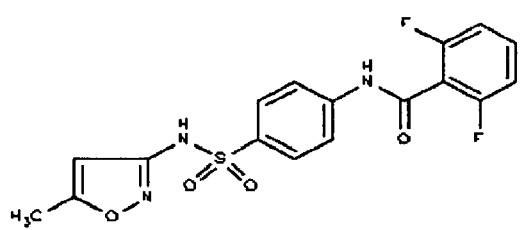 |

Figure 1-17

| # | Compound |
|---|---|
| 79 | |
| 80 | |
| 81 | |
| 82 | |
| 83 | |
| 84 | |

Figure 1-18
| # | Compound |
|---|---|
| 85 | 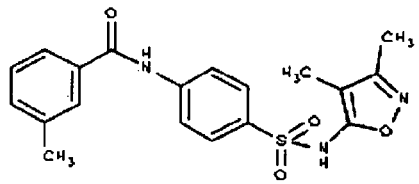 |
| 86 | 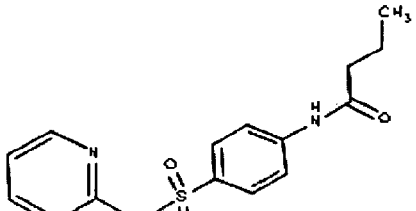 |
| 87 | 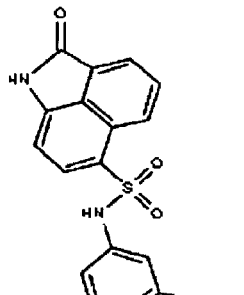 |
| 88 | 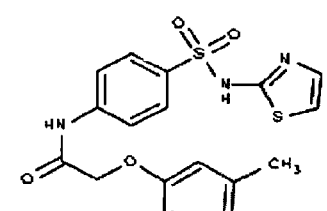 |
| 89 | 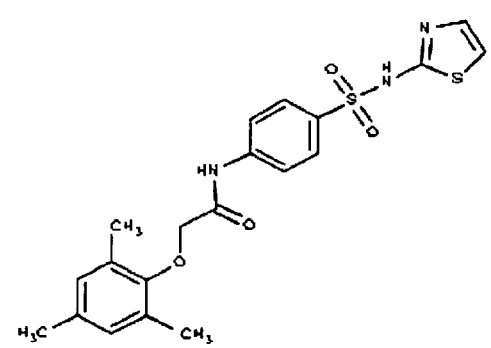 |

Figure 1-19

| # | Compound |
|---|---|
| 90 | |
| 91 | |
| 92 | |
| 93 | |
| 94 | |

Figure 1-20

| # | Compound |
|---|---|
| 95 | |
| 96 | |
| 97 | |
| 98 | |
| 99 | |

Figure 1-21
| # | Compound |
|---|---|
| 100 | 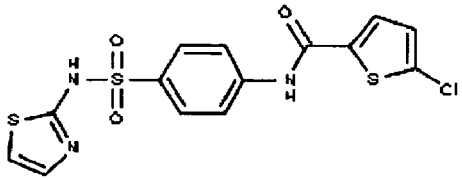 |
| 101 | 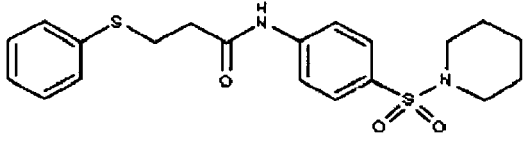 |
| 102 | 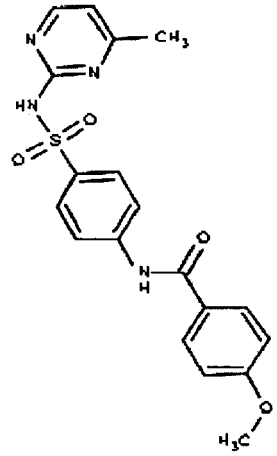 |
| 103 | 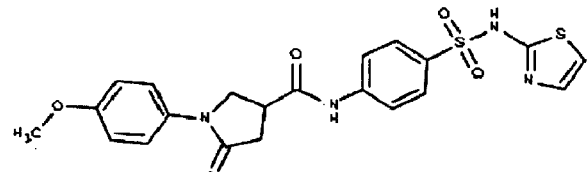 |
| 104 | 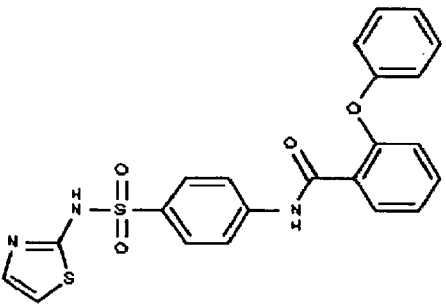 |

Figure 1-22

| # | Compound |
|---|---|
| 105 | |
| 106 | |
| 107 | |
| 108 | |
| 109 | |

Figure 1-23
| # | Compound |
|---|---|
| 110 | 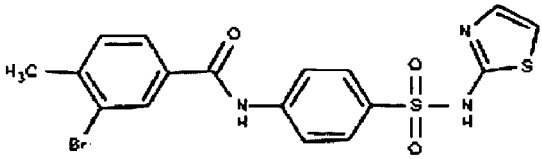 |
| 111 | 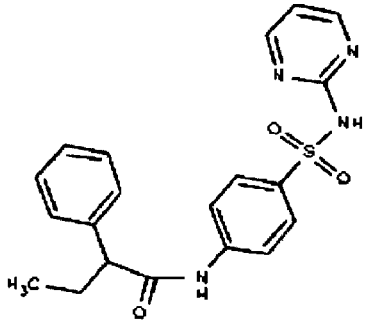 |
| 112 | 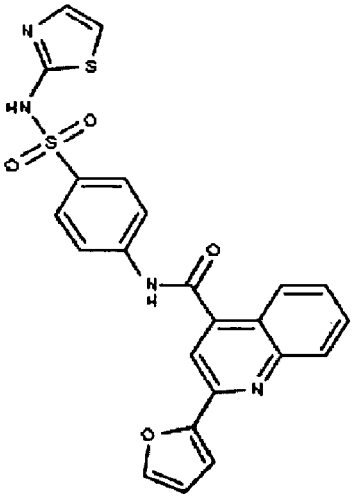 |
| 113 | 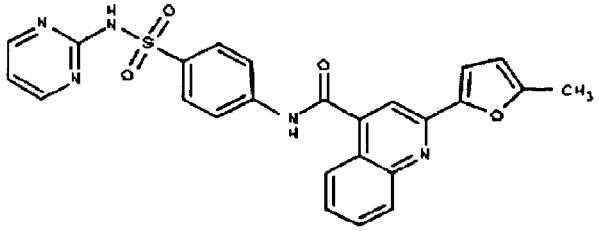 |

Figure 1-24
| # | Compound |
|---|---|
| 114 | 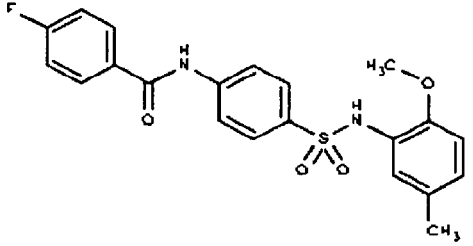 |
| 115 | 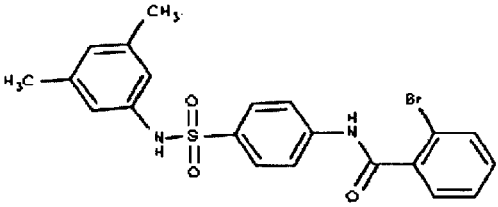 |
| 116 | 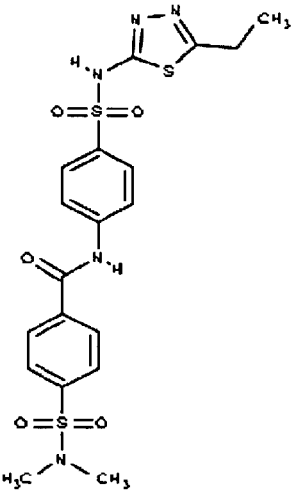 |
| 117 | 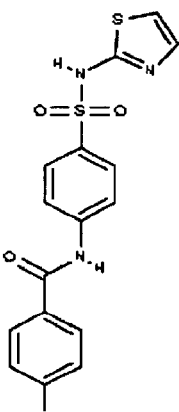 |

Figure 1-25

| # | Compound |
|---|---|
| 118 | |
| 119 | |
| 120 | |

Figure 1-26
| # | Compound |
|---|---|
| 121 | 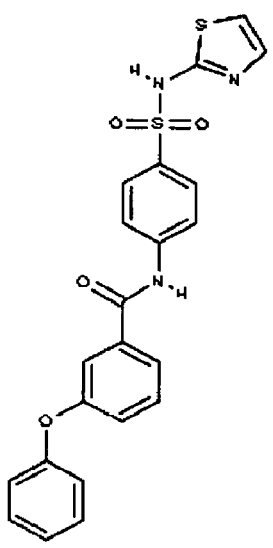 |
| 122 | 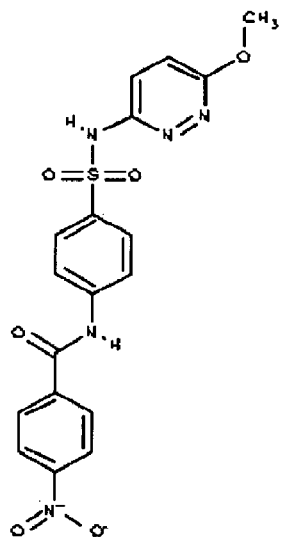 |

Figure 1-27
| # | Compound |
|---|---|
| 123 | 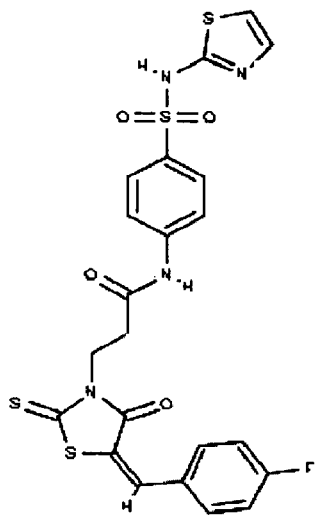 |
| 124 | 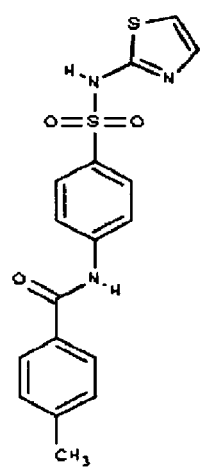 |
| 125 | 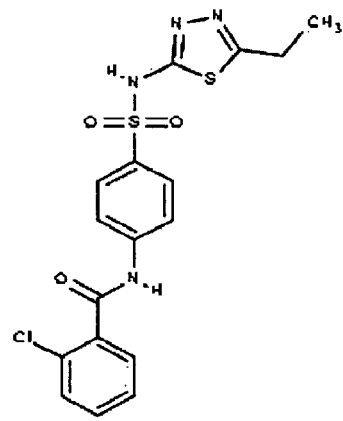 |

Figure 1-28

| # | Compound |
|---|---|
| 126 | |
| 127 | |
| 128 | |

Figure 1-29
| # | Compound |
|---|---|
| 129 | 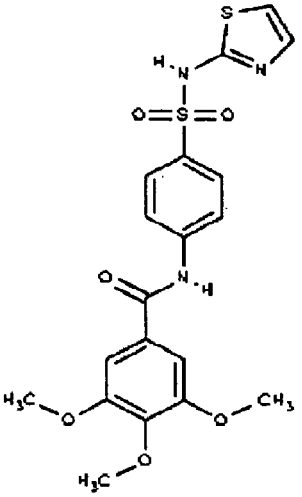 |
| 130 | 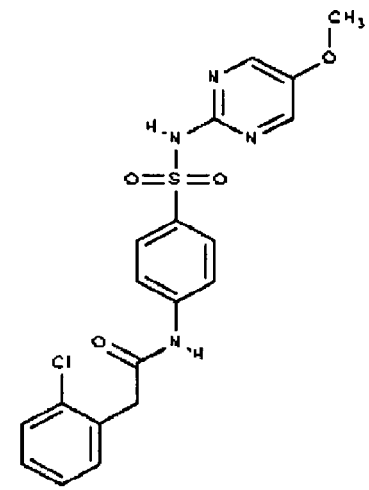 |
| 131 | 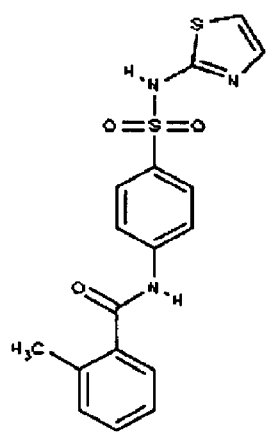 |

Figure 1-30

| # | Compound |
|---|---|
| 132 | |
| 133 | |
| 134 | |

Figure 1-31
| # | Compound |
|---|---|
| 135 | 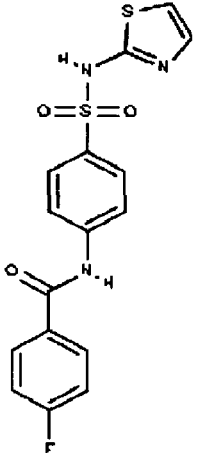 |
| 136 | 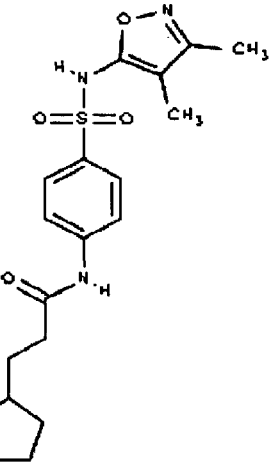 |
| 137 | 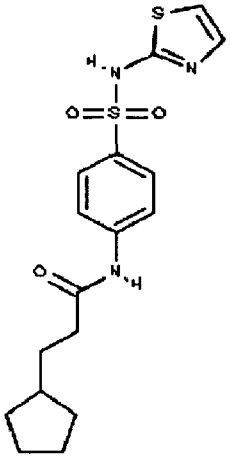 |

Figure 1-32
| # | Compound |
|---|---|
| 138 | 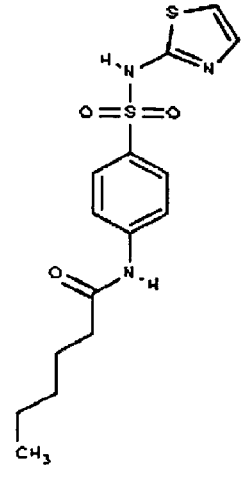 |
| 139 | 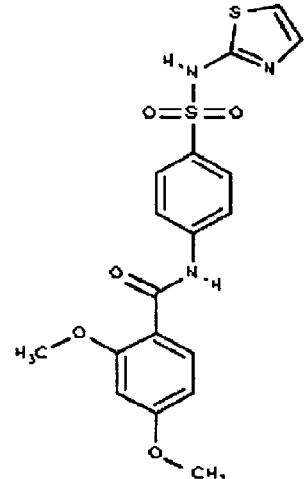 |
| 140 | 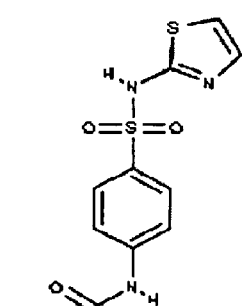 |

Figure 1-33

| # | Compound |
|---|---|
| 141 | |
| 142 | |

Figure 1-34

| # | Compound |
|---|---|
| 143 | (structure: N-(4-(thiazol-2-ylsulfamoyl)phenyl)-4-(2,4-dichlorophenoxy)butanamide) |
| 144 | (structure: 2-(2,4-dichlorophenoxy)-N-(4-(pyrimidin-2-ylsulfamoyl)phenyl)acetamide) |
| 145 | (structure: N-(4-((5-ethyl-1,3,4-thiadiazol-2-yl)sulfamoyl)phenyl)-3,5-dimethylbenzamide) |

Figure 1-35

| # | Compound |
|---|---|
| 146 | (structure: 5-ethyl-1,3,4-thiadiazol-2-yl sulfonamide linked to phenyl-C(O)NH-phenyl-SO2-piperidine) |
| 147 | (structure: CH3-C(O)NH-SO2-phenyl-NHC(O)-CH2CH2CH2-O-(2,4-dichlorophenyl)) |

Figure 1-36
| # | Compound |
|---|---|
| 148 | 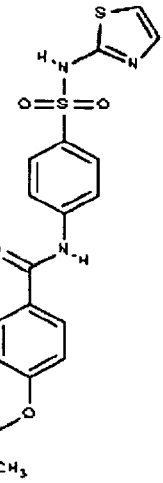 |
| 149 | 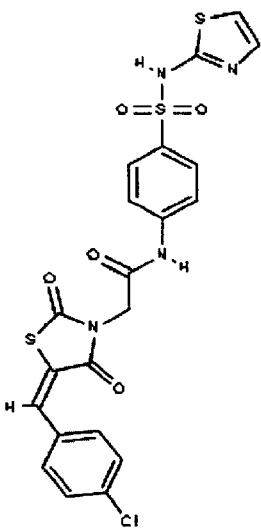 |
| 150 | 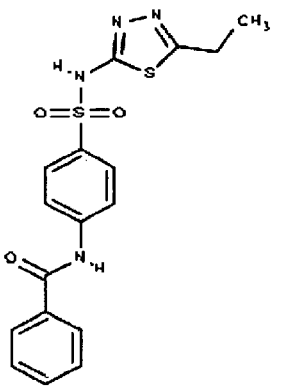 |

Figure 1-37
| # | Compound |
|---|---|
| 151 | 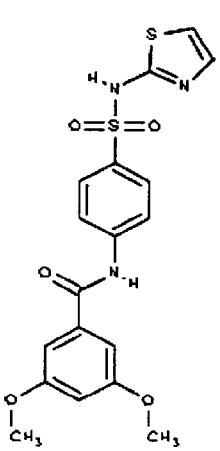 |
| 152 | 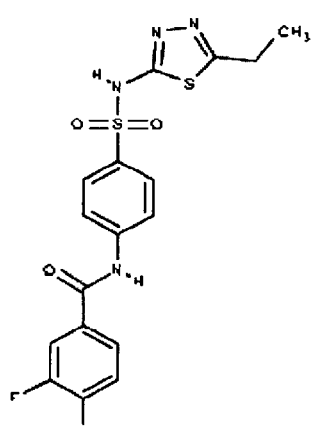 |
| 153 | 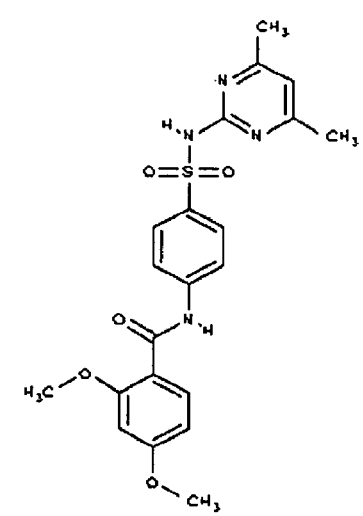 |

Figure 1-38
| # | Compound |
|---|---|
| 154 | 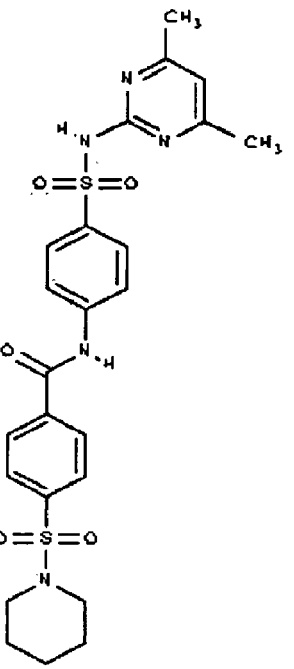 |
| 155 | 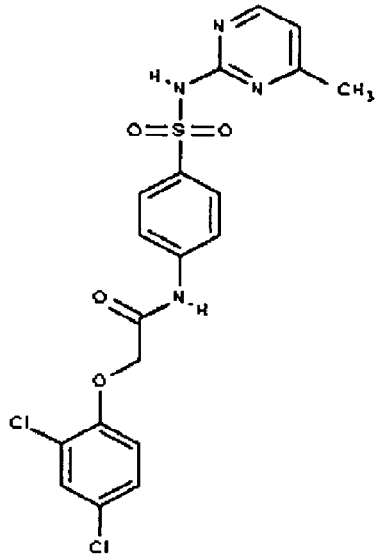 |

Figure 1-39
| # | Compound |
|---|---|
| 156 | 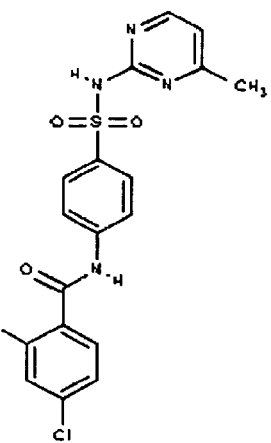 |
| 157 | 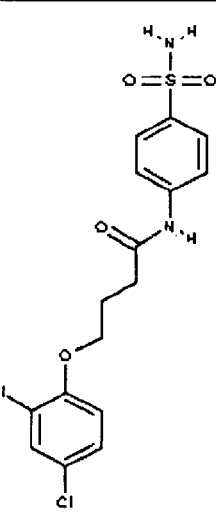 |
| 158 | 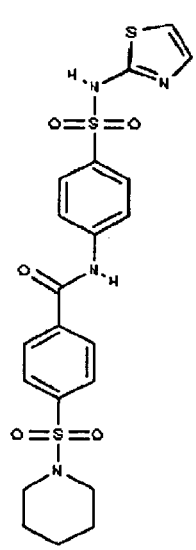 |

Figure 1-40
| # | Compound |
|---|---|
| 159 | 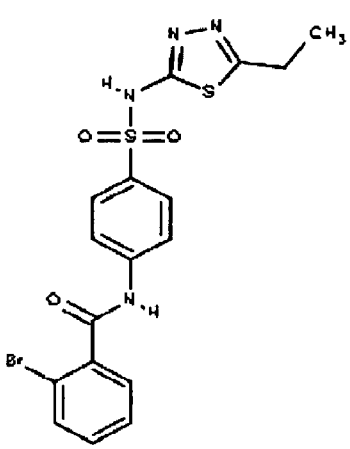 |
| 160 | 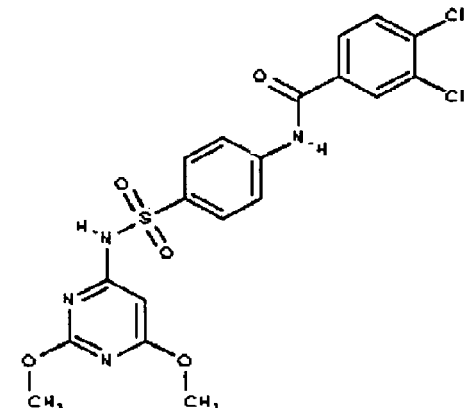 |
| 161 | 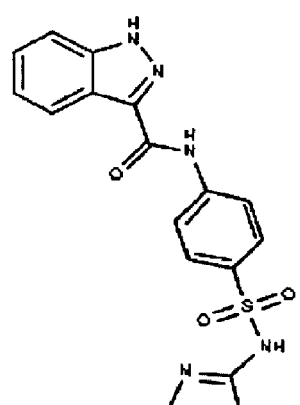 |

Figure 1-41
| # | Compound |
|---|---|
| 162 | 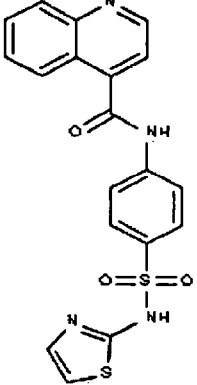 |
| 163 | 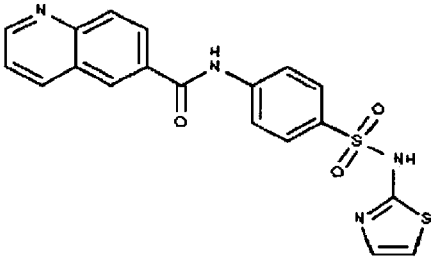 |
| 164 | 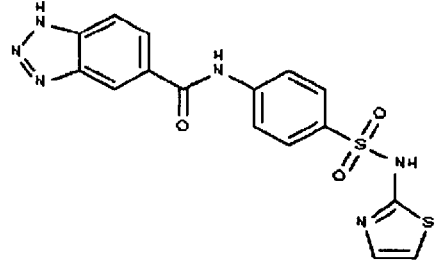 |
| 165 | 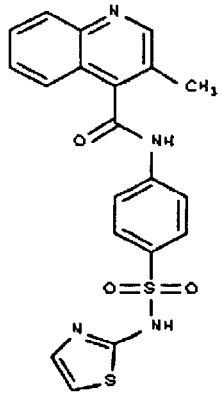 |

Figure 1-42
| # | Compound |
|---|---|
| 166 | 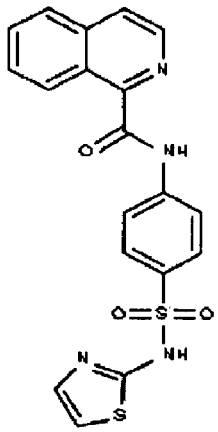 |
| 167 | 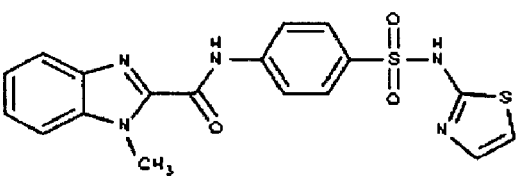 |
| 168 | 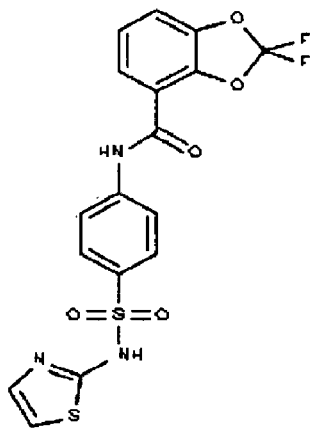 |

Figure 1-43

| # | Compound |
|---|---|
| 170 | |
| 171 | |
| 172 | |
| 173 | |

Figure 1-44

| # | Compound |
|---|---|
| 174 | |
| 175 | |
| 176 | |
| 177 | |

Figure 1-45

| # | Compound |
|---|---|
| 178 | |
| 179 | |
| 180 | |
| 181 | |
| 182 | |

Figure 1-46

| # | Compound |
|---|---|
| 183 | |
| 184 | |
| 185 | |
| 186 | |
| 187 | |

Figure 1-47

| # | Compound |
|---|---|
| 188 | 4-fluorobenzyl group connected via CH2-C(=O)-NH to a para-substituted benzene with sulfonamide (SO2-NH) linked to 4-methylpyrimidin-2-yl |
| 189 | 2-methylbenzoyl-NH-phenyl-SO2-NH-(2,5-dimethylphenyl) |
| 190 | phenyl-CH2-C(=O)-NH-phenyl-SO2-NH-(3-chloro-2-methylphenyl) |
| 191 | (3,5-dimethylphenyl)-NH-SO2-phenyl-NH-C(=O)-phenyl |
| 192 | (3,5-dimethylphenyl)-NH-SO2-phenyl-NH-C(=O)-(4-methoxyphenyl) |

Figure 1-48

| # | Compound |
|---|---|
| 193 | |
| 194 | |
| 195 | |
| 196 | |
| 197 | |

Figure 1-49
| # | Compound |
|---|---|
| 198 | 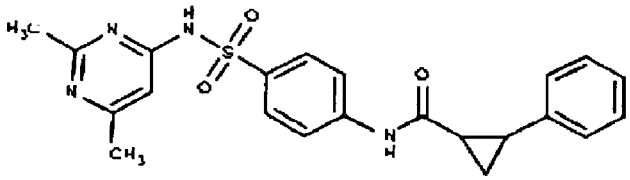 |
| 199 | 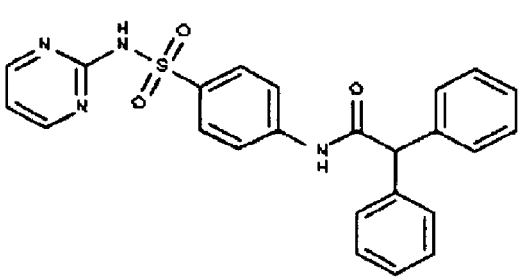 |
| 200 | 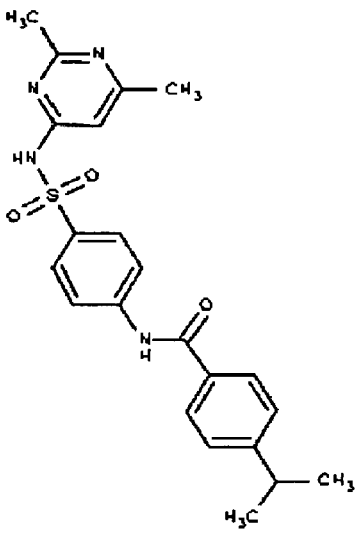 |
| 201 | 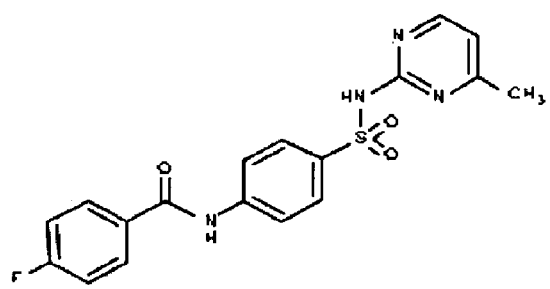 |

Figure 1-50

| # | Compound |
|---|---|
| 202 | |
| 203 | |
| 204 | |
| 205 | |

Figure 1-51
| # | Compound |
|---|---|
| 206 | 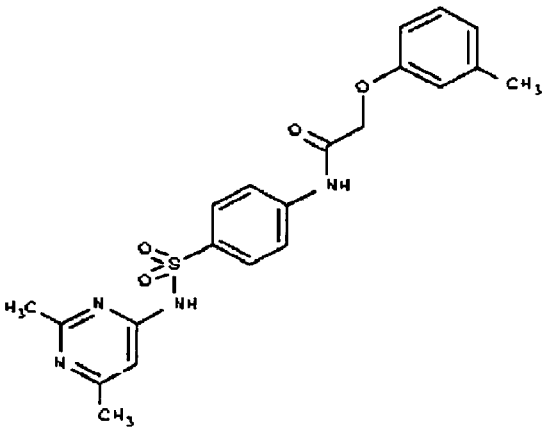 |
| 207 | 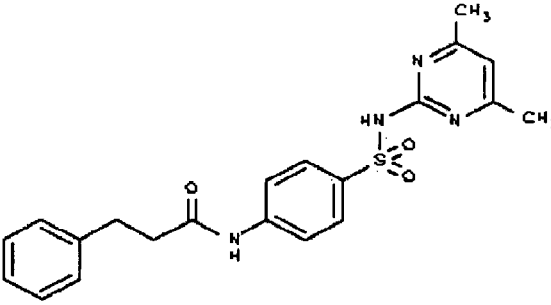 |
| 208 | 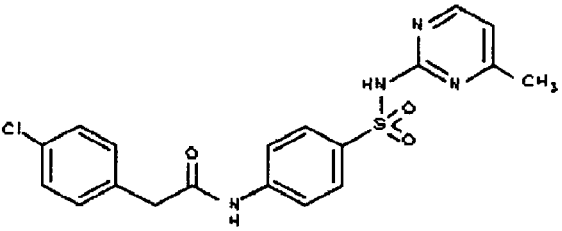 |
| 209 | 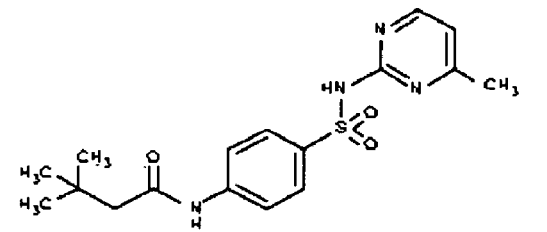 |

Figure 1-52

| # | Compound |
|---|---|
| 210 | |
| 211 | |
| 212 | |
| 213 | |

Figure 1-53

| # | Compound |
|---|---|
| 214 | |
| 215 | |
| 216 | |
| 217 | |

Figure 1-54

| # | Compound |
|---|---|
| 218 | |
| 219 | |
| 220 | |
| 221 | |

Figure 1-55

| # | Compound |
|---|---|
| 222 | |
| 223 | |
| 224 | |
| 225 | |

Figure 1-56
| # | Compound |
|---|---|
| 226 | 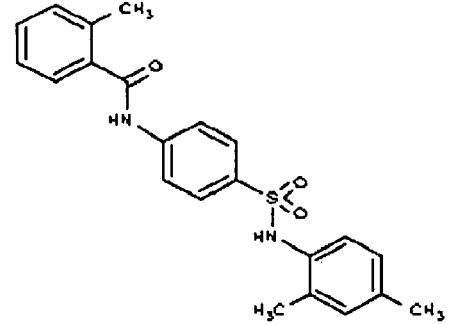 |
| 227 | 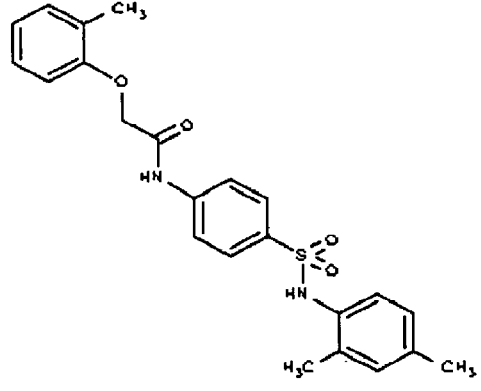 |
| 228 | 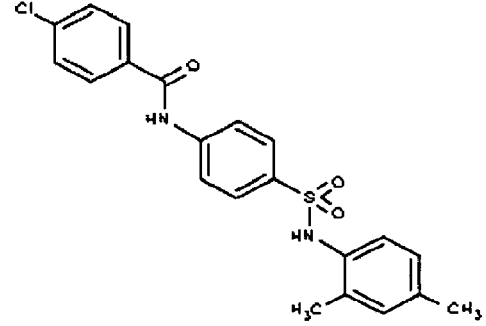 |
| 229 | 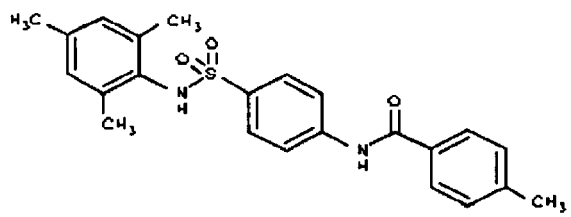 |

Figure 1-57
| # | Compound |
|---|---|
| 230 | 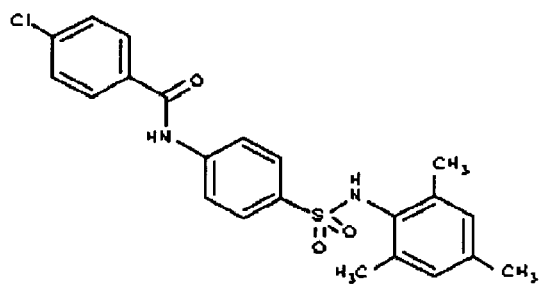 |
| 231 | 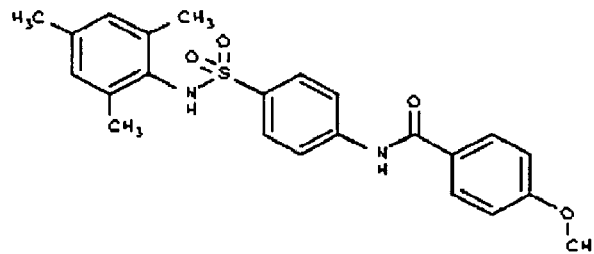 |
| 232 | 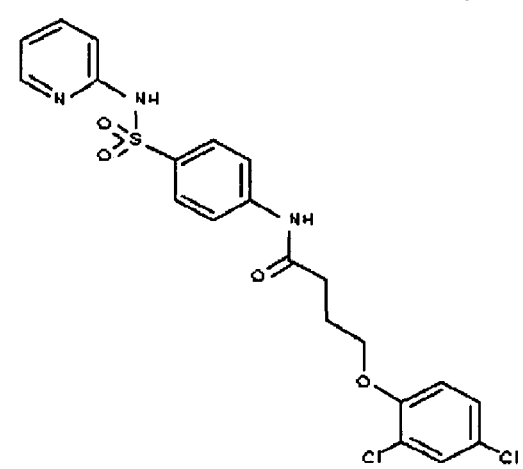 |
| 233 | 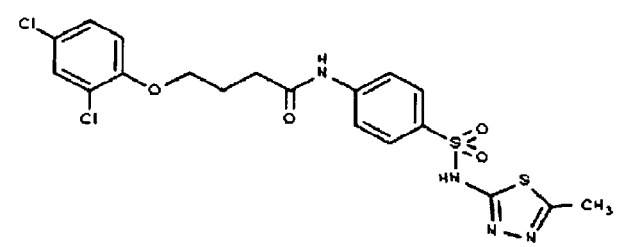 |

Figure 1-58

| # | Compound |
|---|---|
| 234 | |
| 235 | |
| 236 | |

Figure 1-59
| # | Compound |
|---|---|
| 237 | 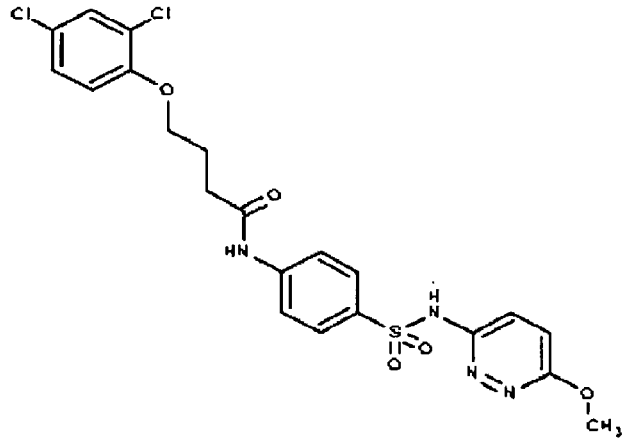 |
| 238 | 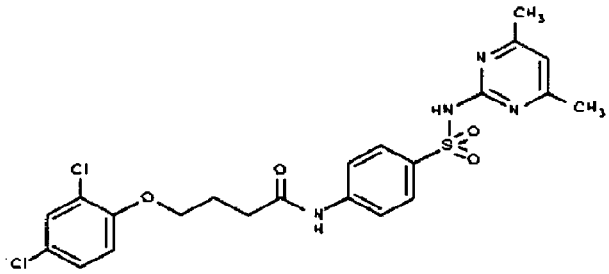 |
| 239 | 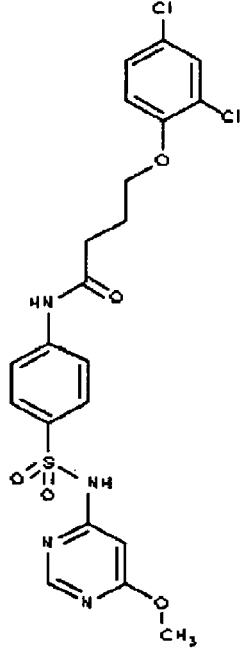 |

Figure 1-60
| # | Compound |
|---|---|
| 240 | 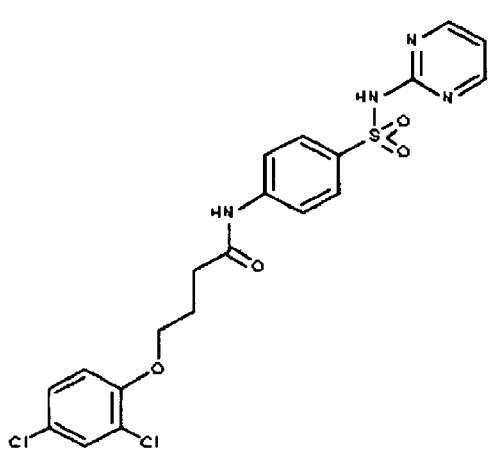 |
| 241 | 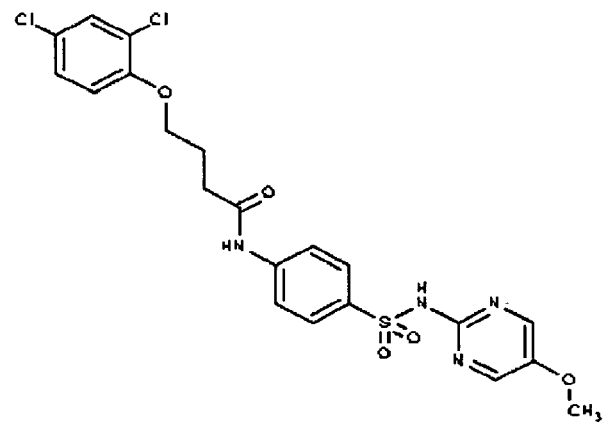 |
| 242 | 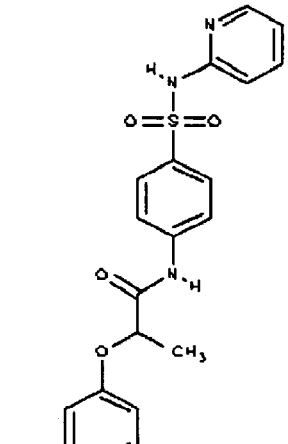 |

Figure 1-61

| # | Compound |
|---|---|
| 243 | |
| 244 | |
| 245 | |

Figure 1-62

| # | Compound |
|---|---|
| 246 | |
| 247 | |

Figure 1-63

| # | Compound |
|---|---|
| 248 | |
| 249 | |
| 250 | |

Figure 1-64
| # | Compound |
|---|---|
| 251 | 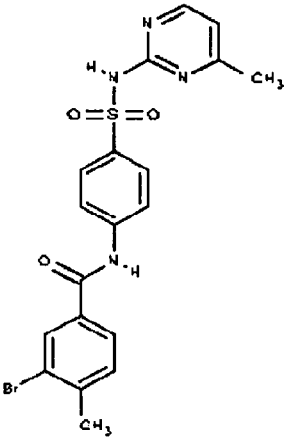 |
| 252 | 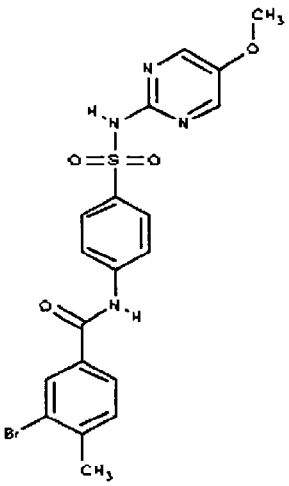 |
| 253 | 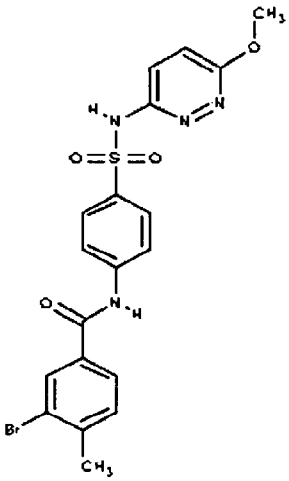 |

| # | Compound |
|---|---|
| 254 |  |
| 255 |  |

| # | Compound |
|---|---|
| 256 |  |
| 257 |  |

Figure 1-67

| # | Compound |
|---|---|
| 258 | (structure: 4-chlorophenylthio-propanamide linked to N-H phenyl sulfonamide N-thiazol-2-yl) |
| 259 | (structure: CH₃C(O)NH-SO₂-phenyl-NHC(O)-phenyl(3-Br, 4-CH₃)) |
| 260 | (structure: pyridin-2-yl-NH-SO₂-phenyl-NHC(O)-phenyl(3-Br, 4-CH₃)) |
| 261 | (structure: 5-methyl-1,3,4-thiadiazol-2-yl-NH-SO₂-phenyl-NHC(O)-phenyl(3-Br, 4-CH₃)) |
| 262 | (structure: 5-methylisoxazol-3-yl-NH-SO₂-phenyl-NHC(O)-phenyl(3-Br, 4-CH₃)) |

Figure 1-68

| # | Compound |
|---|---|
| 263 | |
| 264 | |
| 265 | |

Figure 1-69

| # | Compound |
|---|---|
| 266 | |
| 267 | |
| 268 | |
| 269 | |

Figure 1-70
| # | Compound |
|---|---|
| 270 | 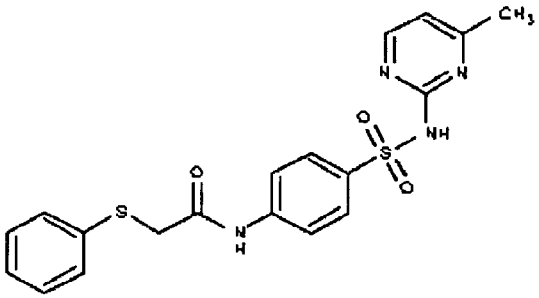 |
| 271 | 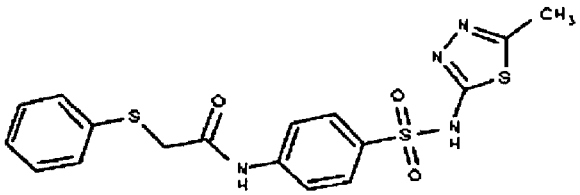 |
| 272 | 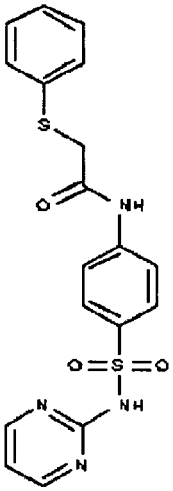 |

Figure 1-71

| # | Compound |
|---|---|
| 273 | |
| 274 | |
| 275 | |
| 276 | |

Figure 1-72
| # | Compound |
|---|---|
| 277 | 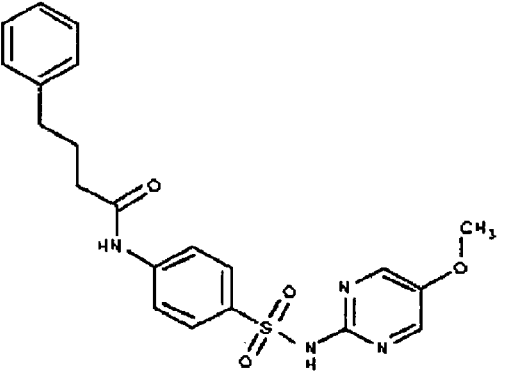 |
| 278 | 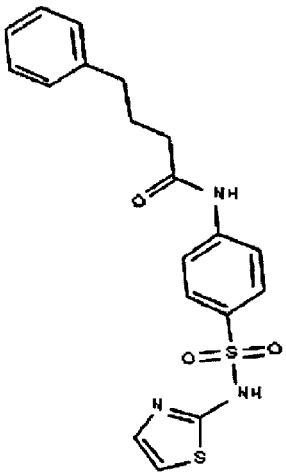 |
| 279 | 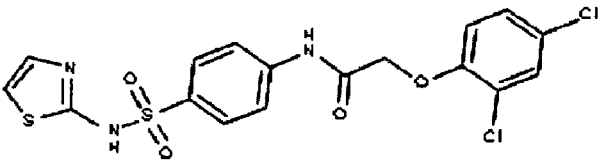 |
| 280 | 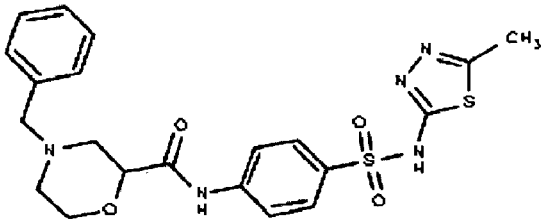 |

Figure 1-73

| # | Compound |
|---|---|
| 281 | |
| 282 | |
| 283 | |

| # | Compound |
|---|---|
| 284 |  |
| 285 |  |

Figure 1-75

| # | Compound |
|---|----------|
| 286 | *(structure: 2-(2,4-dichlorophenoxy)-N-(4-(N-(4,5-dimethyloxazol-2-yl)sulfamoyl)phenyl)propanamide)* |
| 287 | *(structure: 2-(2,4-dichlorophenoxy)-N-(4-(N-(5-methylisoxazol-3-yl)sulfamoyl)phenyl)propanamide)* |

Figure 1-76
| # | Compound |
|---|---|
| 288 | 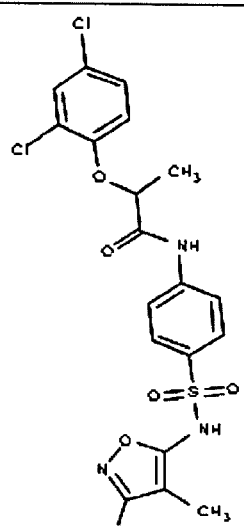 |
| 289 | 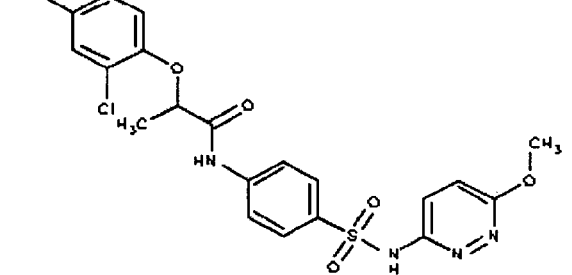 |
| 290 | 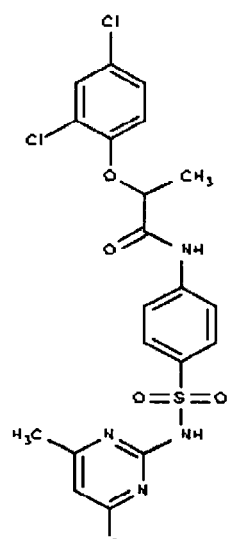 |

Figure 1-77
| # | Compound |
|---|---|
| 291 | 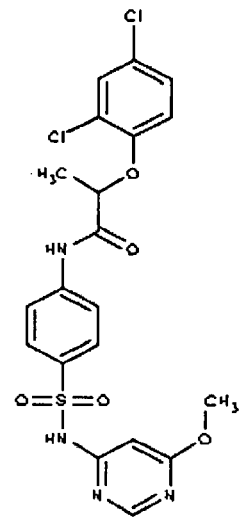 |
| 292 | 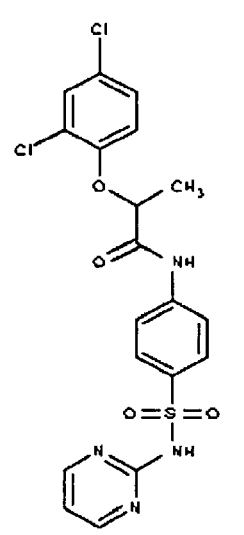 |
| 293 | 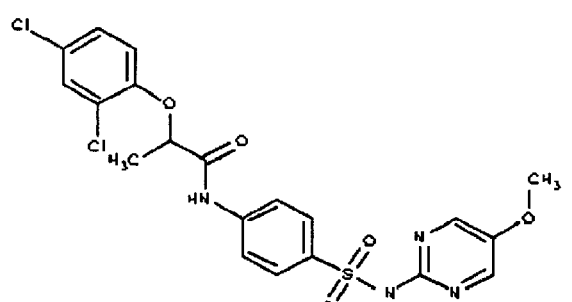 |

Figure 1-78

| # | Compound |
|---|---|
| 294 | |
| 295 | |
| 296 | |

Figure 1-79

| # | Compound |
|---|---|
| 297 | |
| 298 | |
| 299 | |

Figure 1-80
| # | Compound |
|---|---|
| 300 | 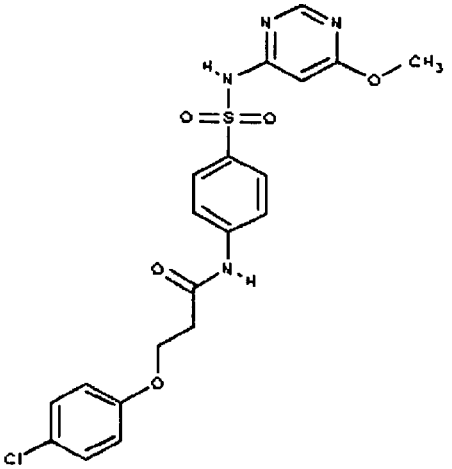 |
| 301 | 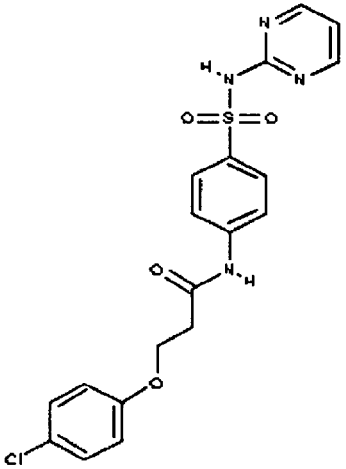 |
| 302 | 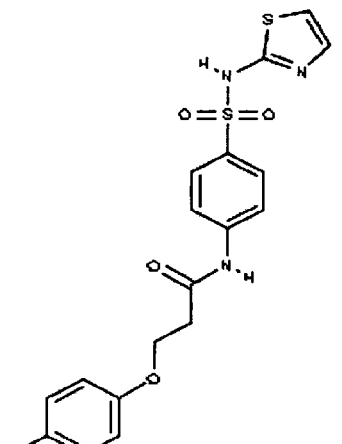 |

Figure 1-81

| # | Compound |
|---|---|
| 303 | |
| 304 | |
| 305 | |
| 306 | |
| 307 | |

Figure 1-82

| # | Compound |
|---|---|
| 308 | |
| 309 | |
| 310 | |
| 311 | |

| # | Compound |
|---|---|
| 312 |  |
| 313 |  |

| # | Compound |
|---|---|
| 314 |  |
| 315 |  |

Figure 1-85

| # | Compound |
|---|---|
| 316 | |
| 317 | |

| # | Compound |
|---|---|
| 318 |  |
| 319 |  |

Figure 1-87
| # | Compound |
|---|---|
| 320 | 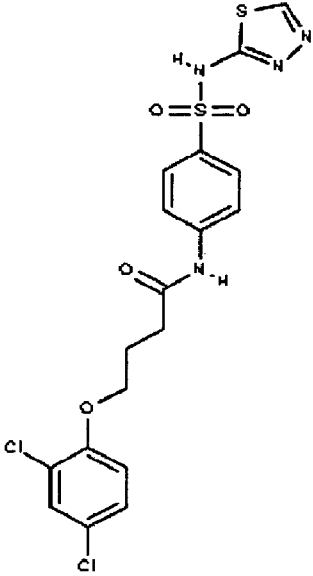 |
| 321 | 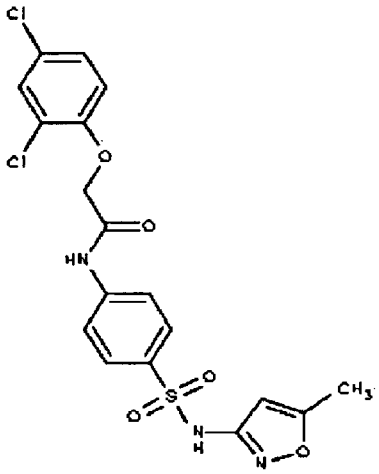 |
| 322 | 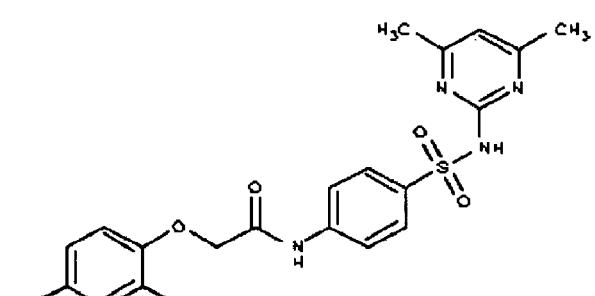 |

Figure 1-88
| # | Compound |
|---|---|
| 323 | 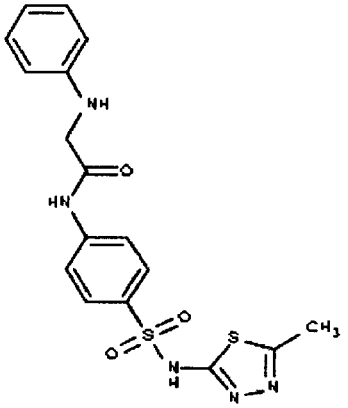 |
| 324 | 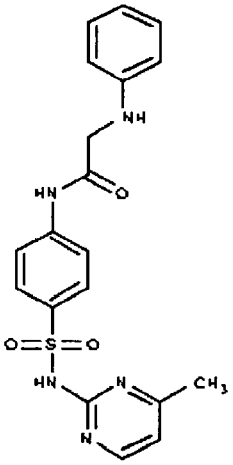 |
| 325 | 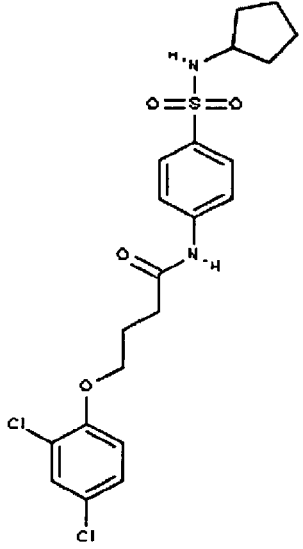 |

Figure 1-89

| # | Compound |
|---|---|
| 326 | |
| 327 | |

| # | Compound |
|---|---|
| 328 |  |
| 329 |  |

Figure 1-91
| # | Compound |
|---|---|
| 330 | 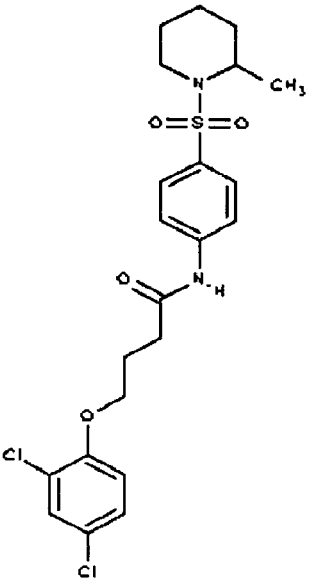 |
| 331 | 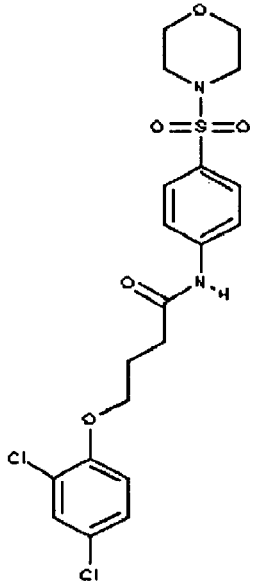 |
| 332 | 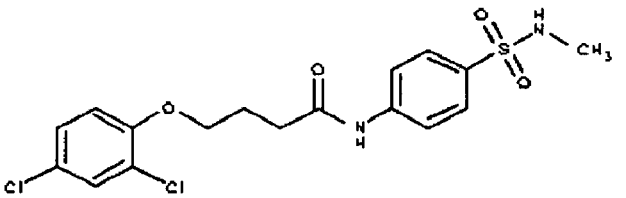 |

Figure 1-92
| # | Compound |
|---|---|
| 333 | 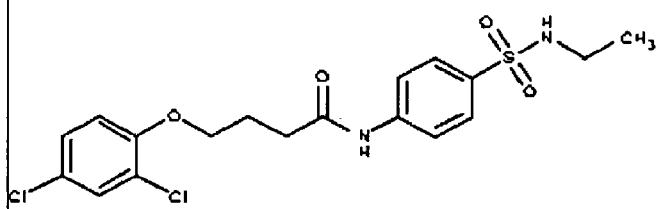 |
| 334 | 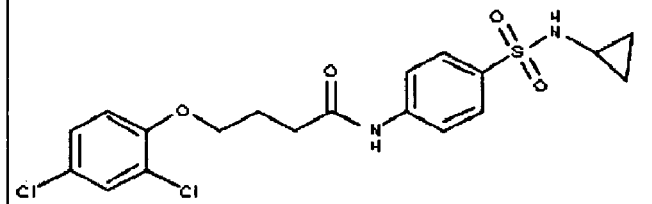 |
| 335 | 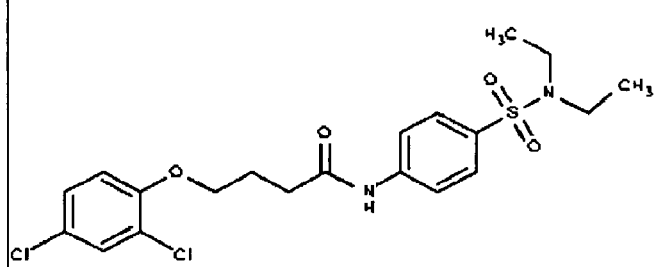 |
| 336 | 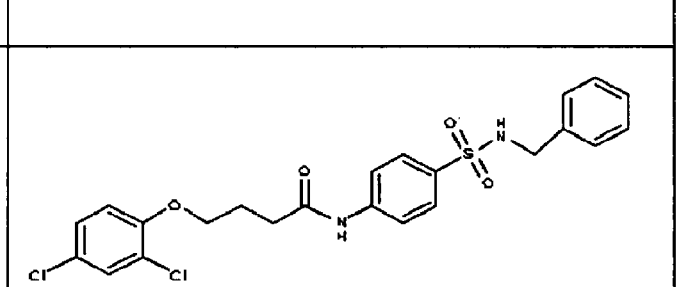 |
| 337 | 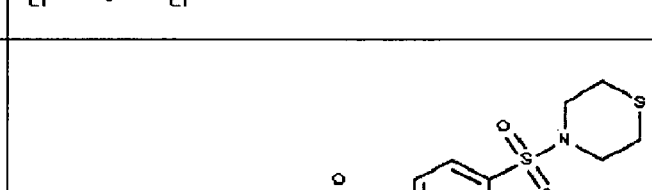 |

Figure 1-93

| # | Compound |
|---|---|
| 338 | |
| 339 | |
| 340 | |
| 341 | |

Figure 1-94

| # | Compound |
|---|---|
| 342 | |
| 343 | |
| 344 | |
| 345 | |
| 346 | |

Figure 1-95

| # | Compound |
|---|---|
| 347 | |
| 348 | |
| 349 | |

Figure 1-96
| # | Compound |
|---|---|
| 350 | 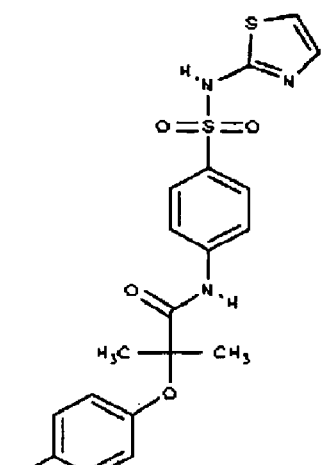 |
| 351 | 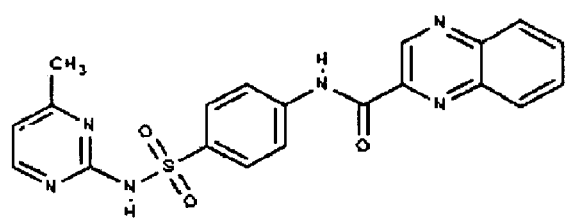 |
| 352 | 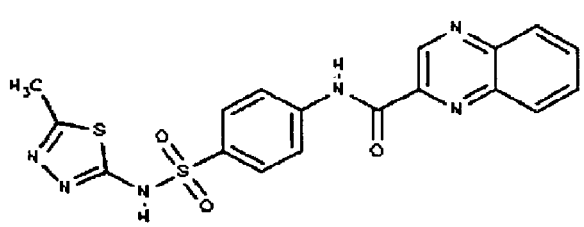 |
| 353 | 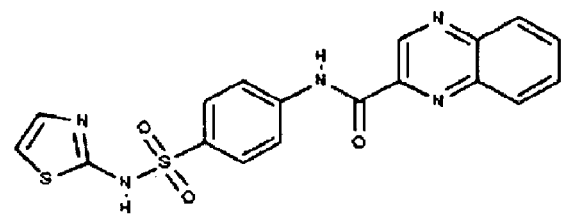 |

Figure 1-97

| # | Compound |
|---|---|
| 354 | |
| 355 | |
| 356 | |

Figure 1-98
| # | Compound |
|---|---|
| 357 | 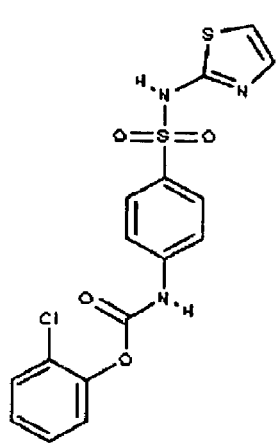 |
| 358 | 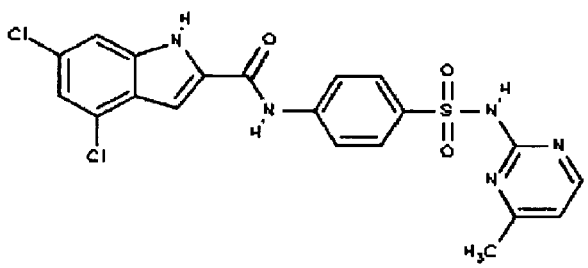 |
| 359 | 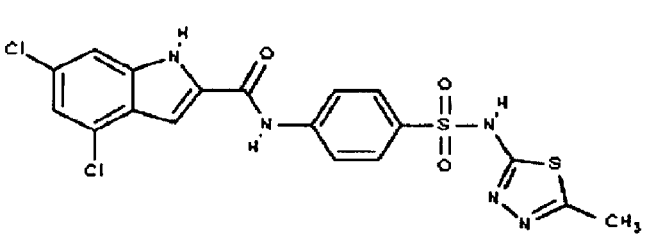 |
| 360 | 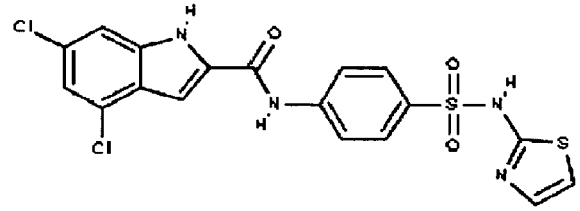 |

Figure 1-99
| # | Compound |
|---|---|
| 361 | 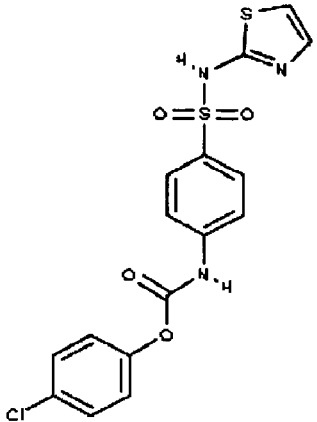 |
| 362 | 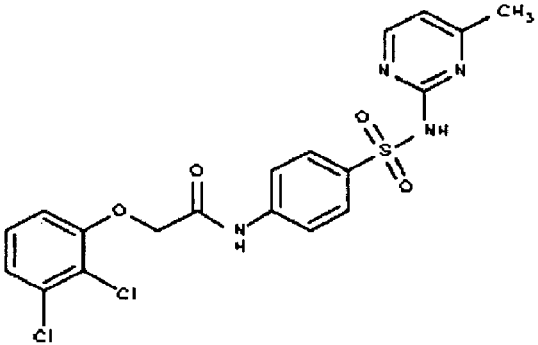 |
| 363 | 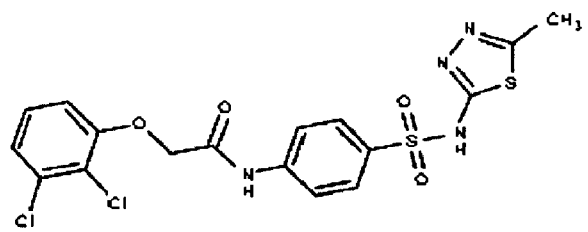 |
| 364 | 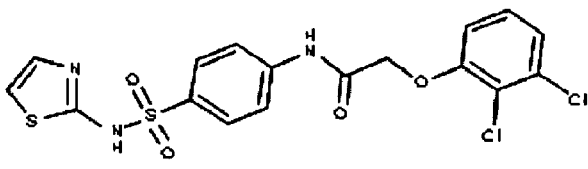 |

Figure 1-100
| # | Compound |
|---|---|
| 365 | 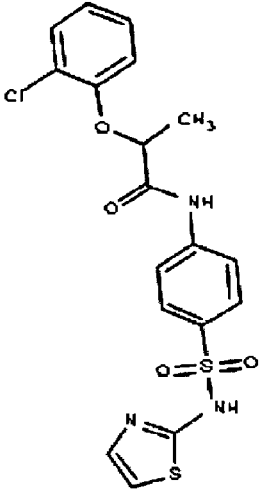 |
| 366 | 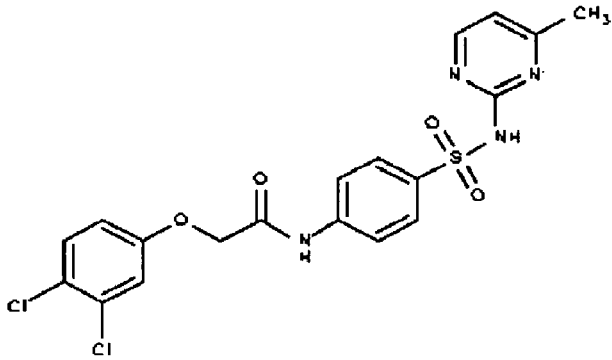 |
| 367 | 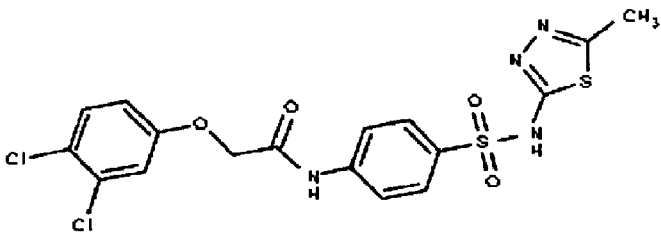 |
| 368 | 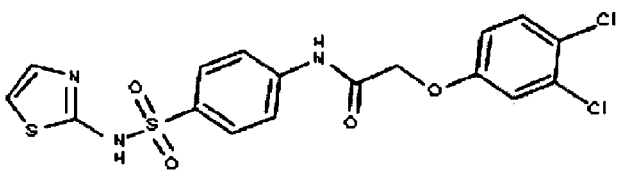 |

Figure 1-101
| # | Compound |
|---|---|
| 369 | 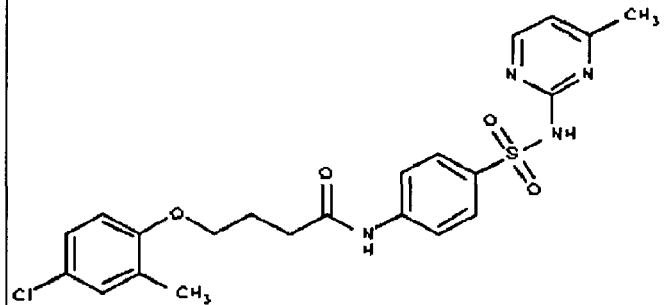 |
| 370 | 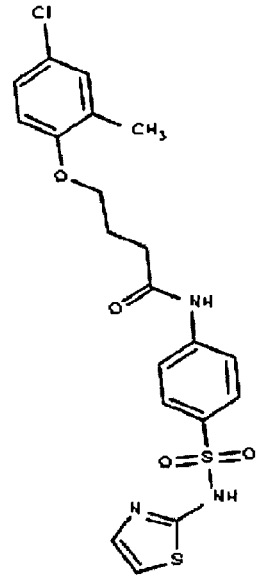 |
| 371 | 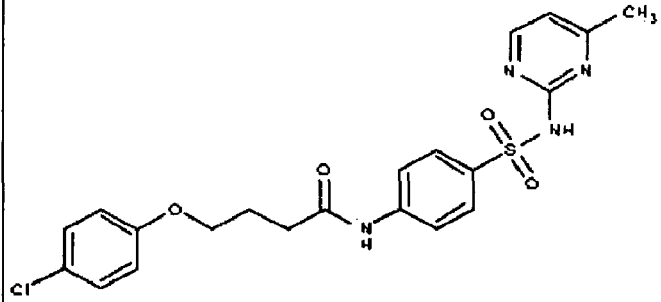 |
| 372 | 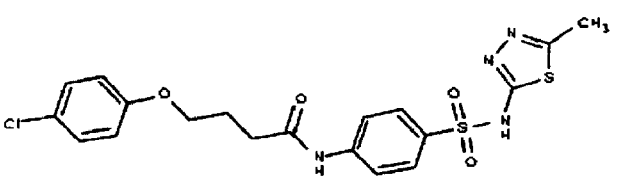 |

Figure 1-102

| # | Compound |
|---|---|
| 373 | |
| 374 | |
| 375 | |

Figure 1-103

| # | Compound |
|---|---|
| 376 | (structure: 2-chlorophenoxy-acetamide linked to phenyl-sulfonamide-thiazole) |
| 377 | (structure: 3-chlorophenoxy-acetamide linked to phenyl-sulfonamide-(5-methyl-1,3,4-thiadiazole)) |
| 378 | (structure: 3-chlorophenoxy-acetamide linked to phenyl-sulfonamide-(4-methylpyrimidin-2-yl)) |
| 379 | (structure: 2-chlorophenoxy-acetamide linked to phenyl-sulfonamide-(4-methylpyrimidin-2-yl)) |

Figure 1-104

| # | Compound |
|---|---|
| 380 | |
| 381 | |
| 382 | |
| 383 | |
| 384 | |

Figure 1-105

| # | Compound |
|---|---|
| 385 | |
| 386 | |
| 387 | |
| 388 | |
| 389 | |
| 390 | |

Figure 1-106
| # | Compound |
|---|---|
| 391 | 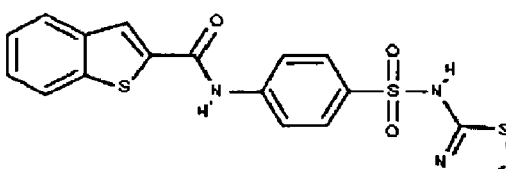 |
| 392 | 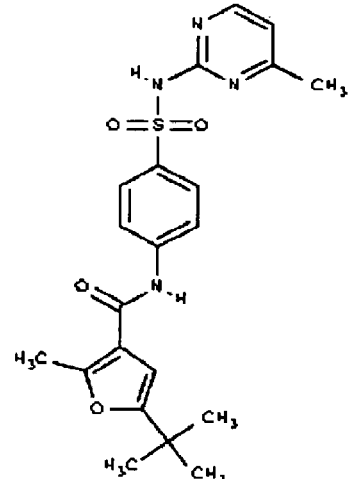 |
| 393 | 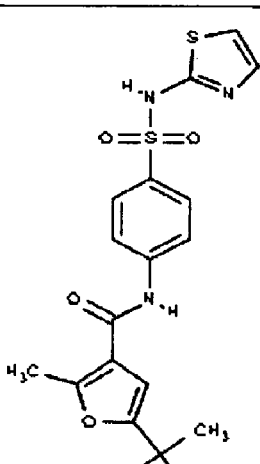 |

Figure 1-107

| # | Compound |
|---|---|
| 394 | |
| 395 | |

Figure 1-108
| # | Compound |
|---|---|
| 396 | 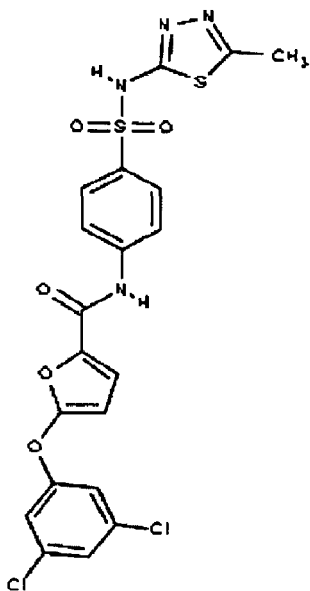 |
| 397 | 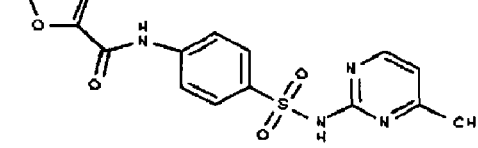 |
| 398 | 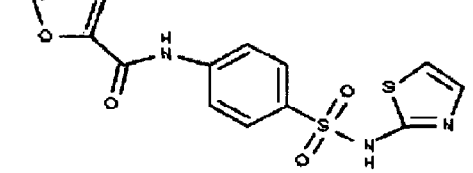 |

Figure 1-109
| # | Compound |
|---|---|
| 399 | 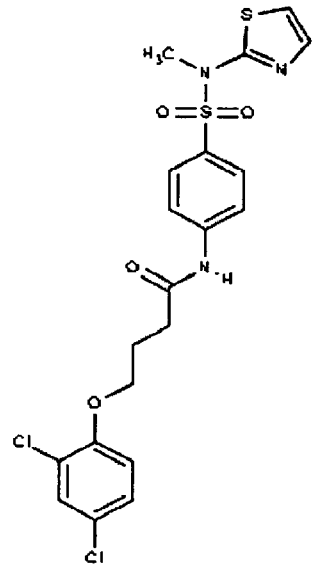 |
| 400 | 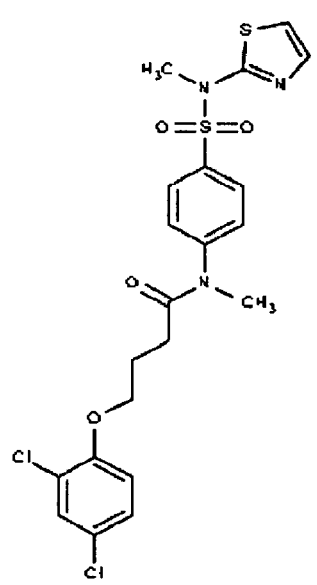 |
| 401 | 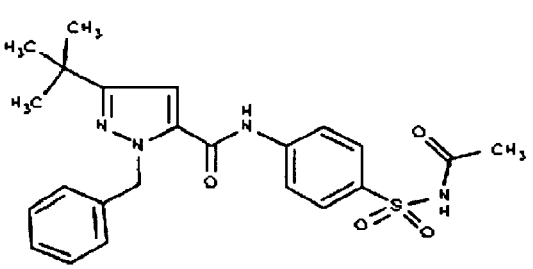 |

Figure 1-110
| # | Compound |
|---|---|
| 402 | 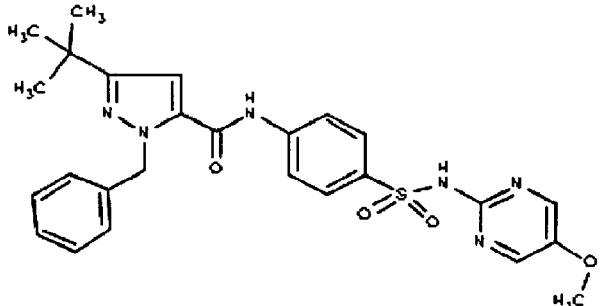 |
| 403 | 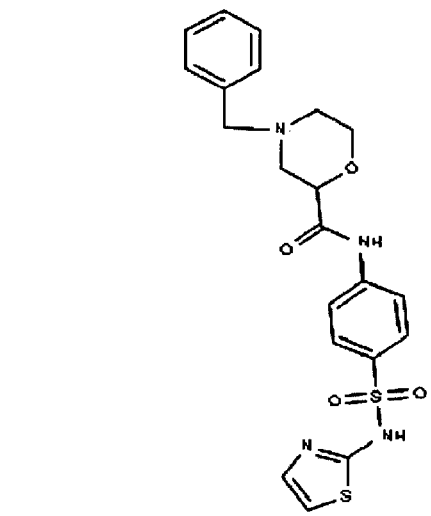 |
| 404 | 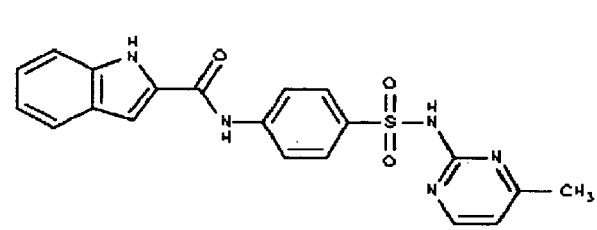 |
| 405 | 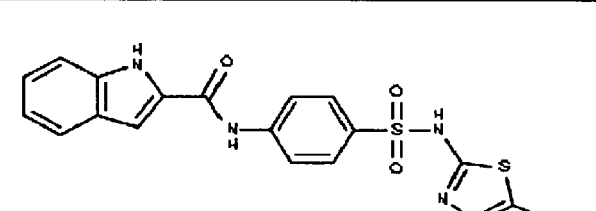 |

Figure 1-111
| # | Compound |
|---|---|
| 406 | 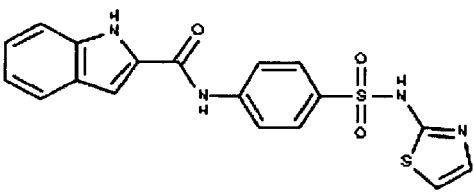 |
| 407 | 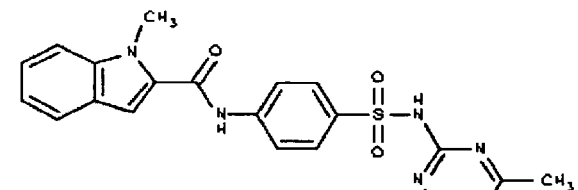 |
| 408 | 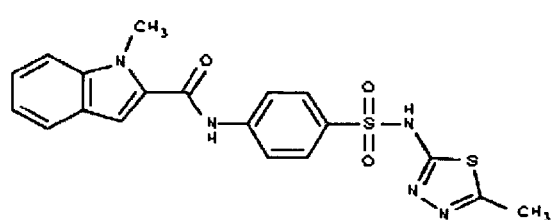 |
| 409 | 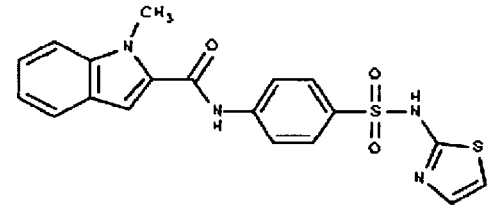 |
| 410 | 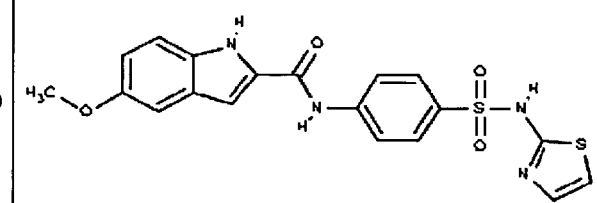 |
| 411 | 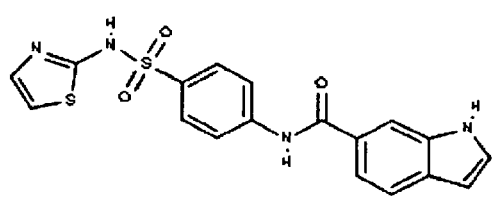 |

Figure 1-112

| # | Compound |
|---|---|
| 412 | 5-fluoro-1H-indole-2-carboxamide linked to N-(4-sulfamoylphenyl)-2-aminothiazole |
| 413 | 5-(trifluoromethoxy)-1H-indole-2-carboxamide linked to N-(4-sulfamoylphenyl)-2-aminothiazole |
| 414 | 5-methyl-1H-indole-2-carboxamide linked to N-(4-sulfamoylphenyl)-2-aminothiazole |
| 415 | quinoline-2-carboxamide linked to N-(4-sulfamoylphenyl)-2-aminothiazole |
| 416 | 5-ethyl-1H-indole-2-carboxamide linked to N-(4-sulfamoylphenyl)-2-aminothiazole |
| 417 | 5,6-dimethoxy-1H-indole-2-carboxamide linked to N-(4-sulfamoylphenyl)-2-aminothiazole |

Figure 1-113

| # | Compound |
|---|---|
| 418 | |
| 419 | |
| 420 | |

Figure 1-114

| # | Compound |
|---|---|
| 421 | |
| 422 | |
| 423 | |
| 424 | |

Figure 1-115
| # | Compound |
|---|---|
| 425 | 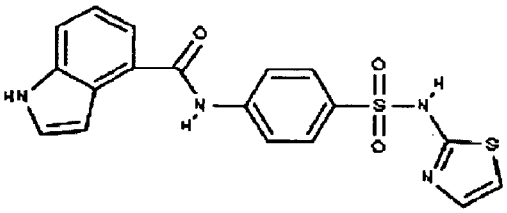 |
| 426 | 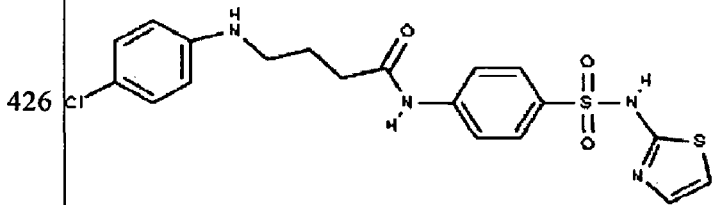 |
| 427 | 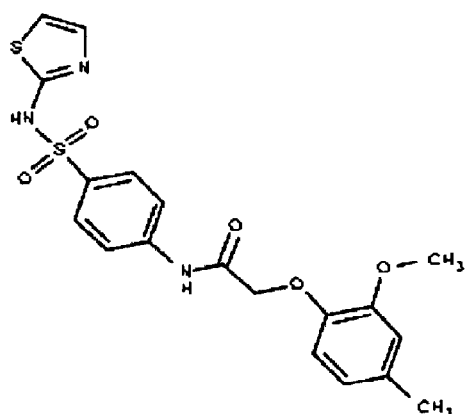 |
| 428 | 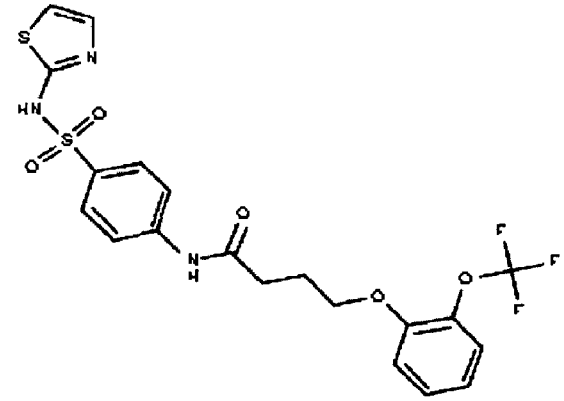 |

Figure 1-116
| # | Compound |
|---|---|
| 429 | 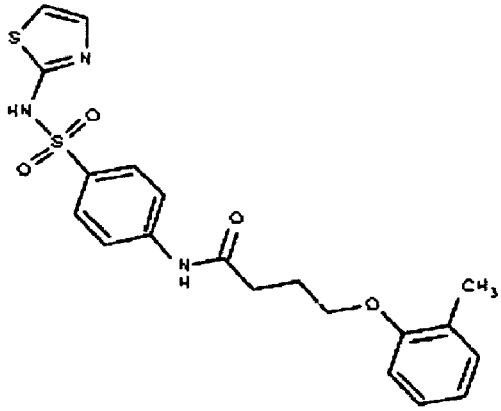 |
| 430 | 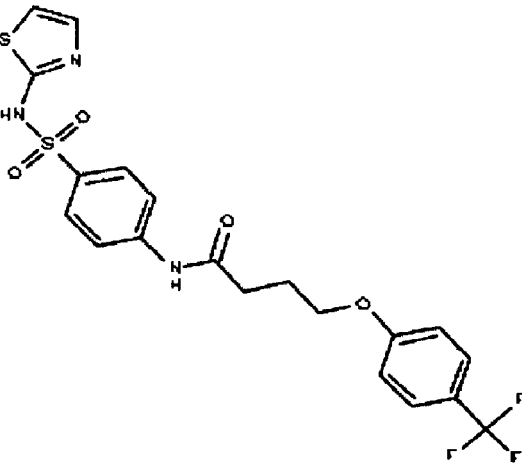 |
| 431 | 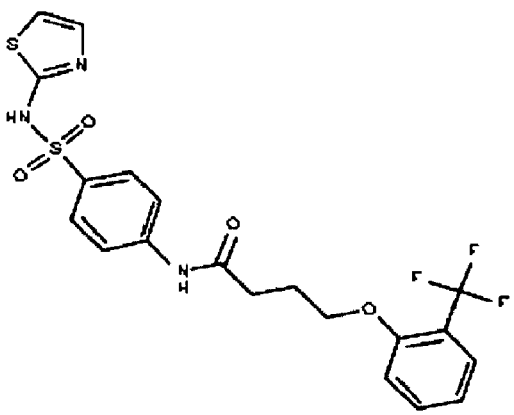 |

Figure 1-117

| # | Compound |
|---|---|
| 432 | |
| 433 | |
| 434 | |

Figure 1-118

| # | Compound |
|---|---|
| 435 | |
| 436 | |
| 437 | |

Figure 1-119

| # | Compound |
|---|---|
| 438 | |
| 439 | |
| 440 | |

Figure 1-120
| # | Compound |
|---|---|
| 441 | 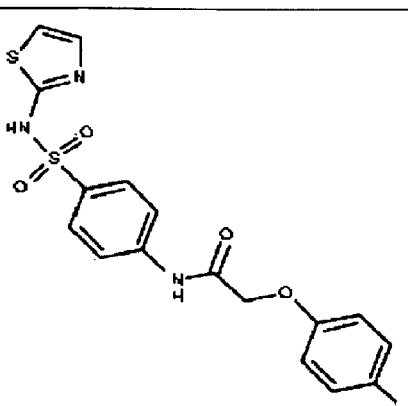 |
| 442 | 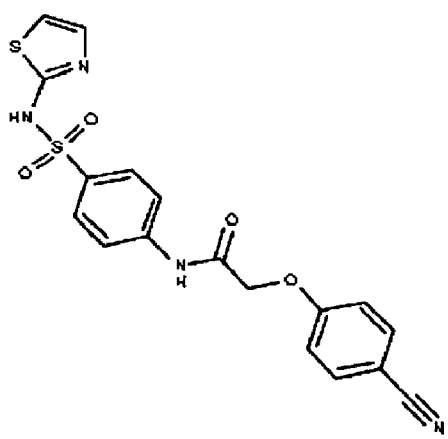 |
| 443 | 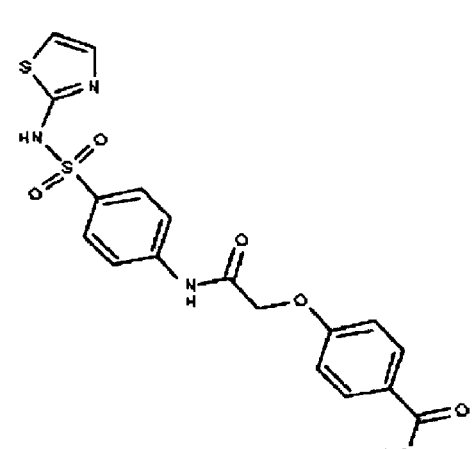 |

Figure 1-121
| # | Compound |
|---|---|
| 444 | 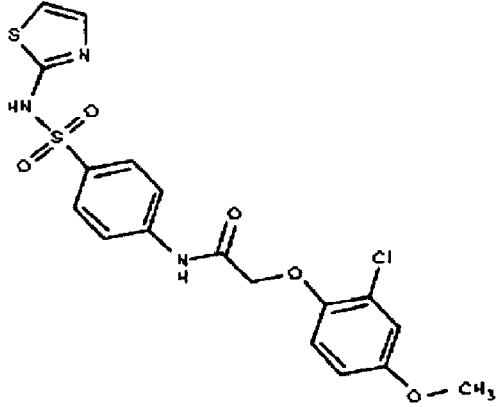 |
| 445 | 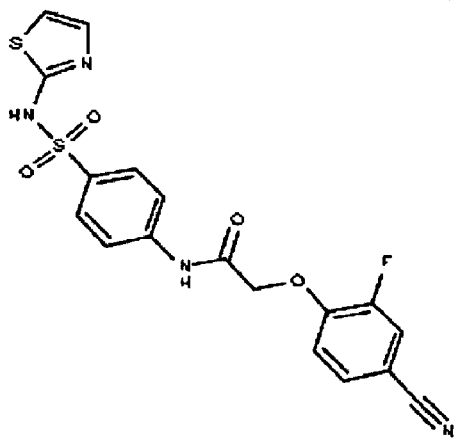 |
| 446 | 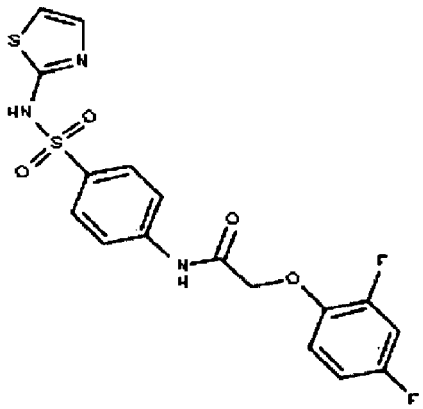 |

Figure 1-122

| # | Compound |
|---|---|
| 447 | |
| 448 | |
| 449 | |

Figure 1-123

| # | Compound |
|---|---|
| 450 | |
| 451 | |
| 452 | |

Figure 1-124
| # | Compound |
|---|---|
| 453 | 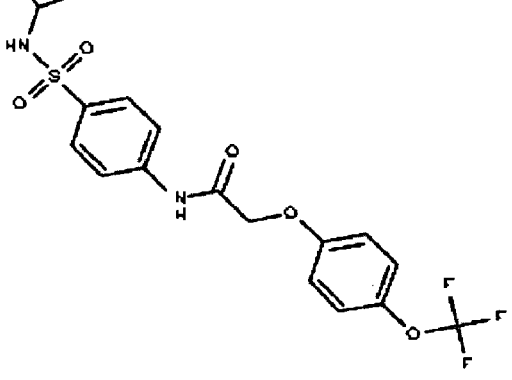 |
| 454 | 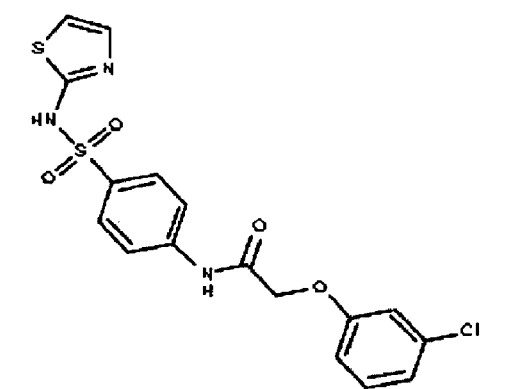 |
| 455 | 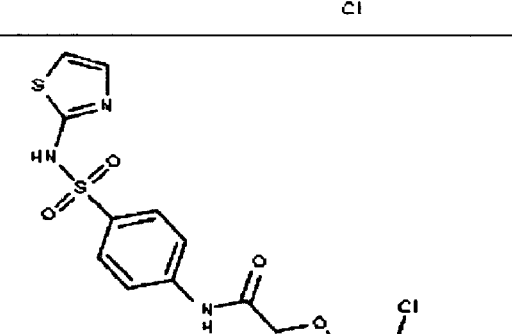 |

Figure 1-125
| # | Compound |
|---|---|
| 456 | 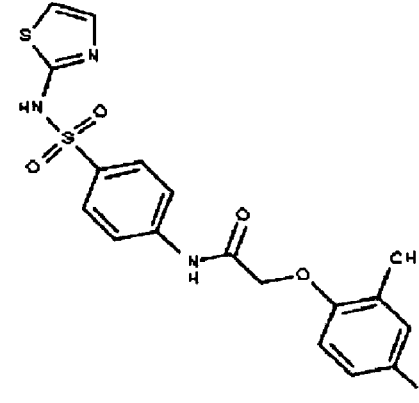 |
| 457 | 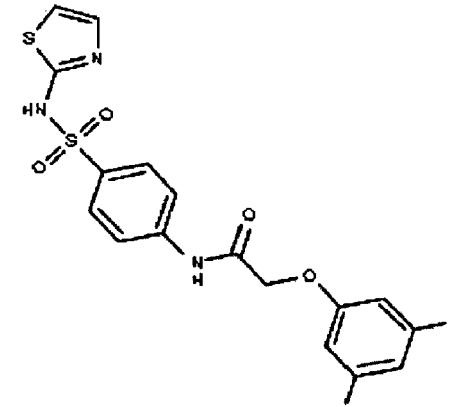 |
| 458 | 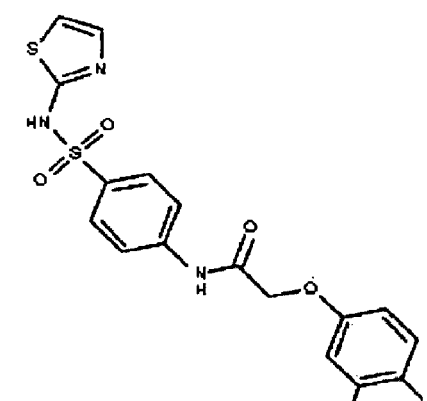 |

Figure 1-126
| # | Compound |
|---|---|
| 459 | 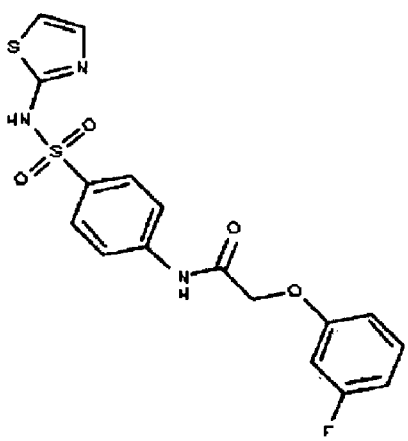 |
| 460 | 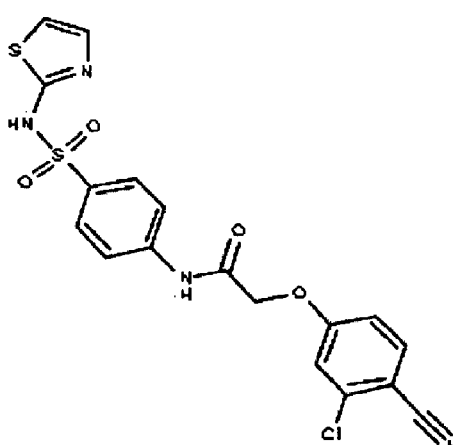 |
| 461 | 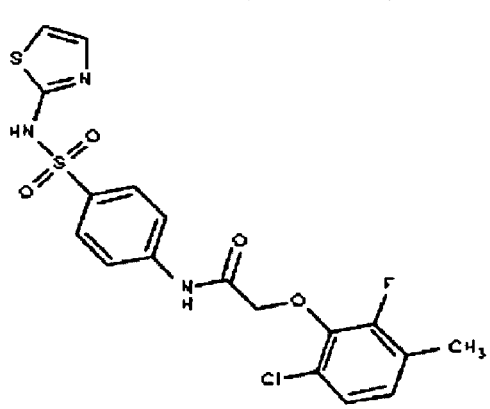 |

Figure 1-127

| # | Compound |
|---|----------|
| 462 | |
| 463 | |
| 464 | |

Figure 1-128

| # | Compound |
|---|---|
| 465 | |
| 466 | |
| 467 | |

Figure 1-129

| # | Compound |
|---|---|
| 468 | |
| 469 | |
| 470 | |
| 471 | |

Figure 1-130

| # | Compound |
|---|---|
| 472 | |
| 473 | |
| 474 | |
| 475 | |
| 476 | |

Figure 1-131
| # | Compound |
|---|---|
| 477 | 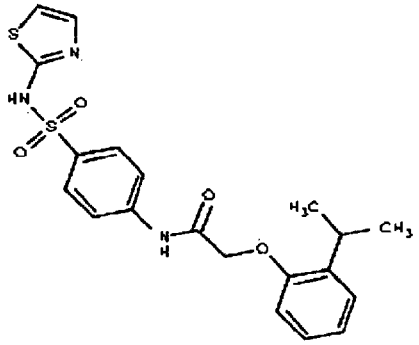 |
| 478 | 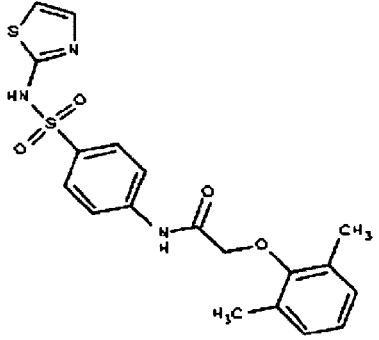 |
| 479 | 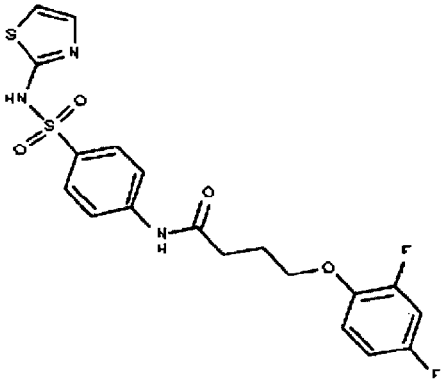 |
| 480 | 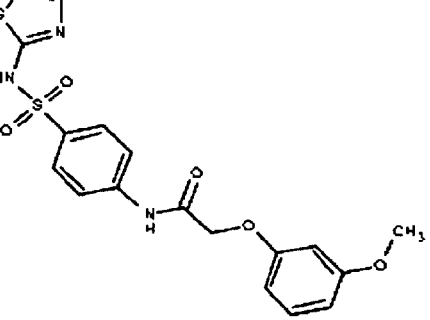 |

Figure 1-132

| # | Compound |
|---|---|
| 481 | |
| 482 | |
| 483 | |

Figure 1-133

| # | Compound |
|---|---|
| 484 | |
| 485 | |
| 486 | |

Figure 1-134

| # | Compound |
|---|---|
| 487 | |
| 488 | |
| 489 | |

Figure 1-135

| # | Compound |
|---|---|
| 490 | |
| 491 | |
| 492 | |

Figure 1-136

| # | Compound |
|---|----------|
| 493 | |
| 494 | |
| 495 | |

Figure 1-137
| # | Compound |
|---|---|
| 496 | 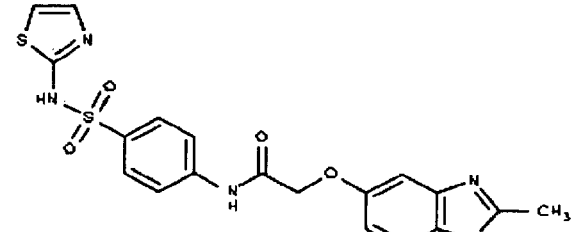 |
| 497 | 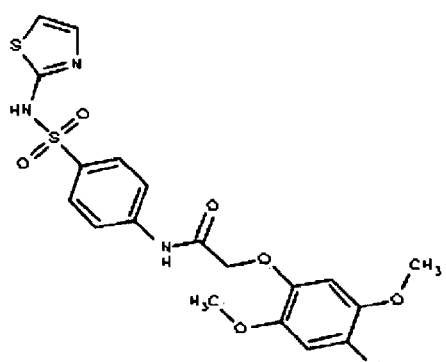 |
| 498 | 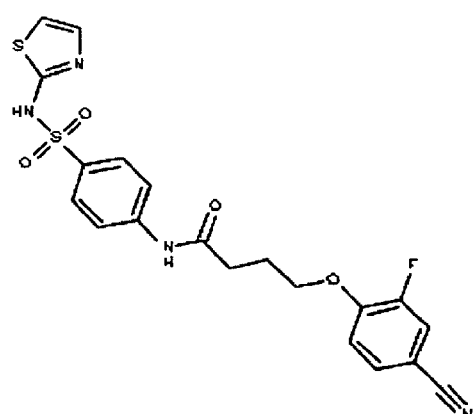 |
| 499 | 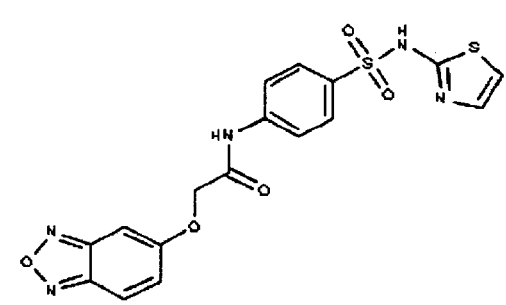 |

Figure 1-138

| # | Compound |
|---|---|
| 500 | |
| 501 | |
| 502 | |

Figure 1-139
| # | Compound |
|---|---|
| 503 | 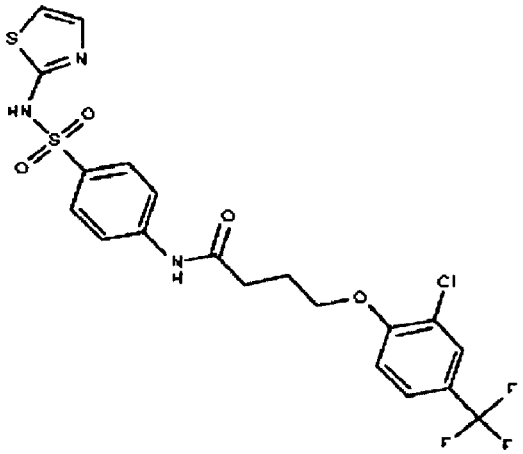 |
| 504 | 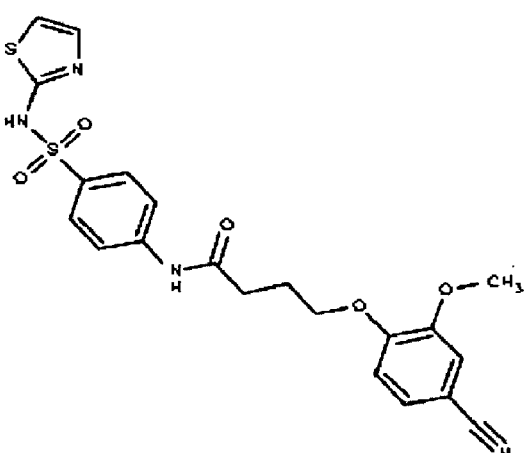 |
| 505 | 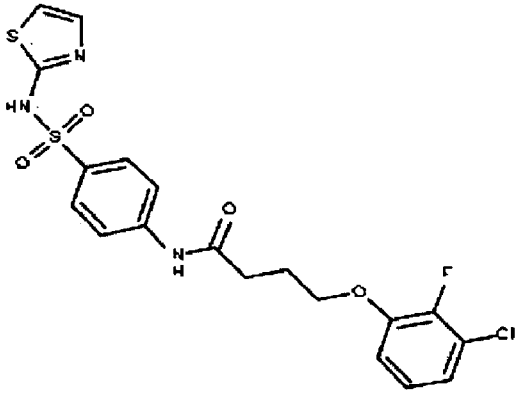 |

Figure 1-140
| # | Compound |
|---|---|
| 506 | 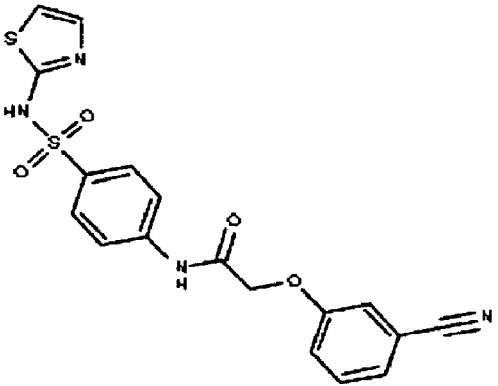 |
| 507 | 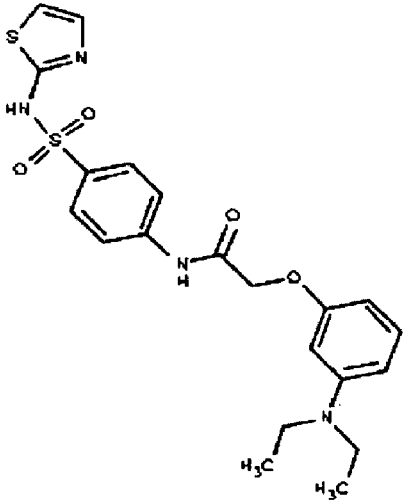 |
| 508 | 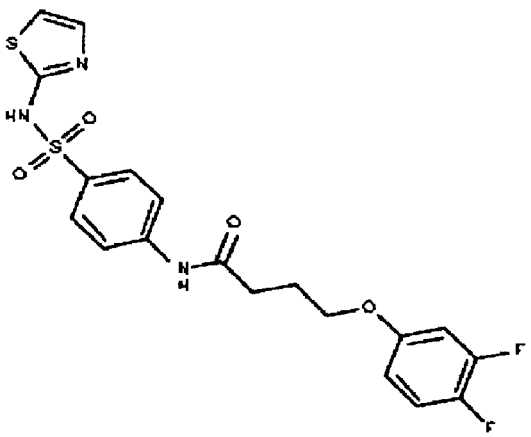 |

Figure 1-141

| # | Compound |
|---|---|
| 509 | |
| 510 | |
| 511 | |
| 512 | |

Figure 1-142

| # | Compound |
|---|---|
| 513 | |
| 514 | |
| 515 | |

Figure 1-143

| # | Compound |
|---|---|
| 516 | |
| 517 | |
| 518 | |

Figure 1-144

| # | Compound |
|---|----------|
| 519 | |
| 520 | |
| 521 | |

Figure 1-145

| # | Compound |
|---|---|
| 522 | |
| 523 | |
| 524 | |

Figure 1-147
| # | Compound |
|---|---|
| 528 | 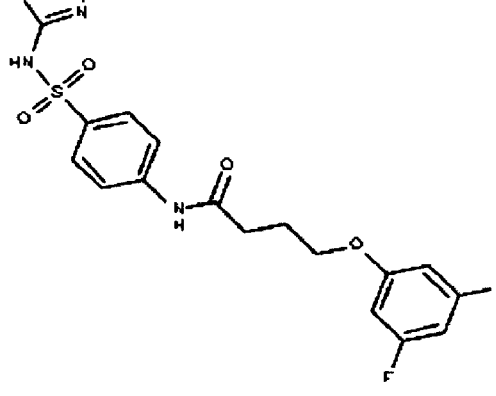 |
| 529 | 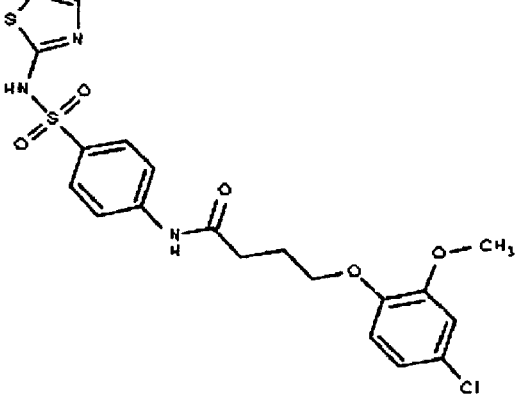 |
| 530 | 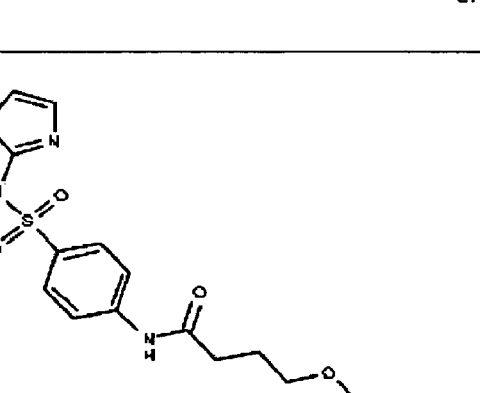 |

Figure 1-148
| # | Compound |
|---|----------|
| 531 | 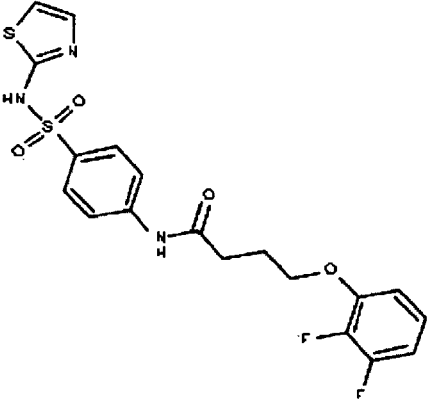 |
| 532 | 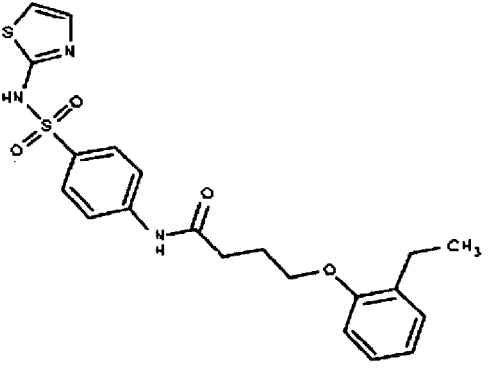 |
| 533 | 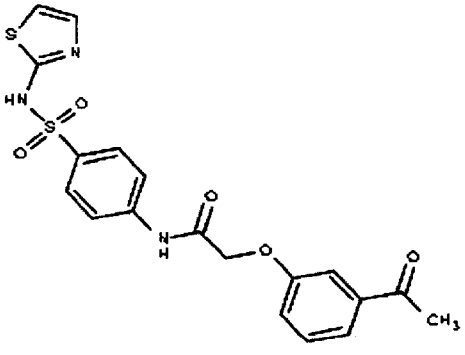 |
| 534 | 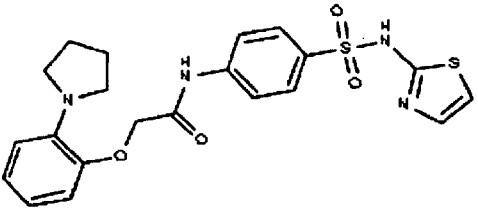 |

Figure 1-149

| # | Compound |
|---|---|
| 535 | |
| 536 | |
| 537 | |

Figure 1-150
| # | Compound |
|---|---|
| 538 | 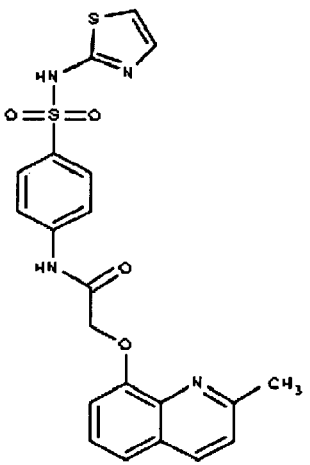 |
| 539 | 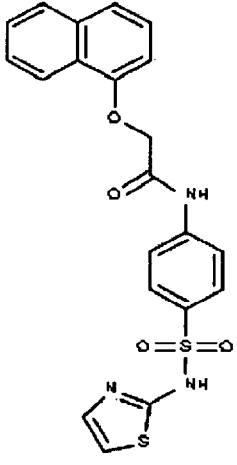 |
| 540 | 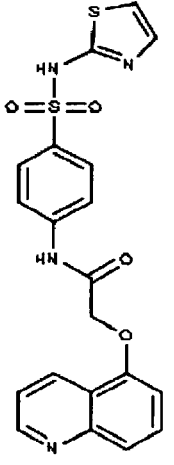 |

Figure 1-151

| # | Compound |
|---|---|
| 541 | |
| 542 | |
| 543 | |

Figure 1-152

| # | Compound |
|---|---|
| 544 | |
| 545 | |
| 546 | |

Figure 1-153
| # | Compound |
|---|---|
| 547 | 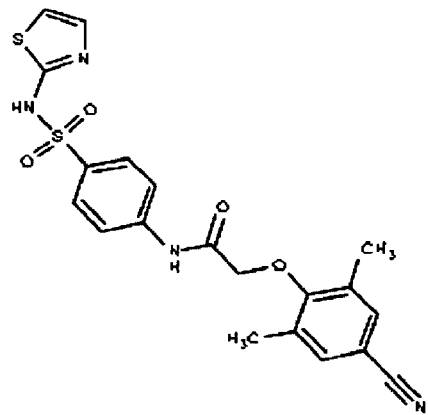 |
| 548 | 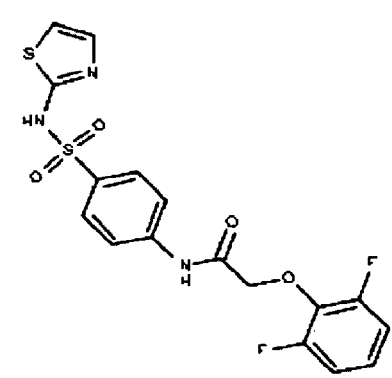 |
| 549 | 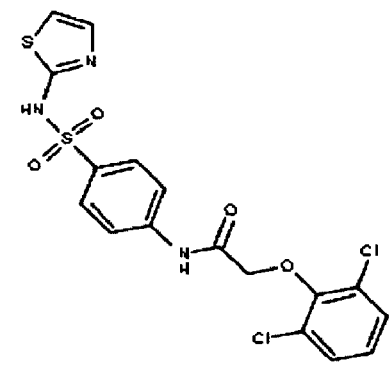 |
| 550 | 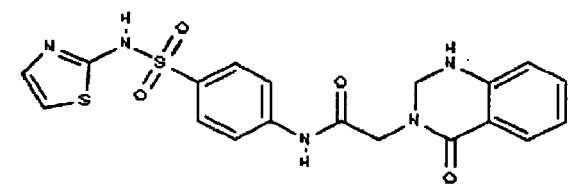 |

Figure 1-154
| # | Compound |
|---|---|
| 551 | 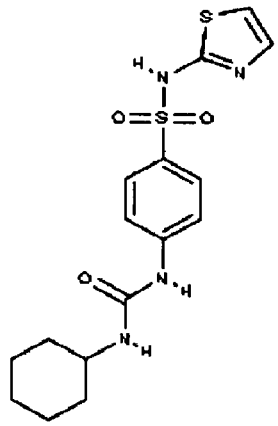 |
| 552 | 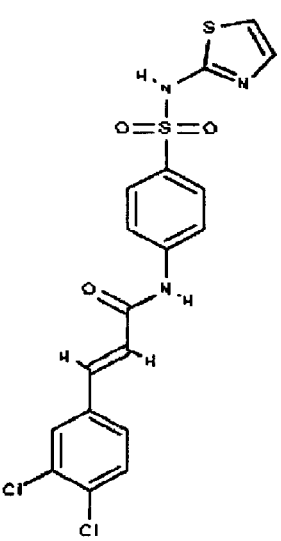 |
| 553 | 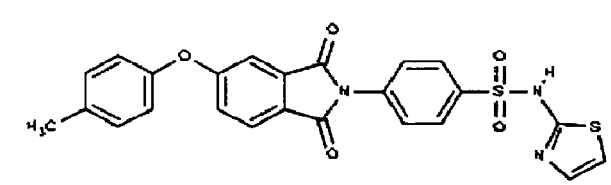 |
| 554 | 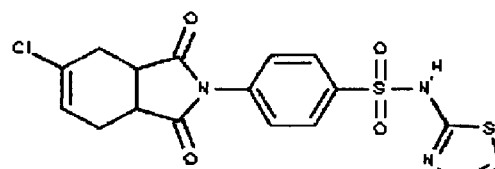 |

Figure 1-155
| # | Compound |
|---|---|
| 555 | 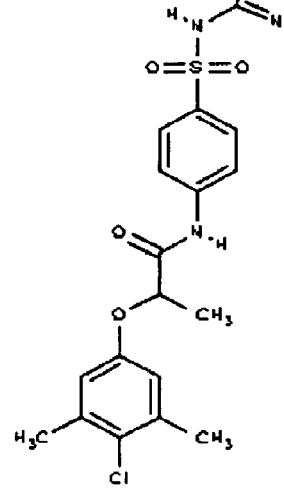 |
| 556 | 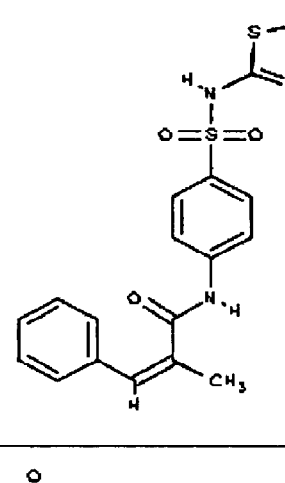 |
| 557 | 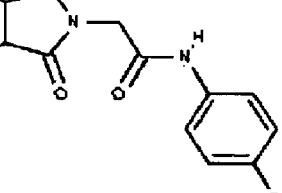 |

Figure 1-156
| # | Compound |
|---|---|
| 558 | 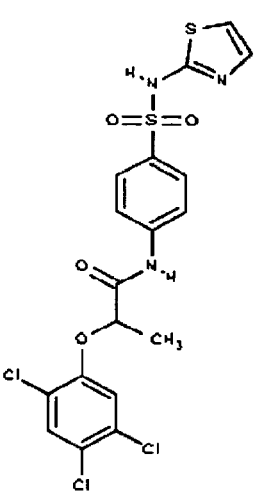 |
| 559 | 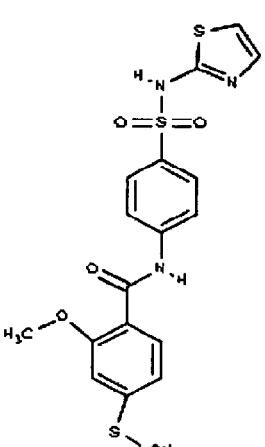 |
| 560 | 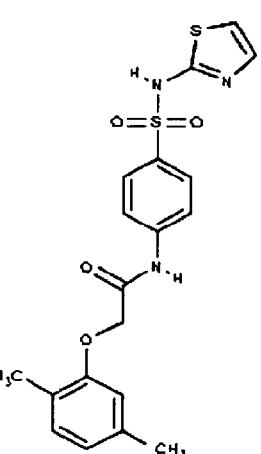 |

Figure 1-157
| # | Compound |
|---|---|
| 561 | 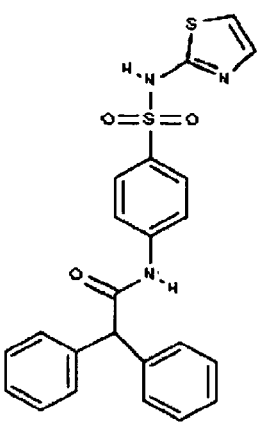 |
| 562 | 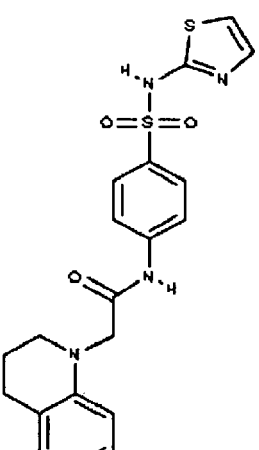 |
| 563 | 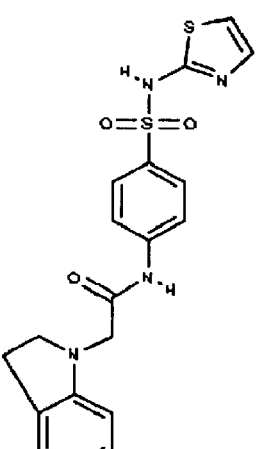 |

Figure 1-158

| # | Compound |
|---|----------|
| 564 | |
| 565 | |
| 566 | |

Figure 1-159
| # | Compound |
|---|---|
| 567 | 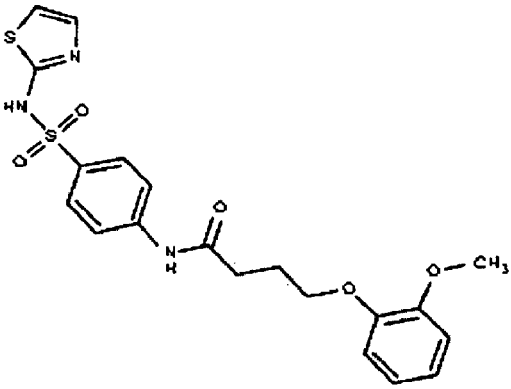 |
| 568 | 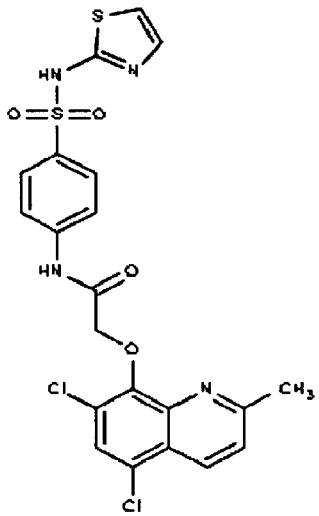 |
| 569 | 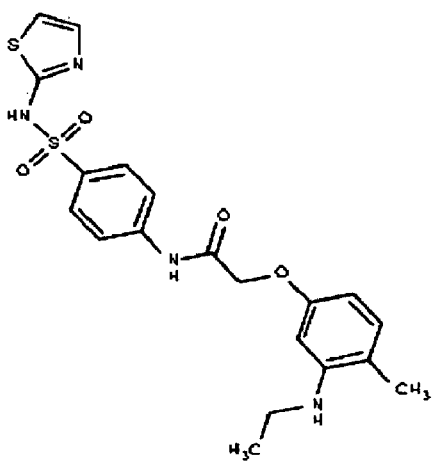 |

Figure 1-160

| # | Compound |
|---|---|
| 570 | |
| 571 | |
| 572 | |

Figure 1-161

| # | Compound |
|---|----------|
| 573 | |
| 574 | |
| 575 | |

Figure 1-162

| # | Compound |
|---|---|
| 576 | |
| 577 | |
| 578 | |
| 579 | |

Figure 1-163

| # | Compound |
|---|---|
| 580 | |
| 581 | |
| 582 | |
| 583 | |

Figure 1-164

| # | Compound |
|---|---|
| 584 | |
| 585 | |
| 586 | |
| 587 | |
| 588 | |

Figure 1-165

| # | Compound |
|---|---|
| 589 | |
| 590 | |
| 591 | |
| 592 | |

Figure 1-166

| # | Compound |
|---|---|
| 593 | |
| 594 | |
| 595 | |
| 596 | |

Figure 1-167
| # | Compound |
|---|---|
| 597 | 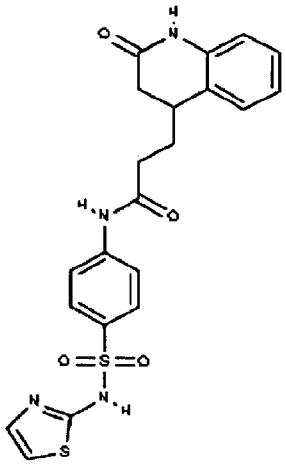 |
| 598 | 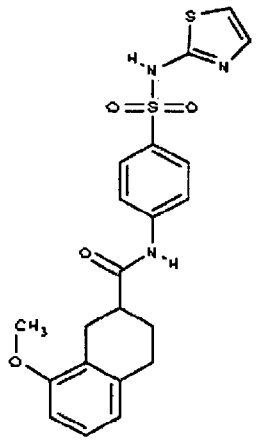 |
| 599 | 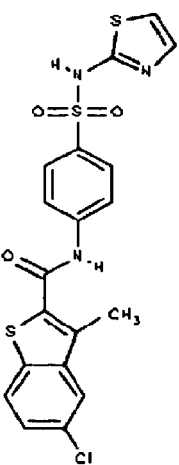 |

Figure 1-168

| # | Compound |
|---|---|
| 600 | |
| 601 | |

| # | Compound |
|---|---|
| 602 |  |
| 603 |  |

Figure 1-170

| # | Compound |
|---|---|
| 604 | |
| 605 | |

Figure 1-171

| # | Compound |
|---|---|
| 606 | |
| 607 | |
| 608 | |

Figure 1-172

| # | Compound |
|---|---|
| 609 | |
| 610 | |
| 611 | |

Figure 1-173

| # | Compound |
|---|---|
| 612 | |
| 613 | |
| 614 | |

Figure 1-174
| # | Compound |
|---|---|
| 615 | 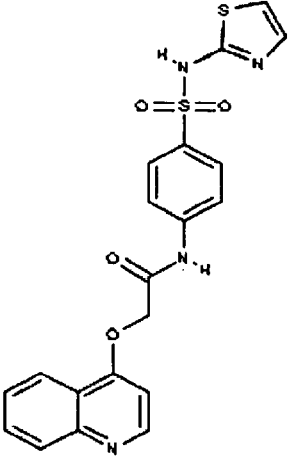 |
| 616 | 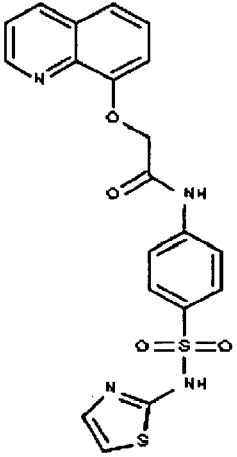 |
| 617 | 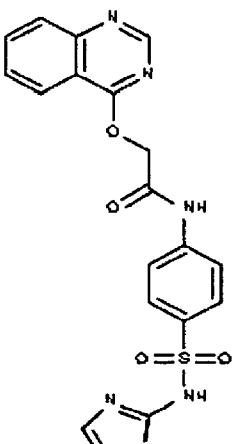 |

Figure 1-175

| # | Compound |
|---|---|
| 618 | |
| 619 | |
| 620 | |
| 621 | |

Figure 1-176

| # | Compound |
|---|---|
| 622 | |
| 623 | |
| 624 | |

Figure 1-177
| # | Compound |
|---|---|
| 625 | 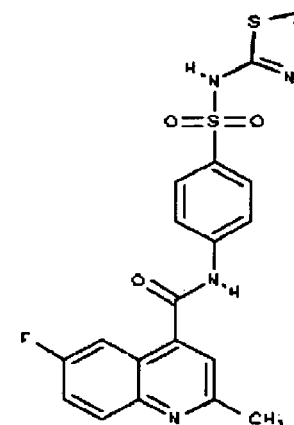 |
| 626 | 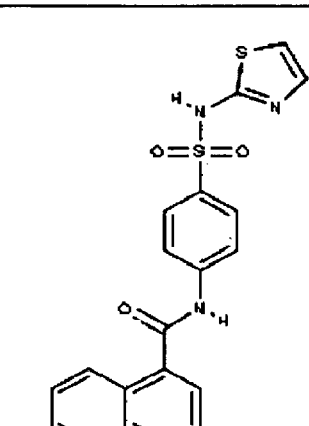 |
| 627 | 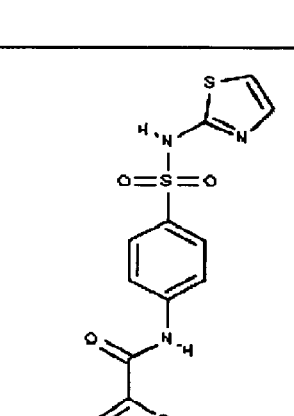 |

Figure 1-178
| # | Compound |
|---|---|
| 628 | 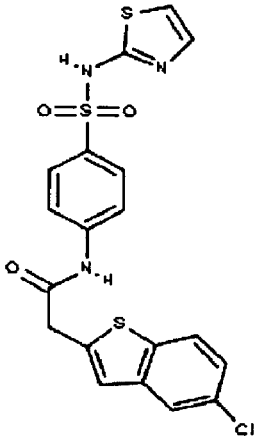 |
| 629 | 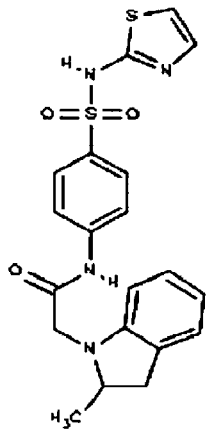 |
| 630 | 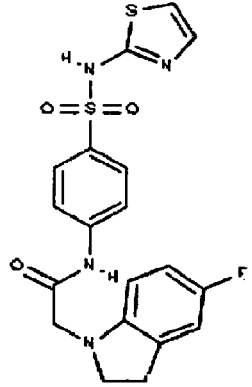 |

Figure 1-179

| # | Compound |
|---|---|
| 631 | |
| 632 | |
| 633 | |

Figure 1-180
| # | Compound |
|---|---|
| 634 | 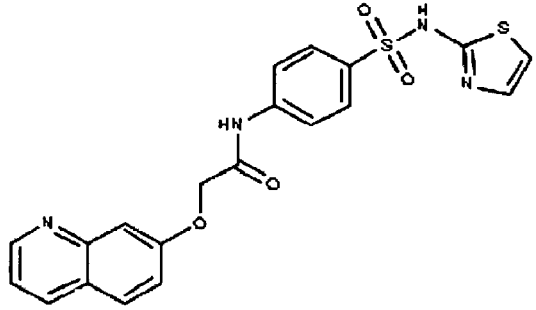 |
| 635 | 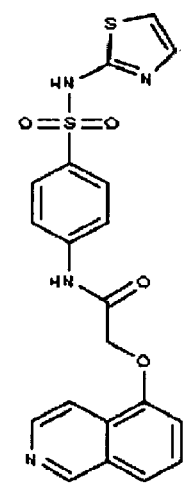 |
| 636 | 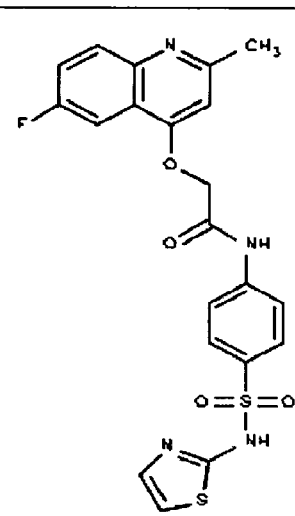 |

Figure 1-181

| # | Compound |
|---|---|
| 637 | |
| 638 | |
| 639 | |

Figure 1-182

| # | Compound |
|---|---|
| 640 | (7-chloroquinolin-4-yloxy)acetamide-N-(4-(N-thiazol-2-ylsulfamoyl)phenyl) structure |
| 641 | (6-fluoroquinolin-4-yloxy)acetamide-N-(4-(N-thiazol-2-ylsulfamoyl)phenyl) structure |
| 642 | (8-fluoroquinolin-4-yloxy)acetamide-N-(4-(N-thiazol-2-ylsulfamoyl)phenyl) structure |

Figure 1-183

| # | Compound |
|---|---|
| 643 | |
| 644 | |
| 645 | |
| 646 | |

Figure 1-184

| # | Compound |
|---|---|
| 647 | |
| 648 | |
| 649 | |

Figure 1-185
| # | Compound |
|---|---|
| 650 | 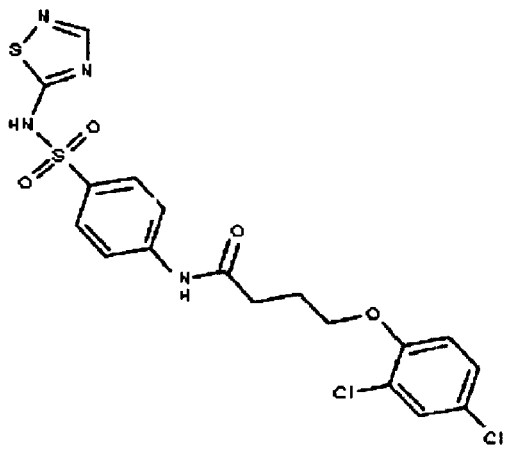 |
| 651 | 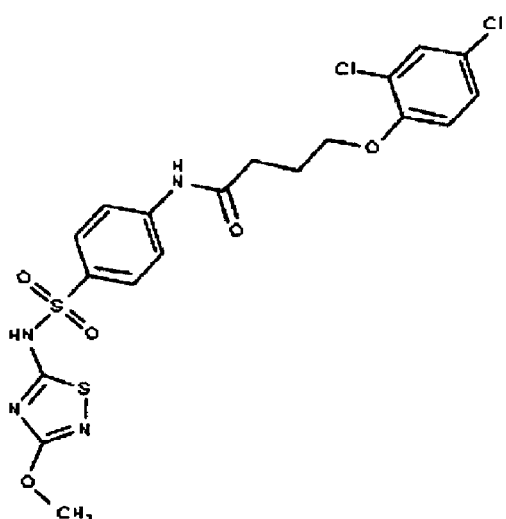 |
| 652 | 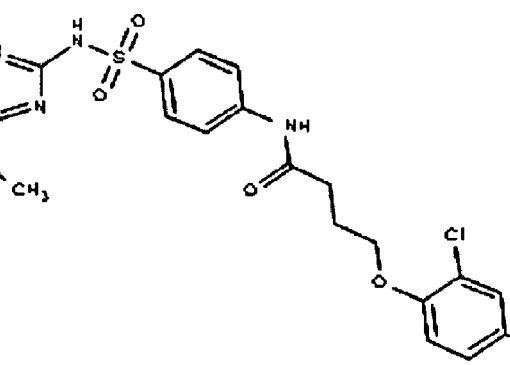 |

Figure 1-186
| # | Compound |
|---|---|
| 653 | 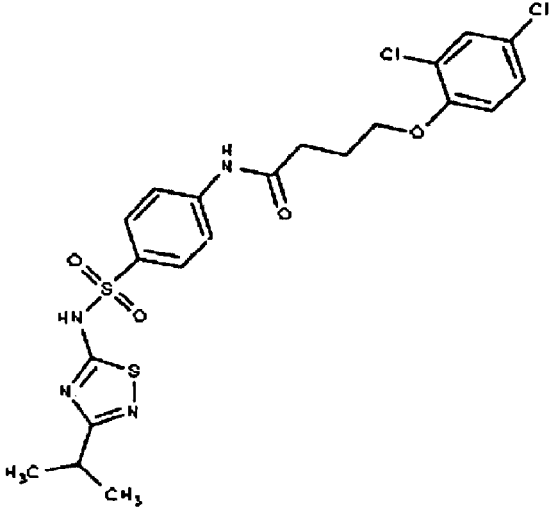 |
| 654 | 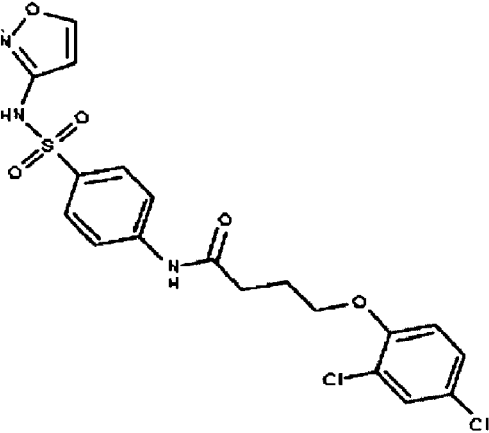 |
| 655 | 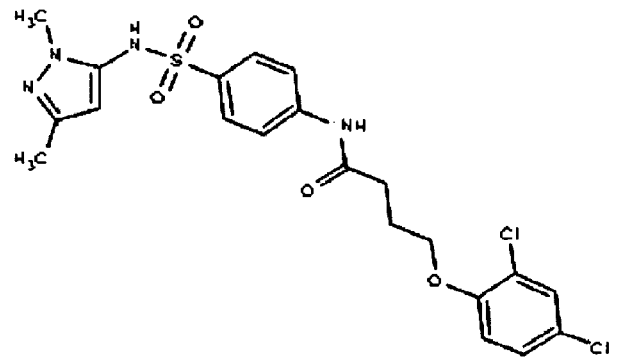 |

Figure 1-187
| # | Compound |
|---|---|
| 656 | 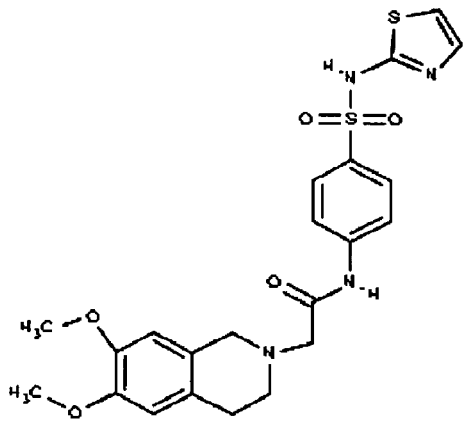 |
| 657 | 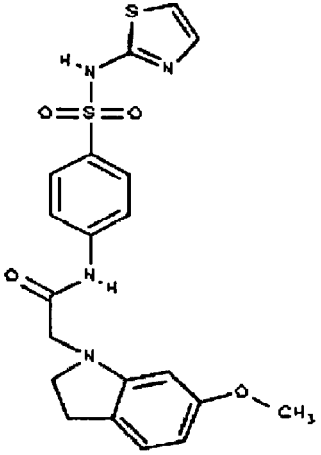 |
| 658 | 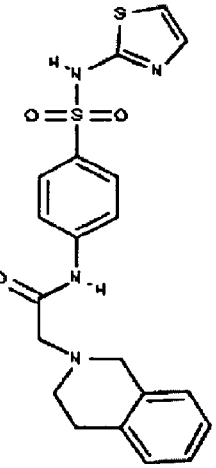 |

Figure 1-188
| # | Compound |
|---|---|
| 659 | 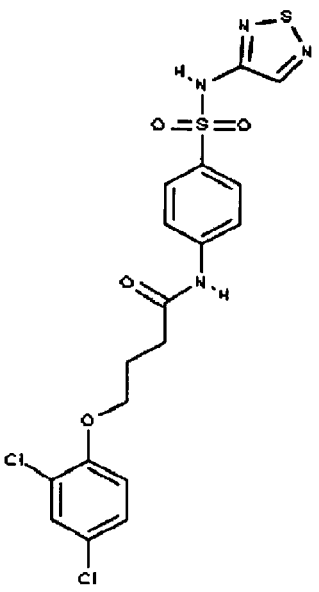 |
| 660 | 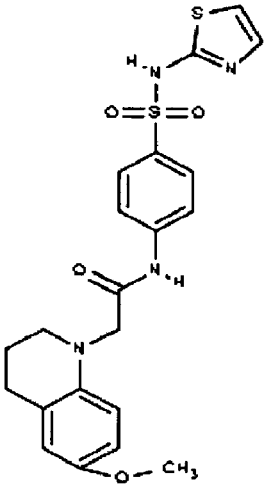 |
| 661 | 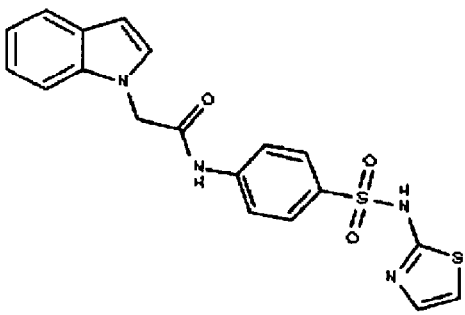 |

Figure 1-189
| # | Compound |
|---|---|
| 662 | 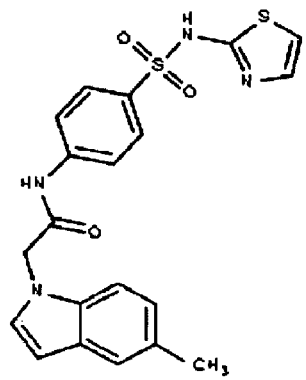 |
| 663 | 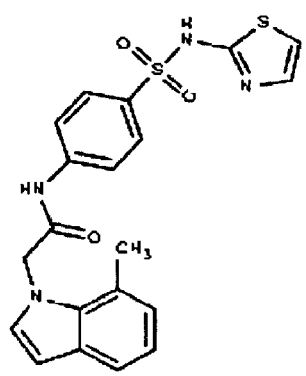 |
| 664 | 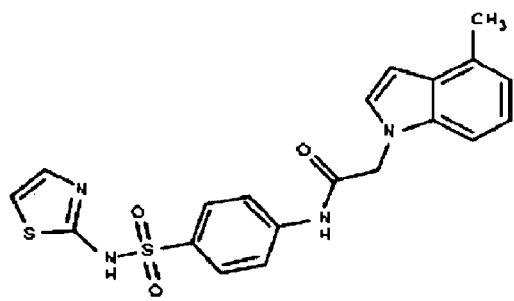 |
| 665 | 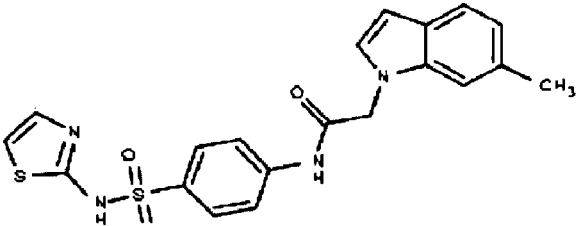 |

Figure 1-190
| # | Compound |
|---|---|
| 666 | 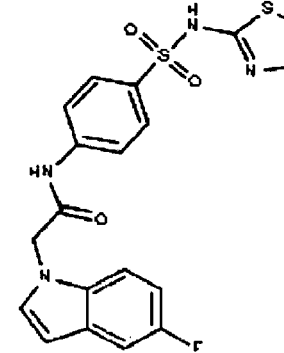 |
| 667 | 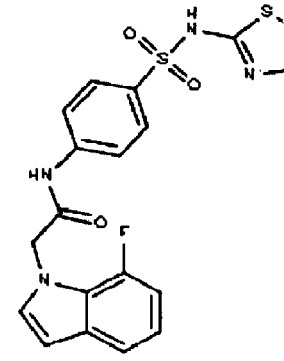 |
| 668 | 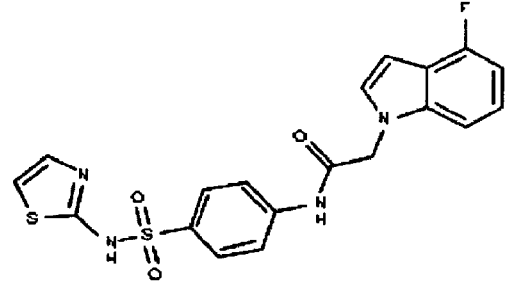 |
| 669 | 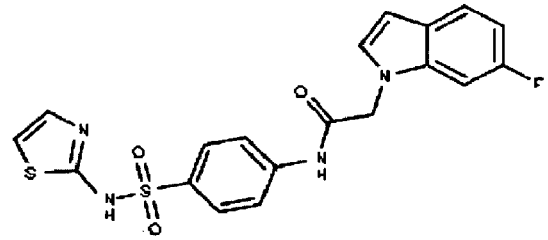 |

Figure 1-191

| # | Compound |
|---|---|
| 670 | |
| 671 | |
| 672 | |
| 673 | |

Figure 1-192
| # | Compound |
|---|---|
| 674 | 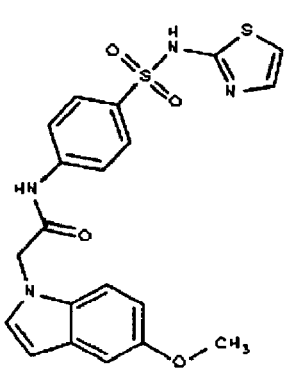 |
| 675 | 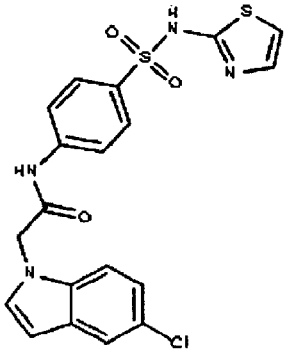 |
| 676 | 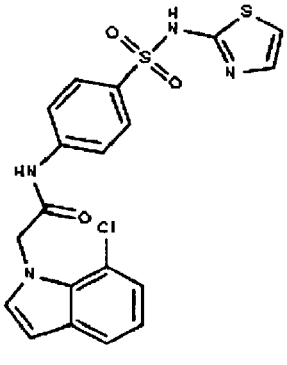 |
| 677 | 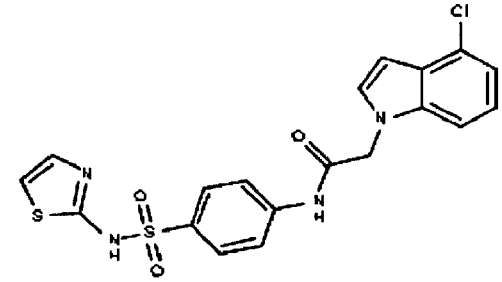 |

Figure 1-193
| # | Compound |
|---|---|
| 678 | 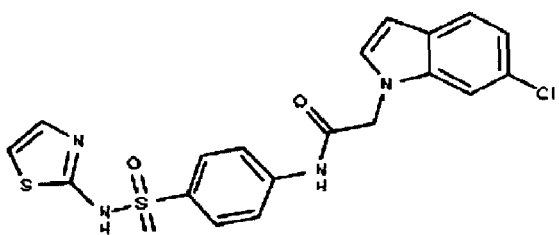 |
| 679 | 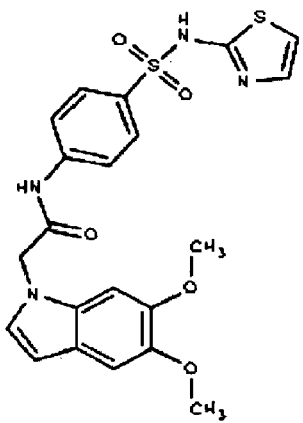 |
| 680 | 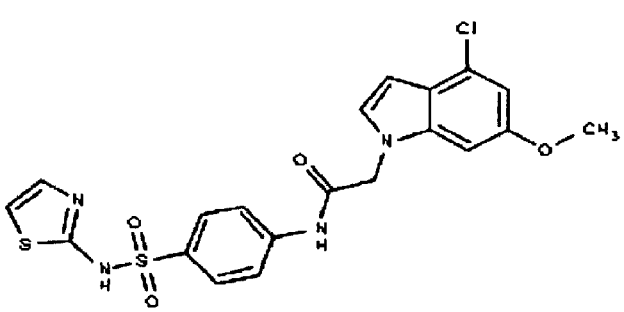 |
| 681 | 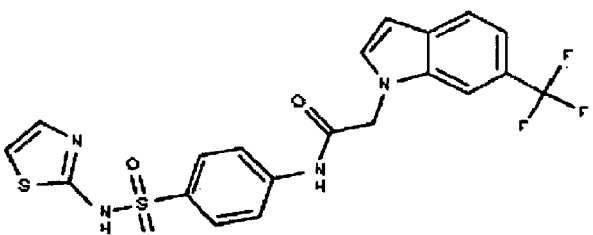 |

Figure 1-194

| # | Compound |
|---|---|
| 682 | |
| 683 | |
| 684 | |
| 685 | |

Figure 1-195

| # | Compound |
|---|---|
| 686 | |
| 687 | |
| 688 | |
| 689 | |

Figure 1-196
| # | Compound |
|---|---|
| 690 | 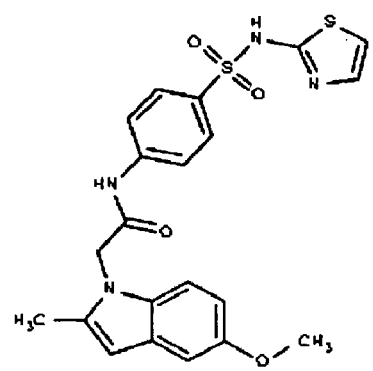 |
| 691 | 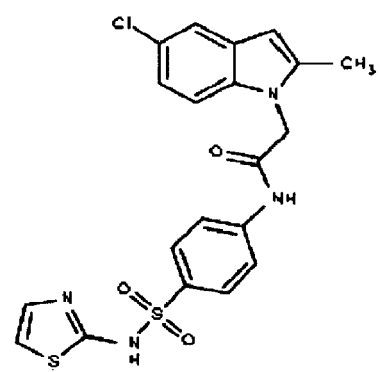 |
| 692 | 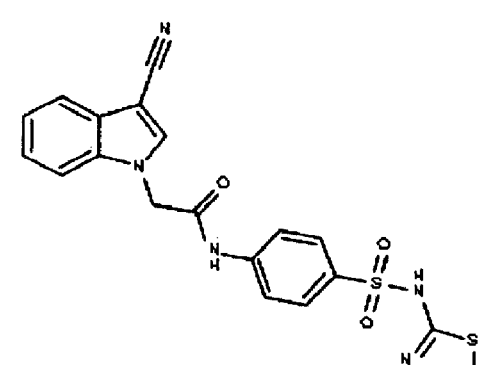 |

Figure 1-197
| # | Compound |
|---|---|
| 693 | 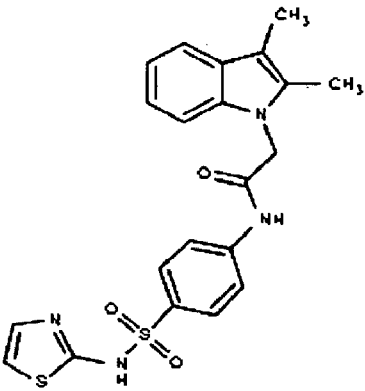 |
| 694 | 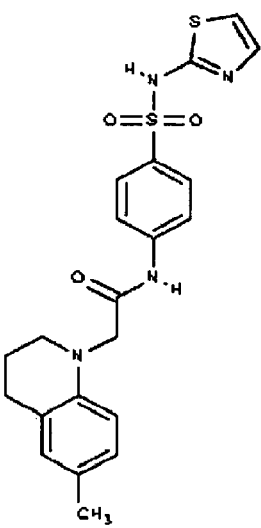 |
| 695 | 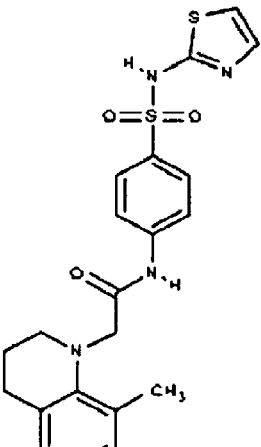 |

Figure 1-198

| # | Compound |
|---|---|
| 696 | |
| 697 | |
| 698 | |
| 699 | |
| 700 | |

| # | Compound |
|---|---|
| 701 |  |
| 702 |  |

| # | Compound |
|---|---|
| 703 |  |
| 704 |  |

Figure 1-201

| # | Compound |
|---|---|
| 705 | |
| 706 | |

Figure 1-202

| # | Compound |
|---|---|
| 707 | |
| 708 | |
| 709 | |

Figure 1-203

| # | Compound |
|---|---|
| 710 | |
| 711 | |
| 712 | |

Figure 1-204

| # | Compound |
|---|---|
| 713 | |
| 714 | |
| 715 | |

Figure 1-205
| # | Compound |
|---|---|
| 716 | 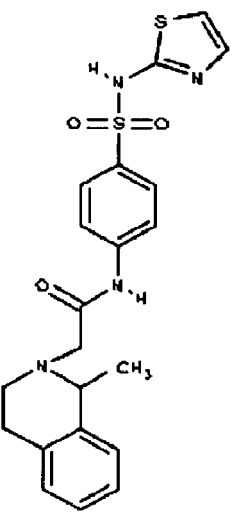 |
| 717 | 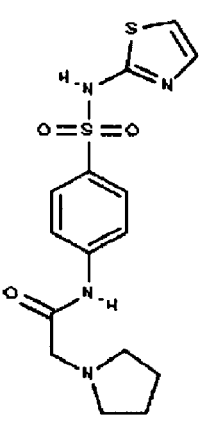 |
| 718 | 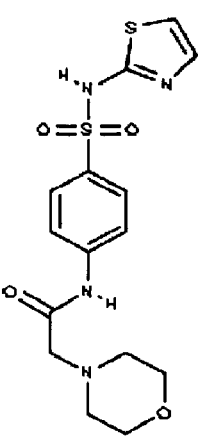 |

Figure 1-206
| # | Compound |
|---|---|
| 719 | 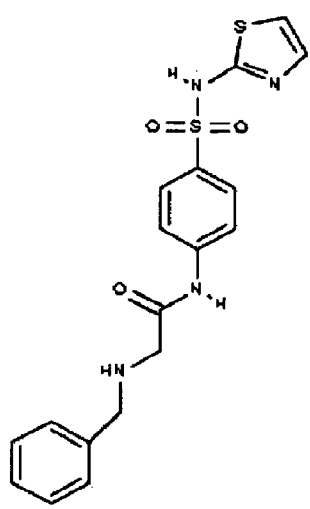 |
| 720 | 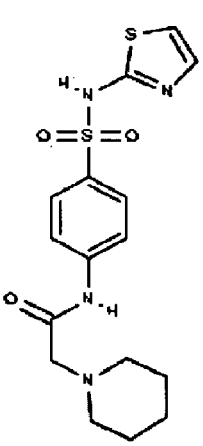 |
| 721 | 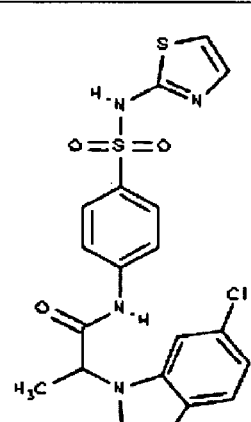 |

Figure 1-207

| # | Compound |
|---|---|
| 722 | *N-(thiazol-2-yl) 4-[3-(3,4-dihydroquinolin-1(2H)-yl)propanamido]benzenesulfonamide* |
| 723 | *N-(thiazol-2-yl) 4-[3-(6-chloro-1H-indol-1-yl)propanamido]benzenesulfonamide* |
| 724 | *N-(thiazol-2-yl) 4-[3-(6-chloro-1H-indol-1-yl)propanamido]benzenesulfonamide* |

Figure 1-208

| # | Compound |
|---|---|
| 725 | |
| 726 | |
| 727 | |

Figure 1-209
| # | Compound |
|---|---|
| 728 | 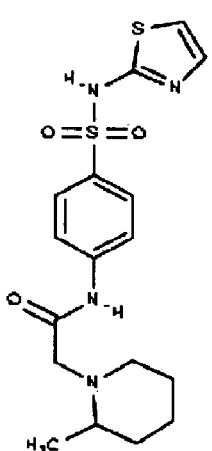 |
| 729 | 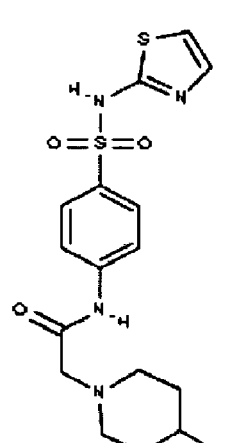 |
| 730 | 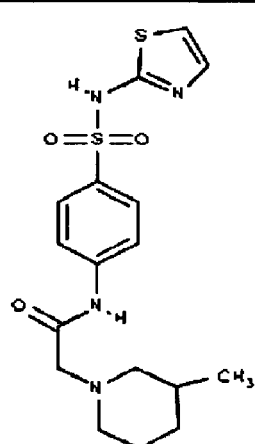 |

Figure 1-210

| # | Compound |
|---|---|
| 731 | |
| 732 | |
| 733 | |

Figure 1-211

| # | Compound |
|---|---|
| 734 | |
| 735 | |
| 736 | |

Figure 1-212

| # | Compound |
|---|---|
| 737 | |
| 738 | |
| 739 | |

Figure 1-213
| # | Compound |
|---|---|
| 740 | 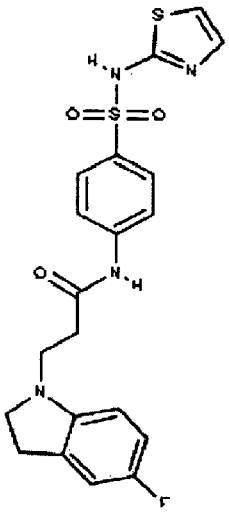 |
| 741 | 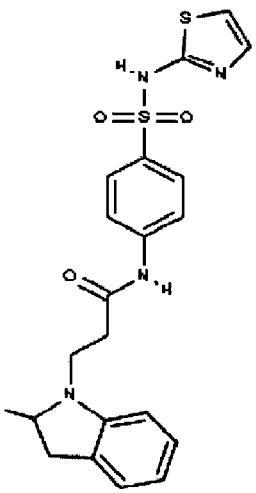 |
| 742 | 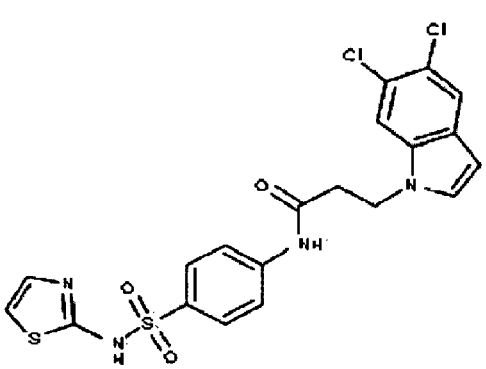 |

Figure 1-214
| # | Compound |
|---|---|
| 743 | 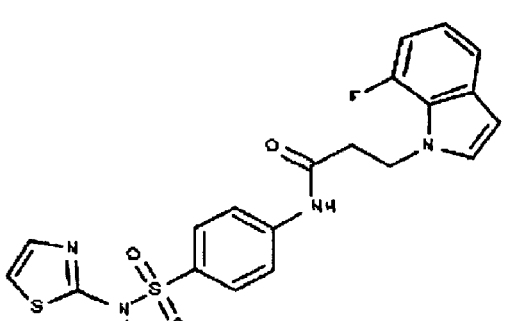 |
| 744 | 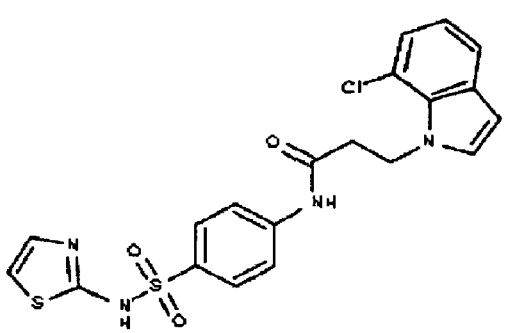 |
| 745 | 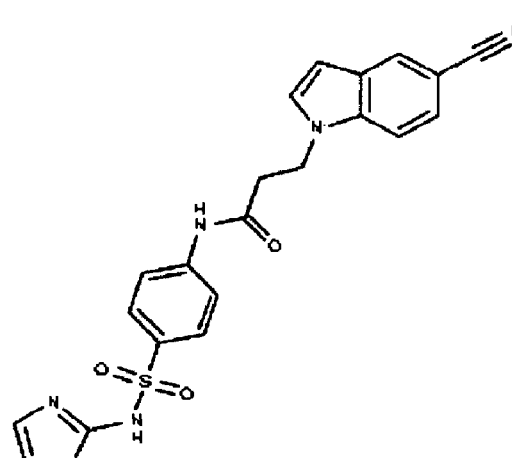 |

Figure 1-215

| # | Compound |
|---|---|
| 746 | |
| 747 | |
| 748 | |
| 749 | |

Figure 1-216

| # | Compound |
|---|---|
| 750 | |
| 751 | |
| 752 | |
| 753 | |

Figure 1-217
| # | Compound |
|---|---|
| 754 | 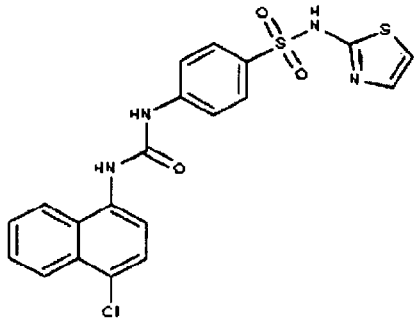 |
| 755 | 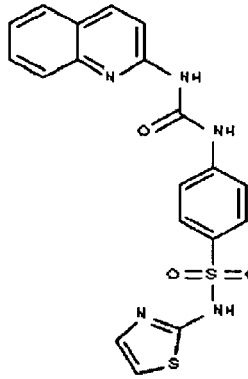 |
| 756 | 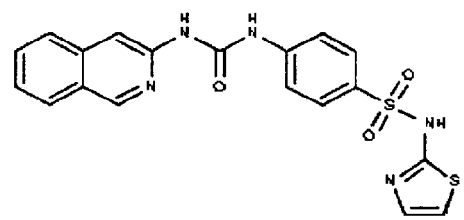 |
| 757 | 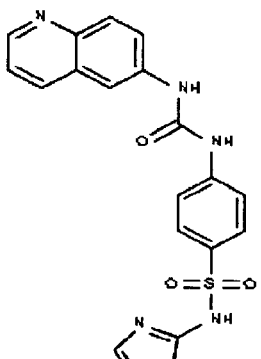 |

Figure 1-218

| # | Compound |
|---|---|
| 758 | |
| 759 | |
| 760 | |

Figure 1-219

| # | Compound |
|---|---|
| 761 | |
| 762 | |
| 763 | |

Figure 1-220

| # | Compound |
|---|---|
| 764 | |
| 765 | |
| 766 | |

Figure 1-221
| # | Compound |
|---|---|
| 767 | 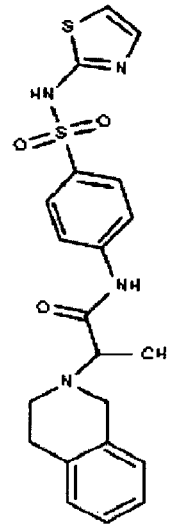 |
| 768 | 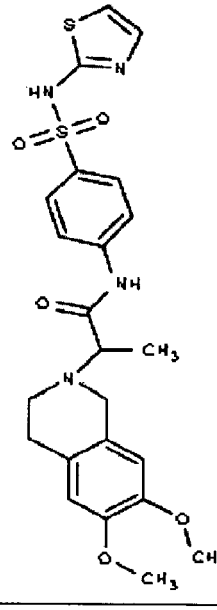 |
| 769 | 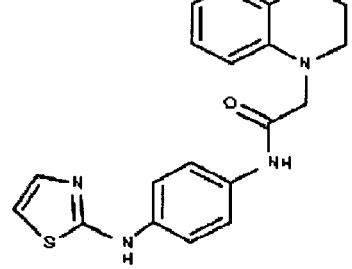 |

Figure 1-222

| # | Compound |
|---|----------|
| 770 | |
| 771 | |
| 772 | |
| 773 | |

| # | Compound |
|---|---|
| 774 |  |

COMPOSITIONS USEFUL AS INHIBITORS OF VOLTAGE-GATED SODIUM CHANNELS

CROSS-REFERENCE TO RELATED APPLICATIONS

The present application is a divisional of U.S. patent application Ser. No. 10/914,988, filed Aug. 9, 2004, which claims the benefit under 35 U.S.C. §119 of U.S. Provisional patent application No. 60/493,659, filed Aug. 8, 2003, and U.S. Provisional patent application No. 60/584,717, filed Jul. 1, 2004, the entire contents of all applications being incorporated herein by reference.

TECHNICAL FIELD OF THE INVENTION

The present invention relates to compounds useful as inhibitors of voltage-gated sodium channels and calcium channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)—null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

Table 1 (Abbreviations: CNS=central nervous system, PNS=peripheral nervous sytem, DRG=dorsal root ganglion, TG=Trigeminal ganglion):

| Na Isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain, Epilepsy |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (Nays) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is significantly upregulated in animal models of neuropathic pain (See, Dib-Hajj, S. D., J. Fjell, et al. (1999) "Plasticity of sodium channel expression in DRG neurons in the chronic constriction injury model of neuropathic pain." *Pain* 83(3): 591-600 and Kim, C. H., Youngsuk, O., et al. (2001) "The changes in expression of three subtypes of TTX sensitive sodium channels in sensory neurons after spinal nerve ligation". *Mol. Brain Res.* 95:153-61.) The timecourse of the increase in NaV1.3 parallels the appearance of allodynia in animal models subsequent to nerve injury. Up-regulation of Nav1.3 transcription is also observed in a rat model of diabetic neuropathy. (See, Craner, M. J., Klein, J. P. et al. (2002) "Changes of sodium channel expression in experimental painful diabetic neuropathy." *Ann Neurol.* 52(6): 786-92. The biophysics of the NaV1.3 channel is distinctive in that it shows very fast repriming after inactivation following an action potential. This allows for sustained rates of high firing as is often seen in the pathophysiological activity accompanying neuropathic pain (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). Human NaV1.3 channel proteins are expressed in the central and peripheral systems of man. (See, Chen, Y. H., Dale, T. J., et al. (2000) "Cloning, distribution and functional analysis of the type III sodium channel from human brain." *Eur. J. Neurosci.* 12: 4281-89). Furthermore, in the periphery, NaV1.3 channel proteins are detectable in injured but not uninjured human nerves indicating that NaV1.3 plays important physiological roles under pathophysiological conditions in humans as well. Given the strong correlation between increased NaV1.3 channel expression and neuronal hyperexcitability, inhibitors of NaV1.3 channels, and in particular selective ones, might therefore provide efficacious therapeutic agents with less-severe side effects than nonselective Na_+ channel inhibitors in the treatment of painful neuropathies. Similarly, NaV1.3 overexpression may also be associated with increased epileptic neuronal activity as it is significantly upregulated in hippocampal pyramidal neurons of epileptic humans (See, Whitaker, W. R. J., Faull, M., et al. (2001) "Changes in the mRNAs encoding voltage-gated sodium channel types II and III in human epileptic hippocampus." *Neurosci.* 106(2): 275-285.); inhibitors with some selectivity against Nav1.3 could also be particularly attractive anticonvulsants and neuroprotectants.

NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33.). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli.

In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir (Wien)* 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L, N, P, Q or R-type). This classification scheme was replaced by a nomenclature based upon the molecular subunit composition, as summarized in Table I (Hockerman, G. H., et. al. (1997) *Annu. Rev. Pharmacol. Toxicol.* 37: 361-96; Striessnig, J. (1999) *Cell. Physiol. Biochem.* 9: 242-69). There are four primary subunit types that make up calcium channels—$\alpha_1$, $\alpha_2\delta$, $\beta$ and $\gamma$ (See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockerman, G. H., et. al. (1997) *Annu. Rev. Pharmacol. Toxicol.* 37: 361-96; Striessnig, J. (1999) *Cell. Physiol. Biochem.* 9: 242-69). Ten isoforms of the $\alpha_1$ subunit are known, as indicated in Table I. The $\alpha_2\delta$ subunit consists of two disulfide linked subunits, $\alpha_2$, which is primarily extracellular and a transmembrane $\delta$ subunit. Four isoforms of $\alpha_2\delta$ are known, $\alpha_2\delta$-1, $\alpha_2\delta$-2, $\alpha_2\delta$-3 and $\alpha_2\delta$-4. The $\beta$ subunit is a non-glycosylated cytoplasmic protein that binds to the $\alpha_1$ subunit. Four isoforms are known, termed $\beta_1$ to $\beta_4$. The $\gamma$ subunit is a transmembrane protein that has been biochemically isolated as a component of $Ca_v1$ and $Ca_v2$ channels. At least 8 isoforms are known ($\gamma_1$ to $\gamma_8$) (Kang, M. G. and K. P. Campbell (2003) *J. Biol. Chem.* 278: 21315-8). The nomenclature for voltage-gated calcium channels is based upon the content of the $\alpha_1$ subunit, as indicated in Table I. Each type of $\alpha_1$ subunit can associate with a variety of $\beta$, $\alpha_2\delta$ or $\gamma$ subunits, so that each $Ca_v$ type corresponds to many different combinations of subunits.

| Cav Nomenclature | $\alpha_1$ subunit | Pharmacological name |
|---|---|---|
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins ω-conotoxin-MVIIC and ω-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek, R. E., et al. (1998) *J. Neurosci.* 18: 6319-30; Cizkova, D, et al. (2002) *Exp. Brain Res.* 147: 456-63). $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain, on the other hand, may last for much longer periods of time and its intensity is more graded. Inflammation may occur for many reasons including tissue damage, autoimmune response, and pathogen invasion. Inflammatory pain is mediated by a variety of agents that are released during inflammation, including substance P, histamines, acid, prostaglandin, bradykinin, CGRP, cytokines, ATP, and other agents (Julius, D. and A. I. Basbaum (2001) *Nature* 413 (6852): 203-10). The third class of pain is neuropathic and involves nerve damage arising from nerve injury or viral infection and results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX-2 inhibitors, opioids, tricyclic antidepressants, and anticonvulsants. Neuropathic pain has been particularly difficult to treat as it does not respond well to opioids until high doses are reached. Gabapentin is currently the most widely used therapeutic for the treatment of neuropathic pain, although it works in only 60% of patients and has modest efficacy. The drug is generally safe, although sedation is an issue at higher doses.

Validation of Cav2.2 as a target for the treatment of neuropathic pain is provided by studies with ziconotide (also known as ω-conotoxin-MVIIA), a selective peptide blocker of this channel (Bowersox, S. S., et al. (1996) *J. Pharmacol. Exp. Ther.* 279: 1243-9; Jain, K. K. (2000) *Exp. Opin. Invest. Drugs* 9: 2403-10; Vanegas, H. and H. Schaible (2000) *Pain* 85: 9-18). In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_v2.1$, $Ca_v2.2$ or $Ca_v2.3$ should also be useful for treating other pathologies of the central nervous system that apparently involve excessive calcium entry. Cerebral ischaemia and stroke are associated with excessive calcium entry due to depolarization of neurons. The $Ca_v2.2$ antagonist ziconotide is effective in reducing infarct size in a focal ischemia model using laboratory animals, suggesting that $Ca_v2.2$ antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances.

$Ca_v2.2$ also mediates release of neurotransmitters from neurons of the sympathetic nervous system and antagonists could be used to treat cardiovascular diseases such as hypertension, cardiac arrhythmia, angina pectoris, myocardial infarction, and congestive heart failure.

However, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, and Ca channel antagonists preferably those with higher potency and fewer side effects.

SUMMARY OF THE INVENTION

It has now been found that compounds of this invention, and pharmaceutically acceptable compositions thereof, are useful as inhibitors of voltage-gated sodium and/or calcium channels. These compounds have the general formula I:

$$T-L_1-A-L_2-Z \qquad (I);$$

or a pharmaceutically acceptable derivative thereof;
wherein:
$L_1$ is $-(X_1)_p-(X_2)_q-R_y-$;
wherein:
$X_1$ is O, S, or $NR_x$
p is 0 or 1;
q is 0 or 1;
$R_x$ is H or $R^2$;
$X_2$ is $R^2$;
$R_y$ is $-C(O)-NR^2-$; or
$L_2$ and Ry are independently selected from OC(O), C(O)O, S(O), $SO_2$, $N(R^5)SO_2$, $N(R^6)SO_2$, $SO_2N(R^5)$, $SO_2N(R^6)$, $C(O)N(R^5)$, $C(O)N(R^6)$, $NR^5C(O)$, $NR^6C(O)$, $C(NOR^5)R^6$, $C(NOR^5)R^6$, $C(NOR^6)R^5$, $C(NOR^6)R^6$, $N(R^5)$, $N(R^6)$, $NR^5C(O)O$, $NR^6C(O)O$, $OC(O)NR^5$, $OC(O)NR^6$, $NR^5C(O)N(R^5)$, $NR^5C(O)N(R^6)$, $NR^6C(O)N(R^5)$, $NR^6C(O)N(R^6)$, $NR^5SO_2N(R^5)$, $NR^5SO_2N(R^6)$, $NR^6SO_2N(R^5)$, $NR^6SO_2N(R^6)$, $N(OR^5)$, or $N(OR^6)$;
Z is hydrogen, cycloaliphatic, heterocyclic, aryl, or heteroaryl ring;
T is aliphatic, cycloaliphatic, aryl, heteroaryl, or heterocyclic ring;
A is aryl or heteroaryl ring;
wherein each of T, A, and Z optionally comprises up to 4 suitable substituents independently selected from $R^1$, $R^2$, $R^3$, $R^4$, or $R^5$;
$R^1$ is oxo, $=NN(R^6)_2$, $=NN(R^7)_2$, $=NN(R^6R^7)$, $R^6$ or $(CH_2)_n-Y$;
n is 0, 1 or 2;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ is optionally substituted with up to 2 substituents independently selected from $R^1$, $R^4$, or $R^5$;
$R^3$ is a cycloaliphatic, aryl, heterocyclic, or heteroaryl ring optionally substituted with up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;

$R^5$ is a cycloaliphatic, aryl, heterocyclic, or heteroaryl ring optionally substituted with up to 3 $R^1$ substituents;

$R^6$ is H or aliphatic, wherein $R^6$ is optionally substituted with a $R^7$ substituent;

$R^7$ is a cycloaliphatic, aryl, heterocyclic, or heteroaryl ring and each $R^7$ is optionally substituted with up to 2 substituents independently chosen from H, aliphatic, or $(CH_2)_n$—Z;

Z' is selected from halo, CN, $NO_2$, $C(halo)_3$, $CH(halo)_2$, $CH_2(halo)$, —$OC(halo)_3$, —$OCH(halo)_2$, —$OCH_2(halo)$, OH, S-aliphatic, S(O)-aliphatic, $SO_2$-aliphatic, $NH_2$, NH-aliphatic, N(aliphatic)$_2$, N(aliphatic)$R^8$, COOH, C(O)O(-aliphatic), or O-aliphatic; and $R^8$ is an amino protecting group.

These compounds and pharmaceutically acceptable compositions thereof are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence.

DETAILED DESCRIPTION OF THE INVENTION

Figure 1:
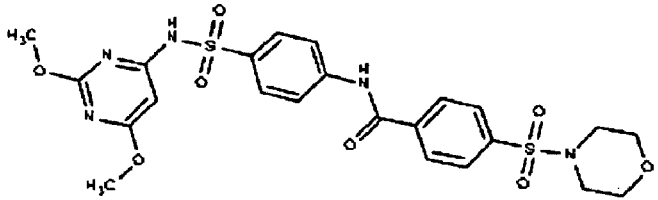
FIG. 1 (FIG. 1-1 to FIG. 1-223) depicts the structures of the compounds of the present invention.
Figure 2:
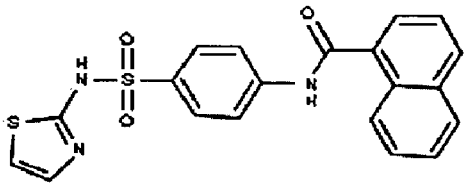
Figure 3:
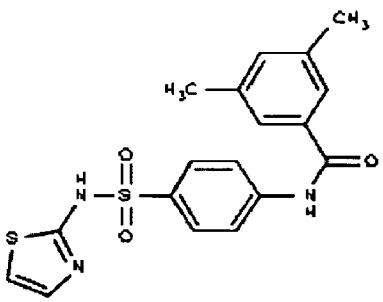
Figure 4:
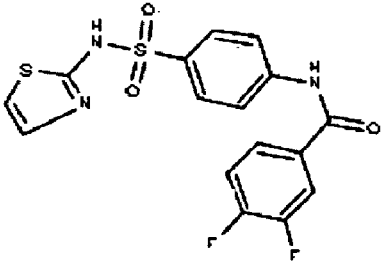
Figure 5:
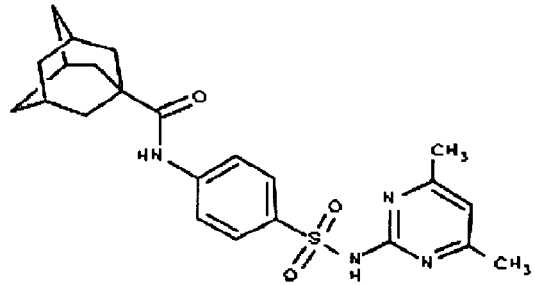
Figure 1:
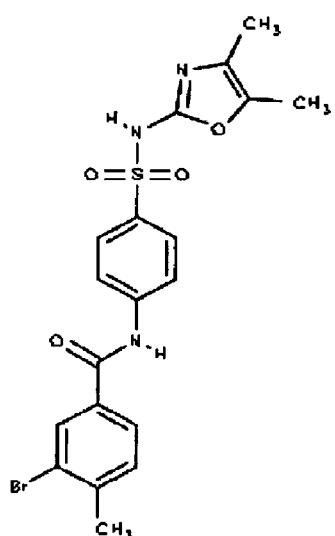
Figure 65:
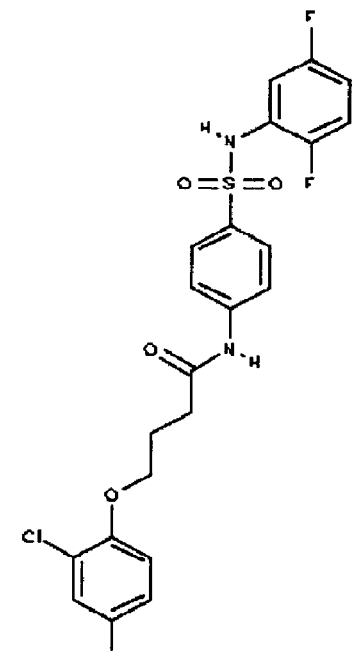
Figure 1:
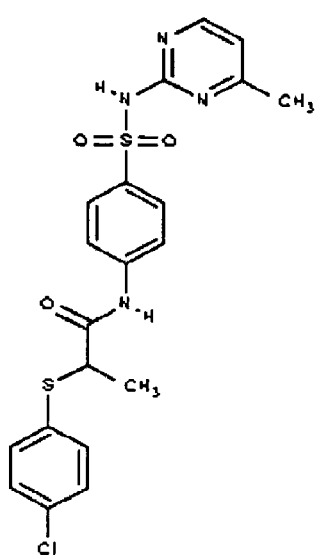
Figure 66:
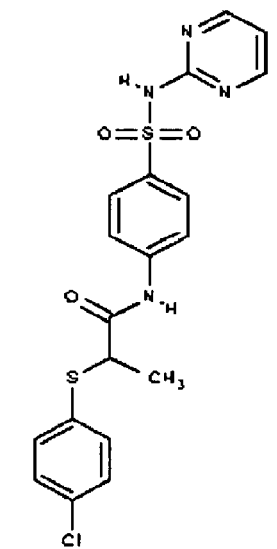
Figure 1:
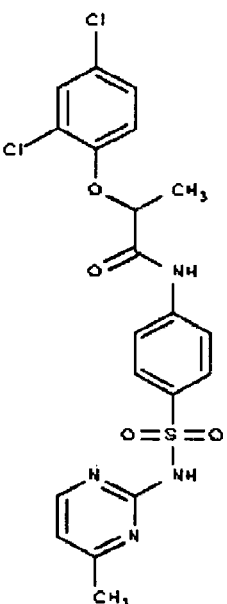
Figure 74:
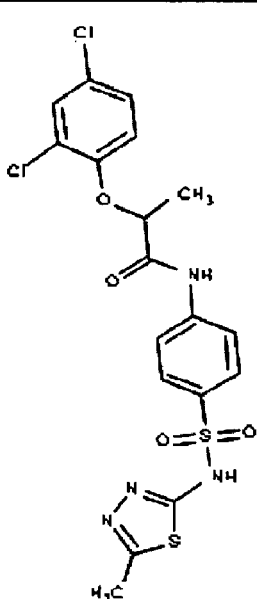
Figure 1:
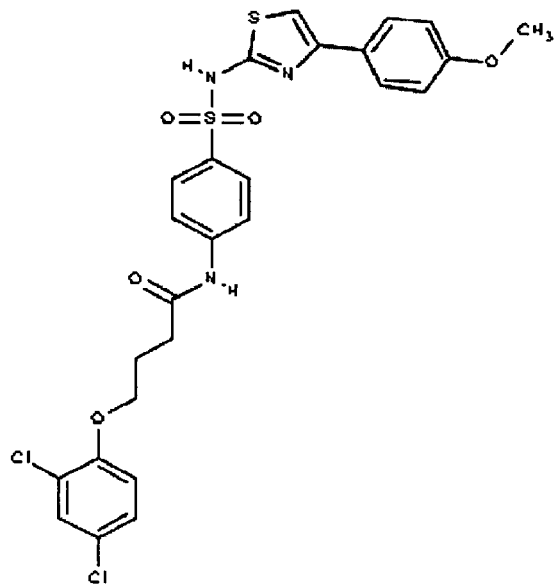
Figure 83:
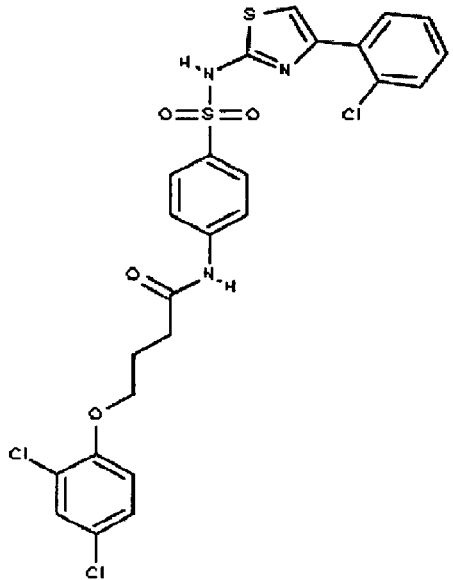
Figure 1:
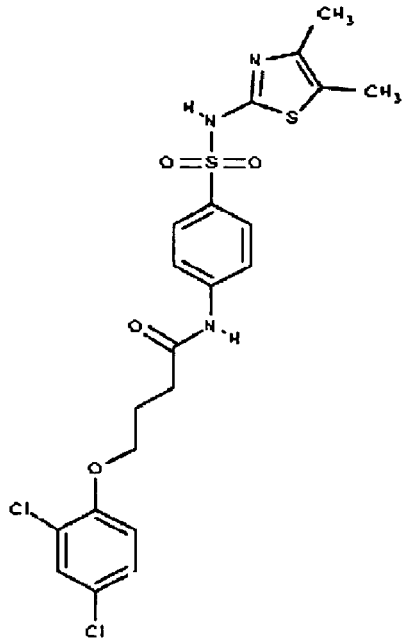
Figure 84:
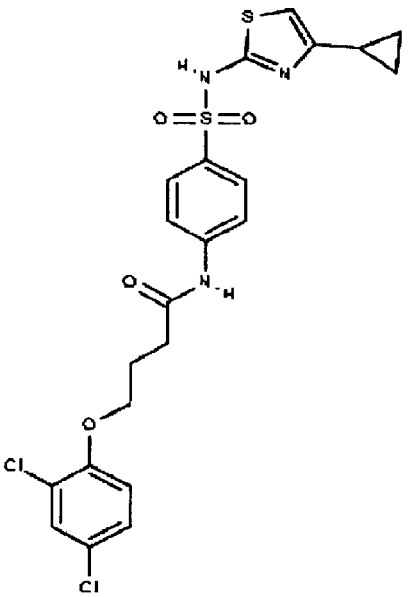
Figure 1:
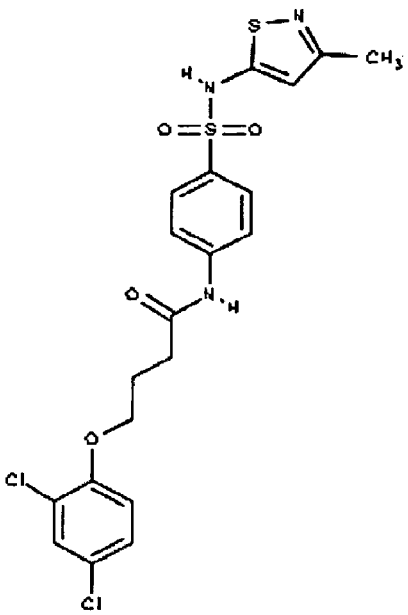
Figure 86:
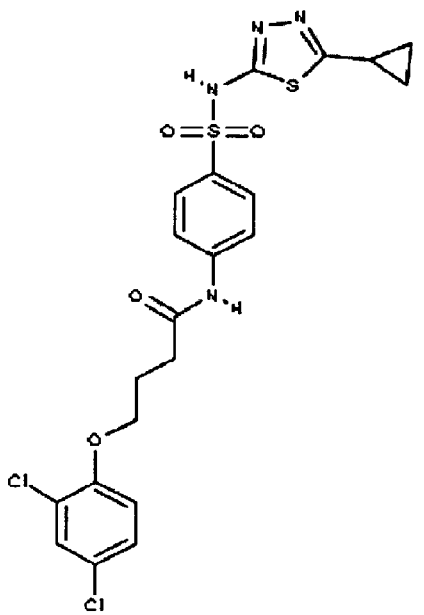
Figure 1:
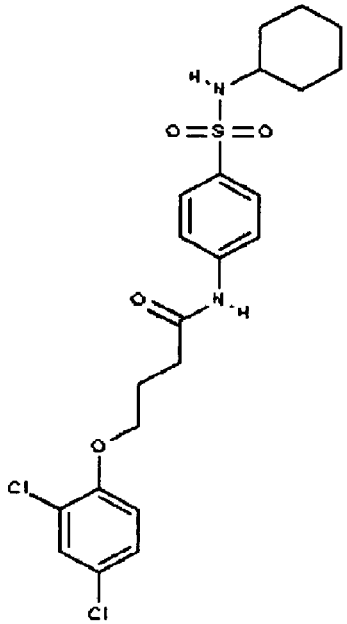
Figure 90:
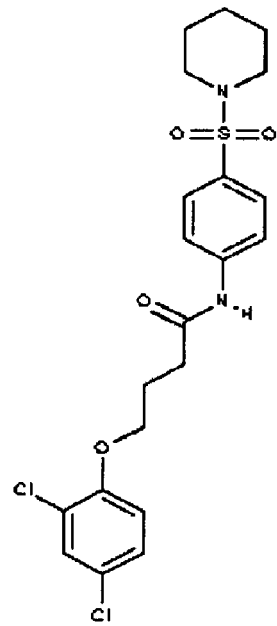
Figures 1, 146:
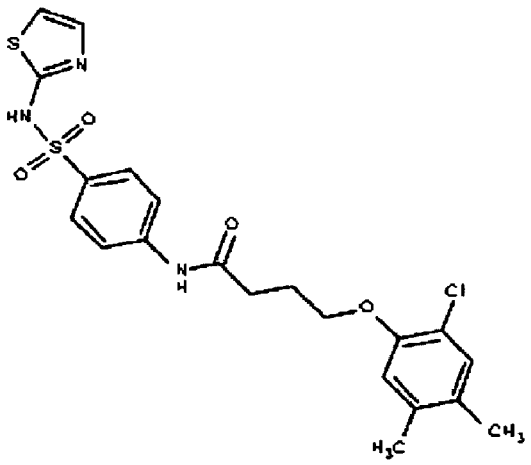
Figure 1:
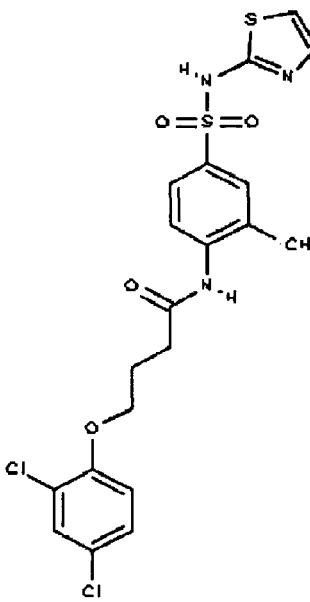
Figure 169:
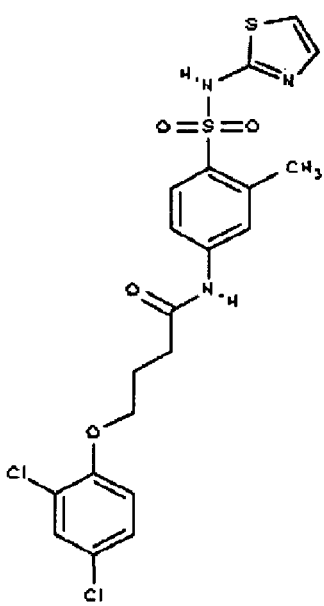
Figure 1:
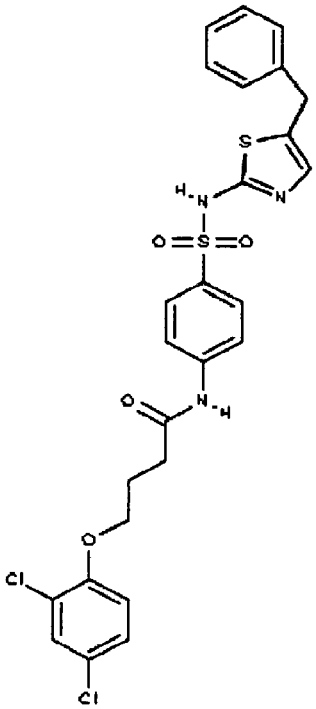
Figure 199:
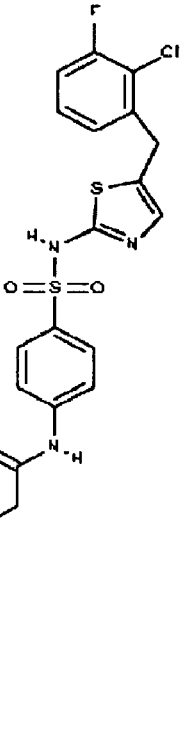
Figure 1:
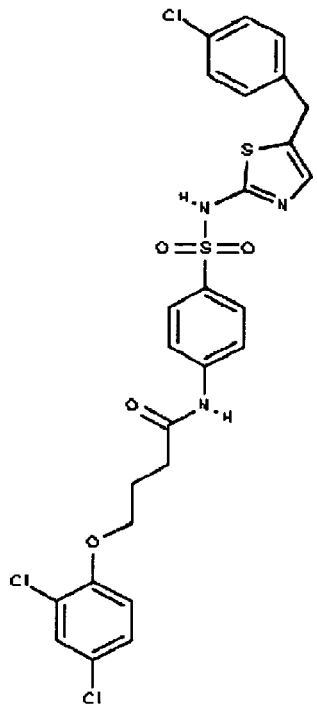
Figure 200:
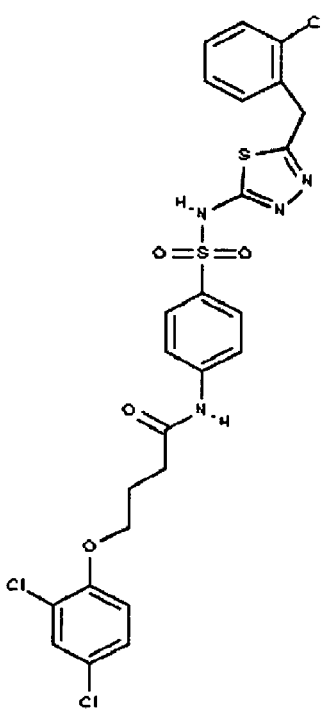
Figures 1, 223:
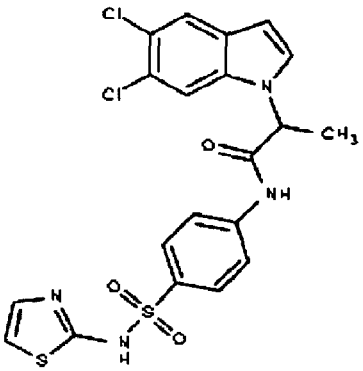

According to one embodiment, the present invention provides compounds of formula (I) useful in inhibiting a sodium and/or calcium channel:

$$T-L_1-A-L_2-Z \quad (I);$$

or a pharmaceutically acceptable salt thereof;
wherein:
$L_1$ is —$(X_1)_p$—$(X_2)_q$—$R_y$—;
wherein:
$X_1$ is O, S, or $NR_x$
p is 0 or 1;
q is 0 or 1;
$R_x$ is H or $R^2$;
$X_2$ is $R^2$;
$R_y$ is —C(O)—$NR^2$—; or
$L_2$ and $R_y$ are independently selected from OC(O), C(O)O, S(O), $SO_2$, $N(R^5)SO_2$, $N(R^6)SO_2$, $SO_2N(R^5)$, $SO_2N(R^6)$, $C(O)N(R^5)$, $C(O)N(R^6)$, $NR^5C(O)$, $NR^6C(O)$, $C(NOR^5)R^6$, $C(NOR^5)R^6$, $C(NOR^6)R^5$, $C(NOR^6)R^6$, $N(R^5)$, $N(R^6)$, $NR^5C(O)O$, $NR^6C(O)O$, $OC(O)NR^5$, $OC(O)NR^6$, $NR^5C(O)N(R^5)$, $NR^5C(O)N(R^6)$, $NR^6C(O)N(R^5)$, $NR^6C(O)N(R^6)$, $NR^5SO_2N(R^5)$, $NR^5SO_2N(R^6)$, $NR^6SO_2N(R^5)$, $NR^6SO_2N(R^6)$, $N(OR^5)$, or $N(OR^6)$;

Z is hydrogen, cycloaliphatic, heterocyclic, aryl, or heteroaryl ring;

T is aliphatic, cycloaliphatic, aryl, heteroaryl, or heterocyclic ring;

A is aryl or heteroaryl ring;

wherein each of T, A, and Z is optionally substituted with up to 4 suitable substituents independently selected from $R^1$, $R^2$, $R^3$, $R^4$, or $R^5$;

$R^1$ is oxo, =$NN(R^6)_2$, =$NN(R^7)_2$, =$NN(R^6R^7)$, $R^6$ or $(CH_2)_n$—Y;

n is 0, 1 or 2;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ is optionally substituted with up to 2 substituents independently selected from $R^1$, $R^4$, or $R^5$;

$R^3$ is a cycloaliphatic, aryl, heterocyclic, or heteroaryl ring is optionally substituted with up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;

$R^5$ is a cycloaliphatic, aryl, heterocyclic, or heteroaryl ring is optionally substituted with up to 3 $R^1$ substituents;

$R^6$ is H or aliphatic, wherein $R^6$ is optionally substituted with a $R^7$ substituent;

$R^7$ is a cycloaliphatic, aryl, heterocyclic, or heteroaryl ring and each $R^7$ is optionally substituted with up to 2 substituents independently chosen from H, aliphatic, or $(CH_2)_n$—Z';

Z' is selected from halo, CN, $NO_2$, $C(halo)_3$, $CH(halo)_2$, $CH_2(halo)$, —$OC(halo)_3$, —$OCH(halo)_2$, —$OCH_2(halo)$, OH, S-aliphatic, S(O)-aliphatic, $SO_2$-aliphatic, $NH_2$, NH-aliphatic, N(aliphatic)$_2$, N(aliphatic)$R^8$, COOH, C(O)O(-aliphatic), or O-aliphatic; and $R^8$ is an amino protecting group.

According to one embodiment, the present invention provides compounds of formula I':

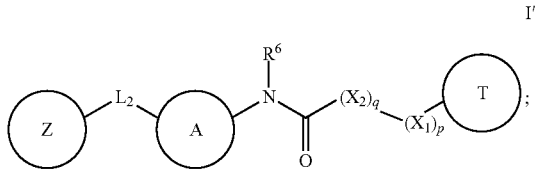

or a pharmaceutically acceptable salt thereof,
wherein:
X₁ is O, S, or NR$_x$;
p is 0 or 1;
q is 0 or 1;
R$_x$ is H or R²;
X₂ is a bond R²;
L₂ is selected from OC(O), C(O)O, S(O), SO₂, N(R⁵)SO₂, N(R⁶)SO₂, SO₂N(R⁵), SO₂N(R⁶), C(O)N(R⁵), C(O)N(R⁶), NR⁵C(O), NR⁶C(O), C(NOR⁵)R⁶, C(NOR⁵)R⁶, C(NOR⁶)R⁵, C(NOR⁶)R⁶, N(R⁵), N(R⁶), NR⁵C(O)O, NR⁶C(O)O, OC(O)NR⁵, OC(O)NR⁶, NR⁵C(O)N(R⁵), NR⁵C(O)N(R⁶), NR⁶C(O)N(R⁵), NR⁶C(O)N(R⁶), NR⁵SO₂N(R⁵), NR⁵SO₂N(R⁶), NR⁶SO₂N(R⁵), NR⁶SO₂N(R⁶), N(OR⁵), or N(OR⁶);
Z is cycloaliphatic, heterocyclic, aryl, or heteroaryl ring;
T is aliphatic, cycloaliphatic, aryl, heteroaryl, or heterocyclic ring;
A is aryl or heteroaryl ring;
wherein each of T, A, and Z is optionally substituted with up to 4 suitable substituents independently selected from R¹, R², R³, R⁴, or R⁵;
R¹ is oxo, =NN(R⁶)₂, =NN(R⁷)₂, =NN(R⁶R⁷), R⁶ or (CH₂)$_n$—Y;
n is 0, 1 or 2;
Y is halo, CN, NO₂, CF₃, OCF₃, OH, SR⁶, S(O)R⁶, SO₂R⁶, NH₂, NHR⁶, N(R⁶)₂, NR⁶R⁸, COOH, COOR⁶ or OR⁶; or
two R¹ on adjacent ring atoms, taken together, form 1,2-methylenedioxy or 1,2-ethylenedioxy;
R² is aliphatic, wherein each R² is optionally substituted with up to 2 substituents independently selected from R¹, R⁴, or R⁵;
R³ is a cycloaliphatic, aryl, heterocyclic, or heteroaryl ring, optionally substituted with up to 3 substituents, independently selected from R¹, R², R⁴ or R⁵;
R⁴ is OR⁵, OR⁶, OC(O)R⁶, OC(O)R⁵, OC(O)OR⁶, OC(O)OR⁵, OC(O)N(R⁶)₂, OC(O)N(R⁵)₂, OC(O)N(R⁶R⁵), OP(O)(OR⁶)₂, OP(O)(OR⁵)₂, OP(O)(OR⁶)(OR⁵), SR⁶, SR⁵, S(O)R⁶, S(O)R⁵, SO₂R⁶, SO₂R⁵, SO₂N(R⁶)₂, SO₂N(R⁵)₂, SO₂NR⁵R⁶, SO₃R⁶, SO₃R⁵, C(O)R⁵, C(O)OR⁵, C(O)R⁶, C(O)OR⁶, C(O)N(R⁶)₂, C(O)N(R⁵)₂, C(O)N(R⁵R⁶), C(O)N(OR⁶)R⁶, C(O)N(OR⁵)R⁶, C(O)N(OR⁶)R⁵, C(O)N(OR⁵)R⁵, C(NOR⁶)R⁶, C(NOR⁶)R⁵, C(NOR⁵)R⁶, C(NOR⁵)R⁵, N(R⁶)₂, N(R⁵)₂, N(R⁵R⁶), NR⁵C(O)R⁵, NR⁶C(O)R⁶, NR⁵C(O)R⁵, NR⁶C(O)OR⁶, NR⁵C(O)OR⁶, NR⁶C(O)OR⁵, NR⁵C(O)OR⁵, NR⁶C(O)N(R⁶)₂, NR⁵C(O)NR⁵R⁶, NR⁶C(O)N(R⁵)₂, NR⁵C(O)N(R⁶)₂, NR⁵C(O)NR⁵R⁶, NR⁵C(O)N(R⁵)₂, NR⁶SO₂R⁶, NR⁶SO₂R⁵, NR⁵SO₂R⁵, NR⁵SO₂N(R⁶)₂, NR⁶SO₂NR⁵R⁶, NR⁶SO₂N(R⁵)₂, NR⁵SO₂NR⁵R⁶, NR⁵SO₂N(R⁵)₂, N(OR⁶)R⁶, N(OR⁶)R⁵, N(OR⁵)R⁵, N(OR⁵)R⁶, P(O)(OR⁶)N(R⁶)₂, P(O)(OR⁶)N(R⁵R⁶), P(O)(OR⁶)N(R⁵)₂, P(O)(OR⁵)N(R⁵R⁶), P(O)(OR⁵)N(R⁶)₂, P(O)(OR⁵)N(R⁵)₂, P(O)(OR⁶)₂, P(O)(OR⁵)₂, or P(O)(OR⁶)(OR⁵);
R⁵ is a cycloaliphatic, aryl, heterocyclic, or heteroaryl ring is optionally substituted with up to 3 R¹ substituents;

R⁶ is H or aliphatic, wherein R⁶ is optionally substituted with a R⁷ substituent;
R⁷ is a cycloaliphatic, aryl, heterocyclic, or heteroaryl ring and each R⁷ is optionally substituted with up to 2 substituents independently chosen from H, aliphatic, or (CH₂)$_n$—Z';
Z' is selected from halo, CN, NO₂, C(halo)₃, CH(halo)₂, CH₂(halo), —OC(halo)₃, —OCH(halo)₂, —OCH₂(halo), OH, S-aliphatic, S(O)-aliphatic, SO₂-aliphatic, NH₂, NH-aliphatic, N(aliphatic)₂, N(aliphatic)R⁸, COOH, C(O)O(-aliphatic), or O-aliphatic; and
R⁸ is an amino protecting group.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable (i.e., having the requisite valency available for a given substituent) position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" means a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic C₃-C₈ hydrocarbon or bicyclic C₈-C₁₂ hydrocarbon that is completely saturated or that contains one or more units of unsaturation, but which is not aromatic, that has a single point of attachment to the rest of the molecule wherein any individual ring in said bicyclic ring system has 3-7 members.

Unless otherwise specified, the term "heterocycle", "heterocyclyl", "heterocycloaliphatic", or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

According to a preferred embodiment, p is 0, and q is 0.
According to another preferred embodiment, p is 0, and q is 1. Or, p is 1, and q is 0.
According to yet another preferred embodiment, p is 1 and q is 1.
According to a preferred embodiment, $X_1$ is O or $NR_x$. More preferably, $X_1$ is O. According to another embodiment, $X_1$ is $NR_x$; preferably $R_x$ is H. Or, $X_1$ is S.
According to a preferred embodiment, $X_2$ is a straight or branched ($C_1$-$C_6$)alkyl or ($C_2$-$C_6$)alkenyl or alkynyl, optionally substituted with up to two substituents independently selected from $R_1$ and $R_5$. More preferably, $X_2$ is a straight or branched ($C_1$-$C_6$)alkyl optionally substituted with up to two substituents independently selected from $R_1$ and $R_5$. Preferred $X_2$ include C1-4 alkyl, such as, —$CH_2$—, $CH_2CH_2$, or —$CH_2CH_2CH_2$—.
According to a preferred embodiment of formula (I), $R_y$ is —C(O)—NH— or —C(O)—$NR^2$—. More preferably, $R^2$ is straight or branched ($C_1$-$C_6$)alkyl or ($C_2$-$C_6$)alkenyl or alkynyl, optionally substituted with up to two substituents independently selected from $R_1$ and $R_5$. More preferably, $R_y$ is —C(O)—NH—.
In one embodiment, $L_2$ is selected from $N(R^5)SO_2$, $N(R^6)SO_2$, $SO_2N(R^5)$, $SO_2N(R^6)$, $C(O)N(R^5)$, $C(O)N(R^6)$, $NR^5C(O)$, $NR^6C(O)$, $NR^5C(O)O$, $NR^6C(O)O$, $OC(O)NR^5$, $OC(O)NR^6$, $NR^5C(O)N(R^5)$, $NR^5C(O)N(R^6)$, $NR^6C(O)N(R^5)$, or $NR^6C(O)N(R^6)$.
In another embodiment, $L_2$ is selected from $N(R^6)SO_2$, $SO_2N(R^6)$, $C(O)N(R^6)$, $NR^6C(O)$, $NR^6C(O)O$, $OC(O)NR^6$, or $NR^6C(O)N(R^6)$. Preferably, $R^6$ is hydrogen.
In another embodiment, $L_2$ is selected from $NHSO_2$, $SO_2NH$, $C(O)NH$, or $NHC(O)$.
According to another preferred embodiment, Z is cycloaliphatic, heterocyclic, aryl, or heteroaryl ring.
According to a preferred embodiment of formula (I), Z is aryl or heteroaryl. More preferably, Z is phenyl or napthyl. According to a more preferred embodiment, Z is heteroaryl. More preferably, Z is selected from thiazole, isothiazole, thiadiazole, thiaphene, furan, oxazole, isooxazole, oxadiazole, triazole, imidazole, pyrazole, pyridine, pyrimidine, pyrazine, pyridazine, triazine, or pyrrolyl.
According to a preferred embodiment of formula (I), A is aryl. More preferably, A is phenyl or naphthyl. Most preferably, A is phenyl.
According to another preferred embodiment of formula (I), A is heteroaryl. More preferably, A is a monocyclic aromatic ring containing 1 to 3 heteroatoms. More preferably, A is pyridyl, pyrazyl, triazinyl, furanyl, pyrrolyl, thiophenyl, oxazolyl, isoxazolyl, isothiazolyl, oxadiazolyl, imidazolyl, triazolyl, thiadiazolyl, or pyrimidinyl. According to another preferred embodiment of formula (I), A is a bicyclic ring system with at least one aromatic ring, wherein said ring system contains 1-5 heteroatoms. More preferably, A is quinolinyl, isoquinolinyl, benzofuranyl, benzothiophenyl, quinolinyl, isoquinolinyl, benzofuranyl, benzothiophenyl, indolizinyl, indolyl, isoindolyl, indolinyl, indazolyl, benzimidazolyl, benzothiazolyl, purinyl, cinnolinyl, phthalazine, quinazolinyl, quinaoxalinyl, naphthylirinyl, or pteridinyl. According to another preferred embodiment, A is a tricyclic ring system with at least one aromatic ring, wherein said ring system contains 1-5 heteroatoms. More preferably, A is dibenzofuranyl, carbazolyl, acridinyl, phenazinyl, phenothiazinyl, or phenoxazinyl.

According to a preferred embodiment of formula (I), T is aliphatic or cycloaliphatic. According to a preferred embodiment T is aliphatic; more preferably, (C1-C6) straight or branched alkyl; yet more preferably, methyl, ethyl, propyl, isopropyl, butyl, isobutyl, or t-butyl. According to another preferred embodiment, T is cycloaliphatic; more preferably, cyclopropyl, cyclobutyl, cyclopentyl, cyclohexyl, norbornyl, or adamantyl. Yet more preferably, T is cyclopropyl, cyclohenxyl, norbornyl, or adamantyl.

According to another preferred embodiment, T is an aryl ring; more preferably, phenyl, napthyl, or anthracenyl. Yet more preferably, T is phenyl or napthyl. According to another preferred embodiment, T is a heteroaryl ring; more preferably, thiophenyl, benzothiophenyl, pyridyl, furanyl, benzofuranyl, oxazolyl, quinolinyl, thiophenyl, benzothiophenyl, pyridiyl, furanyl, benzofuranyl, oxazolyl, quinolinyl, pyrrolyl, thiazolyl, imidazolyl, pyrazolyl, isoxazolyl, isothiazolyl, oxadiazolyl, triazolyl, thiadiazolyl, pyridazinyl, pyrimidinyl, pyrazinyl, triazinyl, indolizinyl, indolyl, isoindolyl, indazolyl, benzimidazolyl, benzthiazolyl, purinyl, isoquinolinyl, cinnolinyl phthalazinyl, quinazolinyl, quinoxalinyl, napthyridinyl, pteridinyl, acridinyl, phenazinyl, phenothiazinyl, phenoxazinyl, carbazolyl.

In one embodiment, T is selected from:

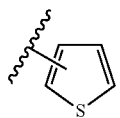 a

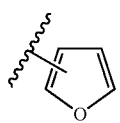 b

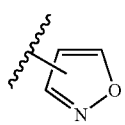 c

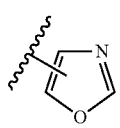 d

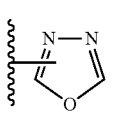 e

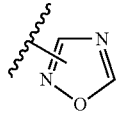 f

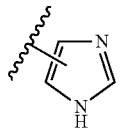 g

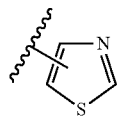 h

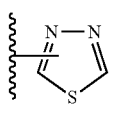 i

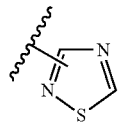 j or

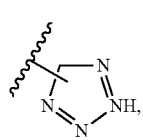 k wherein T is optionally substituted with up to three substituents independently selected from phenyl optionally substituted with $R^1$, halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

According to another preferred embodiment, T is a heterocyclic ring; preferably, tetrahydrofuranyl, pyrrolidinyl, piperidinyl, morpholinyl, dithianyl, thiomorpholinyl, piperazinyl, quinuclidinyl, tetrahydrofuranyl, pyrrolidinyl, piperidinyl, morpholinyl, dithianyl, thiomorpholinyl, piperazinyl, quinuclidinyl, dioxoianyl, imidazolidinyl, pyrazolidinyl, dioxanyl, piperazinyl, or trithianyl.

According to another preferred embodiment of formula (I), $R^1$ is oxo. According to another preferred embodiment, $R^1$ is $R^6$ or $(CH_2)_n$—Y; more preferably, $R^1$ is Y (i.e., n is 0).

According to another preferred embodiment of formula (I), $R^2$ is a straight or branched (C1-C6) alkyl or (C2-C6)alkenyl or alkynyl, optionally substituted with up to two $R^1$ substitutions.

According to one embodiment, $R^1$ is $(CH_2)_n$—Y. Or, $R^1$ is Y. Preferred Y includes halo, CN, $NO_2$, $CF_3$, $OCF_3$, OH, SH, S(C1-4 aliphatic), S(O) (C1-4 aliphatic), $SO_2$(C1-4 aliphatic), $NH_2$, NH(C1-4 aliphatic), N(C1-4 aliphatic)$_2$, NR(C1-4 aliphatic)$R^8$, COOH, COO(C1-4 aliphatic) or O(C1-4 aliphatic). Or two $R^1$ on adjacent ring atoms, taken together, form 1,2-methylenedioxy or 1,2-ethylenedioxy;

According to another embodiment, $R^1$ is selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, 1-pyrrolidinyl, 1-piperidinyl, 1-morpholinyl, or $C(O)C_{1-4}$ alkyl.

According to another preferred embodiment of formula (I):
Z is thiazol-2-yl;
A is phenyl, pyridyl, pyrazinyl, pyridazinyl, pyrimidinyl, triazinyl, or tetrazinyl;
$L_1$ is —$(X_1)_p$—$(X_2)_q$—$R_y$—;
wherein:
$X_1$ is O, S, or $NR_x$
p is 0 or 1;
q is 0 or 1;
$R_x$ is H or $R^2$;
$X_2$ is $R^2$;
R is —C(O)—NH—; and
$L_2$ is $SO_2N(R^5)$ or $SO_2N(R^6)$.

According to one embodiment, the present invention provides a compound of formula I-A:

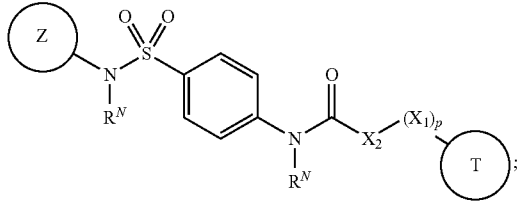

wherein:

X$_1$ is O, S, or NR$^X$ p is 0 or 1;

R$^X$ is H or R$^2$;

R$^N$ is hydrogen or C1-4 aliphatic optionally substituted with up to two substituents selected from R$^1$, R$^4$, or R$^5$;

X$_2$ is C$_{1-3}$ aliphatic, optionally substituted with up to 2 substituents independently selected from R$^1$, R$^4$, or R$^5$;

Z is a 5-7 membered unsaturated or aromatic ring having 1-4 heteroatoms selected from O, S, SO, SO$_2$, N, or NH;

T is a 8-14 membered aromatic or non-aromatic bicyclic or tricyclic ring, having 0-5 heteroatoms selected from O, S, N, NH, S(O) or SO$_2$;

wherein each of Z and T is optionally substituted with up to 4 substituents independently selected from R$^1$, R$^2$, R$^3$, R$^4$, or R$^5$;

wherein the phenylene ring attached to the sulfonyl is optionally substituted with up to 3 substituents selected from R$^1$ and R$^2$;

R$^1$ is oxo, =NN(R$^6$)$_2$, =NN(R$^7$)$_2$, =NN(R$^6$R$^7$), R$^6$ or (CH$_2$)$_n$—Y;

n is 0, 1 or 2;

Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$; or two R$^1$ on adjacent ring atoms, taken together, form 1,2-methylenedioxy or 1,2-ethylenedioxy;

R$^2$ is aliphatic, wherein each R$^2$ is optionally substituted with up to 2 substituents independently selected from R$^1$, R$^4$, or R$^5$;

R$^3$ is a cycloaliphatic, aryl, heterocyclic, or heteroaryl ring is optionally substituted with up to 3 substituents, independently selected from R$^1$, R$^2$, R$^4$ or R$^5$;

R$^4$ is OR$^5$, OR$^6$, OC(O)O, OC(O)R$^5$, OC(O)OR$^6$, OC(O)OR$^5$, OC(O)N(O)$_2$, OC(O)N(R$^5$)$_2$, OC(O)N(R$^6$R$^5$), OP(O)(OR$^6$)$_2$, OP(O)(OR$^5$)$_2$, OP(O)(OR$^6$)(OR$^5$), SR$^6$, SR$^5$, S(O)R$^6$, S(O)R$^5$, SO$_2$O, SO$_2$R$^5$, SO$_2$N(R$^6$)$_2$, SO$_2$N(R$^5$)$_2$, SO$_2$NR$^5$R$^6$, SO$_3$O, SO$_3$R$^5$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^5$, C(O)N(OR$^5$)O, C(O)N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^5$C(O)R$^5$, NR$^6$C(O)R$^6$, NR$^5$C(O)R$^5$, NR$^6$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$SO$_2$R$^6$, NR$^6$SO$_2$R$^5$, NR$^5$SO$_2$R$^5$, NR$^5$SO$_2$R$^6$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, N(OR$^5$)R$^6$, P(O)(OR$^6$)N(R$^6$)$_2$, P(O)(OR$^6$)N(R$^5$R$^6$), P(O)(OR$^6$)N(R$^5$)$_2$, P(O)(OR$^5$)N(R$^5$R$^6$), P(O)(OR$^5$)N(R$^6$)$_2$, P(O)(OR$^5$)N(R$^5$)$_2$, P(O)(OR$^6$)$_2$, P(O)(OR$^5$)$_2$, or P(O)(OR$^6$)(OR$^5$);

R$^5$ is a cycloaliphatic, aryl, heterocyclic, or heteroaryl ring optionally is optionally substituted with up to 3 R$^1$ substituents;

R$^6$ is H or aliphatic, wherein R$^6$ is optionally substituted with a R$^7$ substituent;

R$^7$ is a cycloaliphatic, aryl, heterocyclic, or heteroaryl ring and each R$^7$ is optionally substituted with up to 2 substituents independently chosen from H, aliphatic, or (CH$_2$)$_n$—Z';

Z' is selected from halo, CN, NO$_2$, C(halo)$_3$, CH(halo)$_2$, CH$_2$(halo), —OC(halo)$_3$, —OCH(halo)$_2$, —OCH$_2$(halo), OH, S-aliphatic, S(O)-aliphatic, SO$_2$-aliphatic, NH$_2$, NH-aliphatic, N(aliphatic)$_2$, N(aliphatic)R$^8$, COOH, C(O)O(-aliphatic), or O-aliphatic; and R$^8$ is an amino protecting group.

In certain embodiments, compounds of formula I or formula I-A exclude the following:

a) when both R$^N$ are hydrogen, and T is isoindol-1,3-dione-2-yl optionally substituted with up to 4 halo atoms, then Z is not pyridyl, thiazol-2-yl, 4-(4-methoxyphenyl)thiazol-2-yl, 2-ethyl-1,3,4-thiadiazol-5-yl, optionally substituted pyrimidin-2-yl, 5-methyl-isoxazolyl, 3,4-dimethyl-isoxazoly, or 2-methyl-isoxazolyl;

b) when both R$^N$ are hydrogen, and T is

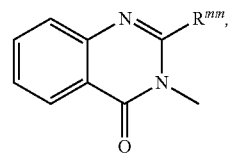

optionally substituted with up to 4 halo atoms, wherein R$^{mm}$ is phenyl optionally substituted with C$_{1-4}$ alkyl or hydrogen, then Z is not optionally substituted pyrimidin-2-yl, 2-pyridyl, or thiazol-2-yl;

c) when both R$^N$ are hydrogen, X$_2$ is —CH$_2$—, p is 1, X$_1$ is S, and T is

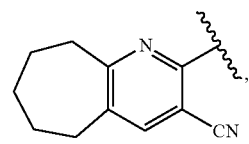

then Z is not 3,4-dimethylisoxazolyl, pyrimidin-2-yl, thiazol-2-yl, or 4,6-dimethyl-pyrimidin-2-yl;

c) when both R$^N$ are hydrogen, X$_2$ is —CH$_2$— and X$_1$ is S, or X$_2$ is CH=CH and X$_1$ is absent, and T is optionally substituted

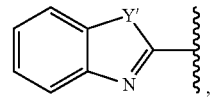

wherein Y' is O, S, or NH, then Z is not pyrimidinyl optionally substituted with up to 2 methyl or methoxy groups, 2-pyridyl, thiazol-2-yl, 2-methoxy-pyrazin-3-yl, 3-chloro-pyridazin-6-yl, 3,4-dimethyl-isoxazolyl, or 2-ethyl-1,3,4-thiadiazol-5-yl;

d) when both $R^N$ are hydrogen, $X_2$ is —CH$_2$—CH$_2$—, $X_1$ is absent, and T is

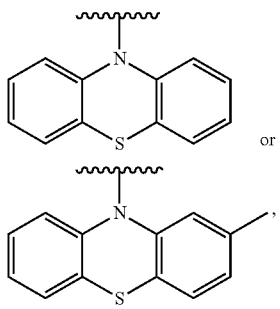

or then Z is not thiazol-2-yl, 2,6-dimethyl-pyrimidin-4-yl, or 3,4-dimethyl-isoxazol-5-yl;

e) when both $R^N$ are hydrogen, $X_2$ is —CH$_2$—, $X_1$ is O or S, and T is

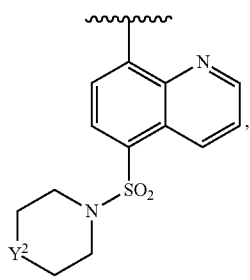

wherein $Y^2$ is O or CH$_2$, then Z is not thiazol-2-yl, or 4,6-dimethyl-pyrimidin-2-yl, or pyrimidin-2-yl;

f) when both $R^N$ are hydrogen, $X_2$ is —CH$_2$—, $X_1$ is O, T is

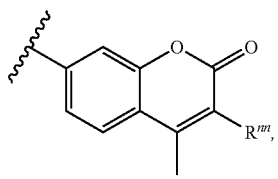

wherein $R''''$ is hydrogen or halo, then Z is not thiazol-2-yl, 4-methyl-pyrimidin-2-yl, 4,6-dimethylpyrimidin-2-yl, pyrimidin-2-yl, or 5-methyl-isoxazol-3-yl;

g) when both $R^N$ are hydrogen, $X_2$ is —CH$_2$—, $X_1$ is absent, T is 1,4-dihydro-quinoxalin-2,3-dione-4-yl, then Z is not 5-methylisoxazol-3-yl, thiazol-2-yl, 4,6-dimethyl-pyrimidin-2-yl, pyrimidin-2-yl, or 2-pyridyl;

h) when both $R^N$ are hydrogen, $X_2$ is —CH$_2$—, $X_1$ is absent, and T is 2,3-dihydro-phthalazin-1,4-dione-2-yl, then Z is not pyridyl, thiazol-2-yl, or optionally substituted pyrimidin-2-yl;

i) when both $R^N$ are hydrogen, $X_2$ is —CH$_2$—, $X_1$ is absent, and T is adamantyl or haloadamantyl, then Z is not 3,4-dimethylisoxazol-5-yl, thiazol-2-yl, or 4-methyl-pyrimidin-2-yl;

j) the following compounds in Table A, wherein $R^N$ is hydrogen, are excluded:

TABLE A

| ring Z | $X_2$ | $X_1$ | ring T |
|---|---|---|---|
| pyrimidin-2-yl | CH$_2$ | NH | 1-naphthyl |
| 4,6-dimethyl-pyrimidin-2-yl | CH$_2$ | NH | 1-naphthyl |
| 5-methyl-isoxazol-3-yl | CH$_2$ | — | 1-naphthyl |
| thiazol-2-yl | CH$_2$ | O | 1-naphthyl, 2-napthyl, 1,7-dibromo-naphth-2-yl |
| 4,6-dimethyl-pyrimidin-2-yl | CH$_2$ | O | 1-naphthyl, 2-napthyl, or 1,7-dibromo-naphth-2-yl |
| 2-methoxy-pyrazin-3-yl | CH$_2$ | O | 2-napthyl |
| 5-ethyl-1,3,4-thiadiazol-2-yl | CH$_2$ | — | 1-napthyl |
| thiazol-2-yl | CH$_2$ | — | 1-naphtyl |
| 5-ethyl-1,3,4-thiadiazol-2-yl | CH$_2$ | O | 2-napthyl |
| 2,6-dimethoxy-pyrimidin-4-yl | CH$_2$ | O | 1-bromo-2-naphthyl |
| 2,6-dimethyl-pyrimidin-4-yl | CH$_2$ | O | 2-naphthyl or 1-bromo-2-naphthyl |
| 2,6-dimethoxy-pyrimidin-4-yl | CH$_2$ | O | 1-naphthyl or 2-naphthyl |
| 2,4-dimethoxy-pyrimidin-6-yl | CH=CH | — | 1-naphthyl |
| 4,6-dimethyl-pyrimidin-2-yl | CH=CH | — | 1-naphthyl |
| 5-methyl-isoxazol-3-yl | CH$_2$ | O | 1-naphthyl or 2-naphthyl |
| 5-methyl-isoxazol-3-yl | CH$_2$ | O | 1-bromo-2-naphthyl or 1,7-dibromo-naphth-2-yl |
| 4,5-dimethyl-isoxazol-3-yl | CH$_2$ | S | 4-bromo-7-chloro-naphth-1-yl |
| thiazol-2-yl | CH$_2$ | S | 4-bromo-7-chloro-naphth-1-yl |
| 4,6-dimethyl-pyrimidin-2-yl | CH$_2$ | O or S | 2-naphtyl |
| 3,4-dimethyl-isoxazol-2-yl | CH$_2$ | O or S | 2-naphtyl |
| 4,6-dimethyl-pyrimidin-2-yl | CH$_2$ | S | quinolin-8-yl |
| 2,6-dimethyl-pyrimidin-2-yl | CH$_2$ | — | 1-naphthyl |
| pyrimidin-2-yl | CH$_2$ | — | 1-naphthyl |
| 6-methoxy-pyrimidin-4-yl | CH$_2$ | — | 1-naphthyl |
| 2-pyridyl | CH$_2$ | — | 1-naphthyl |
| 4-methyl-pyrimidin-2-yl | CH$_2$ | O | 2-naphthyl |
| pyrimidin-2-yl | CH$_2$ | O | 2-naphthyl |
| 2,4-dimethoxy-pyrimidin-2-yl | CH$_2$ | O | 1,7-dibromo-napthh-2-yl |
| 2,4-dimethoxy-pyrimidin-2-yl or 2,4-dimethyl-pyrimidin-2-yl | CH$_2$ | — | 1-naphthyl |
| thiazol-2-yl or 2,4-dimethyl-pyrimidin-4-yl | CH$_2$ | S | isoquinolin-1-yl or 4-methyl-quinazolin-2-yl | k) the following compounds in Table B, wherein $R^N$ is hydrogen, are excluded:

TABLE B

| Ring Z | $X_2$, $X_1$, and T, together |
|---|---|

TABLE B-continued

| Ring Z | X₂, X₁, and T, together |
|---|---|

TABLE B-continued
| Ring Z | X₂, X₁, and T, together |
|---|---|
| 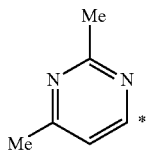 | 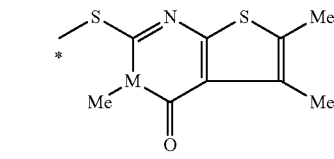 |
|  | 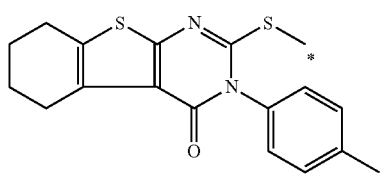 |
|  | 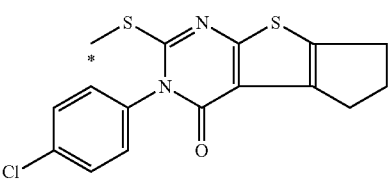 |
|  | 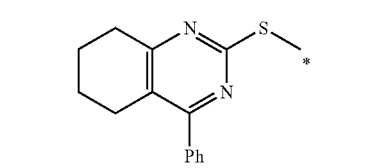 |
| 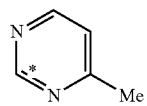 | 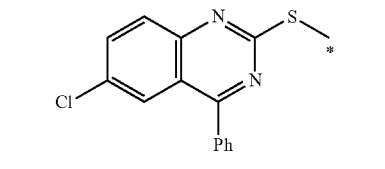 |
|  | 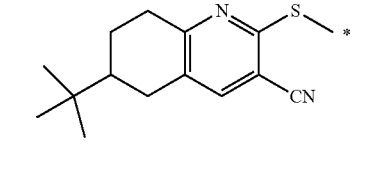 |
|  | 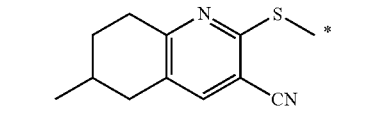 |
|  | 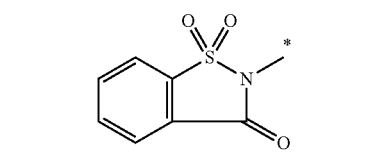 |
| 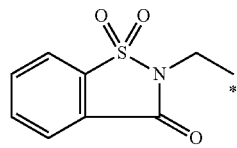 | 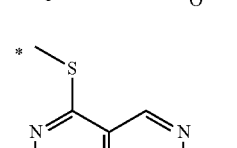 |
| 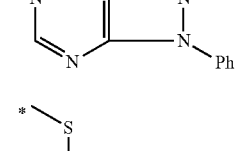 | 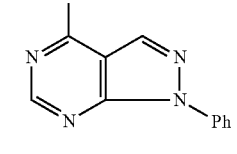 |
| 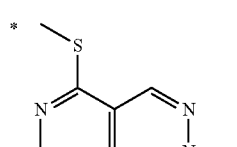 | 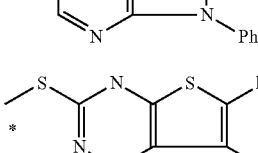 |
| 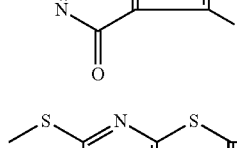 | 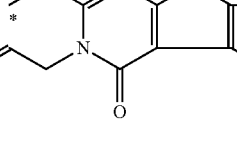 |
| 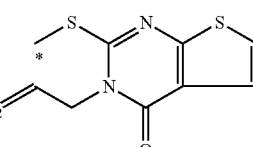 | 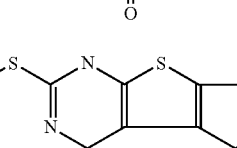 |
| 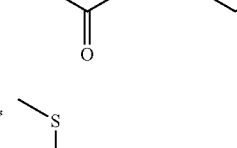 | 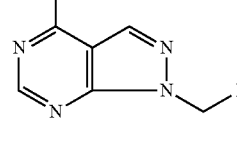 |

TABLE B-continued
| Ring Z | X₂, X₁, and T, together |
|---|---|
| 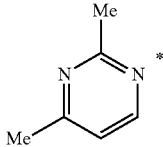 | 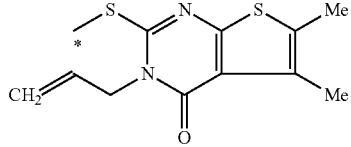 |
|  | 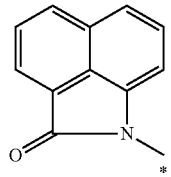 |
| 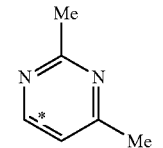 | 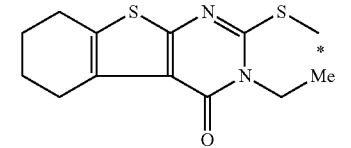 |
| 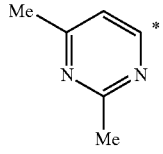 | 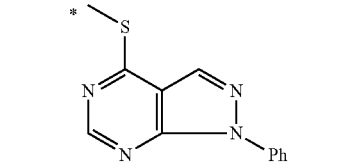 |
| 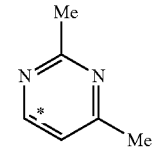 | 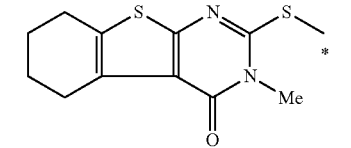 |
| 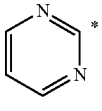 | 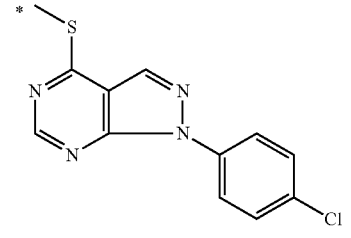 |
| 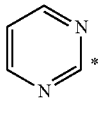 | 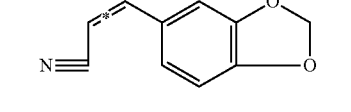 |
|  | 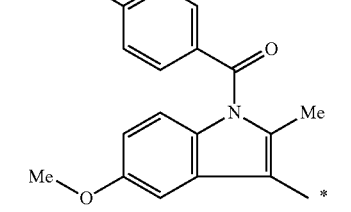 |
TABLE B-continued
| Ring Z | X₂, X₁, and T, together |
|---|---|
| 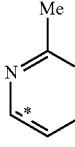 | 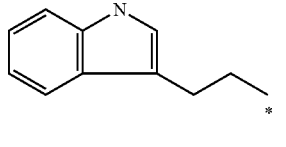 |
|  | 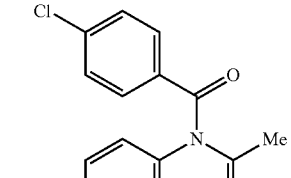 |
| 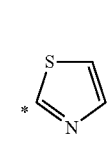 | 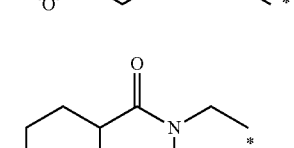 |
| 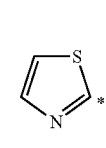 | 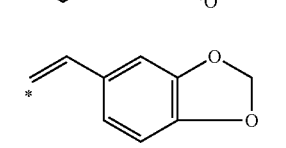 |
| 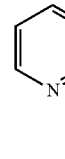 | 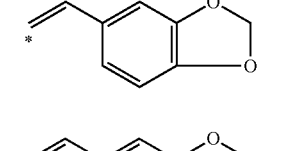 |
| 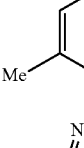 | 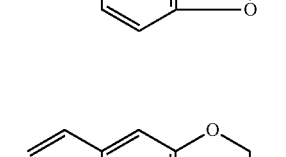 |
|  | 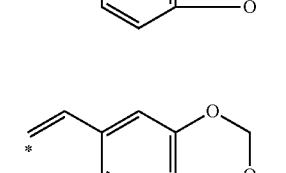 |
| 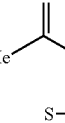 |  |
| 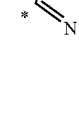 | 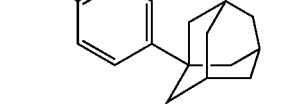 |

TABLE B-continued

| Ring Z | X₂, X₁, and T, together |
|---|---|

TABLE B-continued

| Ring Z | X₂, X₁, and T, together |
|---|---|
| (structures) | (structures) | wherein the asterisk in each structure fragment denotes the carbon atom attached to the remainder of the molecule; e.g., the fragment -* denotes an ethyl group, wherein the second atom of that ethyl group is attached to the remainder of the molecule.

In one embodiment, T is attached to $X_1$ or to $X_2$ (when $X_1$ is absent) through a carbon ring atom in T.

In one embodiment, Z is an optionally substituted ring selected from:

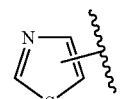

i

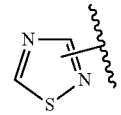

ii

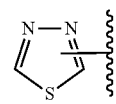

iii

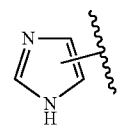

iv

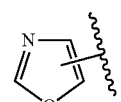

v

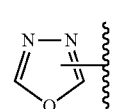

vi

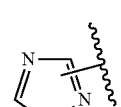

vii

viii

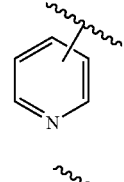

ix

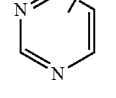

x

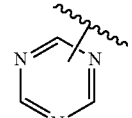

xi

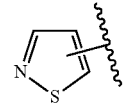

-continued
xii 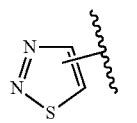
xiii 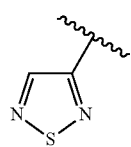
xii 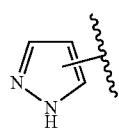
xiii 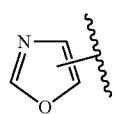
xiv 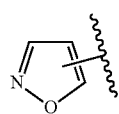
xv 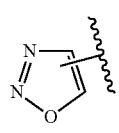
xvi 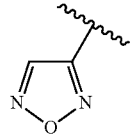
xvii 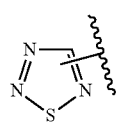
xviii 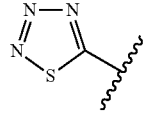
xix 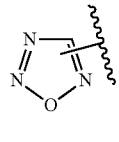
xx 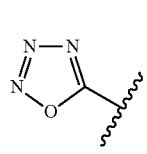
In certain embodiments of the compounds of the present invention, Z is selected from:
i 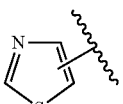
ii 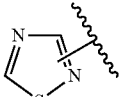
iii 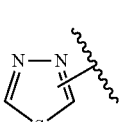
iv 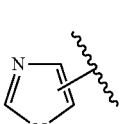
v 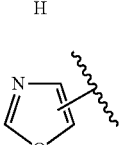
vi 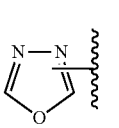
vii 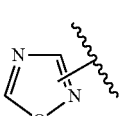
viii 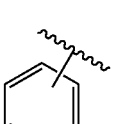
ix 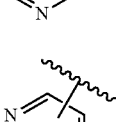
x 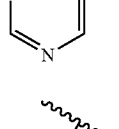
xi 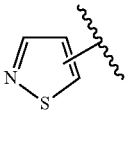

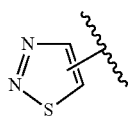
xii
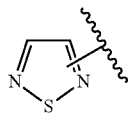
xiii
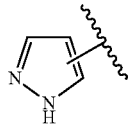
xii
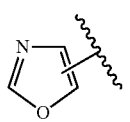
xiii
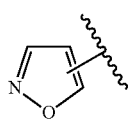
xiv
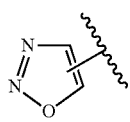
xv
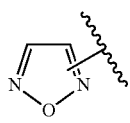
xvi
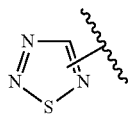
xvii
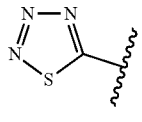
xviii
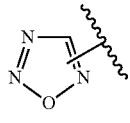
xix
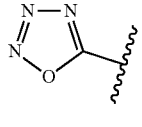
xx
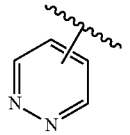
xxi
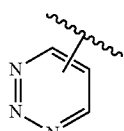
xxii
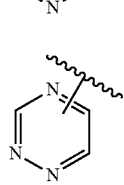
xxiii
wherein Z has up to two substituents selected from $R^1$, $R^2$ or $R^5$.
In other embodiments, Z is selected from:
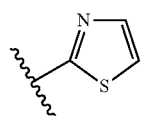
i-a
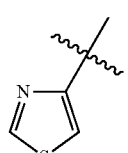
i-b
or
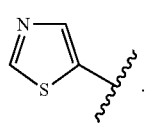
i-c
Or, Z is formula I-a.
In other embodiments, Z is selected from:
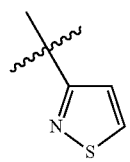
xi-a
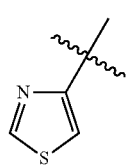
xi-b
or
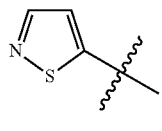
xi-c In certain embodiments of the present invention, Z is selected from:
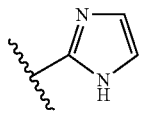
iv-a
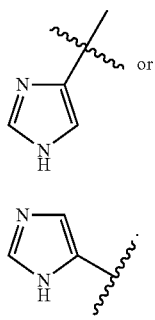
iv-b
or
iv-c
Or, Z is selected from:
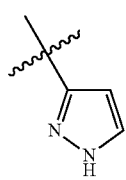
xii-a
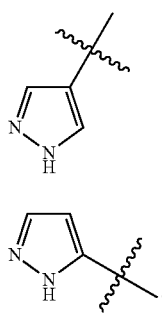
xii-b
or
xii-c
Or, Z is selected from:
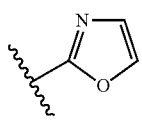
v-a
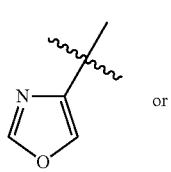
v-b
or
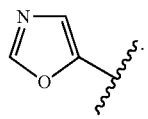
v-c
In certain embodiments, Z is selected from:
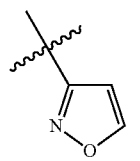
xiv-a
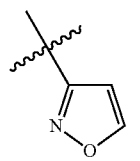
xiv-b
or
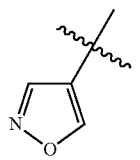
xiv-c
In certain embodiments, Z is selected from:
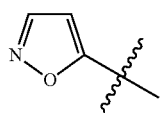
ii-a
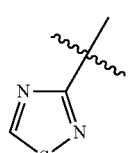
ii-b
or
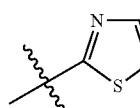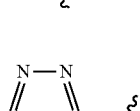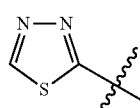
iii-a
In certain embodiments, Z is selected from:
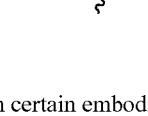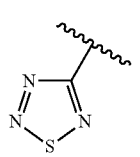
xvii
xvii

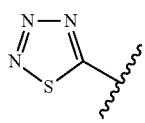
xviii
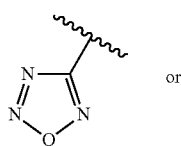
xix
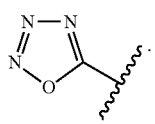
xx
In other embodiments, Z is selected from:
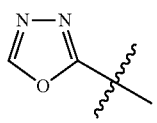
vi-a
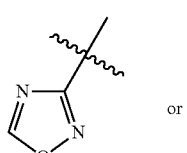
vii-a
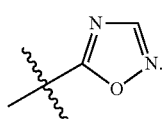
vii-b
In other embodiments, Z is selected from:
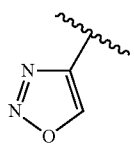
xv-a
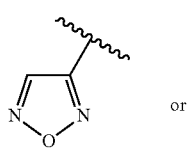
xvi-a
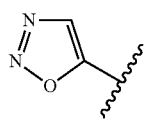
xv-b
In certain embodiments, Z is selected from:
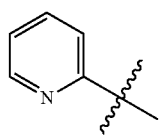
viii-a
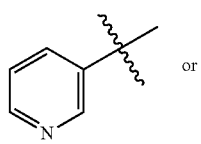
viii-b
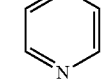
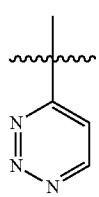
viii-c
In certain embodiments, Z is selected from:
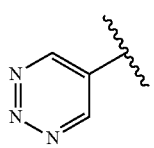
xxii-a
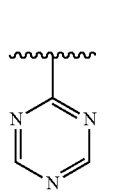
xxii-b
x-a -continued

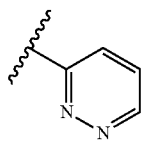
xxi-a

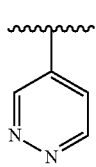
xxi-b

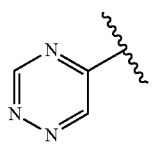
xxii-a

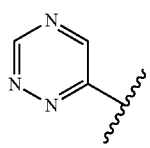
xxii-b

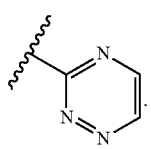
xxii-c

In other embodiments, Z is selected from:

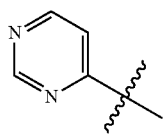
ix-a

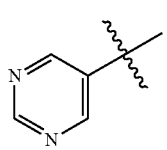
ix-b

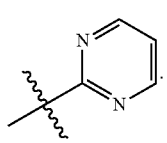
ix-c

In certain embodiments, $R^N$ is hydrogen. Or, $R^N$ is unsubstituted C1-4 alkyl.

In one embodiment, $X^2$ is selected from —CH$_2$—, —CH$_2$—CH$_2$—, —(CH$_2$)$_3$—, —C(Me)$_2$-, —CH(Me)-, —C(Me)=CH—, —CH=CH—, —CH(Ph)-, —CH$_2$—CH(Me)-, —CH(Et)-, —CH(i-Pr)-, or cyclopropylene.

In another embodiment, p is 1 and $X_1$ is O.

In another embodiment, p is 1, and $X_1$ is S.

In another embodiment, p is 1, and $X_1$ is NR$^N$. Preferably, R$^N$ is hydrogen.

In certain embodiments of the present invention, T is naphthyl, tetralinyl, decalinyl, or 6,7,8,9-tetrahydro-5H-benzo[7]annulenyl, optionally substituted with up to 3 substituents independently selected from halo, cyano, trifluoromethyl, OH, C$_{1-4}$ alkyl, C$_{2-4}$ alkenyl, C$_{1-4}$ alkoxy, trifluoromethoxy, C(O)NH$_2$, NH$_2$, NH(C$_{1-4}$ alkyl), N(C$_{1-4}$ alkyl)$_2$, NHC(O) C$_{1-4}$ alkyl, 1-pyrrolidinyl, 1-piperidinyl, 1-morpholinyl, or C(O)C$_{1-4}$ alkyl.

Or, T is optionally substituted napthyl.

In another embodiment, T is selected from:

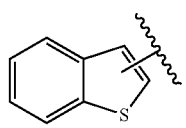
p

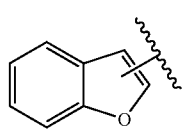
q

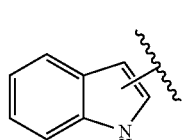
r

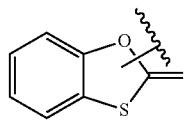
s

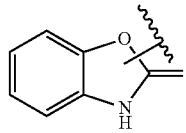
s

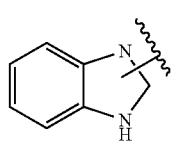
t

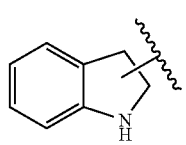
u

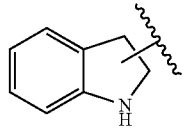
v

-continued

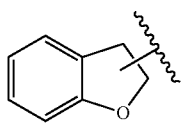 w

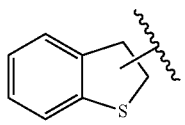 or

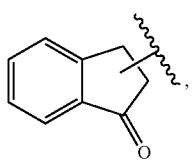, wherein T is optionally substituted with up to three substituents independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In another embodiment, T is a 5-membered ring having up to 4 heteroatoms selected from O, S, N, or NH, optionally fused to a phenyl ring, wherein said phenyl ring is unsubstituted or substituted with up to 4 substituents selected from $R^1$ or $R^2$. Preferred 5-membered rings in such embodiments of T include formula i through xxiii defined above for ring Z that are capable of being fused to a phenyl ring.

In other embodiments, T is selected from:

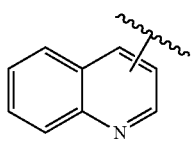 y

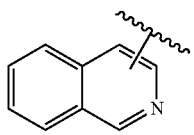 z

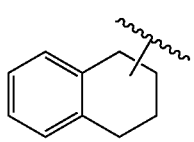 aa

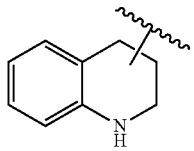 ac

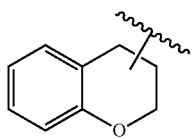 ad or

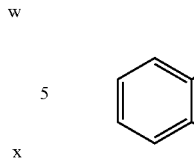 ae wherein T is optionally substituted with up to three substituents independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment, the phenylene ring attached to the sulfonyl group is optionally substituted with up two substituents selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment, the present invention provides compounds wherein:
a. Z is thiazol-2-yl;
b. $R^N$ is hydrogen;
c. $X_2$ is absent or is $C_{1-4}$ alkylene optionally substituted with phenyl;
d. $X_1$ is absent or is O or S;
e. T is selected from quinolin-4-yl, benzofuran-2-yl, benzothiophen-3-yl, phenyl, tetralin-2-yl, tetralin-6-yl, phenyl, indol-2-yl, chroman-3-yl, quinolin-3-yl, benzo[1,3]oxathiol-2-one-6-yl, benzothiophen-2-yl, 1,2,3,4-tetrazol-5-yl, furan-5-yl, quinolin-5-yl, benzothiazol-5-yl, or 5,6,7,8-tetrahydroquinolin-2-yl, optionally substituted with up to three substituents selected from trifluoromethyl, halo, cyano, C1-4 alkoxy, piperidinylsulfonyl, C1-4 alkyl, phenyl optionally substituted with up to three halo, cyano, C1-4 alkyl, or C1-4 alkoxy.

In one embodiment, the present invention provides compounds wherein:
a. Z is thiazol-2-yl;
b. $R^N$ is hydrogen;
c. $X_2$ is absent or is $C_{1-4}$ alkylene optionally substituted with phenyl;
d. $X_1$ is absent or is O or S;
e. T is selected from 8-trifluoromethyl-quinolin-4-yl, benzofuran-2-yl, benzothiophen-3-yl, 3-fluoro-4-chloro-phenyl, 8-methoxy-tetralin-2-yl, tetralin-6-yl, 4-piperidinylsulfonylphenyl, 2,4-dichlorophenyl, 5-fluoroindol-2-yl, 4,6-dichloroindol-2-yl, chroman-3-yl, 2-methyl-6-fluoro-quinolin-4-yl, 2,7-dimethyl-quinolin-3-yl, 4-trifluoromethylphenyl, 2-fluoro-4-chloro-phenyl, benzo[1,3]oxathiol-2-one-6-yl, 5-chloro-benzothiophen-2-yl, 1-phenyl-1,2,3,4-tetrazol-5-yl, 2-(3',5'-dichlorophenyloxy)-furan-5-yl, 5-fluoro-benzothiophen-2-yl, quinolin-5-yl, 2-methyl-quinolin-4-yl, 2-methyl-benzothiazol-5-yl, or 4-cyano-5,6,7,8-tetrahydroquinolin-2-yl.

In one embodiment, the present invention provides compounds wherein:
a. Z is thiazol-2-yl or 1,2,4-thiadiazol-5-yl;
b. $R^N$ is hydrogen;
c. $X_2$ is absent or $C_{1-4}$ alkylene;
d. $X_1$ is absent or O;
e. T is selected from phenyl, benzo[1,3]oxathiol-2-one-5-yl, benzothiophen-2-yl, benzofuran-2-yl, quinolin-4-yl, indolin-2-yl, 1,2,3,4-tetrazol-5-yl, 5,6,7,8-tetrahydroquinolin-2-yl, indol-2-yl, norbornyl, furan-2-yl, 2-naphthyl, benzothiophen-3-yl, phenyl, quinolin-7-yl, tetralin-6-yl, benzothiophen-3-yl, tetralin-2-yl, chroman-3-yl, benzo[1,2,5]oxadiazol-5-yl, quinolin-5-yl, benzothiazol-5-yl, indol-5-yl, quinolin-3-yl, 1,2,3,4-tetrahydroisoquinolin-3-yl, quinolin-2-yl, benzo-[1,3]-dioxolan-5-yl, or benzo-[1,3]dixolan-4-yl, wherein T is optionally substituted with up to three substituents independently selected from trifluoromethyl, trifluoromethoxy, halo, cyano, C1-4 alkoxy, C1-4 alkyl, acyl, N(C1-4alkyl)2, phenyloxy or phenyl optionally substituted with up to three halo, cyano, C1-4 alkyl, or C1-4 alkoxy.

In one embodiment, the present invention provides compounds wherein:
a. Z is thiazol-2-yl or 1,2,4-thiadiazol-5-yl;
b. $R^N$ is hydrogen;
c. $X_2$ is absent or $C_{1-4}$ alkylene;
d. $X_1$ is absent or O;
e. T is selected from 4-trifluoromethylphenyl, 3-fluoro-4-chlorophenyl, 2-chloro-4-cyanophenyl, 2,3-dichlorophenyl, benzo[1,3]oxathiol-2-one-5-yl, 5-fluorobenzothiophen-2-yl, 3,4-dichlorophenyl, benzofuran-2-yl, 8-trifluoromethyl-quinolin-4-yl, 2-chloro-4-cyanophenyl, 1-acyl-indolin-2-yl, 1-phenyl-1,2,3,4-tetrazol-5-yl, 2-fluoro-3-chlorophenyl, 2-methyl-4-fluorophenyl, 2,3-difluorophenyl, 3-cyano-5,6,7,8-tetrahydroquinolin-2-yl, 2-chlorophenyl, 5-fluoro-indol-2-yl, 2,4-dichlorophenyl, 3,5-dichlorophenyl, 3-chlorophenyl, 5-bromo-indol-2-yl, 4-chlorophenyl, 1-norbornyl, 2-methoxy-4-chlorophenyl, 5-(3',5'-dichlorophenyloxy)-furan-2-yl, 2-naphthyl, benzothiophen-3-yl, 2-fluoro-3-trifluoromethylphenyl, 2-methyl-4-chlorophenyl, quinolin-7-yl, 2-fluoro-6-chlorophenyl, 2-methyl-6-fluoro-quinolin-4-yl, 5-methoxy-benzofuran-2-yl, phenyl, 3,4-difluorophenyl, 4,6-dichloroindol-2-yl, 2-trifluoromethoxyphenyl, 4-fluorophenyl, 5-chlorobenzothiophen-2-yl, 2-methyl-quinolin-4-yl, tetralin-6-yl, 2,6-dimethylphenyl, benzothiophen-3-yl, 8-methoxy-tetralin-2-yl, 2-methoxy-4-methylphenyl, chroman-3-yl, 3,4-dicyanophenyl, 2,6-dimethyl-4-cyanophenyl, benzo[1,2,5]oxadiazol-5-yl, 3-diethylaminophenyl, quinolin-5-yl, 2-methyl-benzothiazol-5-yl, 8-fluoro-quinolin-4-yl, 3-trifluoromethoxyphenyl, 2-chloro-3-trifluoromethylphenyl, 2-aminocarbonylphenyl, 2,3-dimethyl-indol-5-yl, 3-cyanophenyl, 7-dimethyl-quinolin-3-yl, 1-acyl-1,2,3,4-tetrahydroisoquinolin-3-yl, 4-methyl-quinolin-2-yl, benzo-[1,3]-dioxolan-5-yl, or 2,2-difluoro-benzo-[1,3]dixolan-4-yl.

In one embodiment, the present invention provides compounds wherein:
a. Z is thiazol-2-yl, oxazol-2-yl, 1,3,4-thiadiazol-2-yl, 1,2,4-thiadiazol-5-yl, wherein Z is optionally substituted with $CF_3$, C1-4 alkyl, or C1-4 alkyl substituted with phenyl having 0-3 halo substituents. Preferably, Z is thiazol-2-yl, 5-benzyl-thiazol-2-yl, 5-(4'-chlorobenzyl)-oxazol-2-yl, 5-trifluoromethyl-1,3,4-thiadiazol-2-yl, 5-(2'-chlorobenzyl)-1,3,4-thiadiazol-2-yl, 5-cyclopropyl-1,3,4-thiadiazol-2-yl, 3-ethyl-1,2,4-thiadiazol-2-yl, or 5-(2',3'-dichlorobenzyl)-thiazol-2-yl;
b. $R^N$ is hydrogen;
c. $X_2$ is $C_{1-3}$ alkylene;
d. $X_1$ is O or is absent; and
e. T is phenyl or 3-methyl-1,2,3,4-tetrahydro-isoquinolin-2-yl, wherein T has up to 2 substituents selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl. Preferably, T is 2,4-dichlorophenyl or 3-methyl-1,2,3,4-tetrahydro-isoquinolin-2-yl.

In one embodiment, the present invention provides compounds wherein:
a. Z is selected from thiazol-2-yl, 1,2,4-thiadiazol-5-yl, 2-pyrazol-3-yl, 1,3,4-thiadiazol-2-yl, 1,2,5-thiadiazol-4-yl, or 1,2,3,4-thiatriazol-5-yl, optionally substituted with up to two substituents selected from C1-4 alkyl, phenyl, or halo. Preferred Z includes 3-isopropyl-1,2,4-thiadiazol-5-yl, thiazol-2-yl, 2,5-dimethyl-1,2-pyrazol-3-yl, 5-phenyl-1,3,4-thiadiazol-2-yl, 1,2,5-thiadiazol-4-yl, 5-ethyl-1,3,4-thiadiazol-2-yl, 2-methyl-1,2-pyrazol-3-yl, 1,2,3,4-thiatriazol-5-yl;
b. $R^N$ is hydrogen;
c. $X_2$ is absent or is $C_{1-3}$ alkylene;
d. $X_1$ is absent or is O; and
e. T is selected from quinolinyl, preferably, quinolin-7-yl, dihalo-substituted phenyl, preferably dichlorophenyl, or naphthyl, preferably, 1-naphthyl.

In one embodiment, the present invention provides compounds wherein:
a. Z is selected from thiazol-2-yl, 1,3,4-thiadiazol-2-yl, pyrimidin-2-yl, pyrimidin-2-yl, 1,2,4-triazol-3-yl, or 3-t-butyl-1,2-pyrazol-5-yl, optionally substituted with C1-4 alkyl, or benzyl;
b. $R^N$ is hydrogen;
c. $X_2$ is absent or C1-4 alkylene or alkenylene;
d. $X_1$ is absent or O;
e. T is selected from phenyl, naphthyl, 2,2,-difluoro-benzo[1,3]dioxol-5-yl, norbornyl, indol-2-yl, benzothiophen-3-yl, benzo[1,3]oxathiol-2-one-5-yl, benzo[1,2,5]oxadiazol-5-yl, quinolinyl, or 1,2,3,4-tetralin-5-yl, optionally substituted with up to 3 substituents selected from halo, cyano, trifluoromethyl, $C_{1-4}$ alkyl, $C_{2-4}$ alkenyl, $C_{1-4}$ alkoxy, trifluoromethoxy, $C(O)NH_2$, $NH(C_{1-4}$ alkyl), $N(C_{1-4}$ alkyl$)_2$, $NHC(O)C_{1-4}$ alkyl, $C(O)C_{1-4}$ alkyl, or 1-piperidyl.

In one embodiment, the present invention provides compounds wherein:
a. Z is selected from thiazol-2-yl, 5-methyl-1,3,4-thiadiazol-2-yl, pyrimidin-2-yl, 4-methyl-pyrimidin-2-yl, 1,2,4-triazol-3-yl, or 1-benzyl-3-t-butyl-1,2-pyrazol-5-yl;
b. $R^N$ is hydrogen;
c. $X_2$ is absent or is $C_{1-4}$ straight or branched alkylene or alkenylene, optionally substituted with phenyl;
d. $X_1$ is absent or is O; and
e. T is selected from phenyl, 2,2,-difluoro-benzo[1,3]dioxol-5-yl, norbornyl, indol-2-yl, benzothiophen-3-yl, benzo[1,3]oxathiol-2-one-5-yl, benzo[1,2,5]oxadiazol-5-yl, quinolinyl, or 1,2,3,4-tetralin-5-yl, optionally substituted with up to 3 substituents selected from halo, cyano, trifluoromethyl, $C_{1-4}$ alkyl, $C_{2-4}$ alkenyl, $C_{1-4}$ alkoxy, trifluoromethoxy, $C(O)NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment, the present invention provides compounds wherein:
a. Z is selected from thiazol-2-yl, 5-methyl-1,3,4-thiadiazol-2-yl, pyrimidin-2-yl, 4-methyl-pyrimidin-2-yl, or 1,2,4-triazol-3-yl;
b. $R^N$ is hydrogen;
c. $X_2$ is absent; or $X_2$ is C1-4 straight or branched alkyl;
d. $X_1$ is absent; or $X_1$ is O;
e. T is 2,6-dichlorophenyl, 3-diethylaminophenyl, 2-methyl, 4-fluorophenyl, 2-cyanophenyl, 2-ethoxyphenyl, 2-chlorophenyl, 4-cyanophenyl, 1-naphthyl, 5-methoxybenzofuran-2-yl, 6-chlorobenzofuran-2-yl, 2-methyl-5,7-dichloro-quinolin-8-yl, 2-piperidinyl-phenyl, 1,2,3,4-tetralin-6-yl, 2-dimethyl-4,7-dimethyl-1,2,3,4-tetrahydroquinolin-1-yl, 2,6-difluorophenyl, 3-fluorophenyl, 2-fluoro-3-chlorophenyl, 2,5-dimethylphenyl, 2,4-dichlorophenyl, 4-chlorophenyl, 2-fluoro-6-chlorophenyl, 3,5,-dimethyl-4-chlorophenyl, 3,5-difluorophenyl, 2,3-dichlorophenyl, 2-fluoro-3-methyl-6-chlorophenyl, isoquinolin-5-yl, 2,6-dimethoxyphenyl, 4-ethoxyphenyl, 5-fluoro-indol-2-yl, 2-methoxy-4-methylphenyl, 3-fluoro-5-trifluoromethylphenyl, 3-fluorophenyl, 1-methyl-5-chloro-indol-2-yl, 2,3-difluorophenyl, 8-methyl-1,2,3,4-tetrahydroquinolin-1-yl, 1,2,3,4-tetrahydroquinolin-1-yl, 2-trifluoromethoxyphenyl, 7-trifluoromethyl-1,2,3,4-tetrahydroquinolin-1-yl, or 2-chloro-3,5-difluorophenyl.

In certain embodiments, the present invention provides compounds of formula IIA-i, formula IIB-i, formula IIC-i, and formula IID-i:

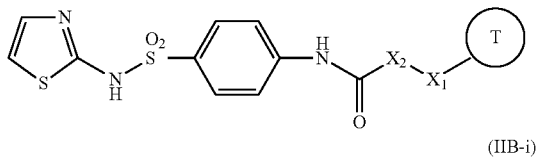

(IIA-i)

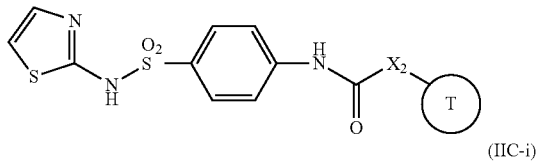

(IIB-i)

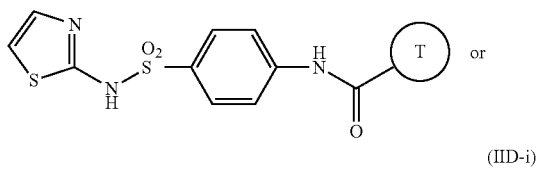

(IIC-i)

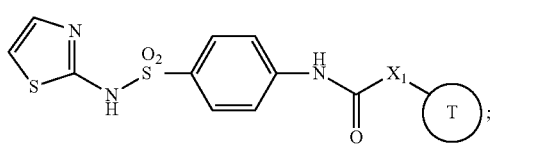

(IID-i)

wherein T is $X_2$, $X_1$, and T are as defined above.

According to another embodiment, the present invention provides a compound of formula III:

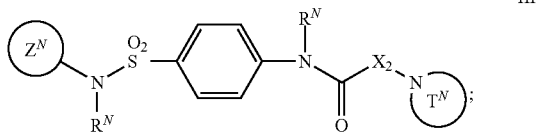

III or a pharmaceutically acceptable salt thereof, wherein:

$Z^N$ is a 5-7 membered monocyclic, unsaturated or aromatic, heterocyclic ring, having up to 4 heteroatoms independently selected from O, N, NH, S, SO, or $SO_2$;

each $R^N$ is independently hydrogen or C1-4 aliphatic optionally substituted with up to two substituents selected from $R^1$, $R^4$, or $R^5$;

$X_2$ is $C_{1-3}$ aliphatic, optionally substituted with up to 2 substituents independently selected from $R^1$, $R^4$, or $R^5$;

$T^N$ is a 3-14 membered monocyclic, bicyclic, or tricyclic, saturated, unsaturated, or aromatic ring system having up to 5 heteroatoms independently selected from O, N, NH, S, SO, or $SO_2$;

wherein $Z^N$ and $T^N$ each is independently and optionally substituted with up to 4 substituents independently selected from $R^1$, $R^2$, $R^3$, $R^4$, or $R^5$;

wherein the phenylene ring attached to the sulfonyl is optionally substituted with up to 3 substituents selected from $R^1$ and $R^2$;

$R^1$ is oxo, $=NN(R^6)_2$, $=NN(R^7)_2$, $=NN(R^6R^7)$, $R^6$ or $(CH_2)_n$—Y;

n is 0, 1 or 2;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ is optionally substituted with up to 2 substituents independently selected from $R^1$, $R^4$, or $R^5$;

$R^3$ is a cycloaliphatic, aryl, heterocyclic, or heteroaryl ring is optionally substituted with up to 3 substituents, independently selected from $R^1$, $R^2$, $R^4$ or $R^5$;

$R^4$ is ORS, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, SRS, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;

$R^5$ is a cycloaliphatic, aryl, heterocyclic, or heteroaryl ring optionally is optionally substituted with up to 3 $R^1$ substituents;

$R^6$ is H or aliphatic, wherein $R^6$ is optionally substituted with a $R^7$ substituent;

$R^7$ is a cycloaliphatic, aryl, heterocyclic, or heteroaryl ring and each $R^7$ is optionally substituted with up to 2 substituents independently chosen from H, aliphatic, or $(CH_2)_n$—Z';

Z' is selected from halo, CN, $NO_2$, C(halo)$_3$, CH(halo)$_2$, $CH_2$(halo), —OC(halo)$_3$, —OCH(halo)$_2$, —$OCH_2$(halo), OH, S-aliphatic, S(O)-aliphatic, $SO_2$-aliphatic, $NH_2$, NH-aliphatic, N(aliphatic)$_2$, N(aliphatic)$R^8$, COOH, C(O)O(-aliphatic), or O-aliphatic; and $R^8$ is an amino protecting group.

In certain embodiments of formula III, the following compounds are excluded:

a) when both $R^N$ are hydrogen, then $T^N$ is not:
  (i) 1,3-dione-isoindol-2-yl, 1,3-dione-isoindol-2-yl substituted with up to 4 halo substituents;

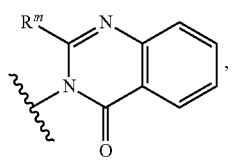 (ii)
wherein R$^m$ is methyl or phenyl optionally substituted with up to 4 halo;
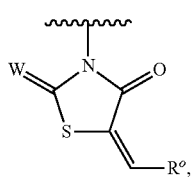 (iii)
wherein W is O or S, and R$^o$ is phenyl or substituted phenyl,
(iv) 4-methyl-1,4-dihydro-quinoxalin-1-yl,
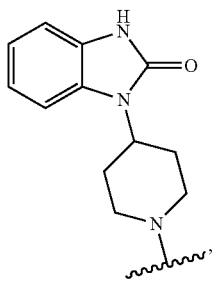 (v)
(b) when both R$^N$ are hydrogen, then the following compounds in Table C are excluded:

TABLE C-continued
| $Z^N$ | $X_2$, together with $T^N$ |
|---|---|
|  | 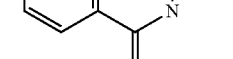 |
|  | 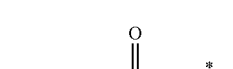 |
|  | 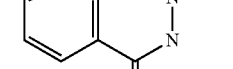 |
| 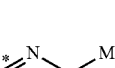 | 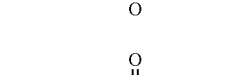 |
|  | 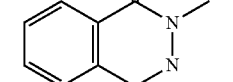 |
| 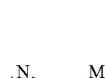 | 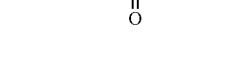 |
|  | 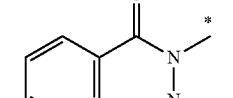 |
|  | 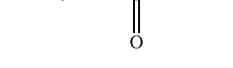 |
TABLE C-continued
| $Z^N$ | $X_2$, together with $T^N$ |
|---|---|
|  | 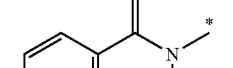 |
|  | 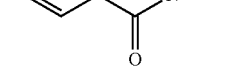 |
|  | 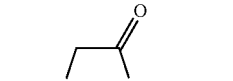 |
|  | 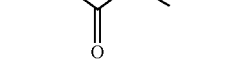 |

TABLE C-continued

| $Z^N$ | $X_2$, together with $T^N$ |
|---|---|

TABLE C-continued

| $Z^N$ | $X_2$, together with $T^N$ |
|---|---|
| thiazole* | N-ethyl-phenothiazine* |
| 2,4-dimethylpyrimidine* | N-ethyl-phenothiazine* |
| 3,4-dimethylisoxazole* | N-ethyl-phenothiazine* | wherein the asterisk denotes the point of attachment of a carbon atom to the rest of the molecule.

In certain embodiments, $Z^N$ is selected from:

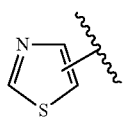

i

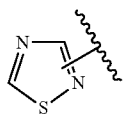

ii

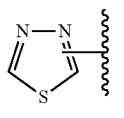

iii

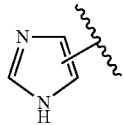

iv

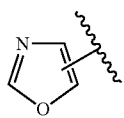

v

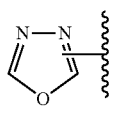

vi

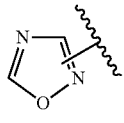

vii

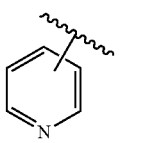

viii

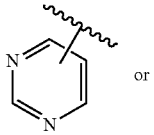 or ix

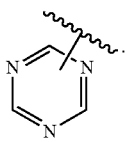.

x

In other embodiments, $Z^N$ is selected from:

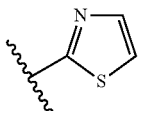

i-a

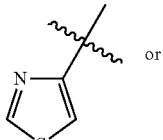 or i-b

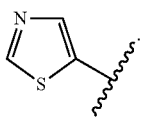.

i-c

Preferably, $Z^N$ is formula I-a.

In certain embodiments, $Z^N$ is selected from:

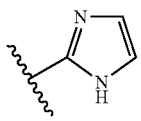

iv-a

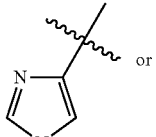 or iv-b

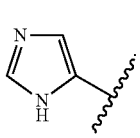

iv-c

In certain other embodiments, $Z^N$ is selected from:

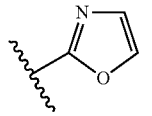

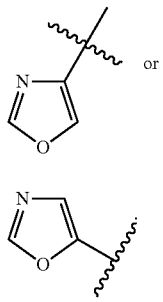

or

In yet other embodiments, $Z^N$ is selected from:

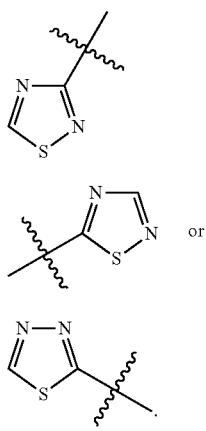

Or, $Z^N$ is selected from:

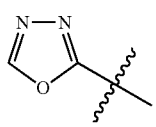

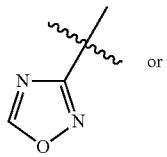

or

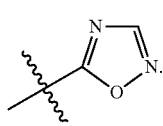

In certain embodiments, $Z^N$ is selected from:

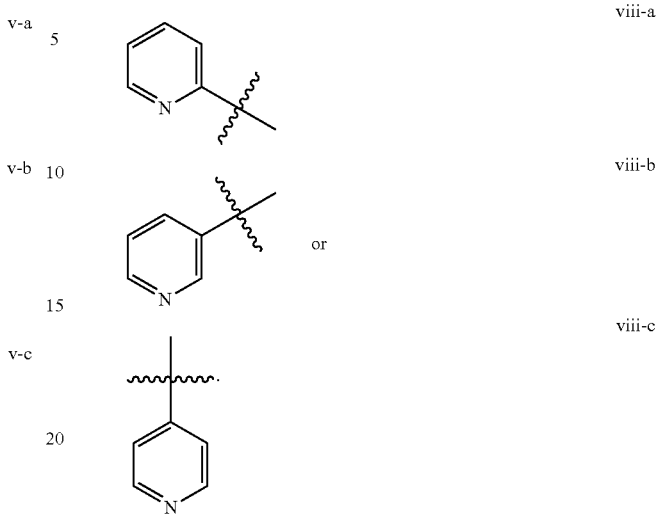

In other embodiments, $Z^N$ is selected from:

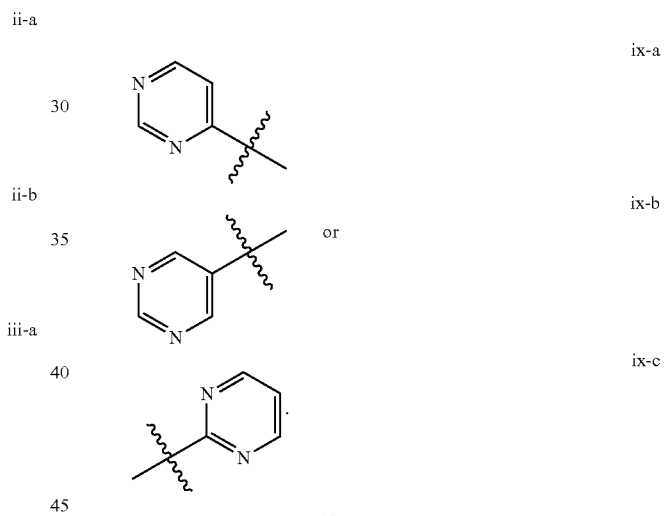

In one embodiment, $Z^N$ is as defined above for Z.

In certain embodiments, $R^N$ is hydrogen. Or, $R^N$ is unsubstituted C1-4 alkyl.

In some embodiments, $X_2$ is selected from —CH$_2$—, —CH$_2$—CH$_2$—, —(CH$_2$)$_3$—, —CH(Me)-, —C(Me)=CH—, —CH=CH—, —CH(Ph)-, —CH$_2$—CH(Me)-, —CH(Et)-, —CH(i-Pr)-, or cyclopropylene.

Preferably, $X_2$ is selected from —CH$_2$—, —CH(Me)-, —CH$_2$—CH$_2$—, or —(CH$_2$)$_3$—. Or, $X_2$ is —CH$_2$—.

In certain embodiments, $T^N$ is an optionally substituted, saturated, unsaturated, or aromatic 5-6 membered monocyclic ring. Preferably $T^N$ is a 5-membered ring with up to 3 heteroatoms, preferably two heteroatoms. Or, $T^N$ is a 6-membered ring with up to 2 heteroatoms, preferably 1 heteroatom. In certain preferred embodiments, $T^N$ has a second heteroatom selected from O, S, N, or NH.

In other embodiments, $T^N$ is an optionally substituted, saturated, unsaturated, or aromatic 8-12 membered bicyclic ring.

In other embodiments, $T^N$ is selected from 1-pyrrolyl, 2,3-dihydro-1H-pyrrol-1-yl, 1-pyrazolyl, 1-imidazolyl, 1-pyrrolidinyl, 1,2,3,4-tetrahydropyrid-1-yl, 1,2,3,6-tetrahydropyrid-1-yl, 1-piperidinyl, 1-piperazinyl, 1-morpholinyl, 1-azepinyl, 1-azepanyl, 1-indolyl, 1-indolinyl, 1,2,3,4-tetrahydroquinolin-1-yl, 1,2,3,4-tetrahydroisoquinolin-2-yl, wherein said ring is optionally substituted with up to 3 substituents. Preferably, $T^N$ is fused to a phenyl ring, wherein said phenyl ring is optionally substituted with up to three substituents.

According to another embodiment, $T^N$ is an optionally substituted ring selected from:

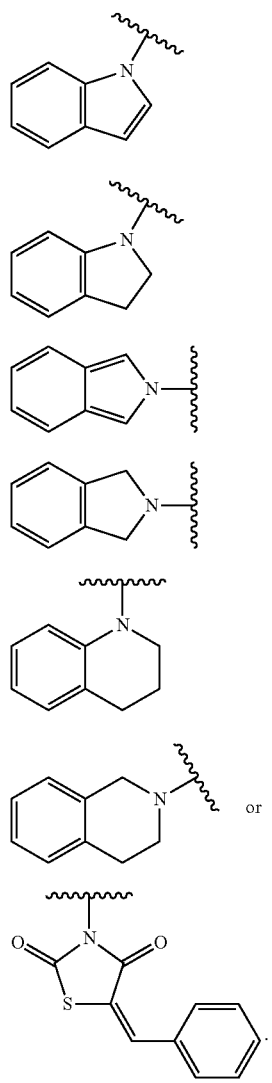

According to one embodiment, $T^N$ is formula i or ii above, optionally substituted as provided above. Or, $T^N$ is formula v or vi above, optionally substituted as provided above. Or, $T^N$ is formula vii, optionally substituted as provided above.

According to another embodiment, $T^N$ is an optionally substituted ring selected from:

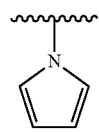

viii

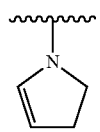

ix

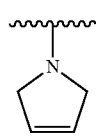

x

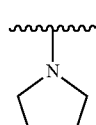

xi

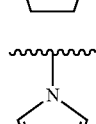

xii

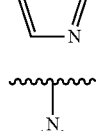

xiii

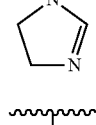

xiv

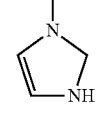

xv

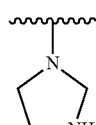

xvi

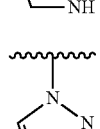

xvii

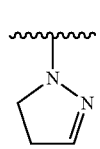

xviii

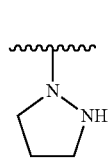

xix

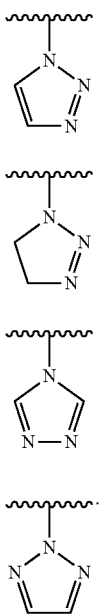

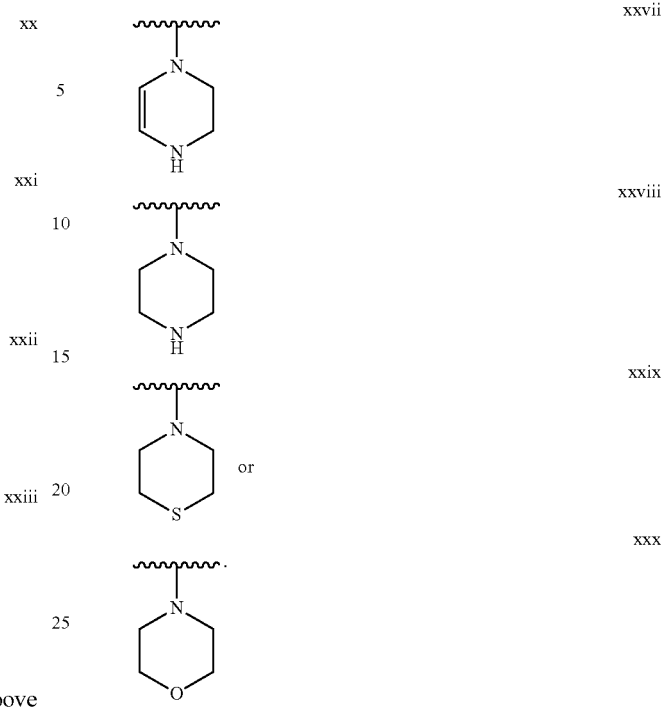

According to another embodiment, $T^N$ is any of the above rings viii to xxiii, optionally fused to an optionally substituted phenyl ring.

According to another embodiment, $T^N$ is any of the above rings viii to xxiii, optionally fused to an optionally substituted 6-membered aromatic heterocyclic ring having up to 3 nitrogen atoms. Preferred such 6-membered rings include pyridyl, pyrimidinyl, pyrazyl, or pyridazinyl.

According to another embodiment, $T^N$ is an optionally substituted ring selected from:

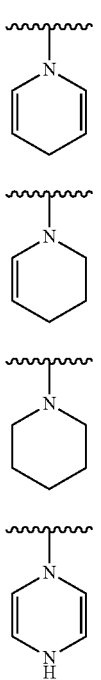

According to another embodiment, $T^N$ is any of the above rings xxiii to xxx, optionally fused to an optionally substituted phenyl ring.

According to another embodiment, $T^N$ is any of the above rings xxiii to xxx, optionally fused to an optionally substituted 6-membered aromatic heterocyclic ring having up to 3 nitrogen atoms. Preferred such 6-membered rings include pyridyl, pyrimidinyl, pyrazyl, or pyridazinyl.

Preferred substituents on $T^N$ are independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment, the phenylene ring attached to the sulfonyl group is optionally substituted with up two substituents selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment, the present invention provides compounds wherein:
a. $Z^N$ is thiazol-2-yl;
b. $R^N$ is hydrogen;
c. $X_2$ is $C_{1-4}$ alkylene, preferably, —$CH_2$— or —$CH_2$—$CH_2$—; and
d. $T^N$ is selected from indol-1-yl, 1,2,3,4-tetrahydroquinolin-1-yl, indolin-1-yl, 1,2,3,4-tetrahydroisoquinolin-2-yl, or 5-benzylidene-thiazolidin-2,4-dione-3-yl, optionally substituted with up to three substituents independently selected from $C_{1-4}$ alkyl, $C_{1-4}$ alkoxy, halo, trifluoromethyl, or cyano.

In one embodiment, the present invention provides compounds wherein:
a. $Z^N$ is thiazol-2-yl;
b. $R^N$ is hydrogen;
c. $X_2$ is $C_{1-4}$ alkylene, preferably, —$CH_2$— or —$CH_2$—$CH_2$—; and d. $T^N$ is selected from 4-fluoro-indol-1-yl, 6-chloro-indol-1-yl, 6-chloro-1,2,3,4-tetrahydroquinolin-1-yl, 5-ethyl-indol-1-yl, 4-fluoro-indol-1-yl, indol-1-yl, 5-methyl-indol-1-yl, 5-fluoro-indolin-1-yl, 7-chloro-indol-1-yl, 1,2,3,4-tetrahydroisoquinolin-2-yl, 6,7-dimethoxy-1,2,3,4-tetrahydroisoquinolin-2-yl, 2-methyl-indolin-1-yl, 5-chloro-indolin-1-yl, 6-methyl-1,2,3,4-tetrahydroquinolin-1-yl, 5,6-dimethoxy-indol-1-yl, 1-methyl-1,2,3,4-tetrahydroisoquinolin-2-yl, 6-methoxy-1,2,3,4-tetrahydroquinolin-1-yl, 5-fluoro-6-chloro-indol-1-yl, 4-methyl-indol-1-yl, 4-chloro-6-methoxy-indol-1-yl, 2-methyl-indol-1-yl, 2,3-dimethyl-indol-1-yl, or 5-(4'-fluoro-benzylidene)-3-methyl-thiazolidin-2,4-dione-3-yl.

In one embodiment, the present invention provides compounds wherein:
a. $Z^N$ is thiazol-2-yl;
b. $R^N$ is hydrogen;
c. $X_2$ is $C_{1-3}$ alkylene, preferably —$CH_2$—;
d. $T^N$ is selected from indol-1-yl, 1,2,3,4-tetrahydroisoquinolin-2-yl, 5-methyl-indol-1-yl, 6-chloroindolin-1-yl, 6-chloro-indol-1-yl, 6-fluoro-indol-1-yl, 6-chloro-1,2,3,4-tetrahydroquinolin-1-yl, 4-fluoro-indol-1-yl, 5-fluoro-indol-1-yl, 4,4-difluoropiperidinyl, 5-cyano-indol-1-yl, 5-ethyl-indol-1-yl, 1,2,3,4-tetrahydroquinolin-1-yl, 6-trifluoromethyl-indol-1-yl, 5,6-dimethoxy-indol-1-yl, 6-fluoro-1,2,3,4-tetrahydroquinolin-1-yl, 5-chloroindolin-1-yl, 1-methyl-1,2,3,4-tetrahydroisoquinolin-2-yl, 3-cyano-indol-1-yl, 3-methyl-indol-1-yl, 2-methyl-6-fluoro-quinolin-4-yl, 5-methoxy-benzofuran-2-yl, 4-methyl-indol-1-yl, 5,6-dichloro-indol-1-yl, 6-methylindol-1-yl, 4,6-dichloroindol-1-yl, 4-methoxy-indol-1-yl, 5-methoxy-indol-1-yl, 7-fluoro-indol-1-yl, 5-fluoro-indolin-1-yl, 5-(4'-fluoro-benzylidene)-1,3-thiolan-2,4-dione-3-yl, 2,3-dimethyl-indol-1-yl, 7-trifluoromethyl-1,2,3,4-tetrahydroquinolin-1-yl, 6-methoxy-1,2,3,4-tetrahydroquinolin-1-yl, 7-ethyl-indol-1-yl, or 2,7-dimethyl-1,2,3,4-tetrahydroquinolin-1-yl.

According to another embodiment, the present invention provides a compound of formula IV:

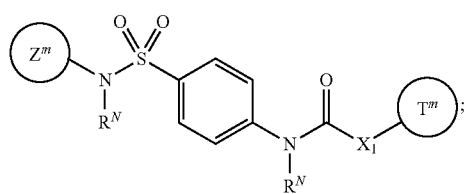

(IV)

or a pharmaceutically acceptable salt thereof;
wherein:
$Z^M$ is a 5-7 membered monocyclic, unsaturated or aromatic, heterocyclic ring, having up to 4 heteroatoms independently selected from O, N, NH, S, SO, or $SO_2$;
each $R^N$ is independently hydrogen or C1-4 aliphatic optionally substituted with up to two substituents selected from R1, R4, or R5;
$X_1$ is O, S, or $NR^N$;
$X_2$ is $C_{1-3}$ aliphatic, optionally substituted with up to 2 substituents independently selected from $R^1$, $R^4$, or $R^5$;
$T^M$ is a 8-14 membered aromatic or non-aromatic bicyclic or tricyclic ring, having 0-5 heteroatoms selected from O, S, N, NH, S(O) or $SO_2$;

wherein the phenylene ring attached to the sulfonyl is optionally substituted with up to 3 substituents selected from $R^1$ and $R^2$;
wherein $Z^M$ and $T^M$ each is independently and optionally substituted with up to 4 substituents independently selected from $R^1$, $R^2$, $R^3$, $R^4$, or $R^5$;
$R^1$ is oxo, =$NN(R^6)_2$, =$NN(R^7)_2$, =$NN(R^6R^7)$, $R^6$ or $(CH_2)_n$—Y;
n is 0, 1 or 2;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ is optionally substituted with up to 2 substituents independently selected from $R^1$, $R^4$, or $R^5$;
$R^3$ is a cycloaliphatic, aryl, heterocyclic, or heteroaryl ring is optionally substituted with up to 3 substituents, independently selected from $R^1$, $R^2$, $R^4$ or $R^5$;
$R^4$ is ORS, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, SRS, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^5C(O)R^6$, $NR^6C(O)R^5$, $NR^6C(O)R^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;
$R^5$ is a cycloaliphatic, aryl, heterocyclic, or heteroaryl ring is optionally substituted with up to 3 $R^1$ substituents;
$R^6$ is H or aliphatic, wherein $R^6$ is optionally substituted with a $R^7$ substituent;
$R^7$ is a cycloaliphatic, aryl, heterocyclic, or heteroaryl ring and each $R^7$ is optionally substituted with up to 2 substituents independently chosen from H, aliphatic, or $(CH_2)_n$—Z';
Z' is selected from halo, CN, $NO_2$, C(halo)$_3$, CH(halo)$_2$, $CH_2$(halo), —OC(halo)$_3$, —OCH(halo)$_2$, —OCH$_2$(halo), OH, S-aliphatic, S(O)-aliphatic, $SO_2$-aliphatic, $NH_2$, NH-aliphatic, N(aliphatic)$_2$, N(aliphatic)$R^8$, COOH, C(O)O(-aliphatic), or O-aliphatic; and
$R^8$ is an amino protecting group.

In one embodiment of formula IV, the following compounds are excluded:
(a) when Z is optionally substituted pyrimidinyl or thiazolyl, both $R^6$ are hydrogen, and X1 is NH, then T is not optionally substituted adamantyl;
(b) when Z is optionally substituted pyridyl, pyrimidinyl, isoxazolyl, or thiazolyl, both $R_6$ are hydrogen, and $X_1$ is NH, then T is not

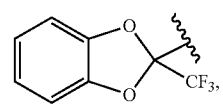

optionally substituted with up to two halo atoms;

(c) when both $R_6$ are hydrogen, and $X_1$ is NH, then T is not 1-naphthyl, 2-naphthyl, or 7-hydroxynaphth-1-yl;

(d) when Z is pyrimidinyl, 5-methylisoxazolyl, or pyridyl, both $R_6$ are hydrogen, and $X_1$ is NH, then T is not substituted purinyl; and (e) when Z is thiazol-2-yl, both $R_6$ are hydrogen, and $X_1$ is NH, then T is not substituted 3H-isobenzofuran-1-one-7-yl.

In one embodiment, $X^1$ is O. Or, $X^1$ is S. Or X1 is $NR^N$.

In one embodiment, each $R^N$ is independently hydrogen. Or, each $R^N$ is independently $C_{1-4}$ alkyl.

In certain embodiments, $Z^M$ is selected from:

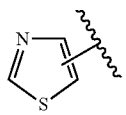
i

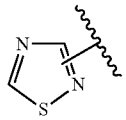
ii

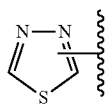
iii

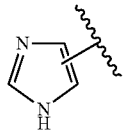
iv

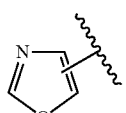
v

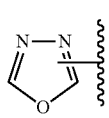
vi

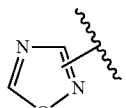
vii

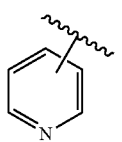
viii

ix or

-continued

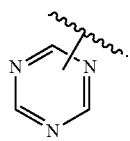
x

In other embodiments, $Z^M$ is selected from:

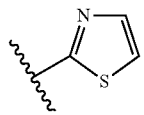
i-a

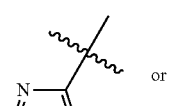
i-b
or

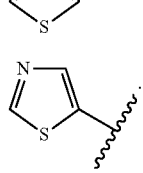
i-c

Preferably, $Z^M$ is formula I-a.

In other embodiments, $Z^M$ is selected from:

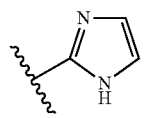
iv-a

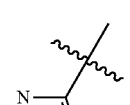
iv-b
or

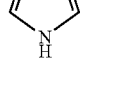
iv-c

In yet other embodiments, $Z^M$ is selected from:

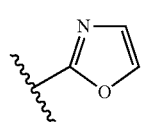
v-a

-continued

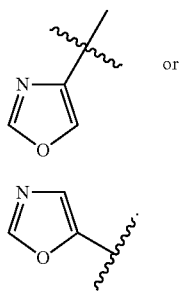

or

Or, $Z^M$ is selected from:

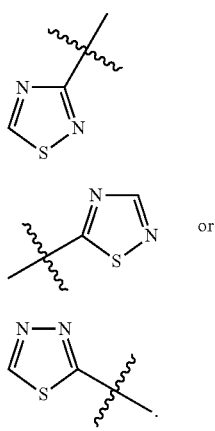

In certain embodiments, $Z^M$ is selected from:

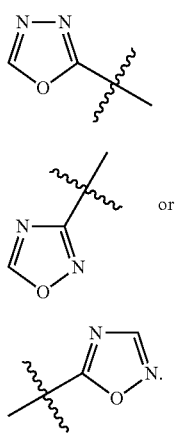

or

In certain other embodiments, $Z^M$ is selected from:

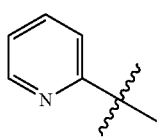

-continued

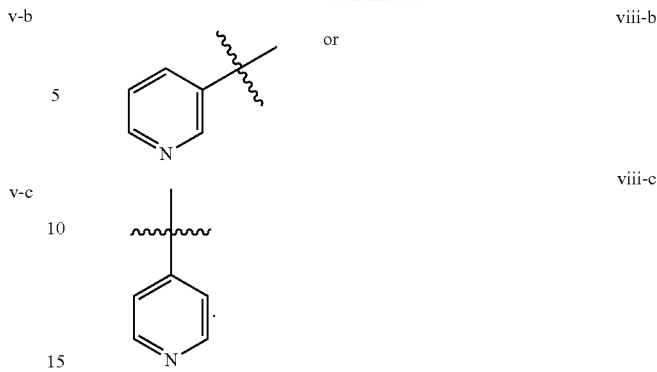

Or, $Z^M$ is selected from:

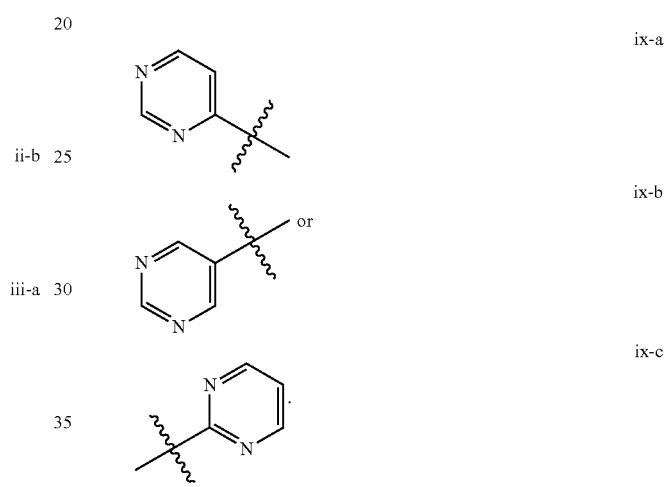

In one embodiments, $Z^M$ is as defined above for Z.

In certain embodiments, $R^N$ is hydrogen. Or, $R^N$ is unsubstituted $C_{1-4}$ alkyl.

In another embodiment, $Z^M$ is an optionally substituted 5-6 membered monocyclic ring.

In one embodiment, $X_1$ is NH. Or, $X_1$ is O.

In certain embodiments, $T^M$ is phenyl or naphthyl, optionally substituted with up to 3 substituents independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl)$_2$, $NHC(O)C_{1-4}$ alkyl, 1-pyrrolidinyl, 1-piperidinyl, 1-morpholinyl, or $C(O)C_{1-4}$ alkyl.

In other embodiments, $T^M$ is selected from:

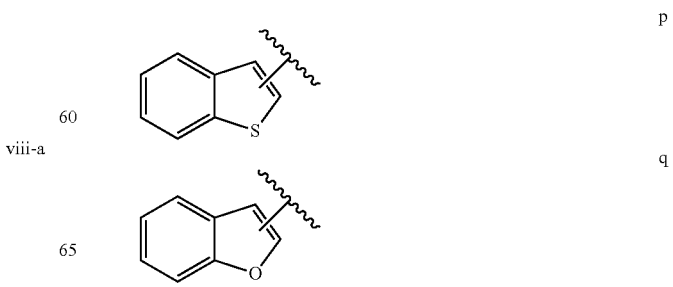

-continued

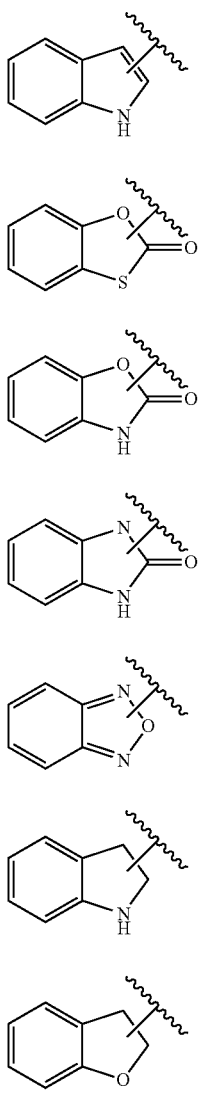

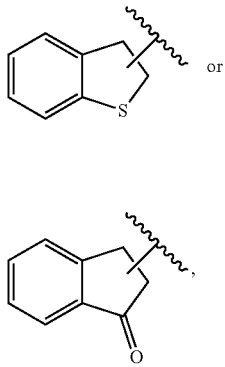

wherein $T^M$ is optionally substituted with up to three substituents independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

Or, $T^M$ is selected from:

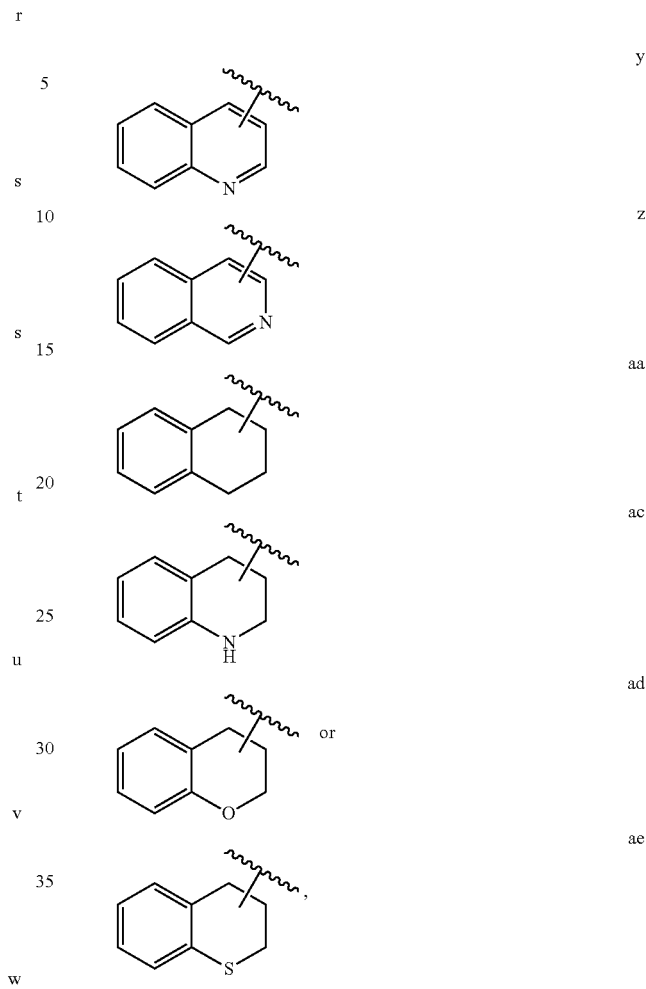

wherein $T^M$ is optionally substituted with up to three substituents independently selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

Or, $T^M$ is a tricyclic ring selected from: dibenzofuranyl, carbazolyl, acridinyl, phenazinyl, phenothiazinyl, or phenoxazinyl, fluorenyl, anthracenyl, or phenoxazinyl.

In certain embodiments, the substituents are independently selected from oxo, halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)C_{1-4}$ alkyl.

In one embodiment of formula (IIA-i):
a. $X_2$ is —$CH_2$—, —$CH_2$—$CH_2$— or —$CH_2CH_2CH_2$—;
b. $X_1$ is O or S; and
c. T is selected from 8-trifluoromethylquinolin-4-yl, 3-chloro-4-fluorophenyl, 1-naphthyl, 4-chloro-3-fluorophenyl, 6-fluoro-2-methyl-quinolin-4-yl, 2,4-dichlorophenyl, 4-chlorophenyl, 2,3-difluorophenyl, 2-chloro-4-methoxyphenyl, 4-trifluoromethylphenyl, 4-chloro-2-fluorophenyl, benzo[1,3]oxathiol-2-one-6-yl, 1-phenyl-tetrazol-5-yl, benzo[1,2,5]oxadiazol-5-yl, 3-cyano-5,6,7,8-tetrahydroquinolin-2-yl, quinolin-2-yl, isoquinolin-5-yl, quinolin-7-yl, or 3,5-dimethyl-4-cyanophenyl.

In one embodiment of formula (IIB-i):
a. $X_2$ is —$CH_2$—, —$CH_2$—$CH_2$—, —$CH_2CH_2CH_2$—, or —CH═CH—;
b. T is selected from benzo[b]thiophen-3-yl, 5-chlorobenzo[b]thiophen-2-yl, 5-chloro-2,3-dihydro-1H-indol-1-yl, 5-fluoro-2,3-dihydro-1H-indol-1-yl, 8-methoxy-1,2,3,4-tetrahydronaphth-2-yl, 1,2,3,4-tetrahydroquinolin-1-yl, 6,7-dimethoxy-1,2,3,4-tetrahydroisoquinolin-2-yl, 2,3-dihydro-1H-indol-1-yl, 1,2,3,4-tetrahydroisoquinolin-2-yl, 2-methyl-2,3-dihydro-1H-indol-1-yl, 6-methoxy-1,2,3,4-tetrahydroquinolin-1-yl, or 3-(t-butylamino carbonyl)-1,2,3,4-tetrahydro isoquinolin-2-yl.

In one embodiment of formula (IIC-i), T is selected from 4,6-dichloroindol-2-yl, benzofuran-2-yl, 1-naphthyl, 2-methyl-6-fluoroquinolin-4-yl, 5-fluoro-indol-2-yl, 5-chlorothiophen-2-yl, benzopyran-3-yl, 3-bromo-4-methylphenyl, 2-(furan-2-yl)-quinolin-4-yl, N-methyl-5-trifluoromethoxy-indol-2-yl, benzothiophen-3-yl, 5-fluoro-benzothiophen-2-yl, 2-methyl-quinolin-4-yl, 6-chloro-indol-2-yl, 6-bromo-indol-2-yl, 2-phenyl-5-methyl-1,2-oxazol-3-yl, N,6-dimethyl-indol-2-yl, or 5-3,5,dichlorophenoxyfuran-2-yl.

In one embodiment of formula (IIA-i):
a. $X_2$ is $CH_2$, —$CH_2CH_2$, or $CH_2CH_2CH_2$;
b. $X_1$ is O, S, or NH; and
c. T is phenyl optionally substituted with up to three substituents selected from halo, cyano, trifluoromethyl, OH, $C_{1-4}$ alkyl, $C_{1-4}$ alkoxy, trifluoromethoxy, $C(O)NH_2$, NH2, NH(C1-4 alkyl), N(C1-4 alkyl)2, NHC(O)C1-4 alkyl, 1-pyrrolidinyl, 1-piperidinyl, 1-morpholinyl, or $C(O)C_{1-4}$ alkyl.

In one embodiment, $X_1$ is O. Or, $X_1$ is S. Or, $X_1$ is NH.

In one embodiment of formula (IIIA-i):
a. $X_2$ is $CH_2$, $CH_2CH_2$, or $CH_2CH_2CH_2$;
b. $X_1$ is O, S, or NH; and
c. T is quinolin-4-yl, quinolin-5-yl, quinolin-6-yl, quinolin-7-yl, quinolin-8-yl, isoquinolin-1-yl, 1-naphthyl, 2-naphthyl, 5a,6,7,8,9,9a-hexahydro-dibenzofuran-2-yl, benzo[1,3]dioxol-6-yl, benzothiazol-5-yl, indan-1-one-4-yl, benzo[1,2,5]oxadiazol-4-yl, indol-4-yl, 4-methyl-chromen-2-one-7-yl, indol-5-yl, benzo-[1,2,3]-triazin-4-yl, or benzimidazol-2-yl, wherein T is optionally substituted with up to three substituents selected from halo, cyano, trifluoromethyl, OH, C1-4 alkyl, $C_{1-4}$ alkoxy, trifluoromethoxy, $C(O)NH_2$, NH2, NH($C_{1-4}$ alkyl), N(C1-4 alkyl)2, NHC(O)C1-4 alkyl, 1-pyrrolidinyl, 1-piperidinyl, 1-morpholinyl, or C(O) $C_{1-4}$ alkyl.

In another embodiment of formula (IIIA-i):
a. $X_2$ is $CH_2$, —$CH_2CH_2$, or $CH_2CH_2CH_2$;
b. $X_1$ is O, S, or NH; and
c. T is quinolin-5-yl, 2-naphthyl, 5a,6,7,8,9,9a-hexahydro-dibenzofuran-2-yl, benzo[1,3]dioxol-6-yl, 8-fluoro-quinolin-4-yl, 2-methyl-benzothiazol-5-yl, 7-trifluoromethyl-quinolin-4-yl, indan-1-one-4-yl, benzo[1,2,5]oxadiazol-4-yl, isoquinolin-1-yl, indol-4-yl, 5,7-dichloro-2-methylquinolin-8-yl, 7-chloro-quinolin-4-yl, 4-methyl-chromen-2-one-7-yl, quinolin-8-yl, 5-chloro-quinolin-8-yl, indol-5-yl, quinolin-6-yl, benzo-[1,2,3]-triazin-4-yl, 7-fluoro-quinolin-4-yl, benzimidazol-2-yl, or 2-methyl-quinolin-8-yl.

According to an alternate embodiment, the present invention provides a compound having formula (V):

$$T_1\text{-}L_{11}\text{-}A\text{-}L_{22}\text{-}Z;$$

wherein:
$T_1$ is a 8-14 membered aromatic or non-aromatic bicyclic or tricyclic ring, having 0-5 heteroatoms selected from O, S, N, NH, S(O) or $SO_2$;
$L_{11}$ is —$(X_1)_p$—$(CHR^1)_r$—$(X_2)$—Ry;
wherein:
p is 0 or 1;
r is 0 or 1;
$X_1$ is O, S, or NRx, wherein $R_x$ is H or $R_2$;
$X_2$ is $R^2$;
Ry is —C(O)—$NR^2$—;
$L_{22}$ is OC(O), C(O)O, S(O), $SO_2$, $N(R^5)SO_2$, $N(R^6)SO_2$, $SO_2N(R^5)$, $SO_2N(R^6)$, $C(O)N(R^5)$, $C(O)N(R^6)$, $NR^5C(O)$, $NR^6C(O)$, $C(NOR^5)R^6$, $C(NOR^5)R^6$, $C(NOR^6)R^5$, $C(NOR^6)$ $R^6$, $N(R^5)$, $N(R^6)$, $NR^5C(O)O$, $NR^6C(O)O$, $OC(O)NR^5$, $OC(O)NR^6$, $NR^5C(O)N(R^5)$, $NR^5C(O)N(R^6)$, $NR^6C(O)N$ $(R^5)$, $NR^6C(O)N(R^6)$, $NR^5SO_2N(R^5)$, $NR^5SO_2N(R^6)$, $NR^6SO_2N(R^5)$, $NR^6SO_2N(R^6)$, $N(OR^5)$, or $N(OR^6)$;
A is a 5-7 membered monocyclic aromatic ring, having 0-4 heteroatoms;
Z is 2-thiazolyl;
wherein each of $T_1$, A, and Z is optionally substituted with up to 4 suitable substituents independently selected from $R^1$, $R^2$, $R^3$, $R^4$, or $R^5$;
$R^1$ is oxo, ═$NN(R^6)_2$, ═$NN(R^7)_2$, ═$NN(R^6R^7)$, $R^6$ or $(CH_2)_n$—Y;
n is 0, 1 or 2;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ is optionally substituted with up to 2 substituents independently selected from $R^1$, $R^4$, or $R^5$;
$R^3$ is a cycloaliphatic, aryl, heterocyclic, or heteroaryl ring is optionally substituted with up to 3 substituents, independently selected from $R^1$, $R^2$, $R^4$ or $R^5$;
$R^4$ is $OR^5$, $OR^6$, $OC(O)R^6$, $OC(O)R^5$, $OC(O)OR^6$, $OC(O)$ $OR^5$, $OC(O)N(R^6)_2$, $OC(O)N(R^5)_2$, $OC(O)N(R^6R^5)$, $OP(O)$ $(OR^6)_2$, $OP(O)(OR^5)_2$, $OP(O)(OR^6)(OR^5)$, $SR^6$, $SR^5$, $S(O)$ $R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N$ $(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C$ $(O)R^5$, $NR^6C(O)OR^6$, $NR^5C(O)OR^6$, $NR^6C(O)OR^5$, $NR^5C$ $(O)OR^5$, $NR^6C(O)N(R^6)_2$, $NR^6C(O)NR^5R^6$, $NR^6C(O)$ $N(R^5)_2$, $NR^5C(O)N(R^6)_2$, $NR^5C(O)NR^5R^6$, $NR^5C(O)$ $N(R^5)_2$, $NR^6SO_2O$, $NR^6SO_2R^5$, $NR^5SO_2R^5$, $NR^6SO_2$ $N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)$ $R^6$, $P(O)(OR^6)N(R^6)_2$, $P(O)(OR^6)N(R^5R^6)$, $P(O)(OR^6)N$ $(R^5)_2$, $P(O)(OR^5)N(R^5R^6)$, $P(O)(OR^5)N(R^6)_2$, $P(O)(OR^5)N$ $(R^5)_2$, $P(O)(OR^6)_2$, $P(O)(OR^5)_2$, or $P(O)(OR^6)(OR^5)$;
$R^5$ is a cycloaliphatic, aryl, heterocyclic, or heteroaryl ring is optionally substituted with up to 3 $R^1$ substituents;
$R^6$ is H or aliphatic, wherein $R^6$ is optionally substituted with a $R^7$ substituent;
$R^7$ is a cycloaliphatic, aryl, heterocyclic, or heteroaryl ring and each $R^7$ is optionally substituted with up to 2 substituents independently chosen from H, aliphatic, or $(CH_2)_n$—Z;
Z is selected from halo, CN, $NO_2$, $CF_3$, $OCF_3$, OH, S-aliphatic, S(O)-aliphatic, $SO_2$-aliphatic, $NH_2$, N-aliphatic, N(aliphatic)$_2$, N(aliphatic)$R^8$, COOH, C(O)O(-aliphatic, or O-aliphatic; and
$R^8$ is an amino protecting group.

In one embodiment of formula V:

(i) when:

$L_{22}$ is $SO_2$, $N(R^5)SO_2$, $N(R^6)SO_2$, $SO_2N(R^5)$, $SO_2N(R^6)$, $C(O)N(R^5)$, $C(O)N(R^6)$, $NR^5C(O)$, or $NR^6C(O)$;

A is optionally substituted 5-6 membered monocyclic aromatic ring with 0-4 heteroatoms independently selected from N, S, or O;

$X_2$ is optionally substituted methylene or ethylene;

$T_1$ is an optionally substituted fused aromatic bicyclic ring system containing 0-4 heteroatoms independently selected from N, O, or S;

then:

r is 1;

(ii) when:

$L_{22}$ is $SO_2$, $N(R^5)SO_2$, $N(R^6)SO_2$, $SO_2N(R^5)$, $SO_2N(R^6)$, $C(O)N(R^5)$, $C(O)N(R^6)$, $NR^5C(O)$, or $NR^6C(O)$;

A is optionally substituted 5-6 membered monocyclic aromatic ring with 0-4 heteroatoms independently selected from N, S, or O;

p is 1;

$X_2$ is optionally substituted methylene, ethylene, or propylene;

$T_1$ is an optionally substituted fused aromatic bicyclic ring system containing 0-4 heteroatoms independently selected from N, O, or S;

then:

$X_1$ is not O or S;

(iii) when:

$L_{11}$ is —O—$CH_2$—C(O)—NH—;

A is phenylene;

$L_{22}$ is —$S(O)_2$—NH—;

then:

$T_1$ is not any of the following:

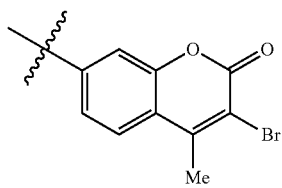

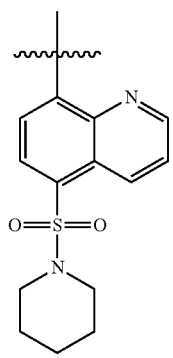

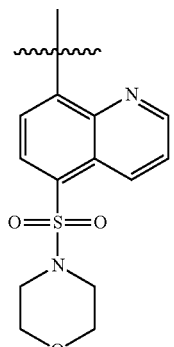

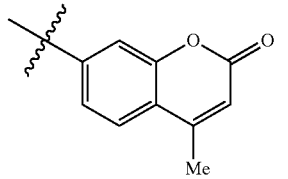

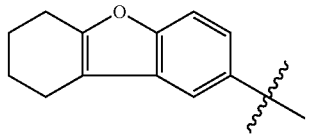

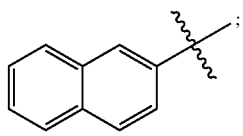

(iv) when:

$L_{11}$ is —S—$CH_2$—C(O)—NH—;

A is phenylene;

$L_{22}$ is —$S(O)_2$—NH—;

then:

$T_1$ is not any of the following:

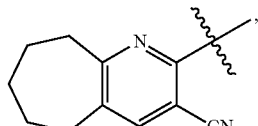

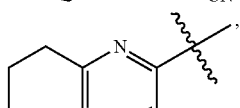

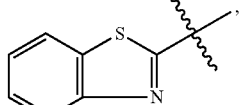

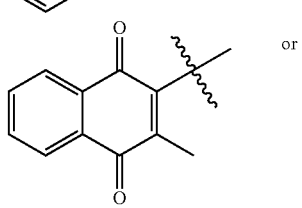 or

-continued

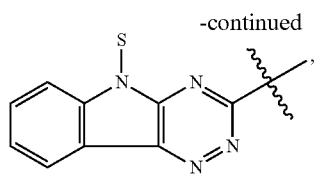

wherein B is hydrogen, methyl, n-propyl, isopropyl, allyl, benzyl, or phenylethyl.

Preferred embodiments of $L_{11}$, $L_{22}$, $R^1$, $R^2$, $R^3$, $R^4$, $R^5$, $R^6$, $R^7$, and $R^8$ in formula (V) are as described above for formula (I).

According to a preferred embodiment, Ry is —C(O)—$NR^2$—.

According to a preferred embodiment, $T_1$ is a 8-14 membered aromatic or non-aromatic bicyclic or tricyclic ring, having 0 heteroatoms. More preferably, $T_1$ is naphthyl. Or, $T_1$ is anthracenyl. According to an alternate more preferred embodiment, $T_1$ is tetralinyl or decalinyl.

According to a preferred embodiment, $T_1$ is a 8-14 membered aromatic or non-aromatic bicyclic or tricyclic ring, having up to 5 heteroatoms, preferably 1 or 2 heteroatoms. More preferably, $T_1$ is a 8-14 membered aromatic bicyclic ring, having up to 5 heteroatoms. Or, $T_1$ is a 8-14 membered non-aromatic bicyclic ring, having up to 5 heteroatoms. Exemplary bicyclic rings include quinolinyl, isoquinolinyl, benzofuranyl, benzothiophenyl, quinolinyl, isoquinolinyl, benzofuranyl, benzothiophenyl, indolizinyl, indolyl, isoindolyl, indolinyl, indazolyl, benzimidazolyl, benzothiazolyl, purinyl, cinnolinyl, phthalazine, quinazolinyl, quinaoxalinyl, naphthylirinyl, or pteridinyl.

According to another preferred embodiment, $T_1$ is a 8-14 membered non-aromatic tricyclic ring, having up to 5 heteroatoms. Or, $T_1$ is a 8-14 membered aromatic tricyclic ring, having up to 5 heteroatoms. Exemplary tricyclic rings include dibenzofuranyl, carbazolyl, acridinyl, phenazinyl, phenothiazinyl, phenoxazinyl, acridinyl, phenazinyl, phenothiazinyl, phenoxainyl, or carbazolyl.

According to a preferred embodiment of formula (II), A is phenyl.

According to another preferred embodiment of formula (II), A is a 5-6 membered monocyclic aromatic ring having 1-4 heteroatoms. More preferably, A is 5-6 membered monocyclic aromatic ring having 1-3 heteroatoms. Exemplary rings include thiazolyl, isothiazolyl, thiadiazolyl, thiaphenyl, furanyl, oxazolyl, isooxazolyl, oxadiazolyl, triazolyl, imidazolyl, pyrazolyl, pyridinyl, pyrimidinyl, pyrazinyl, pyridazinyl, triazinyl, or pyrrolyl.

FIG. 1 recites exemplary compounds of the present invention.

The compounds of the present invention may be readily prepared by methods well known in the art. An exemplary method for synthesizing certain compounds of formula (I) is illustrated below in the schemes.

Scheme 1:

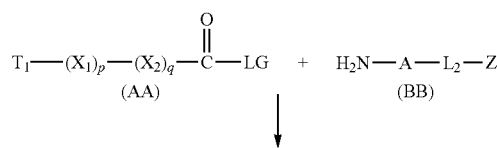

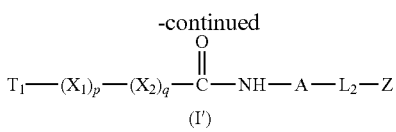

In Scheme 1 above, the synthesis of compounds of formula (I), wherein Ry is an amide (—C(O)—NH—) is illustrated. Compound of formula (AA) is coupled with an amine of formula (BB), wherein $T_1$, $X_1$, $X_2$, p, q, A, $L_2$, and Z have the meaning as defined in formula (I). LG is any suitable leaving group. Suitable leaving groups useful in the method of Scheme 1 are well known in the art. See, e.g., "March's Advanced Organic Chemistry", 5th Ed., Ed.: Smith, M. B. and March, J., John Wiley & Sons, New York: 2001.

Scheme A:

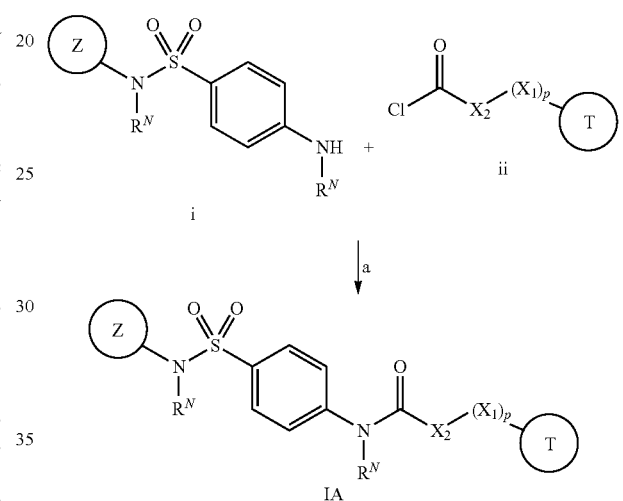

Reaction of i and ii (step a) in pyridine and DCM at room temperature (rt) yields IA.

Scheme B:

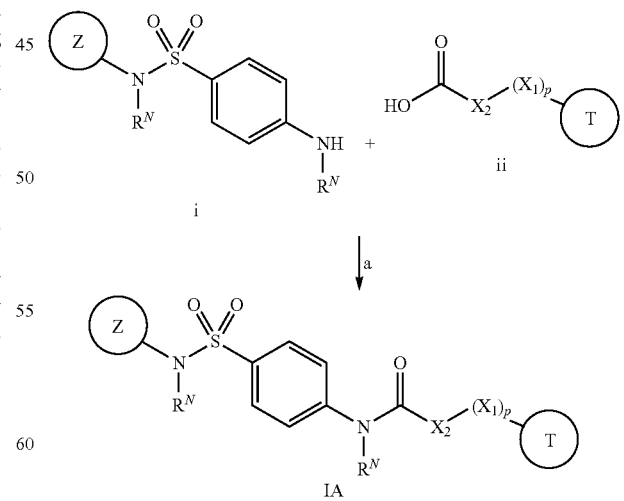

The coupling of i and ii (step a) using CDI and DMA under refluxing conditions, or HATU and TEA in pyridine under mircrowave conditions at 200° C., or BOP and TEA in $CH_3CN$ at rt yields IA.

In the schemes below, $R^6$ is as defined for $R^N$.

Scheme C: Scheme C provides an alternative synthesis for compounds of formula IA.

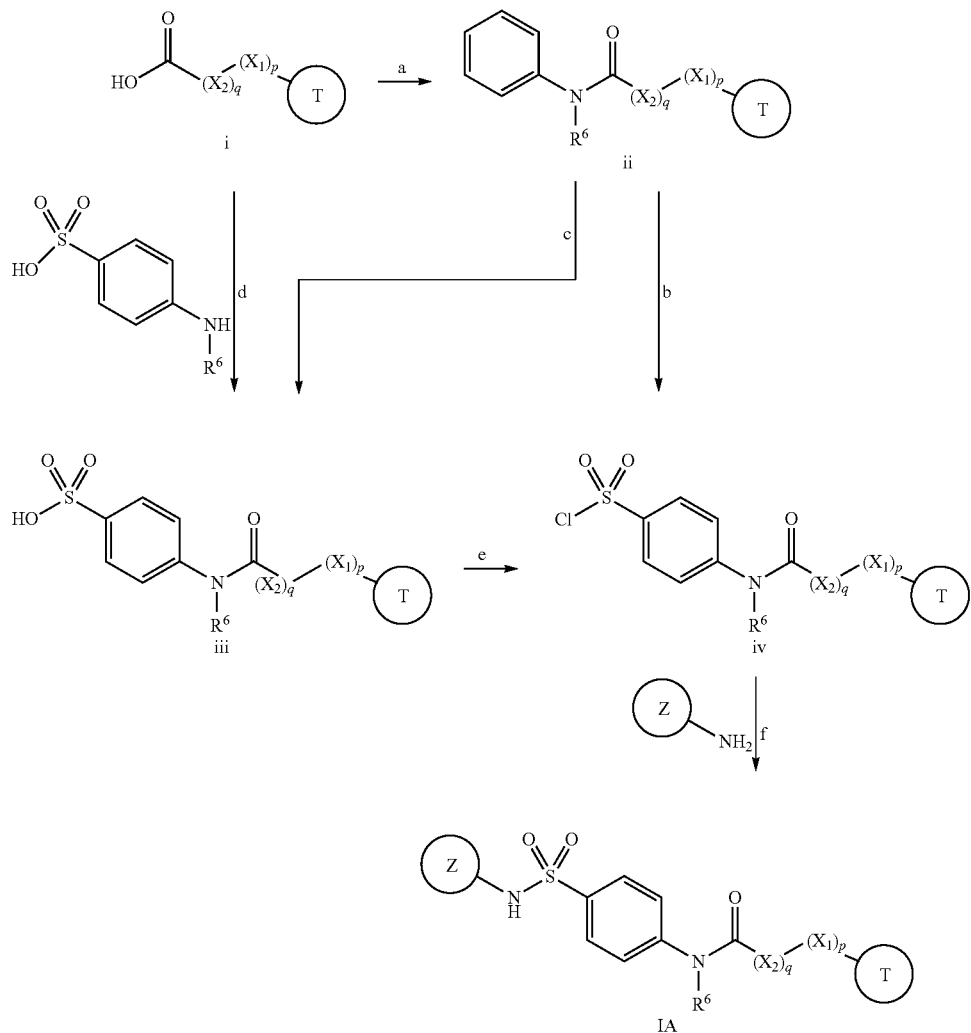

The coupling of i with anilines (step a) using CDI and DMA under refluxing conditions, or HATU and TEA in pyridine under mircrowave conditions at 200° C., or isobutyl chlorocarbonate and TEA in DCM yields ii. Reaction of intermediate ii with $ClSO_3H$ (step b) under refluxing conditions gives iv. Reaction of ii $ClSO_3H$ at 0° C. (step c) gives intermediate iii. Coupling of intermediate i with aminosulfonic acids (step d) using HATU and TEA in pyridine under mircrowave conditions at 200° C., or BOP and TEA in $CH_3CN$ at rt yields iii. Reaction of intermediate iii with $SO_2Cl$ (step e) yields iv. Alternatively, reaction of intermediate iii with cyanuric chloride and TEA in acetone under microwave conditions at 120° C. (step e) provides iv. Reaction of iv with various amines (step f) in pyridine at room temperature yields IA.

Scheme D: Scheme D provides useful intermediates for Schemes A and B.

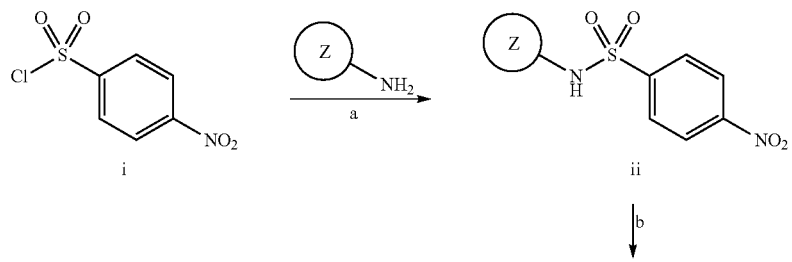

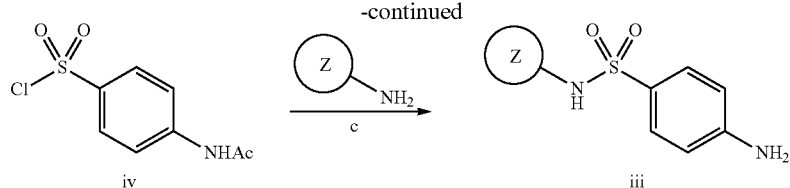

The reaction of intermediate i with amines (step a) in pyridine at rt yields ii. Reaction of intermediate ii with tin in 10% HCl (step b) under refluxing conditions gives iii. Reaction of iv with amines (step c) in pyridine, followed by treatment with 10% NaOH provides iii.

Scheme E: Scheme E provides a synthesis for compounds of Formula IIA.

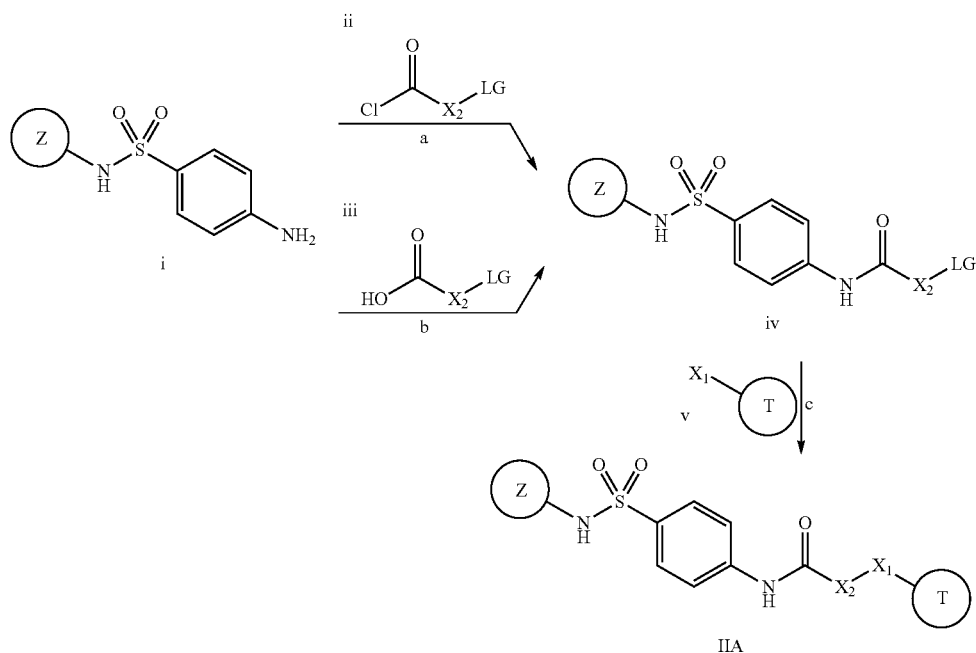

Reaction of i and ii (step a) in pyridine and DCM at rt yields iv. The coupling of i and iii (step b) using CDI and DMA under refluxing conditions, or HATU and TEA in pyridine under microwave conditions at 200° C., or BOP and TEA in CH₃CN at rt yields iv. The reaction of iv and v (step c) under alkylation conditions provides IIA. These alkylation conditions include NaH and K₂CO₃ as bases, DMF, DMSO, and THF as solvents, under rt, microwave, and reflux conditions.

Scheme F: Scheme F provides useful intermediates for Scheme A-C, E.

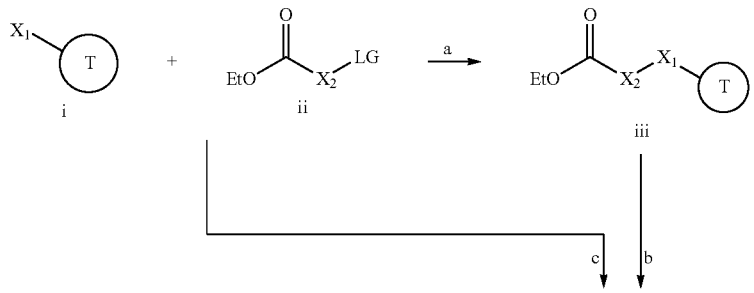

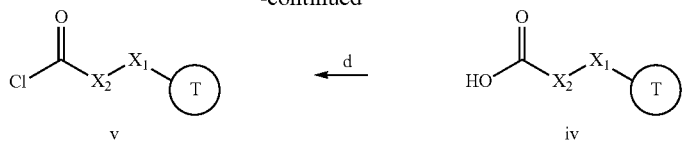

The reaction of i and ii (step a) under alkylation conditions provides intermediate iii. These alkylation conditions include NaH and $K_2CO_3$ as bases, and NaI can be added. Solvents include DMF, DMSO, and THF, and reaction conditions include rt, microwave, and refluxing conditions. The reaction of i and ii (step c) in $H_2O$ and NaOH provides intermediate iv. The reaction of intermediate iii (step b) using 2N NaOH, or $H_2O$ in DMA under microwave conditions yields iv. Treatment of iv with oxalyl chloride or thionyl chloride provides v.

Scheme G: Scheme G provides a synthesis to compounds of Formula IIB.

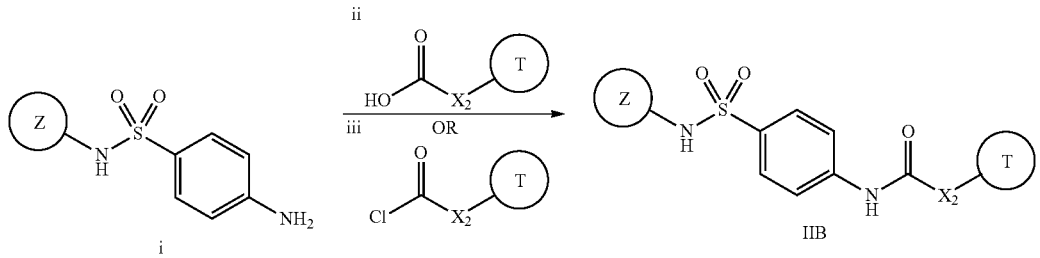

The coupling of i and ii (step a) using CDI and DMA under refluxing conditions, or HATU and TEA in pyridine under mircrowave conditions at 200° C., or BOP and TEA in $CH_3CN$ at rt yields IIB. Reaction of i and iii (step a) in pyridine and DCM at rt yields IIB.

Scheme H: Scheme H provides an alternative synthesis to compounds of Formula IIB.

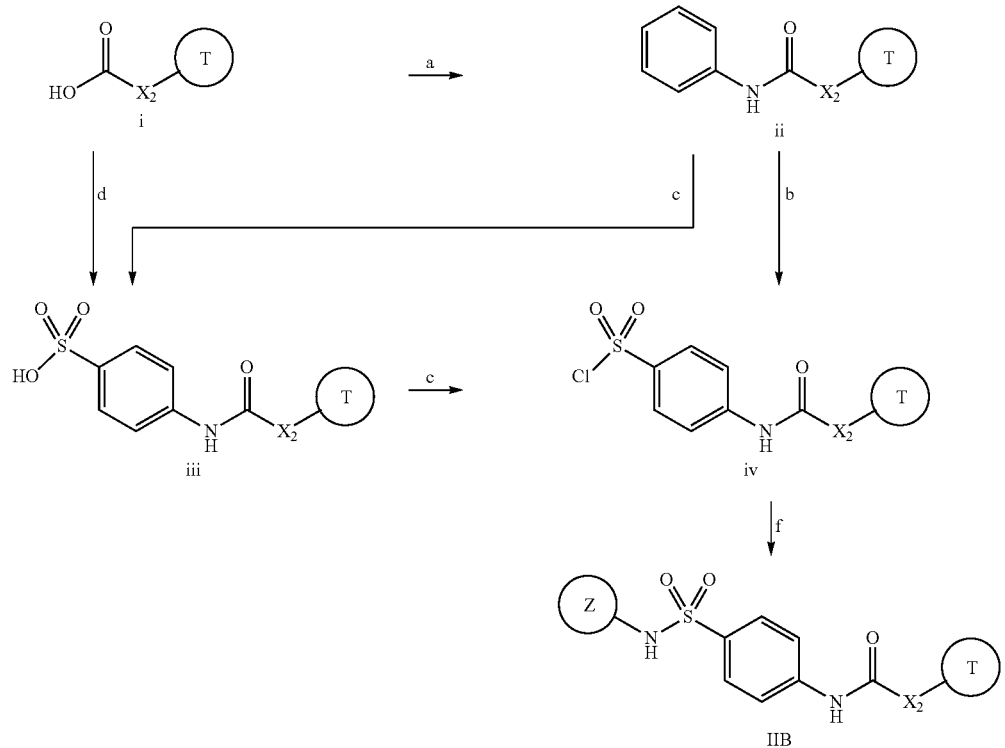

The coupling of i with anilines (step a) using CDI and DMA under refluxing conditions, or HATU and TEA in pyridine under mircrowave conditions at 200° C., or isobutyl chlorocarbonate and TEA in DCM yields ii. Reaction of intermediate ii with ClSO₃H (step b) under refluxing conditions gives iv. Reaction of ii ClSO₃H at 0° C. (step c) gives intermediate iii. Coupling of intermediate i with aminosulfonic acids (step d) using HATU and TEA in pyridine under mircrowave conditions at 200° C., or BOP and TEA in CH₃CN at rt yields iii. Reaction of intermediate iii with SO₂Cl (step e) yields iv. Alternatively, reaction of intermediate iii with cyanuric chloride and TEA in acetone under microwave conditions at 120° C. (step e) provides iv. Reaction of iv with various amines (step f) in pyridine at room temperature yields IIB.

Scheme I: Scheme I provides a synthesis for compounds of Formula IIC.

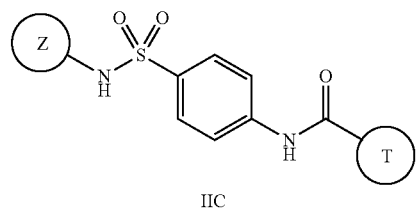

IIC

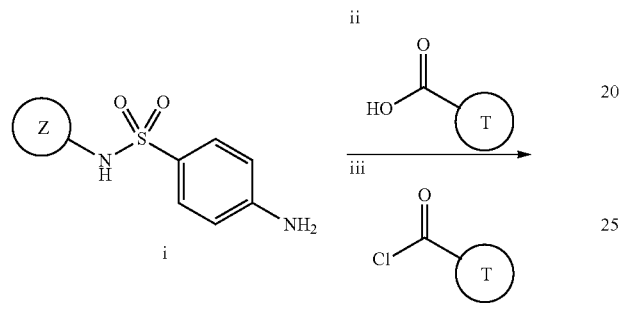

The coupling of i and ii (step a) using CDI and DMA under refluxing conditions, or HATU and TEA in pyridine under mircrowave conditions at 200° C., or BOP and TEA in CH₃CN at rt yields IIC. Reaction of i and iii (step a) in pyridine and DCM at rt yields IIC.

Scheme J: Scheme J provides an alternative synthesis for compounds of Formula IIC.

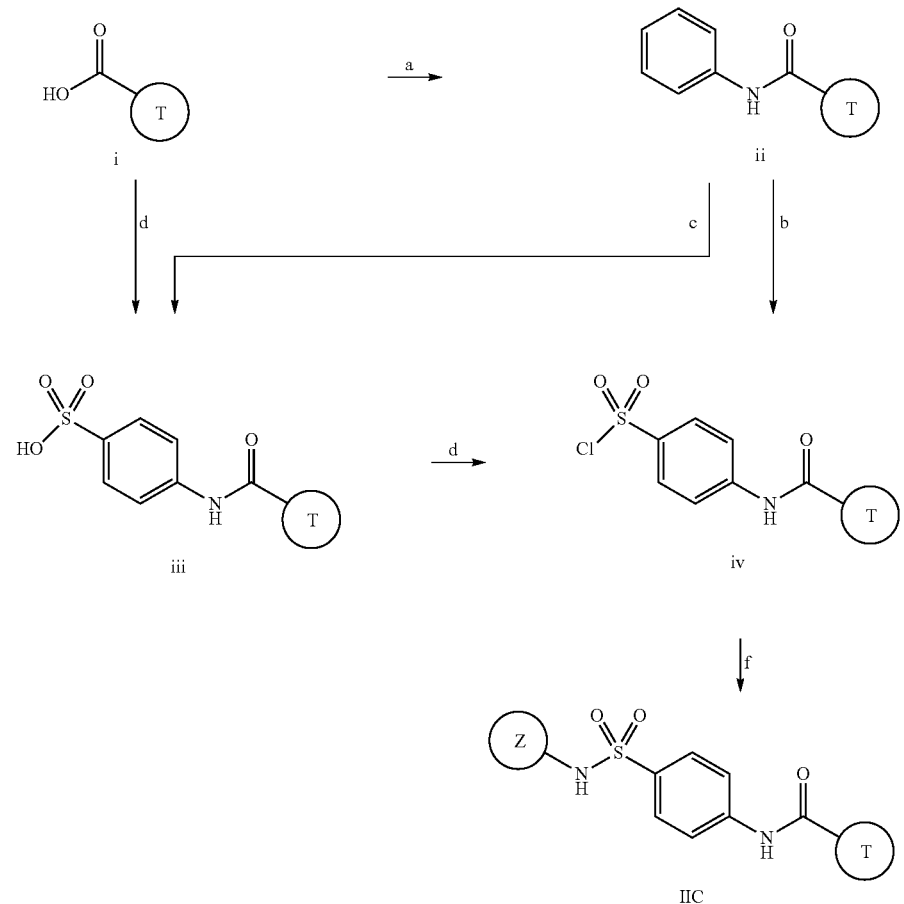

IIC

The coupling of i with anilines (step a) using CDI and DMA under refluxing conditions, or HATU and TEA in pyridine under mircrowave conditions at 200° C., or isobutyl chlorocarbonate and TEA in DCM yields ii. Reaction of intermediate ii with ClSO₃H (step b) under refluxing conditions gives iv. Reaction of ii ClSO₃H at 0° C. (step c) gives intermediate iii. Coupling of intermediate i with aminosulfonic acids (step d) using HATU and TEA in pyridine under mircrowave conditions at 200° C., or BOP and TEA in CH₃CN at rt yields iii. Reaction of intermediate iii with SO₂Cl (step e) yields iv. Alternatively, reaction of intermediate iii with cyanuric chloride and TEA in acetone under microwave conditions at 120° C. (step e) provides iv. Reaction of iv with various amines (step f) in pyridine at room temperature yields IIB.

Scheme K: Scheme K provides a synthesis for compounds of Formula IID.

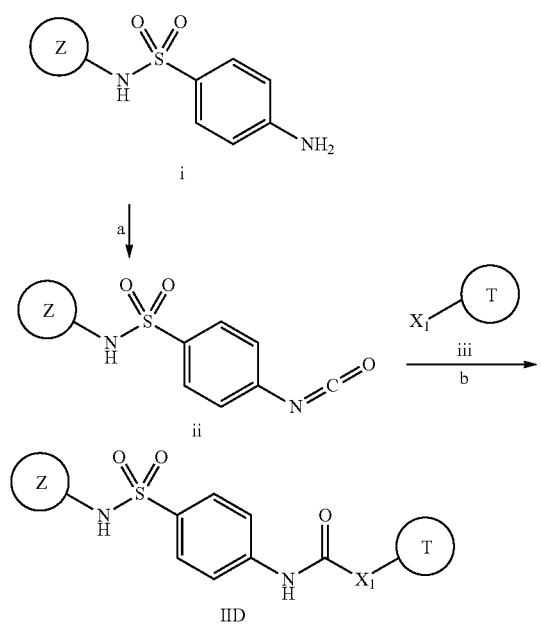

The reaction of intermediate i with 20% diphosgene and TEA (step a) in PhCH₃ with heating provides ii. The treatment of ii with iii (step b) yields IID.

Scheme L: Scheme L provides an alternative synthesis for compounds of Formula IID.

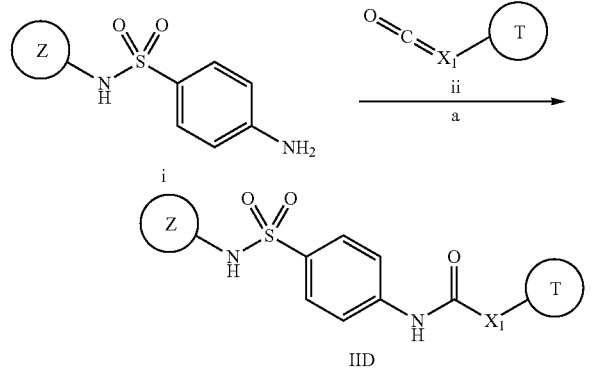

The reaction of intermediate i with ii in TEA/CH₃CN (step a) provides compounds IID.

Scheme M: Scheme M provides an alternative synthesis for compounds of Formula IID.

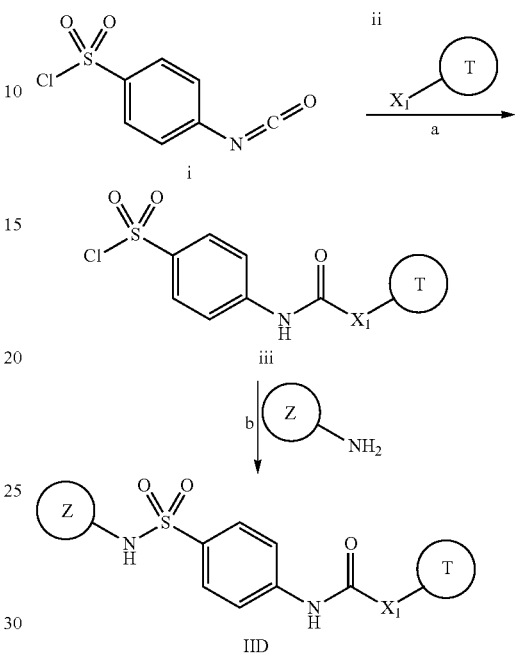

The reactions of intermediate i and ii (step a) in THF at rt provides intermediate iii. The treatment of intermediate iii with various amines (step b) in yridines at rt provides IID.

Scheme N: Scheme N provides a synthesis for compounds of Formula III.

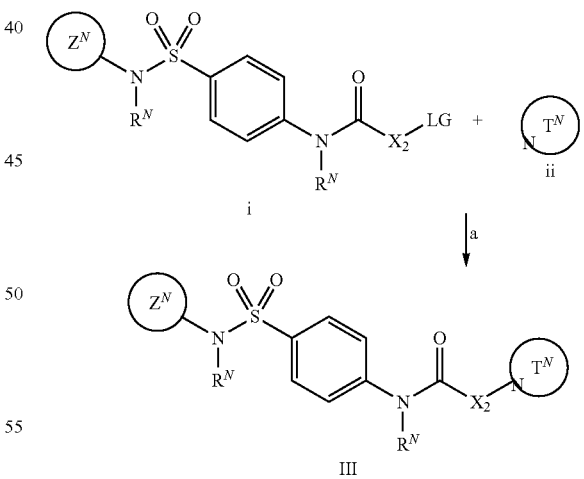

The reaction of i and ii (step a) under alkylation conditions provides III. These alkylation conditions include NaH and K₂CO₃ as bases, and NaI can be added. Solvents include DMF, DMSO, and THF, and reaction conditions include rt, microwave, and refluxing conditions.

One of skill in the art will appreciate that in addition to the above schemes, analogous methods known in the art may be readily used to synthesize other compounds of the present invention.

As discussed above, the present invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence is provided comprising administering an effective amount of a compound, or a pharmaceutically acceptable composition comprising a compound to a subject in need thereof. In certain preferred embodiments, a method for the treatment or lessening the severity of acute, chronic, neuropathic, or inflammatory pain is provided comprising administering an effective amount of a compound or a pharmaceutically acceptable composition to a subject in need thereof. In certain embodiments of the present invention an "effective amount" of the compound or pharmaceutically acceptable composition is that amount effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence.

The compounds and compositions, according to the method of the present invention, may be administered using any amount and any route of administration effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in a proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein, or according to methods available to one of ordinary skill in the art.

In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Examples of additional agents opiois, COX-2 inhibitors, local anesthetics, tricyclic antidepressants, NMDA modulators, cannibaloid receptor agonists, P2X family modulators, VR1 antagonists, and substance P antagonists.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting NaV1.1, NaV1.2, NaV1.3, NaV1.4, NaV1.5, NaV1.6, NaV1.7, NaV1.8 NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES 4-(2,4-Dichloro-phenoxy)-butyric acid ethyl ester

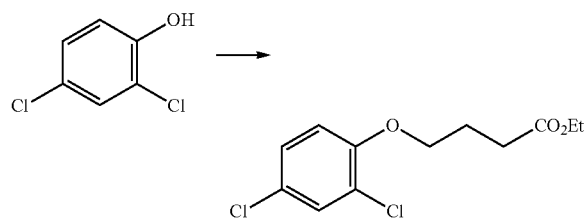

To a mixture of 2,4-dichlorophenol (32.6 g, 0.2 mol), NaI (3 g) and $K_2CO_3$ (69 g, 0.5 mol) in DMF (500 mL) was added dropwise ethyl 4-bromobutyrate (39 g, 0.2 mol) at 80° C. The reaction mixture was stirred at 80° C. for 2 h until the reaction mixture turned to colorless. The cooled mixture was filtered and the filtrate was diluted with EtOAc (1000 mL), washed with water (3×500 mL), dried, and concentrated to give the crude butyrate (57 g) as colorless oil. $^1$H-NMR (CDCl$_3$): δ 7.34 (d, 1H, J=8.8 Hz), 7.16 (dd, 1H, J$_1$=8.8 Hz, J$_2$=2.4 Hz), 6.84 (d, 1H, J=8.8 Hz), 4.15 (q, 2H, J=7.2 Hz), 4.06 (t, 2H, J=7.2 Hz), 2.54 (t, 2H, J=7.2 Hz), 2.17 (p. 2H, 6.4), 1.25 (t, 3H, J=7.2 Hz).

4-(2,4-Dichloro-phenoxy)-butyric acid

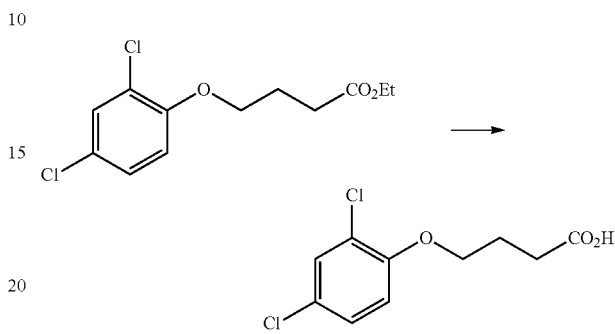

To a solution of ethyl 4-(2,4-dichlorophenoxy)-butyrate (57 g, crude from last step, about 0.2 mol) in THF (500 mL) and water (500 mL) was added LiOH.H$_2$O (12.6 g, 0.3 mol), and the reaction mixture was stirred for 5 h at RT. The mixture was washed with Et$_2$O (3×200 mL), and the aqueous layer was acidified by addition of HCl (20%) to pH ~2. The mixture was extracted with EtOAc (3×400 mL), the combined organic extracts were washed with water and brine, dried over Na$_2$SO$_4$ and concentrated in vacuo to give the butyric acid (37 g, 74.3% from 2,4-dichlorophenol) as a white solid. $^1$H-NMR (CDCl$_3$): δ 7.36 (d, 1H, J=8.8 Hz), 7.18 (dd, 1H, J$_1$=8.8 Hz, J$_2$=2.4 Hz), 6.84 (d, 1H, J=8.8 Hz), 4.07 t, 2H, J=7.2 Hz), 2.64 (t, 2H, J=7.2 Hz), 2.17 (p, 2H, J=6.4 Hz).

4-(2,4-dichlorophenoxy)-N-phenylbutyramide

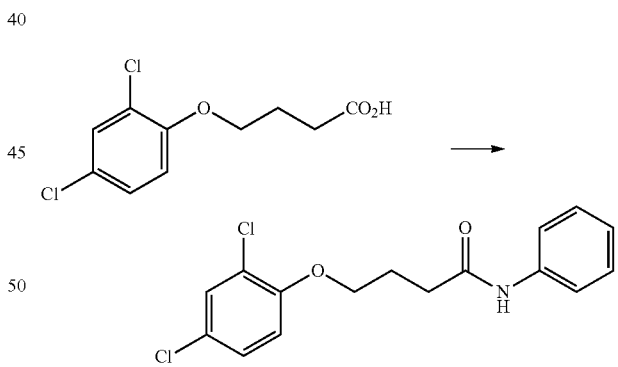

To a solution of the 4-(2,4-dichloro-phenoxy)-butyric acid (9.8 g, 40 mmol) and triethylamine (6.0 ml, 40 mmol) in dichloromethane (150 mL) was added dropwise isobutyl chlorocarbonate (6 mL, 40 mol) at −30° C. After stirring at −30° C. for 3 h, aniline (4 mL 40 mol) was added dropwise. The reaction mixture was stirred for 3 h at −30° C. and then allowed to warm up to RT. Aqueous HCl (5%, 100 mL) was added and stirring was continued for 0.5 h. The phases were separated, the aqueous layer was extracted with dichloromethane (2×200 mL). The combined organic extracts were washed with water and brine, dried over Na$_2$SO$_4$ and concentrated in vacuo to give the product (10 g, 77.5%). $^1$H-NMR (CDCl$_2$): δ 7.49 (d, 2H, J=8.0 Hz), 7.38 (d, 1H, J=2.4 Hz), 7.31 (t, 2H, J=8.0 Hz), 7.18 (dd, 1H, J$_1$=8.8 Hz, J$_2$=2.4 Hz) 7.12 (t, 1H, J=8.0), 6.87 (d, 1H, J=8.8 Hz), 4.12 (t, 2H, J=6.4 Hz), 2.64 (t, 2H, J=6.4 Hz), 2.25 (p, 2H, J=6.4 Hz).

4-[4-(2,4-Dichlorophenoxy)-butyrylamino]-benzenesulfonyl chloride

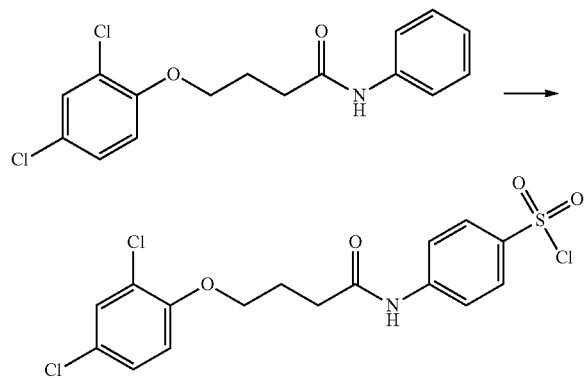

To a solution of 4-(2,4-dichlorophenoxy)-N-phenyl-butyramide (9.8 g, 30 mmol) in chloroform (100 mL) was added chlorosulfonic acid (11.6 g, 100 mmol). The reaction mixture was stirred at RT for 36 h, then water (200 mL) was added to quench the reaction. The mixture was extracted with EtOAc (3×200 mL), the combined organic extracts were washed with water and brine, dried over Na$_2$SO$_4$ and concentrated in vacuo. The residue was purified by chromatography over silica to give the sulfonyl chloride (3.5 g, 32%) as a white solid: $^1$H-NMR (CDCl$_3$): δ 7.97 (d, 2H, J=8.8 Hz), 7.75 (d, 2H, J=8.8 Hz), 7.63 (br, s, 1H), 7.37 (d, 1H, J=2.4 Hz), 7.21 (dd, 1H, J$_1$=8.8 Hz, J$_2$=2.4 Hz), 6.87 (d, 1 H, J=8.8 Hz), 4.12 (t, 2H, J=5.6 Hz), 2.72 (t, 2H, J=6.8 Hz), 2.31 (p, 2H, J=6.4 Hz).

4-(2,4-Dichloro-phenoxy)-N-[(4-[1,2,4]thiadiazol-5-ylsulfamoyl)-phenyl]butyramide

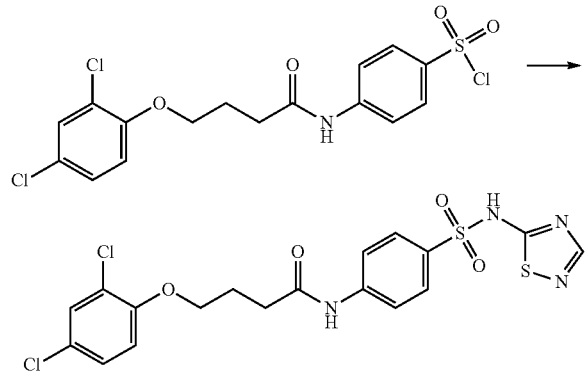

To a solution of the sulfonyl chloride (84 mg, 0.2 mmol) in pyridine (1 mL) was added 5-amino-1,2,4-thiazole (40 mg, 0.4 mmol) and the reaction mixture stirred at rt for 24 h. The reaction mixture was quenched with 50% DMSO and MeOH (3 mL) and purified by HPLC (gradient 10-99% CH$_3$CN/water). LC/MS (10-99%) M/Z: M$^+$1 obs=487.0; t$_R$=3.23 min.

5,7-Dichloro-1H-indol-2-carboxylic acid [4-(thiazol-2-ylsulfamoyl)-phenyl]-amide

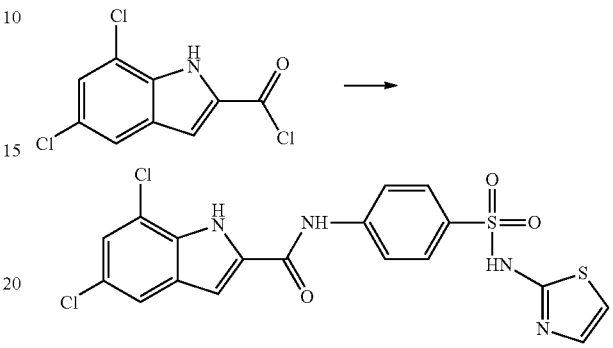

To a solution of 5,7-dichloro-indole-2-carbonylchloride (186 mg, 0.75 mmol) in pyridine (0.8 mL, 1 mmol) and DCM (5.2 mL) was added N'-(2-thiazolyl)sulfanilamide (128 mg, 0.5 mmol) and the reaction mixture stirred at rt for 16 h. The resulting solid was filtered, washed with DCM (3×5 mL), and dried under vacuum overnight to provide the product (0.21 g; yield=90%) as a white-green solid. $^1$H-NMR (DMSO-d$_6$) 12.78 (s, 1H), 12.33 (s, 1H), 10.67 (s, 1H), 7.97 (d, J=7.0 Hz, 2H), 7.82 (d, J=7.0 Hz, 2H), 7.62 (d, J=1.5 Hz, 1H), 7.47 (s, 1H), 7.30 (d, J=1.7 Hz, 1H), 7.27 (d, J=4.6 Hz, 1H), 6.84 (d, J=4.6 Hz, 1H). LC/MS (10-99%) M/Z: obs=467.0; t$_R$=3.12 min.

2-(4-Fluoro-phenoxy)-N-[4-thiazol-2-ylsulfamoyl)-phenyl]-acetamide

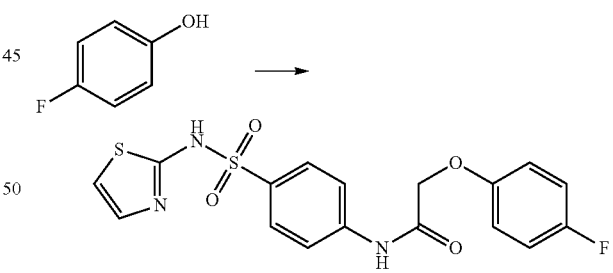

4-Fluorophenol (0.050 g, 0.45 mmol) was dissolved in 1.0 mL dimethylacetamide containing K$_2$CO$_3$ (0.15 g, 2.5 equiv). tert-Butyl chloroacetate (0.081 g, 85 pit, 1.2 equiv) was added neat and the mixture was microwave irradiated at 150° C. for 30 min. After cooling, the contents of the tube were filtered through Celite into a clean microwave tube, the bed was rinsed with 1.0 mL dimethylacetamide, 1.0 mL H$_2$O was added to the tube and this mixture was irradiated for 3 min at 190° C. Volatiles were evaporated. To the crude residue was added carbonyldiimidazole (0.68 mL of 1.0 M in DMA). The solution was placed on the shaker for 1.0 h at rt, after which N'-(2-thiazolyl)sulfanilamide (1.8 mL of 1.0 M in DMA) was

2-(2-Ethyl-phenoxy)-N-[4-thiazol-2-ylsulfamoyl)-phenyl]-acetamide

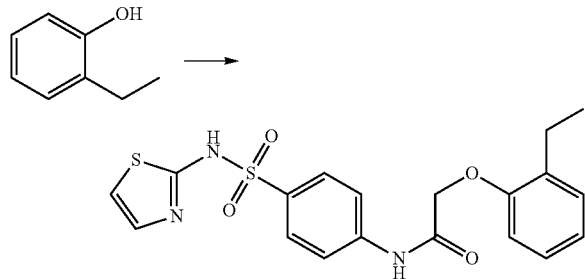

2-Ethylphenol (0.061 g, 0.50 mmol) was dissolved in DMSO (0.5 mL) and powdered K$_2$CO$_3$ (0.070 g, 0.50 mmol) was added followed by ethyl bromoacetate (0.12 g, 86 µL neat, 1.2 equiv). The mixture was shaken at rt for 16 h. NaOH (1.0 mL of 2 N) was added and shaking continued for 4 h. Aryloxybutanoic acid was precipitated by adding HCl (2.0 mL of 2 N) and collected by centrifugation and decantation of supernatant. A water wash was similarly employed prior to evaporation of volatiles. The dry crude product was weighed and assumed to be pure as it was treated with carbonyldiimidazole (1.0 equiv of 0.50 M in DMA) for 1 h at 45° C., then N'-(2-thiazolyl)sulfanilamide (1.0 equiv of 1.0 M in DMA) was added and shaking continued overnight overnight at rt. Volatiles were again evaporated, and the product isolated by HPLC purification.

2-(4-Chloro-2-fluoro-phenoxy)-N-[4-thiazol-2-ylsulfamoyl)-phenyl]-acetamide

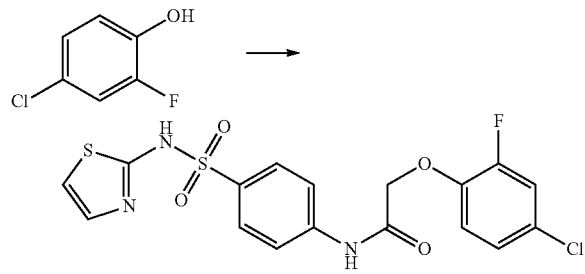

4-Chloro-2-fluorophenol (0.073 g, 0.50 mmol) was suspended in 0.62 mL H$_2$O and NaOH (0.10 mL, 10 N) was added. The mixture was shaken until homogenous, chloroacetic acid (0.50 mL of 1.0 M) was added and the solution was heated to 110° C. in a test tube equipped with a rubber cap punctured by a syringe needle. Water was allowed to distill out. After 4-5 h, the temperature was increased to about 120° C. and most of the rest of the water was distilled off. When the volume reduction was about 75%, the tube was cooled and 1.0 mL of 6 N HCl was added to precipitate product which was collected by centrifugation and decantation of supernatant. Water washes (2×2 mL) were similarly employed prior to evaporation of volatiles. The dry crude product was weighed and assumed to be pure as it was treated with carbonyldiimidazole (1.0 equiv of 0.50 M in dimethylamine) for 1 h at 45° C., then N'-(2-thiazolyl)sulfanilamide (1.0 equiv of 1.0 M in dimethylamine) was added and shaking continued overnight at rt. Volatiles were again evaporated, and the product isolated by HPLC purification.

(8-Trifluoromethyl-quinolin-4-yloxy)-acetic acid

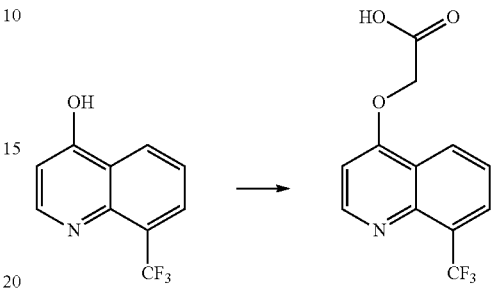

4-Hydroxy-8-trifluoromethylquinoline (0.50 g, 2.35 mmol) was dissolved in DMSO (2 mL). Potassium carbonate was added (0.32 g, 2.35 mmol) and the mixture was stirred vigorously for 2 h. Ethyl bromoacetate (0.32 mL, 1.2 equiv) was added dropwise and heat was applied at 50° C. for 6 h. At 50° C., 2N NaOH (2 mL) was added and stirring continued for 4 h. The mixture was cooled and quenched with water (4 mL). Glacial acetic acid (1.4 mL) was added to ~pH 4 resulting in precipitation of product. After stirring the suspension for 6 h, the solid was collected by vacuum filtration, rinsed with water, and dried in a vacuum dessicator over CaCl. The yield of white solid was 0.56 g (87%). $^1$H-NMR (DMSO-d$_6$) 5.04 (s, 2H), 7.11 (d, J=5.2 Hz, 1H), 7.69 (t, J=8.0 Hz, 1H), 8.15 (d, J=8.0 Hz, 1H), 8.47 (d, J=8.0 Hz, 1H), 8.83 (d, J=5.2 Hz, 1H), 13.3 (br s, 1H); LC/MS (10-99%) M/Z: obs=333.5; t$_R$=2.63 min.

N-[4-(Thiazol-2-ylsulfamoyl)-phenyl]-2-(8-trifluoromethyl-quinolin-4-yloxy)-acetamide

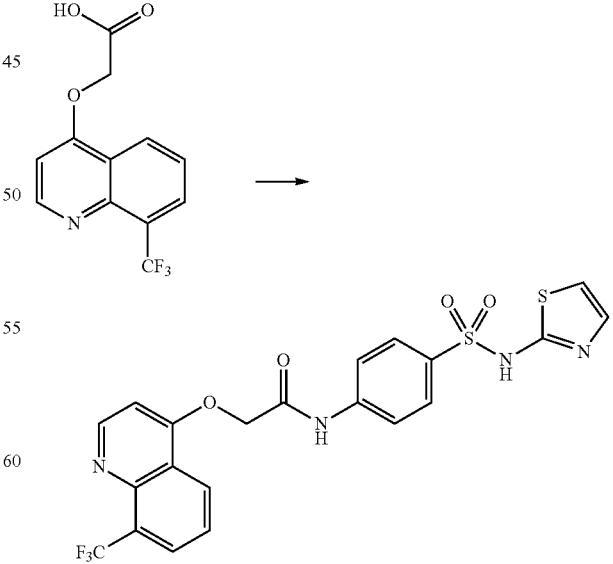

(8-Trifluoromethylquinolin-4-yloxy)-acetic acid (0.50 g, 1.84 mmol) was suspended in 20 mL DCM with rapid stirring. At rt, oxalyl chloride (0.19 mL, 1.2 equiv) was added dropwise and stirring continued for 4 h. Solvent and excess oxalyl chloride were removed in vacuo, the white residue was re-suspended in DCM, and the mixture cooled to 0° C. N'-(2-thiazolyl)sulfanilamide (0.47 g, 1.0 equiv) was added followed by pyridine (0.30 mL, 2.0 equiv). The mixture was allowed to warm to rt overnight. The solid was collected and rinsed with fresh DCM. Further purification was effected by suspending the solid in 20 mL methanol, stirring vigorously for 4 h, and filtration. After drying under vacuum, white solid 0.65 g (69%) was obtained. $^1$H-NMR (DMSO-$d_6$) 5.11 (s, 2H), 6.79 (d, J=4.8 Hz, 1H), 7.12 (d, J=5.2 Hz, 1H), 7.22 (d, J=4.8 Hz, 1H), 7.71 (t, J=8.0 Hz, 1H), 8.17 (d, J=8.0 Hz, 1H), 8.55 (d, J=8.0 Hz, 1H), 8.85 (d, J=5.2 Hz, 1H); $^{13}$C-NMR (DMSO-$d_6$) 68.0, 103.6, 108.8, 120.0, 122.0, 124.8 (q, J=270 Hz), 125.1, 125.4, 126.4 (q, J=33 Hz), 127.7, 127.8, 129.2, 137.7, 142.1, 145.6, 153.2, 161.2, 166.5, 169.4 LC/MS (10-99%) M/Z: M$^+$1 obs=509.5; $t_R$=3.13 min.

6-Chloro-1,2,3,4-tetrahydroquinoline

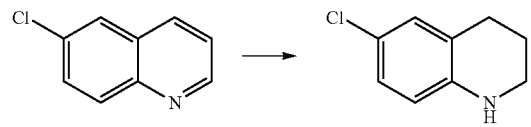

Method A: To a solution of 6-chloroquinoline (2.0 g, 12.2 mmol) in anhydrous MeOH (500 mL) under nitrogen was added PtO$_2$ (0.2 g, 1.6 mmol). Hydrogen gas was then passed through the reaction mixture and the mixture stirred for 45 min. The reaction mixture was filtered and the filtrate evaporated. The product was taken up in DCM, filtered through celite and chromatographed (gradient of 0-10% EtOAc/Hex) to afford 0.9 g (41%) as clear colorless oil. HNMR (CDCl$_3$): δ 6.85-6.83 (m, 2H), 6.42-6.39 (m, 1H), 5.82 (s, 1H), 3.17-3.13 (m, 2H), 2.63 (t, J=6.3 Hz, 2H), 1.75 (q, J=5.9 Hz, 2H), LC/MS (10-99%) M/Z: M$^+$1 obs=168.3; $t_R$=1.74 min.

Method B: A mixture of 6-chloroquinoline (0.82 g, 0.5 mmol), indium powder (0.53 g, 4.6 mmol), and saturated aq. NH$_4$Cl (789 µL) in absolute EtOH (2.5 mL) was microwaved at 160° C. for 8 h. The mixture was then filtered and the filtrate concentrated to give a crude yield of 0.10 g. The product was taken up in DCM, filtered through celite and chromatographed (gradient of 0-10% EtOAc/Hex) to afford 0.01 g (12%) as clear colorless oil. LC/MS (10-99%) M/Z: M$^+$1 obs=168.3; $t_R$=1.74 min.

1-Methyl-1,2,3,4-tetrahydro-isoquinoline

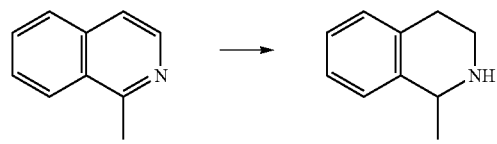

To a solution of 1-methylisoquinoline (133 µL, 1.0 mmol) in THF under nitrogen was added dropwise a solution of LiBEt$_3$H in THF (1.0M, 2.2 mL, 2.2 mmol) to give a yellow solution. After stirring 1.5 h, MeOH (1.2 mL) was added dropwise to produce a clear colorless solution, which was then diluted with 1M aq. HCl and ether. The aqueous layer was extracted three times with ether, then made basic (pH 14) by addition of 1M aq. NaOH. The aqueous layer was extracted five times with DCM, dried over MgSO$_4$, filtered and concentrated to give the desired product in 77% yield, which was used without further purification. LC/MS (10-99%) M/Z: M$^+$1 obs=148.3; $t_R$=0.62 min.

6-Methoxy-1,2,3,4-tetrahydro-quinoline

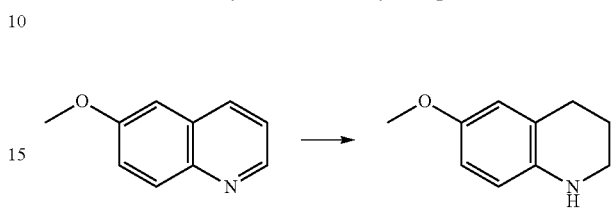

A mixture of 6-methoxyquinoline (69 µL, 0.5 mmol), ammonium formate (0.32 g, 5.0 mmol), and 10% Pd/C (0.05 g) in anhydrous MeOH (5 mL) was microwaved for 900 s at 100° C. The mixture was filtered and 2M HCl in Et$_2$O (1.5 mL) was added. The product was redissolved in H$_2$O/DCM and the aqueous layer basified with 0.1M aq. NaOH (pH 8). After extracting three times with DCM, the organic layer was concentrated to give the product in 89% yield. The product was used without further purification. LC/MS (10-99%) M/Z: M$^+$1 obs=164.0; $t_R$=0.40 min.

2-Chloro-N-[4-(thiazol-2-ylsulfamoyl)-phenyl]-acetamide

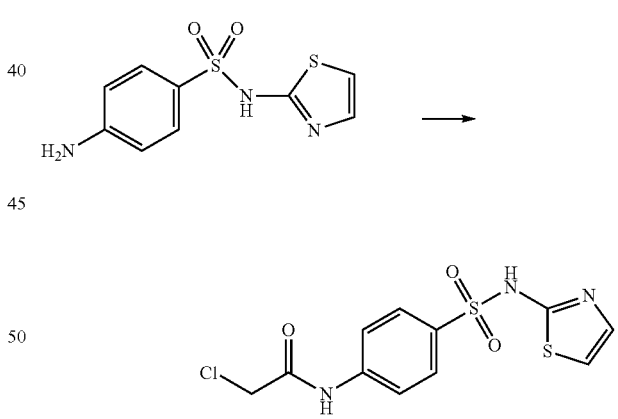

General procedure 1: N'-(2-thiazolyl)sulfanilamide (10.0 g, 39.2 mmol) was suspended in DCM containing pyridine (3.80 mL, 1.2 equiv) and chilled in an ice bath. Chloroacetyl chloride (5.3 g, 3.74 mL, 1.2 equiv) was added dropwise with vigorous stirring. The mixture was allowed to warm to rt overnight. The solid was filtered, rinsed with fresh DCM, and air dried to give 11.6 g (89%) white solid. $^1$H-NMR (DMSO-$d_6$) 4.56 (s, 2H), 6.78 (d, J=4.8 Hz, 1H), 7.21 (d, J=4.8 Hz, 1H), 7.70 (d, J=9.0 Hz, 2H), 7.75 (d, J=9.0 Hz, 2H), 10.61 (s, 1H); $^{13}$C-NMR (DMSO-$d_6$) δ4.2, 108.8, 119.7, 125.1, 127.7, 137.7, 142.3, 165.8, 169.4; LC/MS (10-99%) M/Z: M$^+$1 obs=333.6; $t_R$=2.63 min.

2-(3,4-Dihydro-2H-quinolin-1-yl)-N-[4-(thiazol-2-ylsulfamoyl)-phenyl]-acetamide

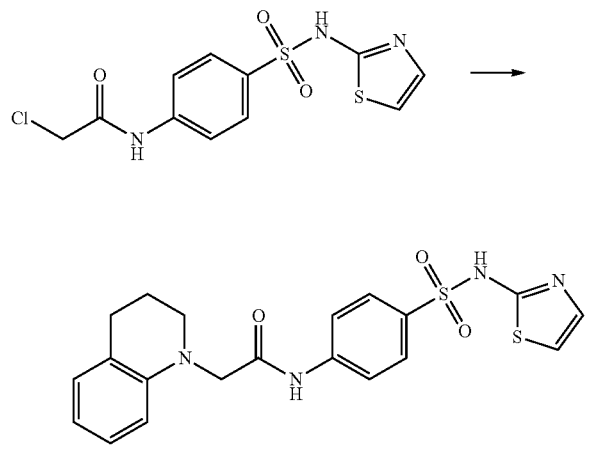

General procedure 2: To the 2-chloroacetamide (2.00 g, 6.03 mmol) in DMF (15 mL) was added tetrahydroquinoline (2.27 mL, 18.09 mmol) and the reaction mixture was microwaved at 200° C. for 300 s. The reaction mixture was taken up in DCM, filtered through celite and chromatographed (gradient of 0-10% MeOH/DCM) to provide 1.53 g (59%) of a white solid. $^1$H-NMR (DMSO-$d_6$) 12.70 (s, 1H), 10.37 (s, 1H), 7.74 (s, 4H), 7.25 (d, J=5.6 Hz, 1H), 6.87-6.95 (m, 2H), 6.82 (d, J=4.6 Hz, 1H), 6.50 (t, J=7.3 Hz, 1H), 6.42 (d, J=7.9 Hz, 1H), 3.41 (t, J=5.6 Hz, 2H), 2.73 (t, J=6.3 Hz, 2H), 1.86-1.95 (m, 2H). LC/MS (10-99%) M/Z: M$^+$1 obs=429.0; $t_R$=2.79 min.

2-(6-Chloro-3,4-dihydro-2H-quinoline-1-yl)-N-[4-(thiazol-2-ylsulfamoyl)-phenyl]-acetamide

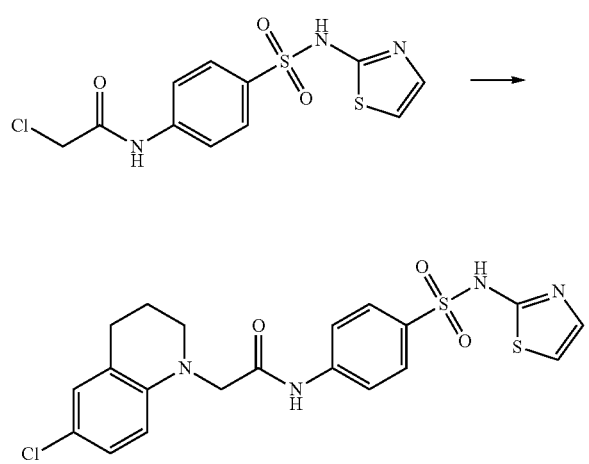

Synthesized according to general procedure 2: 2-chloroacetamide (1.0 g, 3.0 mmol), 6-chloro-tetrahydro-quinoline (0.85 g, 5.0 mmol) in DMF (15 mL). Purified by column chromatography (5-10% MeOH/DCM), followed by HPLC purification (1-99% CH$_3$CN/H$_2$O). LC/MS (10-99%) M/Z: M$^+$1 obs=463.3; $t_R$=2.93 min.

2-Indol-1-yl-N-[4-(thiazol-2-ylsulfamoyl)-phenyl]-acetamide

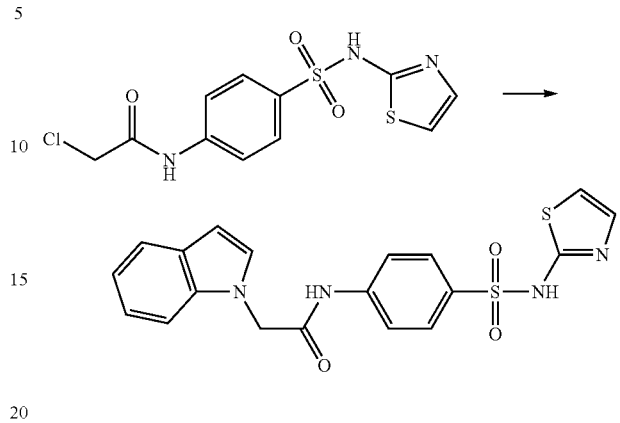

General procedure 3: A dry, 10 mL borosilicate glass reaction vessel was put under an inert atmosphere of argon and loaded with sodium hydride (60% wt. dispersion in mineral oil, 5 equiv) to which dry DMF (1 mL) was added. The resulting suspension was cooled to 0° C. Subsequently, a solution of the indole in dry DMF (0.1M, 1 mL, 0.1 mmol) was added to the vessel and the reaction mixture was stirred for 30 min. at 0° C. Next, a solution of the 2-chloro-N-[4-(thiazol-2-ylsulfamoyl)-phenyl]-acetamide in dry DMF (0.1M, 1 mL, 1 equiv) was added. The reaction mixture was allowed to warm to room temperature and stirred for 72 h, after which the reaction was quenched by the addition of water (5 mL). The work-up consisted of washing the aqueous phase with heptane (2×5 mL), addition of aqueous HCl (1M, 1 mL) and extraction with DCM (2×4 mL). Finally, removal of the DCM under reduced pressure and stripping the resulting solid with CH$_3$CN (5 times), afforded the final product. $^1$H-NMR (DMSO-$d_6$): δ 10.73 (s, 1H), 7.78-7.71 (m, 4H), 7.55 (d, J=7.7 Hz, 1H), 7.41 (d, J=8.3 Hz, 1H), 7.38 (d, J=3.0 Hz, 1H), 7.23 (d, J=4.7 Hz, 1H), 7.12 (t, J=7.4 Hz, 1H), 7.02 (t, J=7.4 Hz, 1H), 6.80 (d, J=4.7 Hz, 1H), 6.46 (d, J=3.0 Hz, 1H), 5.09 (s, 2H). LC/MS (10-99%) M/Z: M$^+$1 obs=412.2; $t_R$=3.43 min.

2-(2-Methyl-2,3-dihydro-indol-1-yl)-N-[4-(thiazol-2-ylsulfamoyl)-phenyl]-acetamide

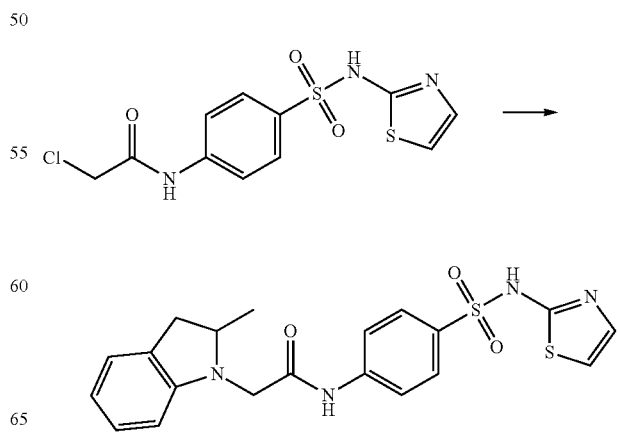

Synthesized according to general procedure 2: 2-chloroacetamide (0.5 g, 1.5 mmol), 2-methylindoline (1.0 mL, 7.5 mmol) in DMF (5 mL). Purified by chromatography (gradient of 0-10% MeOH/DCM) to provide 640 mg (100%) of a white solid. $^1$H-NMR (DMSO-$d_6$) 12.70 (bs, 1H), 10.26 (s, 1H), 7.72-7.78 (m, 4H), 7.25 (d, J=4.6 Hz, 1H), 7.01 (d, J=7.2 Hz, 1H), 6.95 (t, J=7.6 Hz, 1H), 6.82 (d, J=4.6 Hz, 1H), 6.57 (dt, J=0.8 Hz, 1H), 6.39 (d, $J_d$=0.8 Hz, $J_t$=8.0 Hz, 1H) (3.41 (t, J=5.6 Hz, 2H), 2.73 (t, J=6.3 Hz, 2H), 1.86-1.95 (m, 2H). LC/MS (10-99%) M/Z: M$^+$1 obs=429.2; $t_R$=2.97 min.

2-Chloro-N-[4-(thiazol-2-ylsulfamoyl)-phenyl]-propionylamide

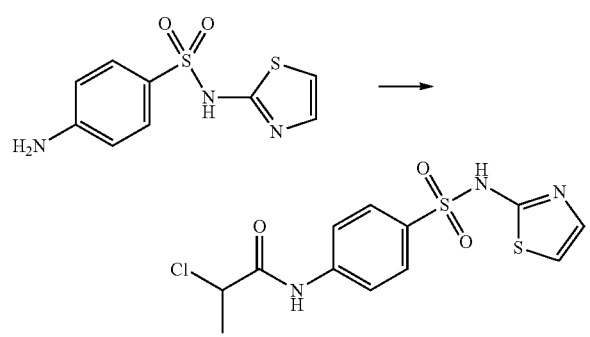

Synthesized according to general procedure 1: N'-(2-thiazolyl)sulfanilamide (1.00 g, 3.9 mmol), pyridine (0.6 mL), 2-Chloropropionyl chloride (0.5 mL, 4.7 mmol, 1.2 equiv) in DCM (50 mL). Yield: 1.34 g (99%) of a crude white solid. $^1$H-NMR (DMSO-$d_6$) 10.65 (s, 1H), 7.73-7.79 (m, 4H), 7.25 (d, J=4.3, 1H), 6.83 (d, J=4.6 Hz, 1H), 4.69 (q, J=3.3, 1H), 1.61 (d, J=6.6, 3H). LC/MS (10-99%) M/Z: M$^+$1 obs=346.1; $t_R$=2.22 min.

2-(3,4-Dihydro-2H-quinolin-1-yl)-N-[4-(thiazol-2-ylsulfamoyl)-phenyl]-propionamide

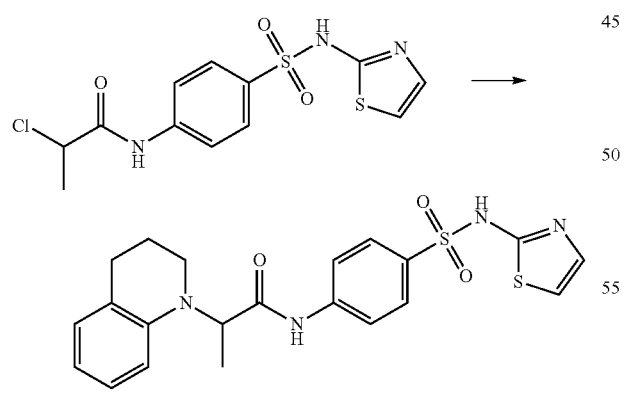

Synthesized according to general procedure 2: 2-chloropropionylamde (173 mg, 0.5 mmol), tetrahydro-quinoline (0.19 mL, 1.5 mmol) in DMF (1 mL), microwaved at 200° C. for 450 s. The reaction mixture was diluted with 50% MeOH/DMSO and purified by HPLC (gradient of 1-99% CH$_3$CN/water). $^1$H-NMR (DMSO-$d_6$) 10.29 (s, 1H), 7.72-7.79 (m, 4H), 7.25 (d, J=4.6, 1H), 6.81-6.99 (m, 2H), 6.82 (d, J=4.6, 1H), 6.65 (d, 8.2, 1H), 6.54 (td, $J_d$=0.6, $J_t$=7.3, 1H), 4.58 (q, J=6.8, 1H), 3.47 (bs, 1H), 3.25 (t, J=5.5, 2H), 2.70 (t, J=6.2, 2H), 1.81-1.96 (m, 2H), 1.35 (d, J=6.9, 3H). LC/MS (10-99%) M/Z: M$^+$1 obs=443.3; $t_R$=3.13 min.

2-(5-Chloro-indol-1-yl)-N-[4-(thiazol-2-ylsulfamoyl)-phenyl]-propionamide

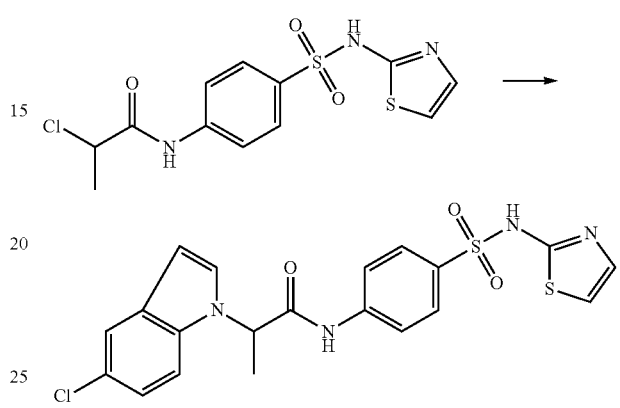

Synthesized according to general procedure 3: 6-Chloroindole (0.1 g, 0.7 mmol), NaH (60% in oil, 0.14 g, 3.6 mmol), 2-chloropropionylamide (250 mg, 0.7 mmol). The product was isolated by HPLC (gradient of 10-99% CH$_3$CN/water). $^1$H-NMR (DMSO-$d_6$) 10.71 (bs, 1H), 7.71-7.83 (m, 4H), 7.65 (d, J=1.6, 1H), 7.58-7.59 (m, 1H), 7.56 (s, 1H), 7.24 (d, 4.6, 1H), 7.05 (dd, J=1.8, 8.4, 1H), 6.81 (d, J=4.6, 1H), 6.53 (dd, J=0.5, 2.8, 1H), 5.37 (q, J=7.0, 1H), 1.75 (d, J=6.9, 3H). LC/MS (10-99%) M/Z: M$^+$1 obs=461.3; $t_R$=2.90 min.

2-Chloro-2-phenyl-N-[4-(thiazol-2-ylsulfamoyl)-phenyl]-acetamide

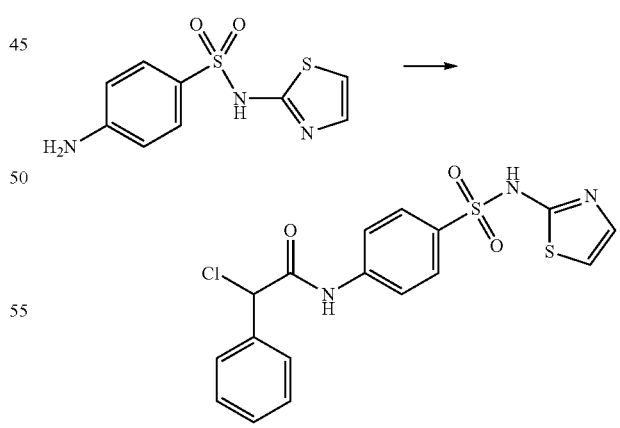

Synthesized according to general procedure 1: N'-(2-thiazolyl)sulfanilamide (5.60 g, 22 mmol), pyridine (3.6 mL, 44 mmol), 2-chloro-2-phenyl acetylchloride (3.8 mL, 26.4 mmol, 1.2 equiv) in DCM (400 mL). Yield: 6.73 g (75%) of a white solid. $^1$H-NMR (DMSO-$d_6$) δ 10.85 (s, 1H), 7.78-7.72 (m, 4H), 7.60-7.57 (m, 2H), 7.45-7.37 (m, 3H), 7.25 (d, J=4.6

Hz, 1H), 6.82 (d, J=4.6 Hz, 1H), 5.77 (s, 1H). LC/MS (10-99%) M/Z: M⁺1 obs=408.1; $t_R$=2.61 min.

2-(3,4-Dihydro-2H-quinolin-1-yl)-2-phenyl-N-[4-(thiazol-2-ylsulfamoyl)-phenyl]-acetamide

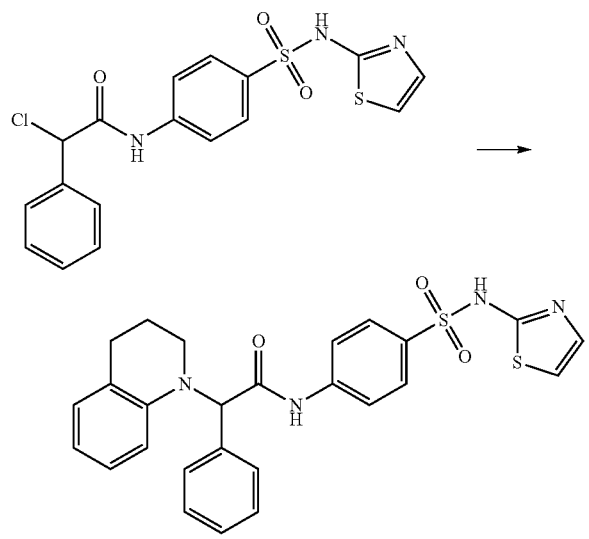

Synthesized according to general procedure 2: 2-chloro-2-phenyl acetamide (61 mg, 0.15 mmol), tetrahydroquinoline (94 μL, 0.75 mmol) in DMF (0.75 mL), microwaved at 200° C. for 300 s. The reaction mixture was diluted with 50% MeOH/DMSO (0.75 mL) and purified by HPLC (gradient of 1-99% CH₃CN/water). ¹H-NMR (DMSO-d₆) δ 10.74 (s, 1H), 7.79-7.74 (m, 4H), 7.44-7.31 (m, 5H), 7.25 (d, J=4.6 Hz, 1H), 6.99 (d, J=7.4 Hz, 1H), 6.95 (d, J=7.6 Hz, 1H), 6.82 (d, J=4.6 Hz, 1H), 6.70 (d, J=8.1 Hz, 1H), 6.58-6.55 (m, 1H), 5.75 (s, 1H), 3.40-3.36 (m, 1H), 2.94-2.89 (m, 1H), 2.79-2.61 (m, 2H), 1.83-1.67 (m, 2H). LC/MS (10-99%) M/Z: M⁺1 obs=505.3; $t_R$=3.20 min.

3-Chloro-N-[4-(thiazol-2-ylsulfamoyl)-phenyl]-propionamide

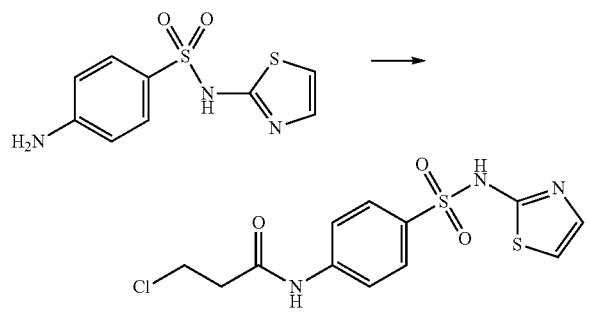

Synthesized according to general procedure 1: N″-(2-thiazolyl)sulfanilamide (8.37 g, 32.8 mmol), pyridine (5.3 mL, 65.6 mmol), 2-chloro-propionylchloride (3.8 mL, 39.4 mmol, 1.2 equiv) in DCM (400 mL). Yield: 2.70 g (24%) of a white solid. 1H-NMR (DMSO-d₆) δ 10.41 (s, 1H), 7.77-7.72 (m, 4H), 7.25 (d, J=4.6 Hz, 1H), 6.82 (d, J=4.6 Hz, 1H), 3.88 (t, J=6.2 Hz, 2H), 2.86 (t, J=6.2 Hz, 2H). LC/MS (10-99%) M/Z: M⁺1 obs=346.1; $t_R$=1.94 min.

2-(3,4-Dihydro-2H-quinolin-1-yl)-N-[4-(thiazol-2-ylsulfamoyl)-phenyl]-propionamide

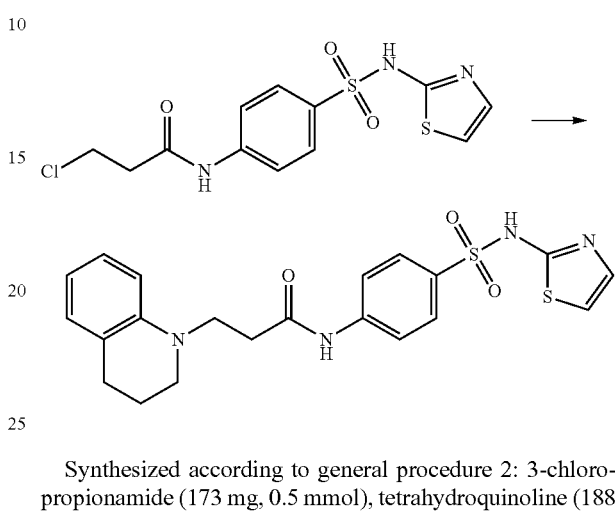

Synthesized according to general procedure 2: 3-chloropropionamide (173 mg, 0.5 mmol), tetrahydroquinoline (188 μL, 1.5 mmol) in DMF (5.0 mL), microwaved at 200° C. for 300 s. The reaction mixture was diluted with 50% MeOH/DMSO (5.0 mL) and purified by HPLC (gradient of 1-99% CH₃CN/water). ¹H-NMR (DMSO-d₆) δ 10.32 (s, 1H), 7.75-7.70 (m, 4H), 7.25 (d, J=4.6 Hz, 1H), 7.00-6.96 (m, 1H), 6.87 (dd, J=7.3, 1.4 Hz, 1H), 6.82 (d, J=4.6 Hz, 1H), 6.64 (d, J=7.9 Hz, 1H), 6.48 (dt, J=10.0, 3.6 Hz, 1H), 3.59 (t, J=7.0 Hz, 2H), 3.25 (t, J=5.6 Hz, 2H), 2.69-2.53 (m, 4H), 1.86-1.80 (m, 2H). LC/MS (10-99%) M/Z: obs=443.3; $t_R$=2.42 min.

3-(6-Chloro-indol-1-yl)-N-[4-(Thiazol-2-ylsulfamoyl)-phenyl]-propionamide

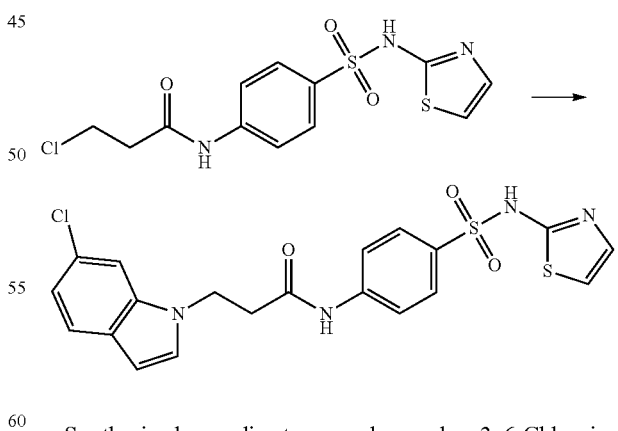

Synthesized according to general procedure 3: 6-Chloroindole (109 mg, 0.72 mmol), NaH (60% in oil, 144 mg, 3.60 mmol), 3-chloropropionamide (250 mg, 0.72 mmol). The product was isolated by HPLC (gradient of 10-99% CH₃CN/water). ¹H-NMR (DMSO-d₆) δ 10.25 (s, 1H), 7.73-7.64 (m, 4H), 7.53 (d, J=8.3 Hz, 1H), 7.37 (d, J=3.1 Hz, 1H), 7.21 (d, J=4.5 Hz, 1H), 7.02 (dd, J=8.4, 1.9 Hz, 1H), 6.43 (d, J=0.8 Hz, 1H), 4.50 (t, J=6.6 Hz, 2H), 2.84 (t, J=6.7 Hz, 2H). LC/MS (10-99%) M/Z: M+1 obs=461.1; $t_R$=2.84 min.

[4-(Thiazol-2-ylsulfamoyl)-phenyl]-carbamic acid 8-trifluoromethyl-quinolin-4-yl ester

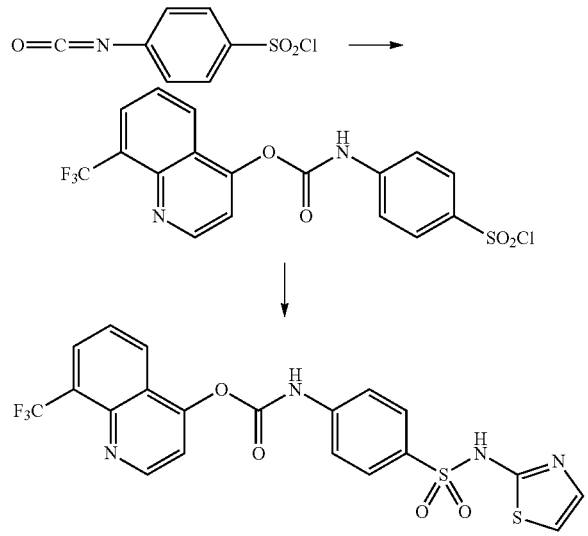

To a solution of 8-trifluoromethyl-quinolin-4-ol (107 mg, 0.50 mmol) in THF (5 mL) was added 4-isocyanatobenzenesulfonyl chloride (109 mg, 0.50 mmol) at RT. The resulting mixture was stirred at ambient temperature for 1 h. Then, a solution of 2-aminothiazole (50 mg, 0.50 mmol) in pyridine (5 mL) was added and stirring was continued for 65 h. The solvents were evaporated under a stream of nitrogen, the residue was dissolved in DMSO (2 mL) and purified by preparative LC/MS (gradient of 5-95% CH$_3$CN/water). $^1$H-NMR (DMSO-d$_6$) δ 9.63 (s, 1H), 9.10 (s, 1H), 8.28-8.22 (m, 2H), 7.97-7.95 (m, 2H), 7.81-7.77 (m, 3H), 7.52-7.51 (m, 1H), 7.41-7.40 (m, 2H), 7.15-7.14 (m, 1H). LC/MS (5-95%) M/Z: M+1 obs=495.4; $t_R$=10.45.

4-(3-Quinolin-8-yl-ureido)-N-thiazol-2-yl-benzenesulfonamide

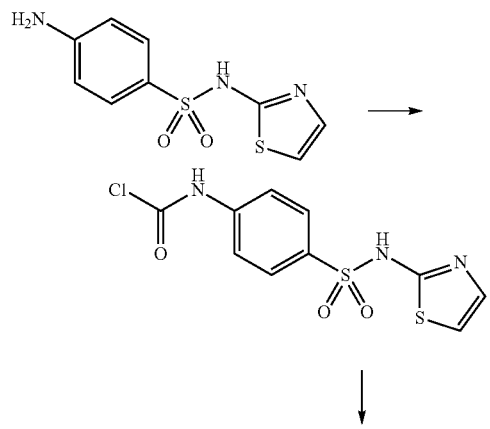

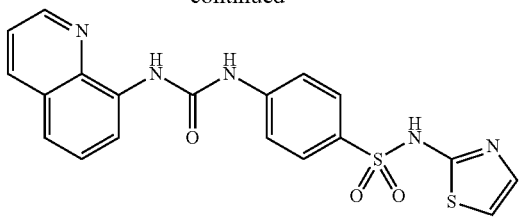

Method A: To a solution of sulfathiazole (102 mg, 0.40 mmol) and N,N-diisopropylethylamine (0.17 mL, 0.95 mmol) in acetonitrile (10 mL) was added a 20% phosgene solution in toluene (20% w/w in toluene, 1 mL). The reaction mixture was stirred under reflux for 2 h. The excess of phosgene and solvent were evaporated in vacuo and coevaporated with acetonitrile (5 mL). Then, the crude product was suspended in acetonitrile (5 mL), and a solution of 8-aminoquinoline (58 mg, 0.40 mmol) in acetonitrile (1 mL) was added. The resulting mixture was stirred at reflux for 16 h. After cooling to RT, the reaction mixture was filtered and washed with acetonitrile (5 mL), water (2×5 mL) and diisopropylether (5 mL). The urea precipitated during the washing steps and was collected by filtration. The solid was washed with water (5 mL) and diisopropylether (5 mL) and dried in vacuo to give the product (18 mg, 11%). $^1$H-NMR (DMSO-d$_6$) δ 10.24 (s, 1H), 9.80 (s, 1H), 8.94-8.93 (m, 1H), 8.57-8.55 (m, 1H), 8.42-8.40 (m, 1H), 7.76-7.57 (m, 7H), 7.25-7.24 (m, 1H), 6.82-6.81 (m, 1H). LC/MS (5-95%) M/Z: M+1 obs=424.6; $t_R$=8.44.

Method B: To a solution of 8-aminoquinoline (72 mg, 0.50 mmol) in acetonitrile (5 mL) was added diphosgene (66 μL, 0.55 mmol). The mixture was stirred under reflux for 2 h. Then, sulfathiazole (125 mg, 0.49 mmol) and triethylamine (167 μL, 1.12 mmol) were added. The mixture was stirred under reflux for another 2 h and then allowed to reach ambient temperature overnight. Water (5 mL) was added, and the solid was filtered off, washed with water and cold acetonitrile and dried in vacuo.

(4-Nitrophenyl)-thiazol-2-yl-amine

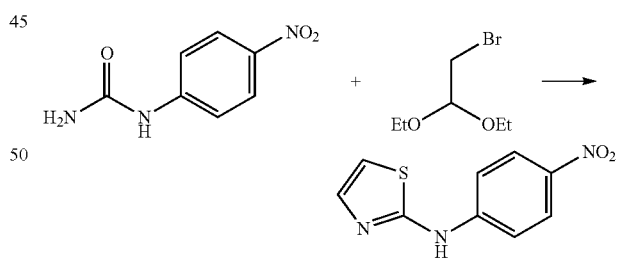

To a suspension of 1-(4-nitrophenyl)-2-thiourea (5.00 g, 25.4 mmol) in acetic acid (40 mL) was added bromoacetaldehyde diethyl acetal (3.94 mL, 25.4 mmol) at RT. The resulting mixture was heated to 100° C. for 2 h. After cooling to RT, the solvent was removed in vacuo. The residue was diluted with 1M NaOH (100 mL) and EtOAc (100 mL). The phases were separated, and the aqueous phase was extracted with EtOAc (2×100 mL). The combined organic extracts were dried over MgSO$_4$ and concentrated. Purification by column chromatography (20-80% EtOAc in hexanes) afforded the product as a yellow solid (2.75 g, 49%). $^1$H-NMR (400 MHz, DMSO-d$_6$) δ 11.02 (s, 8.231H), 8.23 (d, J=9.3 Hz, 2H), 7.85

(d, J=9.3 Hz, 2H), 7.41 (d, J=3.6 Hz, 1H), 7.15 (d, J=3.6 Hz, 1H). LC/MS (10-99%) M/Z: M+1 obs=222.1; $t_R$=2.50 min.

N-Thiazol-2-yl-benzene-1,4-diamine

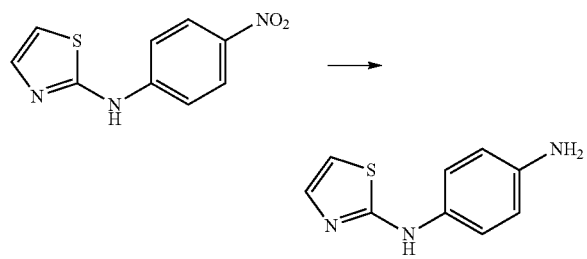

A mixture of 4-Nitrophenyl)-thiazol-2-yl-amine (917 mg, 4.15 mmol) and tin(II) chloride (2.36, 12.5 mmol) in EtOH (40 mL) and 1M HCl (40 mL) was heated to 80° C. for 6 h. After cooling to RT, water (100 mL) and EtOAc (100 mL) were added and the phases were separated. The aqueous phase was neutralized by addition of 1M NaHCO$_3$ and extracted with EtOAc (4×150 mL). The combined organic extracts were dried over MgSO$_4$ and concentrated. The residue was filtered through a silica pad (hexanes:EtOAc, 1:1), and the filtrate was concentrated to give the product as a yellow-white solid (340 mg, 39%). $^1$H-NMR (400 MHz, DMSO-d$_6$) δ 9.56 (s, 1H), 7.21 (d, J=6.6 Hz, 2H), 7.12 (d, J=3.6 Hz, 1H), 6.70 (d, J=3.7 Hz, 1H), 6.53 (d, J=6.6 Hz, 2H), 4.81 (s, 2H). LC/MS (10-99%) M/Z: obs=192.3; $t_R$=0.39 min.

{4-[(Thiazole-2-carbonyl)-amino]-phenyl}-carbamic acid tert-butyl ester

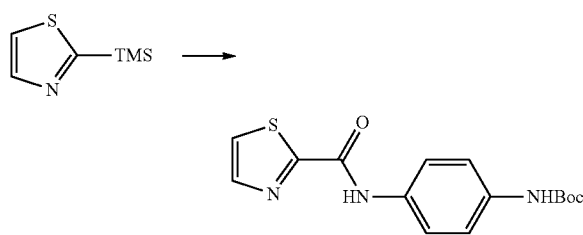

To a solution of 2-TMS-thiazole (2.25 mL, 14.1 mmol) in DCM (5 mL) at 0° C. was slowly added a solution of phosgene in toluene (20%, 7.45 mL, 14.1 mmol) over 15 Min. After stirring for 2 h at RT, the resulting solution was slowly added via syringe to a solution of N-BOC-1,4-phenylenediamine (4.42 g, 21.2 mmol) and pyridine (2.3 mL, 28.2 mmol) in DCM (100 mL) at 0° C. After stirring for 20 h at RT, the reaction mixture was quenched by addition of sat. NaHCO$_3$ (100 mL), EtOAc (150 mL) was added, and the phases were separated. The aqueous phase was extracted with EtOAc (2×75 mL), and the combined organic extracts were dried over MgSO$_4$ and concentrated in vacuo. Purification by column chromatography (10-50% EtOAc in hexanes) afforded the product as an orange solid (452 mg, 10%). $^1$H-NMR (400 MHz, DMSO-d$_6$) δ 10.66 (s, 1H), 9.34 (s, 1H), 8.12 (d, J=3.1 Hz, 1H), 8.09 (d, J=3.1 Hz, 1H), 7.72 (d, J=7.0 Hz, 2H), 7.42 (d, J=8.9 Hz, 2H), 1.48 (s, 9H). LC/MS (10-99%) M/Z: M+1 obs=320.3; $t_R$=2.90 min.

Thiazole-2-carboxylic acid (4-amino-phenyl)-amide

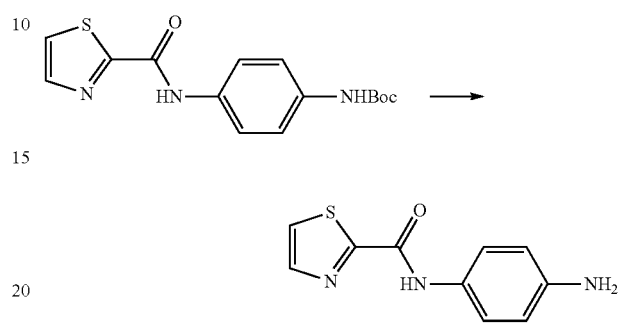

To a solution of the N-BOC-protected amine (452 mg, 1.42 mmol) in DCM (2.5 mL) was added TFA (2.5 mL). After stirring for 1 h at RT, the reaction mixture was poured into sat. NaHCO$_3$ (50 mL) and extracted with EtOAc (2×50 mL). The combined organic extracts were dried over MgSO$_4$, concentrated in vacuo and used without further purification in the next reaction. $^1$H-NMR (400 MHz, DMSO-d$_6$) δ 10.26 (s, 1H), 7.99 (d, J=3.1 Hz, 1H), 7.97 (d, J=3.1 Hz, 1H), 7.37 (d, J=8.8 Hz, 2H), 6.45 (d, J=8.8 Hz, 2H), 4.92 (s, 2H). LC/MS (10-99%) M/Z: M+1 obs=220.3; $t_R$=0.57 min.

Thiazole-2-carboxylic acid 4-tert-butoxycarbonylamino-phenyl ester

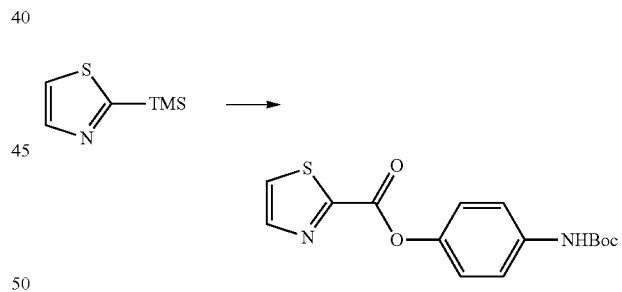

To a solution of 2-TMS-thiazole (2.25 mL, 14.1 mmol) in DCM (5 mL) at 0° C. was slowly added a solution of phosgene in toluene (20%, 7.45 mL, 14.1 mmol) over 15 Min. After stirring for 2 h at RT, the resulting solution was slowly added via syringe to a solution of N-BOC-4-hydroxyaniline (4.39 g, 21.2 mmol) and pyridine (2.3 mL, 28.2 mmol) in DCM (100 mL) at 0° C. After stirring for 20 h at RT, the reaction mixture was quenched by addition of sat. NaHCO$_3$ (100 mL), EtOAc (150 mL) was added, and the phases were separated. The aqueous phase was extracted with EtOAc (2×75 mL), and the combined organic extracts were dried over MgSO$_4$ and concentrated in vacuo. Purification by column chromatography (10-50% EtOAc in hexanes) afforded the product as a green solid (518 mg, 12%). $^1$H-NMR (400 MHz, DMSO-d$_6$) δ 9.49 (s, 1H), 8.29 (d, J=3.0 Hz, 1H), 8.22

(d, J=3.0 Hz, 1H), 7.53 (d, J=8.9 Hz, 2H), 7.23 (d, J=6.9 Hz, 2H), 1.48 (s, 9H). LC/MS (10-99%) M/Z: M$^+$1 obs=321.1; $t_R$=2.94 min.

Thiazole-2-carboxylic 4-amino-phenyl ester

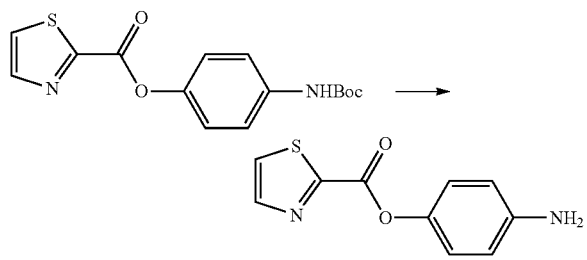

To a solution of the N-BOC-protected amine (515 mg, 1.61 mmol) in DCM (2.5 mL) was added TFA (2.5 mL). After stirring for 1 h at RT, the reaction mixture was poured into sat. NaHCO$_3$ (50 mL) and extracted with EtOAc (2×50 mL). The combined organic extracts were dried over MgSO$_4$, concentrated in vacuo and used without further purification in the next reaction. $^1$H-NMR (400 MHz, DMSO-d$_6$) δ 8.25 (d, J=3.0 Hz, 1H), 8.19 (d, J=3.0 Hz, 1H), 6.94 (d, J=8.8 Hz, 2H), 6.59 (d, J=8.8 Hz, 2H), 5.17 (s, 2H). LC/MS (10-99%) M/Z: M$^+$1 obs=221.1; $t_R$=0.59 min.

3-(3,4-Dihydro-2H-quinolin-1-yl)-propionic acid

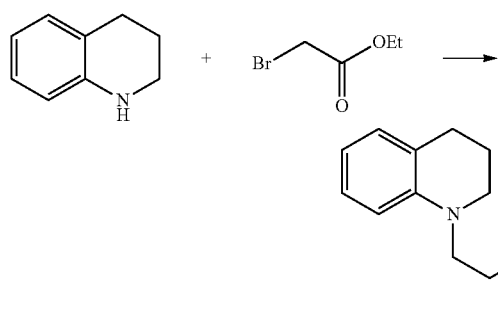

A solution of ethyl bromoacetate (0.75 g, 4.5 mmol) and 1,2,3,4-tetrahydroquinoline (0.57 mL, 4.5 mmol) in DMF (10 mL) was microwaved at 200° C. for 300 s. The solvent was removed in vacuo, and the residue was redissolved in MeOH (12.5 mL). 1M NaOH (12.5 mL) was added, and the reaction mixture was heated to 80° C. for 2.5 h. After cooling to RT, EtOAc (30 mL) and water (30 mL) were added, the phases were separated, the aqueous layer was acidified to pH 2-3 by addition of 6M HCl and extracted with EtOAc (3×30 mL). The combined organic extracts were dried over MgSO$_4$ and concentrated in vacuo to give the product (640 mg, 75%) as a white solid. $^1$H-NMR (400 MHz, DMSO-d$_6$) δ 6.94-6.88 (m, 2H), 1H), 6.38 (d, J=8.2 Hz, 1H), 3.98 (s, 2H), 3.32 (t, J=5.6 Hz, 2H), 2.69 (t, J=6.3 Hz, 2H), 1.92-1.84 (m, 2H). LC/MS (10-99%) M/Z: M$^+$1 obs=192.3; $t_R$=2.39 min.

General Procedure 4 for Amide Couplings:

A mixture of the corresponding acid (0.2 mmol), amine (0.2 mmol), triethylamine (28 μL, 0.2 mmol) and HATU (76 mg, 0.2 mmol) in pyridine (0.5 mL) was microwaved at 200° C. for 420 s. The reaction mixture was diluted with 50% DMSO/MeOH (0.5 mL), filtered and purified by HPLC (gradient of 10-99% CH$_3$CN/water).

4-(2,4-Dichloro-phenoxy)-N-[4-(thiazol-2-ylamino)-phenyl]-butyramide

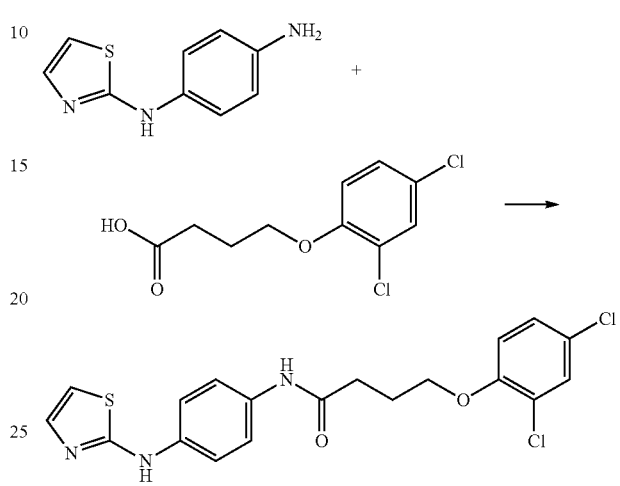

Synthesized according to general procedure 4. $^1$H-NMR (400 MHz, DMSO-d$_6$) δ 10.09 (s, 1H), 9.86 (s, 1H), 7.58-7.50 (m, 5H), 7.37 (dd, J=8.9, 2.6 Hz, 1H), 7.23-7.19 (m, 2H), 6.86 (d, J=3.7 Hz, 1H), 4.12 (t, J=6.3 Hz, 2H), 2.56-2.45 (m, 2H), 2.09-2.02 (m, 2H). LC/MS (10-99%) M/Z: M$^+$1 obs=422.1; $t_R$=2.67 min.

2-(3,4-Dihydro-2H-quinolin-1-yl)-N-[4-thiazol-2-ylamino)-phenyl]-acetamide

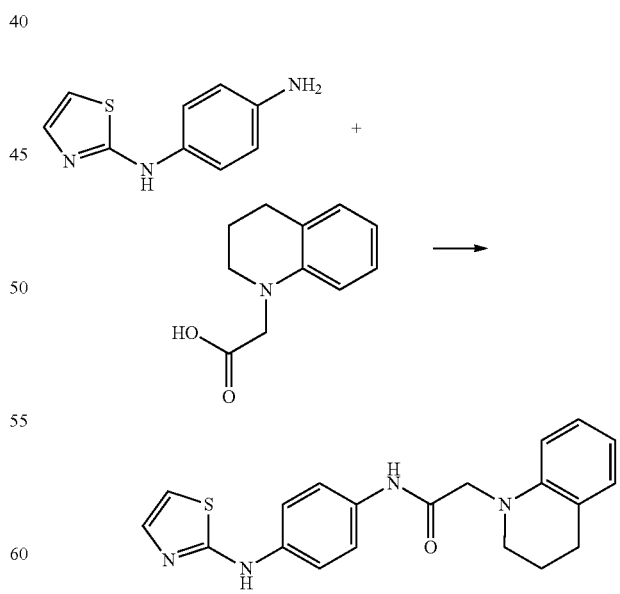

Synthesized according to general procedure 4. $^1$H-NMR (400 MHz, DMSO-d$_6$) δ 10.15 (s, 1H), 9.88 (s, 1H), 7.56-7.51 (m, 4H), 7.23 (d, J=3.7 Hz, 1H), 6.95-6.87 (m, 3H), 6.50 (td, J=7.3, 0.9 Hz, 1H), 6.44 (d, J=8.1 Hz, 4.02 (s, 2H), 3.42 (t, J=5.6 Hz, 2H), 2.72 (t, J=6.3 Hz, 2H), 1.96-1.90 (m, 2H). LC/MS (10-99%) M/Z: M⁺1 obs=365.1; $t_R$=2.41 min.

N-[4-(Thiazol-2-ylamino)-phenyl]-2-(8-trifluoromethyl-quinolin-4-yloxy)-acetamide

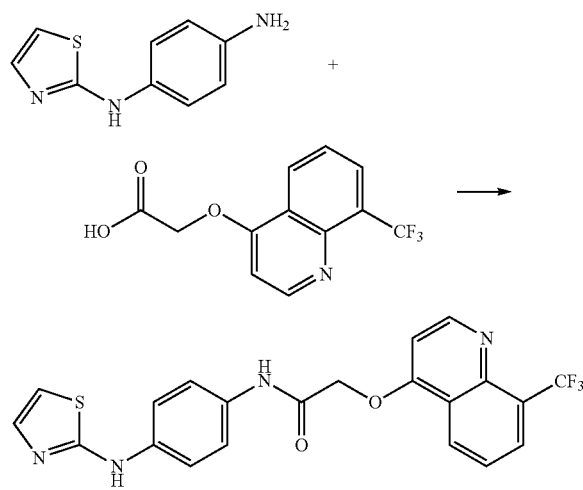

Synthesized according to general procedure 4. ¹H-NMR (400 MHz, DMSO-d₆) δ 10.23 (s, 1H), 10.19 (s, 1H), 8.90 (d, J=5.3 Hz, 1H), 8.63 (d, J=7.6 Hz, 1H), 8.22 (d, J=6.8 Hz, 1H), 7.75 (t, J=7.9 Hz, 1H), 7.61-7.52 (m, 4H), 7.24 (d, J=3.7 Hz, 1H), 7.17 (d, J=5.3 Hz, 1H), 6.89 (d, J=3.7 Hz, 1H), 5.08 (s, 2H). LC/MS (10-99%) M/Z: M¹-1 obs=445.3; $t_R$=2.29 min.

Thiazole-2-carboxylic acid {4-[4-(2,4-dichloro-phenoxy)-butyrylamino]phenyl}-amide

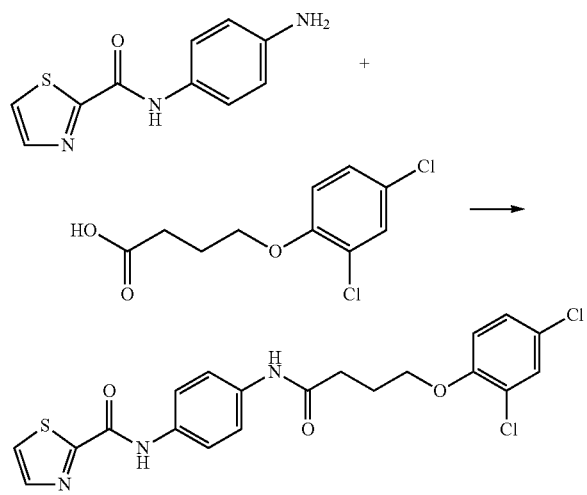

Synthesized according to general procedure 4. ¹H-NMR (400 MHz, DMSO-d₆) δ H NMR (400 MHz, DMSO-d6) δ 10.72 (s, 1H), 9.98 (s, 1H), 8.13 (d, J=3.1 Hz, 1H), 8.10 (d, J=3.1 Hz, 1H), 7.79-7.75 (m, 2H), 7.59-7.56 (m, 3H), 7.37 (dd, J=8.9, 2.6 Hz, 1H), 7.20 (d, J=8.9 Hz, 1H), 4.13 (t, J=6.3 Hz, 2H), 3.37-3.31 (m, 2H), 2.09-2.03 (m, 2H). LC/MS (10-99%) M/Z: M⁺1 obs=450.3; $t_R$=3.34 min.

Thiazole-2-carboxylic acid [4-(2,3,4-dihydro-2H-quinolin-1-yl-acetylamino)-phenyl]-amide

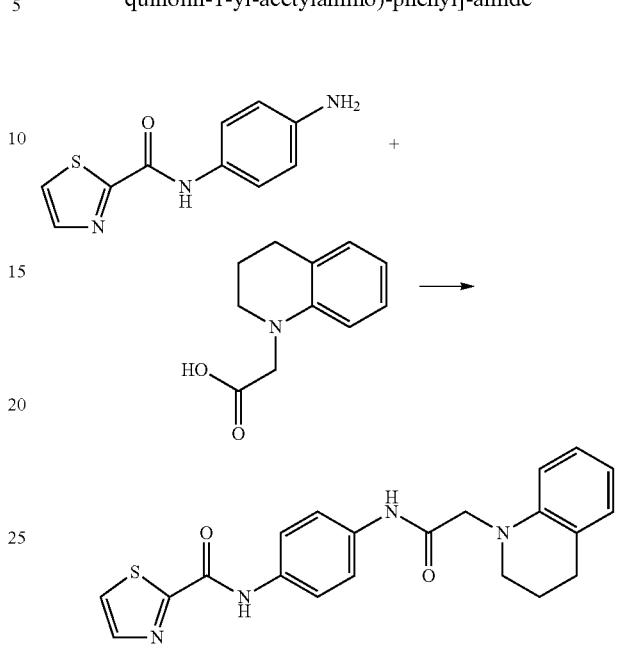

Synthesized according to general procedure 4. ¹H-NMR (400 MHz, DMSO-d₆) δ H NMR (400 MHz, DMSO-d6) δ 10.73 (s, 1H), 10.00 (s, 1H), 8.13 (d, J=3.1 Hz, 1H), 8.10 (d, J=3.1 Hz, 1H), 7.78 (d, J=9.0 Hz, 2H), 7.58 (d, J=9.0 Hz, 2H), 6.96-6.89 (m, 2H), 6.52-6.44 (m, 2H), 4.05 (s, 2H), 3.42 (t, J=5.6 Hz, 2H), 2.73 (t, J=6.3 Hz, 2H), 1.96-1.90 (m, 2H). LC/MS (10-99%) M/Z: M⁺1 obs=393.1; $t_R$=3.07 min.

Thiazole-2-carboxylic acid {4-[2-(8-trifluoromethyl-quinolin-4-yloxy)-acetylamino]-phenyl}-amide

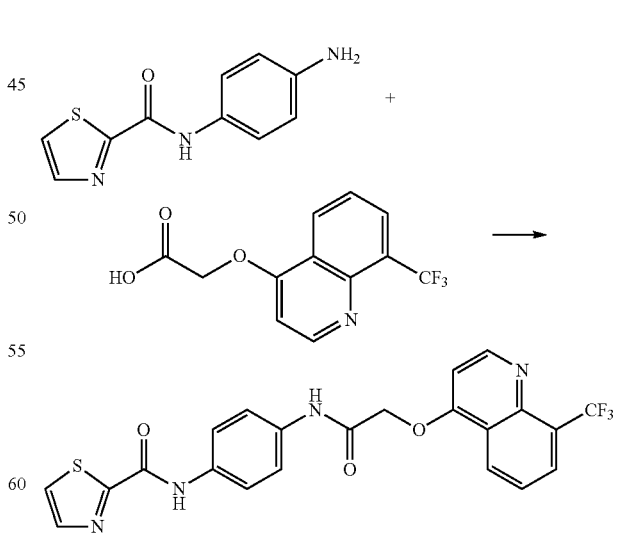

Synthesized according to general procedure 4. ¹H-NMR (400 MHz, DMSO-d₆) δ 10.78 (s, 1H), 10.34 (s, 1H), 8.90 (d, J=5.3 Hz, (d, J=8.1 Hz, 1H), 8.22 (d, J=7.0 Hz, 1H), 8.14 (d, J=3.1 Hz, 1H), 8.11 (d, J=3.1 Hz, 1H), 7.84-7.82 (m, 2H), 7.76 (t, J=7.9 Hz, 1H), 7.63-7.61 (m, 2H), 7.18 (d, J=5.3 Hz, 1H), 5.11 (s, 2H). LC/MS (10-99%) M/Z: M+1 obs=473.1; $t_R$=2.82 min.

Thiazole-2-carboxylic acid 4-[4-(2,4-dichloro-phenoxy)-butyrylamino]-phenyl ester

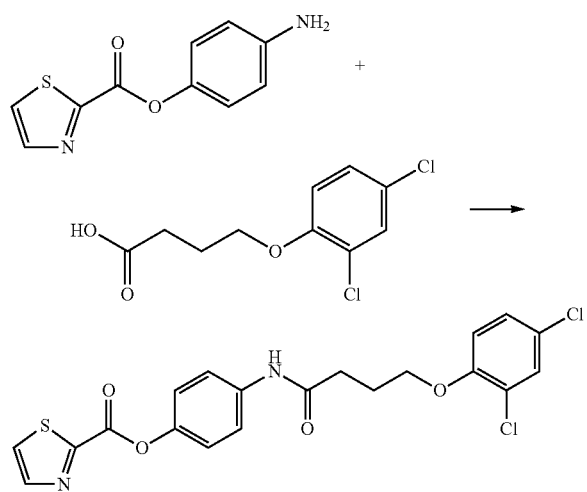

Synthesized according to general procedure 4. $^1$H-NMR (400 MHz, DMSO-$d_6$) δ H NMR (400 MHz, DMSO-d6) δ 10.11 (s, 1H), 8.30 (d, J=3.0 Hz, 1H), 8.24 (d, J=3.0 Hz, 1H), 7.71-7.67 (m, 2H), 7.58 (d, J=2.6 Hz, 1H), 7.38 (dd, J=8.9, 2.6 Hz, 1H), 7.30-7.26 (m, 2H), 7.21 (d, J=8.9 Hz, 1H), 4.14 (t, J=6.3 Hz, 2H), 2.55 (t, 2H), 2.34-2.30 (m, 2H). LC/MS (10-99%) M/Z: M+1 obs=451.0; $t_R$=3.58 min.

Thiazole-2-carboxylic acid 4-(2,3,4-dihydro-2H-quinolin-1-yl-acetylamino)-phenyl ester

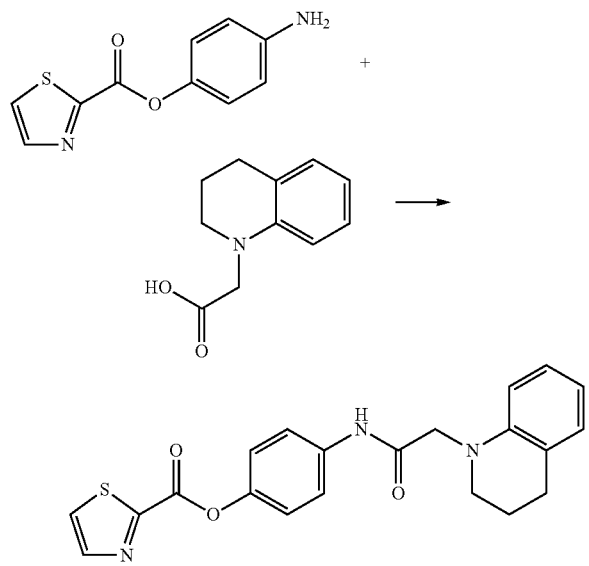

Synthesized according to general procedure 4. $^1$H-NMR (400 MHz, DMSO-$d_6$) δ H NMR (400 MHz, DMSO-d6) δ 10.14 (s, 1H), 8.30 (d, J=3.0 Hz, 1H), 8.23 (d, J=3.0 Hz, 1H), 7.72-7.68 (m, 2H), 7.31-7.27 (m, 2H), 6.96-6.90 (m, 2H), 6.51 (dt, J=9.7, 3.9 Hz, 1H), 6.45 (d, J=8.1 Hz, 1H), 4.08 (s, 2H), 3.43 (t, J=5.6 Hz, 2H), 2.73 (t, J=6.3 Hz, 2H), 1.96-1.90 (m, 2H). LC/MS (10-99%) M/Z: M+1 obs=394.2; $t_R$=3.30 min.

Thiazole-2-carboxylic acid 4-[2-(8-trifluoromethyl-quinolin-4-yloxy)-acetylamino]-phenyl ester

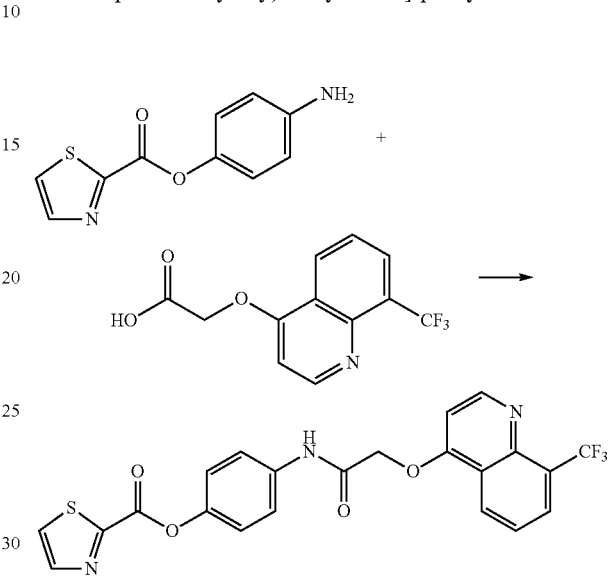

Synthesized according to general procedure 4. $^1$H-NMR (400 MHz, DMSO-$d_6$) δ H NMR (400 MHz, DMSO-d6) δ 10.47 (s, 1H), 8.90 (d, J=5.3 Hz, 1H), 8.63 (d, J=7.7 Hz, 1H), 8.31 (d, J=3.0 Hz, 1H), 8.24 (d, J=3.0 Hz, 1H), 8.22 (d, J=7.0 Hz, 1H), 7.78-7.71 (m, 3H), 7.36-7.32 (m, 2H), 7.19 (d, J=5.3 Hz, 1H), 5.14 (s, 2H). LC/MS (10-99%) M/Z: M+1 obs=474.0; $t_R$=3.06 min.

The analytical data for selected compounds recited in FIG. 1 are shown below in Table 2.

TABLE 2

| Cmpd # | LC/MS M+ | RT (min) |
| --- | --- | --- |
| 4 | 390.20 | 2.51 |
| 36 | 440.00 | 4.30 |
| 38 | 441.00 | 2.43 |
| 43 | 388.00 | 2.56 |
| 63 | 447.20 | 3.06 |
| 74 | 408.00 | 3.95 |
| 91 | 440.30 | 2.96 |
| 110 | 454.10 | 2.97 |
| 124 | 374.00 | 2.59 |
| 127 | 428.00 | 2.87 |
| 142 | 495.00 | 3.23 |
| 143 | 486.20 | 2.96 |
| 144 | 453.00 | 3.01 |
| 147 | 445.20 | 3.23 |
| 155 | 467.20 | 3.11 |
| 157 | 403.00 | 3.16 |
| 161 | 400.00 | 2.63 |
| 162 | 411.00 | 2.18 |
| 163 | 411.00 | 1.99 |
| 164 | 401.00 | 2.18 |
| 165 | 425.00 | 2.13 |
| 166 | 411.00 | 2.86 |
| 167 | 414.00 | 2.81 |
| 168 | 440.00 | 2.90 |

TABLE 2-continued

| Cmpd # | LC/MS M+ | RT (min) |
|---|---|---|
| 170 | 442.20 | 1.85 |
| 171 | 427.10 | 3.09 |
| 172 | 402.30 | 2.53 |
| 173 | 447.30 | 3.03 |
| 174 | 427.30 | 2.61 |
| 175 | 404.00 | 2.55 |
| 186 | 408.00 | 2.62 |
| 193 | 475.00 | 3.11 |
| 225 | 426.00 | 2.86 |
| 232 | 480.00 | 3.16 |
| 233 | 501.20 | 3.29 |
| 234 | 498.20 | 3.25 |
| 235 | 484.00 | 3.49 |
| 236 | 498.20 | 3.51 |
| 237 | 511.20 | 3.26 |
| 238 | 509.20 | 3.26 |
| 239 | 511.20 | 3.31 |
| 240 | 481.00 | 3.24 |
| 241 | 511.20 | 3.34 |
| 242 | 432.20 | 2.97 |
| 243 | 453.00 | 3.12 |
| 244 | 450.00 | 3.07 |
| 245 | 436.20 | 3.32 |
| 246 | 463.20 | 3.09 |
| 247 | 461.20 | 3.05 |
| 248 | 463.20 | 3.13 |
| 249 | 433.20 | 3.03 |
| 250 | 428.20 | 2.89 |
| 251 | 461.20 | 3.07 |
| 252 | 479.00 | 3.25 |
| 253 | 479.00 | 3.12 |
| 254 | 466.00 | 3.10 |
| 255 | 515.00 | 3.84 |
| 256 | 463.20 | 3.15 |
| 257 | 449.20 | 3.10 |
| 258 | 454.00 | 3.04 |
| 259 | 411.00 | 3.11 |
| 260 | 446.20 | 3.02 |
| 261 | 469.00 | 3.20 |
| 262 | 452.00 | 3.41 |
| 263 | 397.00 | 3.04 |
| 264 | 450.00 | 3.37 |
| 265 | 463.20 | 3.19 |
| 266 | 469.00 | 3.07 |
| 267 | 473.00 | 3.19 |
| 268 | 483.00 | 3.17 |
| 269 | 405.20 | 2.70 |
| 270 | 415.00 | 2.59 |
| 271 | 420.80 | 2.72 |
| 272 | 401.00 | 2.56 |
| 273 | 406.00 | 2.55 |
| 274 | 411.20 | 2.81 |
| 275 | 417.20 | 2.90 |
| 276 | 397.20 | 2.76 |
| 277 | 427.20 | 2.96 |
| 278 | 402.20 | 2.75 |
| 279 | 458.20 | 2.98 |
| 280 | 474.20 | 1.98 |
| 281 | 389.00 | 3.05 |
| 282 | 431.20 | 3.15 |
| 283 | 465.80 | 3.14 |
| 284 | 481.00 | 3.21 |
| 285 | 487.00 | 3.27 |
| 286 | 484.20 | 3.21 |
| 287 | 470.20 | 3.46 |
| 288 | 484.20 | 3.47 |
| 289 | 497.20 | 3.21 |
| 290 | 495.20 | 3.20 |
| 291 | 497.20 | 3.24 |
| 292 | 466.80 | 3.16 |
| 293 | 497.20 | 3.28 |
| 294 | 472.20 | 3.09 |
| 295 | 432.20 | 2.79 |
| 296 | 447.20 | 2.90 |
| 297 | 453.20 | 2.95 |
| 298 | 463.20 | 2.92 |
| 299 | 461.40 | 2.89 |
| 300 | 463.20 | 3.00 |
| 301 | 433.40 | 2.85 |
| 302 | 438.20 | 2.79 |
| 303 | 389.20 | 2.35 |
| 304 | 374.60 | 2.92 |
| 305 | 417.00 | 3.06 |
| 306 | 470.20 | 3.07 |
| 307 | 470.00 | 3.34 |
| 308 | 485.20 | 3.08 |
| 309 | 483.00 | 3.15 |
| 310 | 452.00 | 2.95 |
| 311 | 536.20 | 3.48 |
| 312 | 592.20 | 3.55 |
| 313 | 596.20 | 3.62 |
| 314 | 514.20 | 3.27 |
| 315 | 526.20 | 3.31 |
| 316 | 542.40 | 3.53 |
| 317 | 562.40 | 3.53 |
| 318 | 500.00 | 3.37 |
| 319 | 527.20 | 3.37 |
| 320 | 487.00 | 3.09 |
| 321 | 455.80 | 3.31 |
| 322 | 481.00 | 3.05 |
| 323 | 404.20 | 2.49 |
| 324 | 397.20 | 2.37 |
| 325 | 471.20 | 3.66 |
| 326 | 457.40 | 3.60 |
| 327 | 471.20 | 3.74 |
| 328 | 485.40 | 3.78 |
| 329 | 471.20 | 3.81 |
| 330 | 485.40 | 3.87 |
| 331 | 473.20 | 3.42 |
| 332 | 417.20 | 3.22 |
| 333 | 431.40 | 3.36 |
| 334 | 443.40 | 3.42 |
| 335 | 459.40 | 3.72 |
| 336 | 493.20 | 3.67 |
| 337 | 489.00 | 3.69 |
| 338 | 432.20 | 3.00 |
| 339 | 417.20 | 2.81 |
| 340 | 435.20 | 2.43 |
| 341 | 441.20 | 2.57 |
| 342 | 426.00 | 2.39 |
| 343 | 409.20 | 2.69 |
| 344 | 415.00 | 2.82 |
| 345 | 400.00 | 2.65 |
| 346 | 459.20 | 3.10 |
| 347 | 465.00 | 3.18 |
| 348 | 461.20 | 3.18 |
| 349 | 466.80 | 3.26 |
| 350 | 452.00 | 3.07 |
| 351 | 421.00 | 2.55 |
| 352 | 427.00 | 2.69 |
| 353 | 411.60 | 2.51 |
| 354 | 385.00 | 2.62 |
| 355 | 391.20 | 2.69 |
| 356 | 376.00 | 2.55 |
| 357 | 410.20 | 2.62 |
| 358 | 476.20 | 3.22 |
| 359 | 482.20 | 3.26 |
| 360 | 467.00 | 3.12 |
| 361 | 410.20 | 2.78 |
| 362 | 467.90 | 4.06 |
| 363 | 474.86 | 4.05 |
| 364 | 459.86 | 3.87 |
| 365 | 437.89 | 3.79 |
| 366 | 467.90 | 4.10 |
| 367 | 474.85 | 4.23 |
| 368 | 459.84 | 3.95 |
| 369 | 475.99 | 4.30 |
| 370 | 465.92 | 4.13 |
| 371 | 460.95 | 3.95 |
| 372 | 467.96 | 4.00 |
| 373 | 451.92 | 3.83 |
| 374 | 466.90 | 4.29 |
| 375 | 451.95 | 4.10 |
| 376 | 424.90 | 3.63 |

TABLE 2-continued

| Cmpd # | LC/MS M+ | RT (min) |
|---|---|---|
| 377 | 438.90 | 3.93 |
| 378 | 433.20 | 2.80 |
| 379 | 433.20 | 2.80 |
| 380 | 424.00 | 2.85 |
| 381 | 443.20 | 2.94 |
| 382 | 449.00 | 3.10 |
| 383 | 434.00 | 2.96 |
| 384 | 487.20 | 2.57 |
| 385 | 472.20 | 2.41 |
| 386 | 439.20 | 2.71 |
| 387 | 445.40 | 2.84 |
| 388 | 430.10 | 2.79 |
| 389 | 425.20 | 2.89 |
| 390 | 431.00 | 2.98 |
| 391 | 416.20 | 2.82 |
| 392 | 429.20 | 3.27 |
| 393 | 420.20 | 3.15 |
| 394 | 537.20 | 3.58 |
| 395 | 528.20 | 3.50 |
| 396 | 525.40 | 3.45 |
| 397 | 519.00 | 3.40 |
| 398 | 510.20 | 3.29 |
| 399 | 500.00 | 3.19 |
| 400 | 514.00 | 3.04 |
| 401 | 455.40 | 3.74 |
| 402 | 521.40 | 3.79 |
| 403 | 459.00 | 1.70 |
| 404 | 408.20 | 2.63 |
| 405 | 414.20 | 2.74 |
| 406 | 399.00 | 2.60 |
| 407 | 422.20 | 2.89 |
| 408 | 428.20 | 2.96 |
| 409 | 413.00 | 2.84 |
| 410 | 429.50 | 2.68 |
| 411 | 399.10 | 2.51 |
| 412 | 417.10 | 2.78 |
| 413 | 483.30 | 3.08 |
| 414 | 413.30 | 2.83 |
| 415 | 411.30 | 2.83 |
| 416 | 427.00 | 2.90 |
| 417 | 459.00 | 2.32 |
| 418 | 509.00 | 3.32 |
| 419 | 475.00 | 3.10 |
| 420 | 500.00 | 3.23 |
| 421 | 500.00 | 3.21 |
| 422 | 470.00 | 3.19 |
| 423 | 447.00 | 3.05 |
| 424 | 433.00 | 2.86 |
| 425 | 399.00 | 2.58 |
| 426 | 451.00 | 2.81 |
| 428 | 502.00 | 4.42 |
| 429 | 432.00 | 4.29 |
| 430 | 486.00 | 4.41 |
| 431 | 486.00 | 4.36 |
| 432 | 436.00 | 4.09 |
| 439 | 462.00 | 4.54 |
| 440 | 434.00 | 4.09 |
| 441 | 424.00 | 4.19 |
| 442 | 415.00 | 3.82 |
| 443 | 432.00 | 3.72 |
| 444 | 454.00 | 4.19 |
| 448 | 404.00 | 4.15 |
| 471 | 100.00 | 3.30 |
| 472 | 497.20 | 3.60 |
| 473 | 443.40 | 3.15 |
| 474 | 100.00 | 3.37 |
| 475 | 158.00 | 2.98 |
| 476 | 436.00 | 4.12 |
| 477 | 432.00 | 4.49 |
| 478 | 418.00 | 4.27 |
| 479 | 454.00 | 4.12 |
| 480 | 420.00 | 3.97 |
| 481 | 442.00 | 4.20 |
| 482 | 537.00 | 3.40 |
| 484 | 456.00 | 4.07 |
| 485 | 470.00 | 4.30 |
| 486 | 466.00 | 4.02 |
| 487 | 434.00 | 3.92 |
| 488 | 484.00 | 4.44 |
| 489 | 447.00 | 3.47 |
| 490 | 444.00 | 3.69 |
| 491 | 472.00 | 4.52 |
| 492 | 520.00 | 4.47 |
| 493 | 458.00 | 3.70 |
| 494 | 509.00 | 3.60 |
| 495 | 445.00 | 3.84 |
| 496 | 461.00 | 3.82 |
| 497 | 464.00 | 4.15 |
| 498 | 461.00 | 4.00 |
| 499 | 432.00 | 3.95 |
| 500 | 504.00 | 4.41 |
| 501 | 504.00 | 4.44 |
| 502 | 472.00 | 4.44 |
| 503 | 520.00 | 4.38 |
| 504 | 473.00 | 3.45 |
| 505 | 471.00 | 3.62 |
| 506 | 416.00 | 3.45 |
| 507 | 462.00 | 3.38 |
| 508 | 454.00 | 3.80 |
| 509 | 459.00 | 3.99 |
| 510 | 451.00 | 3.26 |
| 511 | 475.00 | 4.02 |
| 512 | 443.00 | 5.27 |
| 513 | 492.00 | 5.43 |
| 514 | 435.00 | 3.63 |
| 515 | 477.00 | 3.74 |
| 516 | 487.00 | 4.39 |
| 517 | 521.00 | 4.39 |
| 518 | 500.00 | 4.19 |
| 519 | 482.00 | 3.77 |
| 520 | 470.00 | 3.87 |
| 521 | 488.00 | 4.30 |
| 522 | 470.00 | 3.94 |
| 523 | 451.00 | 4.01 |
| 524 | 453.00 | 4.02 |
| 525 | 480.00 | 4.07 |
| 526 | 470.00 | 3.89 |
| 527 | 463.00 | 3.95 |
| 528 | 521.00 | 4.39 |
| 529 | 482.00 | 4.04 |
| 530 | 502.00 | 4.46 |
| 531 | 454.00 | 4.15 |
| 532 | 447.00 | 3.74 |
| 533 | 433.00 | 3.40 |
| 534 | 460.00 | 3.32 |
| 535 | 474.00 | 3.50 |
| 536 | 434.00 | 3.34 |
| 537 | 476.00 | 4.12 |
| 538 | 455.00 | 3.41 |
| 539 | 441.00 | 5.36 |
| 540 | 442.00 | 3.12 |
| 541 | 510.00 | 4.44, |
| 542 | 450.00 | 5.70 |
| 543 | 443.00 | 4.72 |
| 544 | 451.00 | 4.31 |
| 545 | 441.00 | 5.10 |
| 546 | 444.00 | 3.81 |
| 547 | 444.00 | 4.72 |
| 548 | 426.00 | 3.57 |
| 549 | 459.00 | 3.95 |
| 550 | 442.30 | 0.57 |
| 551 | 381.10 | 2.36 |
| 552 | 456.30 | 2.98 |
| 553 | 492.30 | 3.17 |
| 554 | 424.10 | 2.46 |
| 555 | 466.10 | 3.07 |
| 556 | 400.30 | 2.70 |
| 557 | 479.10 | 2.23 |
| 558 | 506.10 | 3.12 |
| 559 | 436.00 | 2.55 |
| 560 | 418.00 | 2.68 |
| 561 | 450.00 | 2.79 |
| 562 | 429.00 | 2.71 |
| 563 | 415.00 | 2.59 |

TABLE 2-continued

| Cmpd # | LC/MS M+ | RT (min) |
|---|---|---|
| 564 | 460.00 | 3.63 |
| 565 | 462.00 | 5.07 |
| 566 | 436.00 | 3.69 |
| 567 | 448.00 | 3.45 |
| 568 | 523.00 | 5.15 |
| 569 | 448.00 | 3.57 |
| 570 | 504.00 | 4.00 |
| 571 | 500.00 | 4.14 |
| 572 | 448.00 | 3.52 |
| 573 | 477.00 | 3.67 |
| 574 | 465.00 | 4.97 |
| 575 | 467.00 | 2.58 |
| 576 | 444.00 | 4.38 |
| 577 | 490.00 | 4.79 |
| 578 | 399.10 | 2.29 |
| 579 | 413.30 | 2.43 |
| 580 | 400.30 | 1.73 |
| 581 | 428.30 | 1.88 |
| 582 | 427.30 | 2.65 |
| 583 | 427.30 | 2.51 |
| 584 | 477.10 | 2.93 |
| 585 | 431.30 | 2.55 |
| 586 | 411.10 | 2.75 |
| 587 | 414.30 | 2.86 |
| 588 | 442.00 | 4.89 |
| 589 | 470.00 | 3.42 |
| 590 | 260.10 | 3.20 |
| 591 | 246.30 | 3.10 |
| 592 | 430.30 | 2.68 |
| 593 | 234.10 | 2.71 |
| 594 | 416.30 | 2.60 |
| 595 | 425.10 | 1.79 |
| 596 | 425.10 | 1.78 |
| 597 | 457.30 | 2.18 |
| 598 | 444.00 | 2.84 |
| 599 | 464.00 | 3.07 |
| 600 | 484.00 | 3.10 |
| 601 | 494.00 | 3.04 |
| 602 | 500.00 | 3.00 |
| 603 | 500.00 | 3.05 |
| 604 | 530.00 | 3.18 |
| 605 | 470.00 | 4.51 |
| 606 | 473.00 | 4.66 |
| 607 | 457.00 | 2.78 |
| 608 | 418.00 | 3.09 |
| 609 | 397.00 | 2.01 |
| 610 | 429.00 | 2.14 |
| 611 | 486.00 | 3.29 |
| 612 | 500.00 | 3.37 |
| 613 | 474.00 | 3.01 |
| 614 | 446.00 | 3.68 |
| 615 | 441.00 | 1.87 |
| 616 | 442.00 | 2.29 |
| 617 | 443.00 | 2.67 |
| 618 | 442.00 | 2.21 |
| 619 | 430.00 | 3.04 |
| 620 | 442.00 | 2.77 |
| 621 | 430.00 | 2.80 |
| 622 | 430.00 | 3.06 |
| 623 | 414.00 | 1.93 |
| 624 | 439.00 | 2.19 |
| 625 | 443.00 | 2.31 |
| 626 | 425.00 | 2.11 |
| 627 | 434.00 | 2.85 |
| 628 | 464.00 | 2.93 |
| 629 | 429.00 | 2.78 |
| 630 | 433.00 | 2.71 |
| 631 | 449.00 | 2.87 |
| 632 | 497.00 | 3.03 |
| 633 | 485.00 | 3.28 |
| 634 | 442.00 | 2.29 |
| 635 | 442.00 | 2.25 |
| 636 | 473.00 | 2.62 |
| 637 | 475.00 | 2.93 |
| 638 | 442.00 | 2.91 |
| 639 | 442.00 | 3.05 |
| 640 | 475.00 | 2.12 |
| 641 | 459.00 | 2.02 |
| 642 | 459.00 | 1.84 |
| 643 | 430.00 | 2.14 |
| 644 | 509.00 | 2.43 |
| 645 | 413.00 | 2.55 |
| 646 | 399.00 | 2.36 |
| 647 | 528.00 | 2.30 |
| 648 | 563.30 | 4.71 |
| 649 | 563.30 | 4.71 |
| 650 | 487.30 | 3.13 |
| 651 | 517.10 | 3.28 |
| 652 | 517.10 | 3.32 |
| 653 | 528.90 | 3.45 |
| 654 | 308.10 | 3.25 |
| 655 | 497.10 | 3.12 |
| 656 | 489.00 | 1.98 |
| 657 | 445.00 | 2.64 |
| 658 | 429.00 | 1.92 |
| 659 | 487.00 | 3.41 |
| 660 | 459.00 | 2.83 |
| 682 | 480.00 | 3.19 |
| 683 | 438.00 | |
| 684 | 426.00 | |
| 685 | 426.00 | |
| 686 | 440.00 | |
| 687 | 464.00 | |
| 688 | 440.00 | |
| 689 | 444.00 | |
| 690 | 456.00 | |
| 691 | 460.00 | |
| 693 | 440.00 | |
| 694 | 443.00 | 2.99 |
| 695 | 443.00 | 2.83 |
| 696 | 463.00 | 3.08 |
| 697 | 457.00 | 2.44 |
| 698 | 471.00 | 2.57 |
| 699 | 443.00 | 2.48 |
| 700 | 471.00 | 2.49 |
| 701 | 576.00 | 3.54 |
| 702 | 628.00 | 3.67 |
| 703 | 610.00 | 3.69 |
| 704 | 611.00 | 3.68 |
| 705 | 594.00 | 3.52 |
| 706 | 555.00 | 3.64 |
| 707 | 515.00 | 3.36 |
| 708 | 447.00 | 2.82 |
| 709 | 443.00 | 2.00 |
| 710 | 457.00 | 3.10 |
| 711 | 457.00 | 3.13 |
| 712 | 443.00 | 3.13 |
| 713 | 443.00 | 3.16 |
| 714 | 523.00 | 2.64 |
| 715 | 463.00 | 3.04 |
| 716 | 443.00 | 1.92 |
| 717 | 367.00 | 0.68 |
| 718 | 383.00 | 0.62 |
| 719 | 403.00 | 1.68 |
| 720 | 381.00 | 1.17 |
| 721 | 461.00 | 2.90 |
| 722 | 443.00 | 2.42 |
| 723 | 461.00 | 2.84 |
| 724 | 461.00 | 2.84 |
| 725 | 429.00 | 2.76 |
| 726 | 443.00 | 2.67 |
| 727 | 505.00 | 3.20 |
| 728 | 395.00 | 1.55 |
| 729 | 395.00 | 1.68 |
| 730 | 409.00 | 1.82 |
| 731 | 417.00 | 1.65 |
| 732 | 399.00 | 1.40 |
| 733 | 417.00 | 1.56 |
| 734 | 445.00 | 2.70 |
| 735 | 445.00 | 2.70 |
| 736 | 409.00 | 1.40 |
| 737 | 424.00 | 0.86 |
| 738 | 424.00 | 0.67 |
| 739 | 395.00 | 1.49 |

TABLE 2-continued

| Cmpd # | LC/MS M+ | RT (min) |
|---|---|---|
| 740 | 447.00 | 2.41 |
| 741 | 443.00 | 2.58 |
| 742 | 495.00 | 3.00 |
| 743 | 445.00 | 2.70 |
| 744 | 461.00 | 2.80 |
| 745 | 452.00 | 2.50 |
| 746 | 449.00 | 2.70 |
| 747 | 444.00 | 2.88 |
| 748 | 424.60 | 4.37 |
| 749 | 424.60 | 4.54 |
| 750 | 424.60 | 8.44 |
| 751 | 423.60 | 5.40 |
| 752 | 494.60 | 7.21 |
| 753 | 448.60 | 5.50 |
| 754 | 459.40 | 9.11 |
| 755 | 424.60 | 5.39 |
| 756 | 424.60 | 5.28 |
| 757 | 424.60 | 4.55 |
| 758 | 424.40 | 4.92 |
| 759 | 495.40 | 10.29 |
| 760 | 422.00 | 2.66 |
| 761 | 475.00 | 2.95 |
| 762 | 475.00 | 2.95 |
| 763 | 462.00 | 2.94 |
| 764 | 429.00 | 2.76 |
| 765 | 443.00 | 2.67 |
| 766 | 457.00 | 3.03 |
| 767 | 443.00 | 1.75 |
| 768 | 503.00 | 1.74 |
| 769 | 365.00 | 2.42 |
| 770 | 445.00 | 2.29 |
| 771 | 450.00 | 3.59 |
| 772 | 393.00 | 3.07 |
| 773 | 473.00 | 2.82 |
| 774 | 495.00 | 3.09 |

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" Drug Discov Today 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 µL of the CC2-DMPE solution. Plates are incubated in the dark for 30 minutes at room temperature.
4) While the cells are being stained with coumarin, a 15 µL oxonol solution in BS#2 is prepared. In addition to DiSBAC$_2$(3), this solution should contain 0.75 mM ABSC1 and 30 µL veratridine (prepared from 10 mM EtOH stock, Sigma #V-5754).
5) After 30 minutes, CC2-DMPE is removed and the cells are washed twice with 225 µL of BS#2. As before, the residual volume should be 40 µL.
6) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.
7) Once the incubation is complete, the cells are ready to be assayed on VIPR® with a sodium addback protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\,nm} - \text{background}_{460\,nm})}{(\text{intensity}_{580\,nm} - \text{background}_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R = R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound
Solutions [mM]
Bath Solution #1: NaCl 160, KCl 4.5, CaCl$_2$ 2, MgCl$_2$ 1, HEPES 10, pH 7.4 with NaOH
Bath Solution #2 TMA-Cl 160, CaCl$_2$ 0.1, MgCl$_2$ 1, HEPES 10, pH 7.4 with KOH (final K concentration 5 mM)

CC2-DMPE: prepared as a 5 mM stock solution in DMSO and stored at −20° C.

DiSBAC$_2$(3): prepared as a 12 mM stock in DMSO and stored at −20° C.

ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM DiSBAC$_2$(3) (Aurora #00-100-010) in dry DMSO 10 mM CC2-DMPE (Aurora #00-100-008) in dry DMSO 200 mM ABSC1 in H$_2$O Hank's Balanced Salt Solution (Hyclone #SH30268.02) supplemented with 10 mM HEPES (Gibco #15630-080)

Loading Protocol:

2×CC2-DMPE=20 μM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 μL of 2×CC2-DMPE is to wells containing washed cells, resulting in a 10 μM final staining concentration. The cells are stained for 30 minutes in the dark at RT.

2×DISBAC$_2$(3) with ABSC1=6 μM DISBAC$_2$(3) and 1 mM ABSC1: The required amount of 10 mM DISBAC$_2$(3) is added to a 50 ml conical tube and mixed with 1 μL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 μL. Add 50 uL/well of the 2×DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay Buffer #1

140 mM NaCl, 4.5 mM KCl, 2 mM CaCl$_2$, 1 mM MgCl$_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water Assay Protocol 1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\,nm} - \text{background}_{460\,nm})}{(\text{intensity}_{580\,nm} - \text{background}_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R_r = R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27; glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 M$\Omega$ using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), CdCl2 (0.4), NiCl2 (0.1), TTX ($0.25 \times 10^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM): 150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Compounds of the invention as depicted generally herein and in Table 2 were found to inhibit voltage-gated sodium channels at 25.0 µM or less.

Assays for Detecting and Measuring CaV Inhibition Properties of Compounds

A) Optical Methods for Assaying CaV Inhibition Properties of Compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM $DiSBAC_6(3)$ (Aurora #00-100-010) in dry DMSO
10 mM CC2-DMPE (Aurora #00-100-008) in dry DMSO
200 mM Acid Yellow 17 (Aurora #VABSC) in $H_2O$
370 mM Barium Chloride (Sigma Cat# B6394) in $H_2O$
Bath X
160 mM NaCl (Sigma Cat# S-9888)
4.5 mM KCl (Sigma Cat# P-5405)
1 mM MgCl2 (Fluka Cat#63064)
10 mM HEPES (Sigma Cat# H-4034)
pH 7.4 using NaOH Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×CC2DMPE & $DISBAC_6(3)$=8 µM CC2DMPE & 2.5 µM $DISBAC_6(3)$: Vortex together both dyes with an equivalent volume of 10% pluronic (in DMSO). Vortex in required amount of Bath X with beta-cyclodextrin. Each 96 well cell plate will require 5 ml of 2×CC2DMPE. Wash plate with ELx405 with Bath X, leaving a residual volume of 50 µL/well. Add 50 µL of 2XCC2DMPE & $DISBAC_6(3)$ to each well. Stain for 30 minutes in the dark at RT.

1.5×AY17=750 µM AY17 with 15 mM $BaCl_2$: Add Acid Yellow 17 to vessel containing Bath X. Mix well. Allow solution to sit for 10 minutes. Slowly mix in 370 mM $BaCl_2$. This solution can be used to solvate compound plates. Note that compound plates are made at 1.5× drug concentration and not the usual 2×. Wash CC2 stained plate, again, leaving residual volume of 50 µL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\,nm} - \text{background}_{460\,nm})}{(\text{intensity}_{580\,nm} - \text{background}_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R = R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound.

Electrophysiology Assays for CaV Activity and Inhibition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

Voltage-Clamp Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 M using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $BaCl_2$ (10), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10).

Following these procedures, representative compounds of the present invention were found to possess desired N-type calcium channel modulation activity and selectivity.

The invention claimed is:

1. A method of inhibiting one or more of NaV1.1, NaV1.2, NaV1.3, NaV1.4, NaV1.5, NaV1.6, NaV1.7, NaV1.8, NaV1.9, or CaV2.2 activity in:

(a) a patient; or (b) a biological sample;

which method comprising administering to said patient, or contacting said biological sample with a compound selected from the following:

| # | Compound |
|---|----------|
| 223 | |
| 385 | |

129
-continued
| # | Compound |
|---|---|
| 487 | 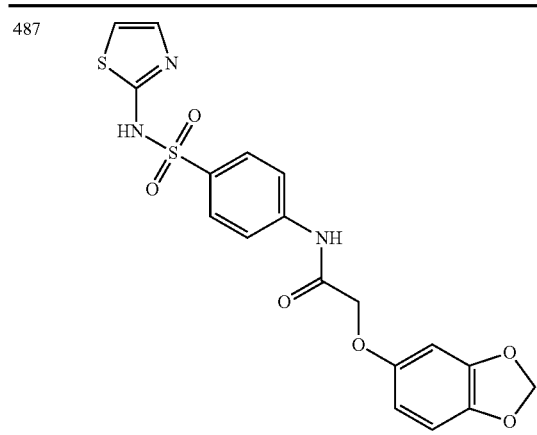 |
| 494 | 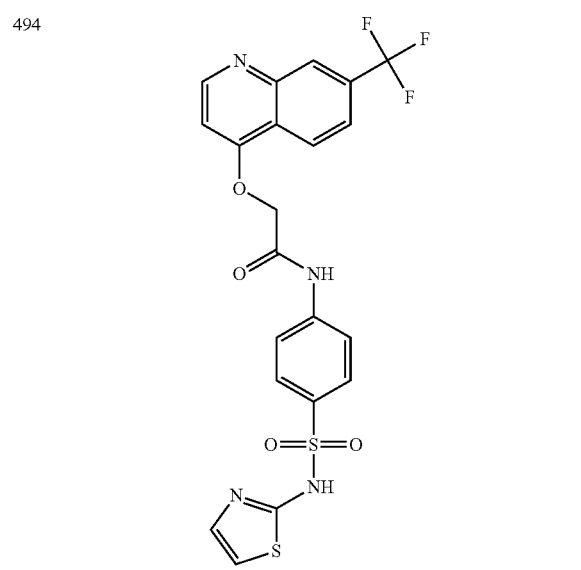 |
| 496 | 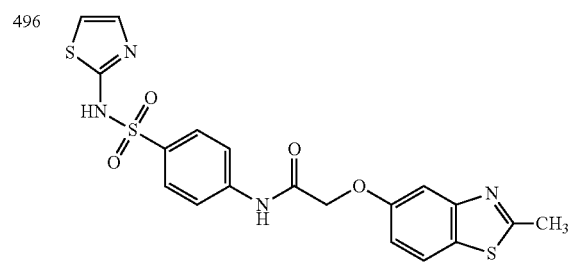 |
| 499 | 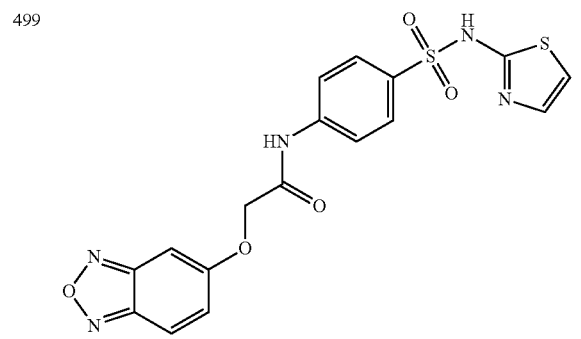 |
130
-continued
| # | Compound |
|---|---|
| 538 | 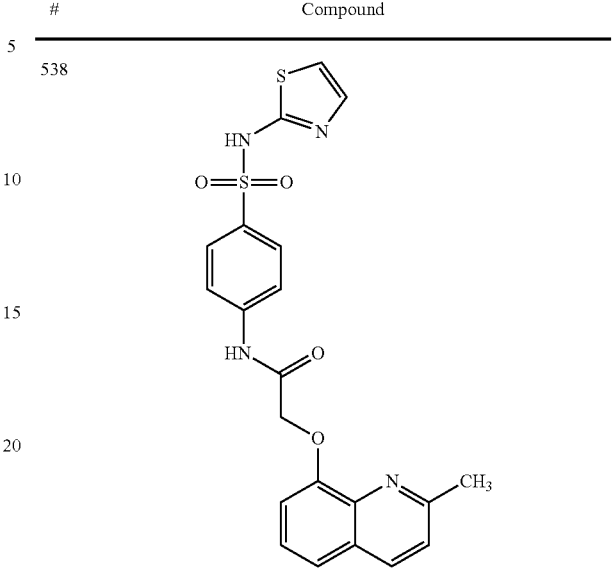 |
| 540 | 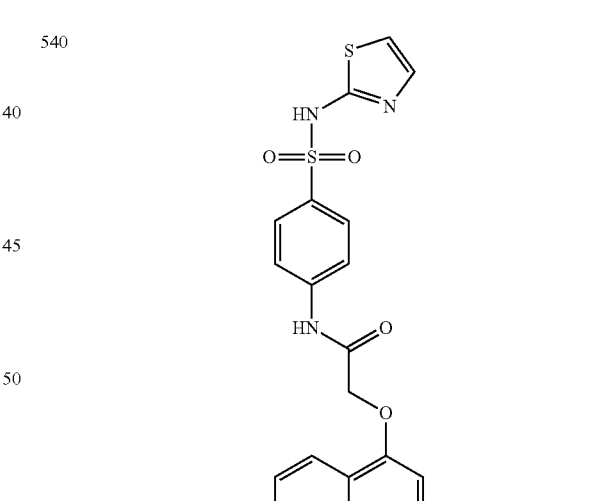 |

131
-continued
| # | Compound |
|---|---|
| 541 | 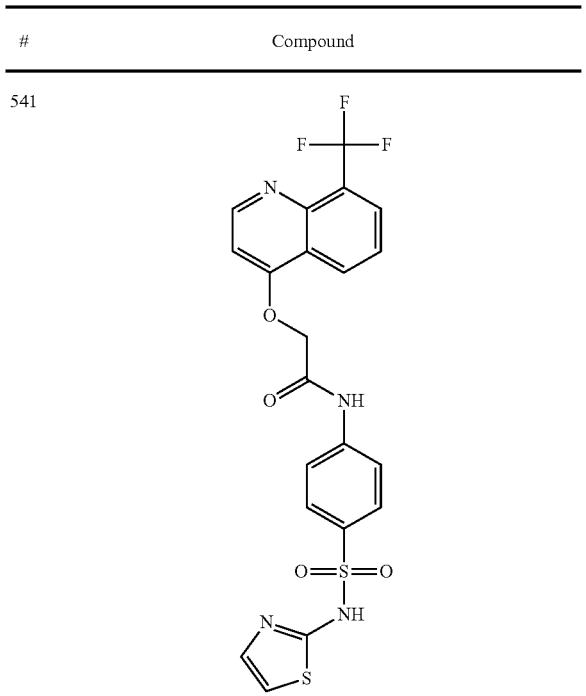 |
| 550 | |
| 557 | 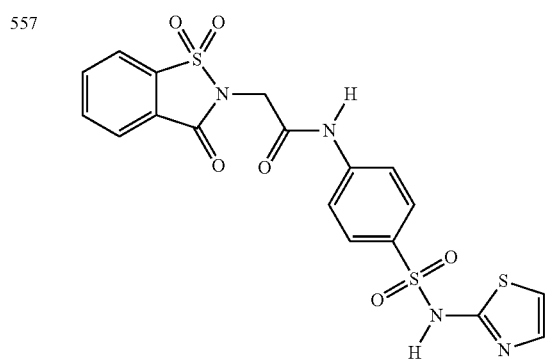 |
132
-continued
| # | Compound |
|---|---|
| 562 | 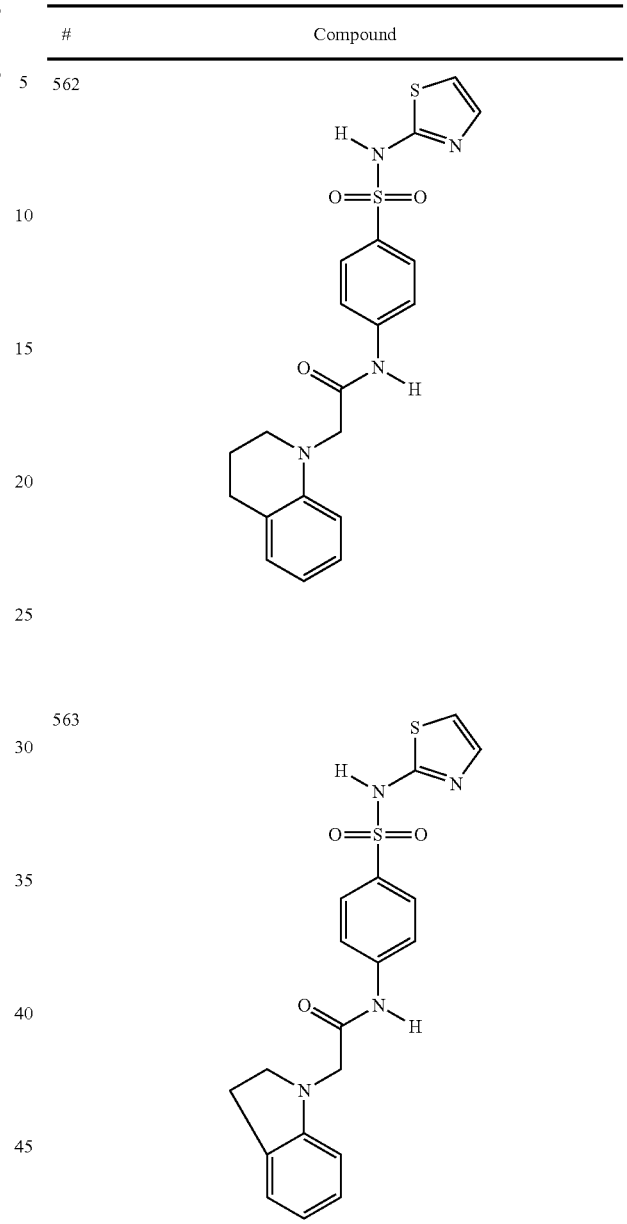 |
| 563 | |
| 564 | |

-continued

| # | Compound |
|---|---|
| 568 | |
| 574 | |
| 575 | |
| 576 | |
| 577 | |
| 579 | |
| 581 | |

| # | Compound |
|---|---|
| 582 | 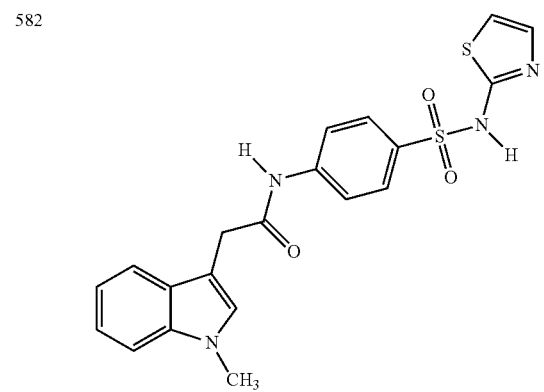 |
| 583 | 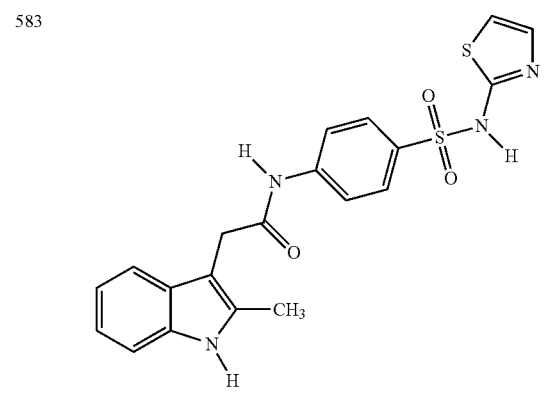 |
| 585 | 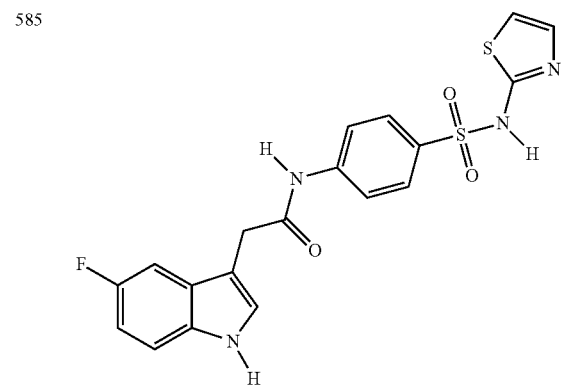 |
| 588 | 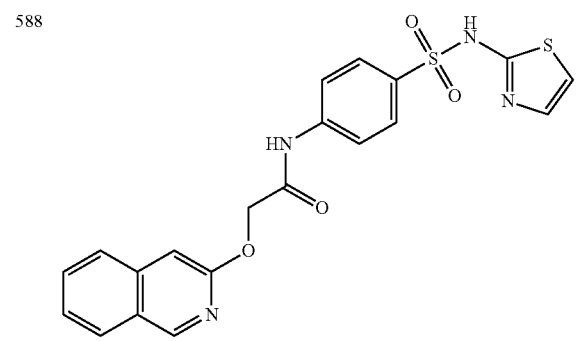 |
| # | Compound |
|---|---|
| 589 | 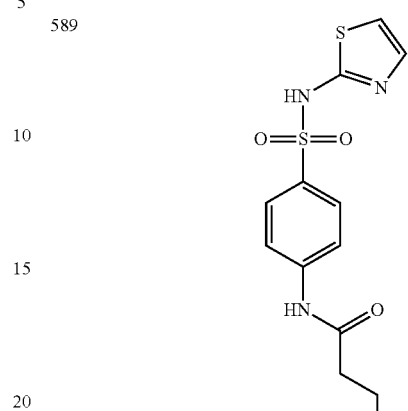 |
| 592 | 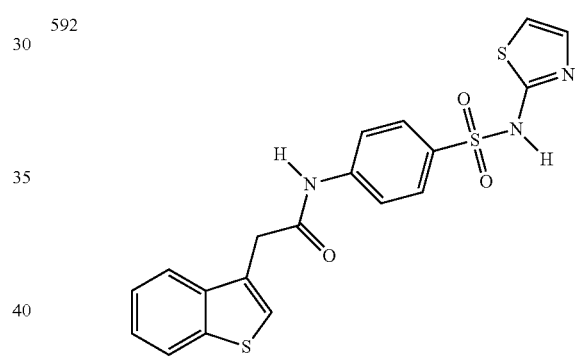 |
| 597 | 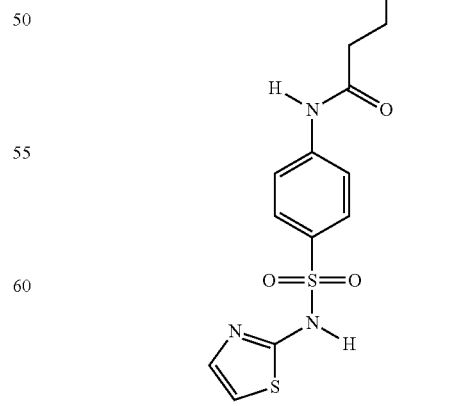 |

TABLE-continued
| # | Compound |
|---|---|
| 605 | 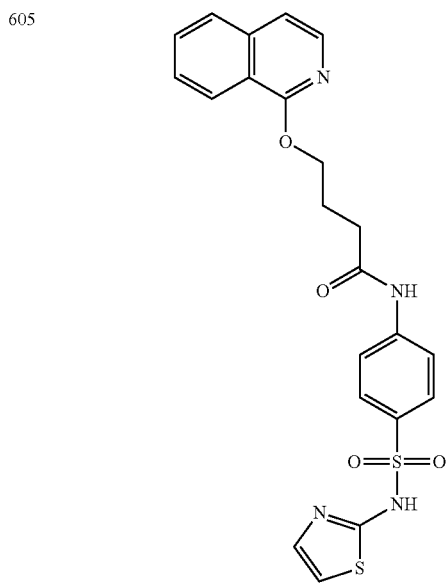 |
| 607 | 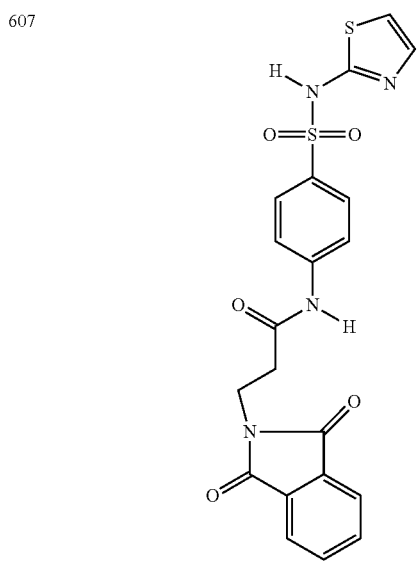 |
TABLE-continued
| # | Compound |
|---|---|
| 611 | 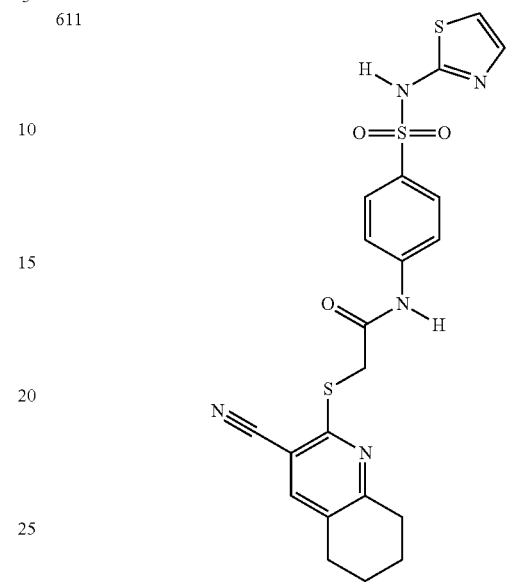 |
| 612 | 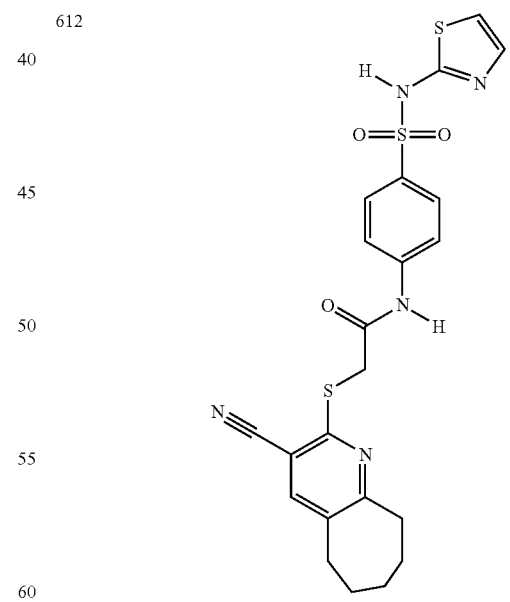 |

-continued

| # | Compound |
|---|---|
| 615 | (structure: thiazol-2-yl sulfonamide – phenyl – NHC(=O)CH2O – quinolin-4-yl) |
| 616 | (structure: quinolin-8-yloxy – CH2C(=O)NH – phenyl – SO2NH-thiazol-2-yl) |
| 617 | (structure: quinazolin-4-yloxy – CH2C(=O)NH – phenyl – SO2NH-thiazol-2-yl) |

-continued

| # | Compound |
|---|---|
| 618 | (structure: quinolin-6-yloxy – CH2C(=O)NH – phenyl – SO2NH-thiazol-2-yl) |
| 619 | (structure: thiazol-2-yl-NHSO2 – phenyl – NHC(=O)CH2O – 1H-indol-5-yl) |
| 620 | (structure: quinolin-2-yloxy – CH2C(=O)NH – phenyl – SO2NH-thiazol-2-yl) |
| 621 | (structure: 1H-indol-2-yloxy – CH2C(=O)NH – phenyl – SO2NH-thiazol-2-yl) |

| # | Compound |
|---|---|
| 622 | 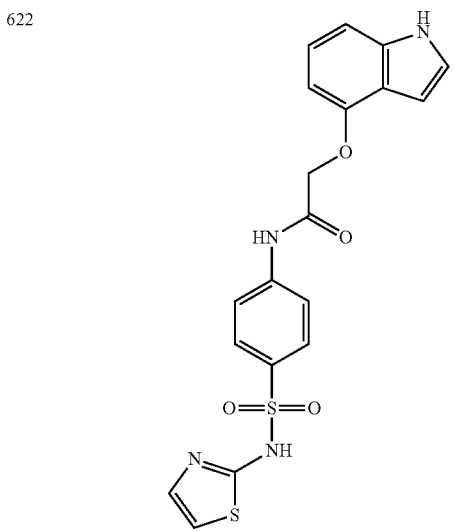 |
| 628 | 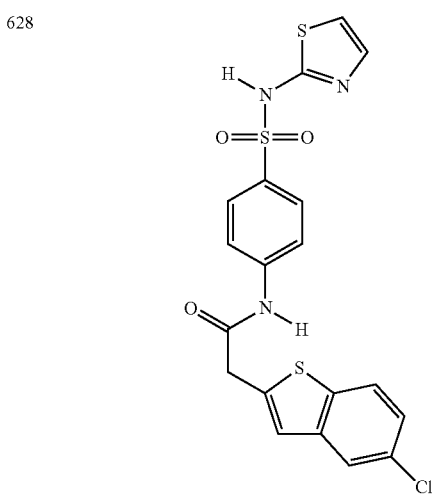 |
| 629 | 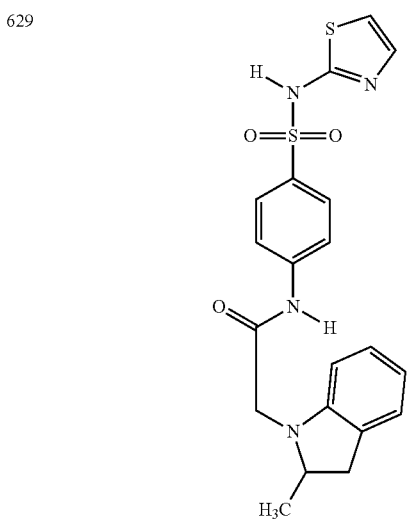 |
| # | Compound |
|---|---|
| 630 | 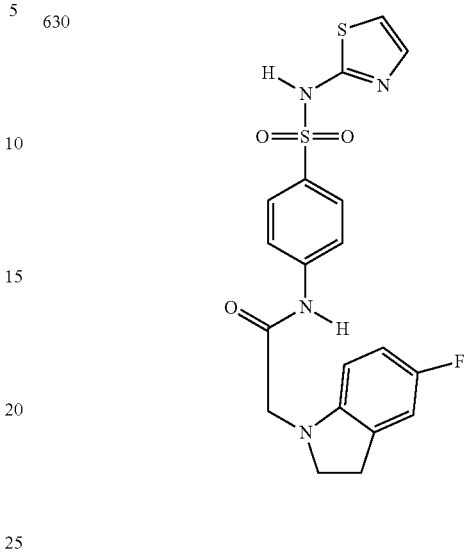 |
| 631 | 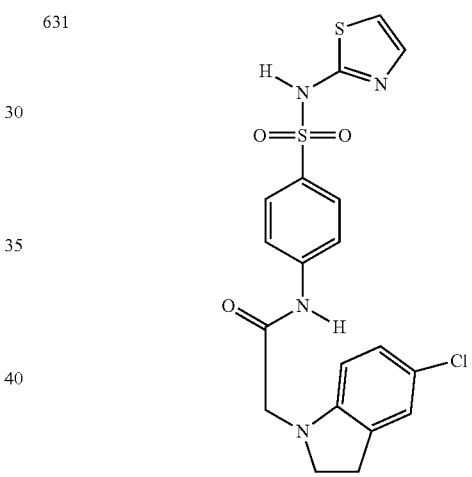 |
| 632 | 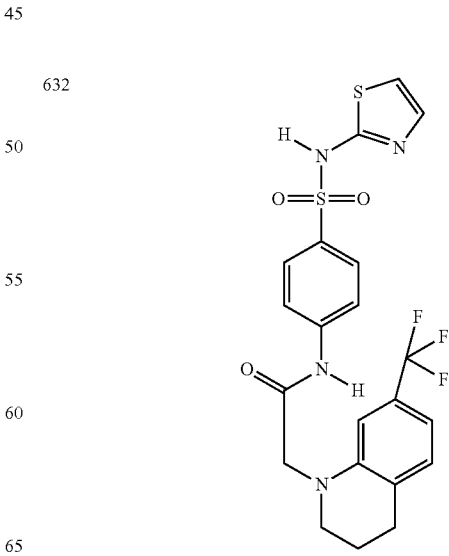 |

| # | Compound |
|---|---|
| 633 | 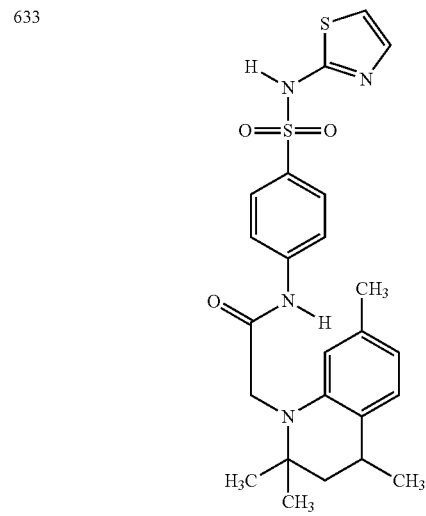 |
| 634 | 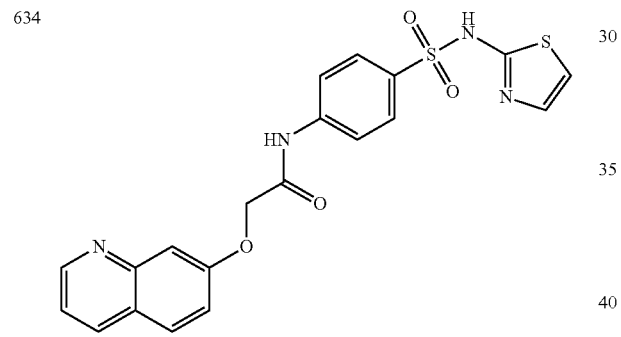 |
| 635 | 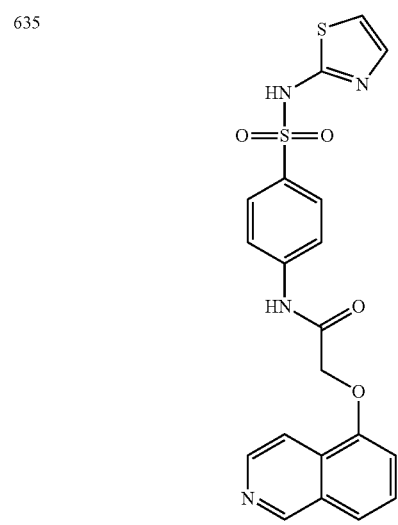 |
| # | Compound |
|---|---|
| 636 | 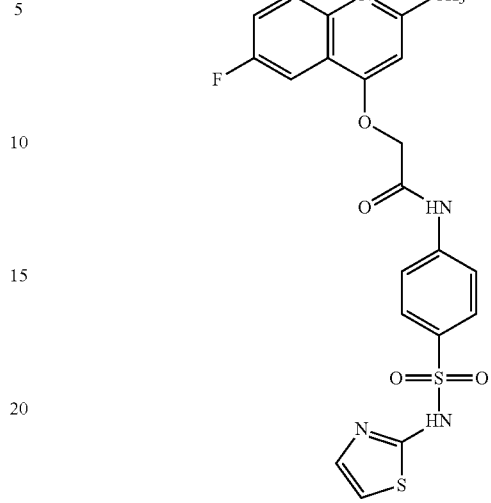 |
| 637 | 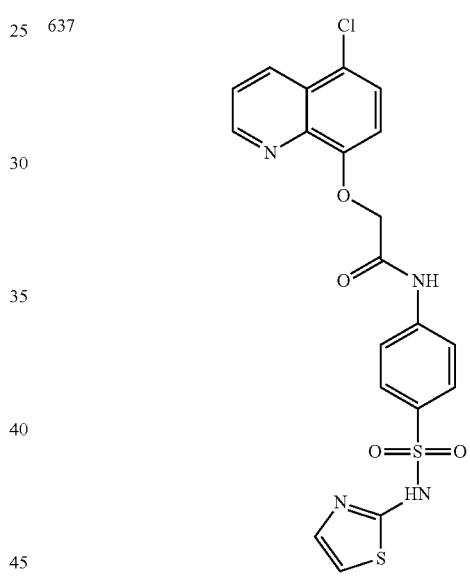 |
| 638 | 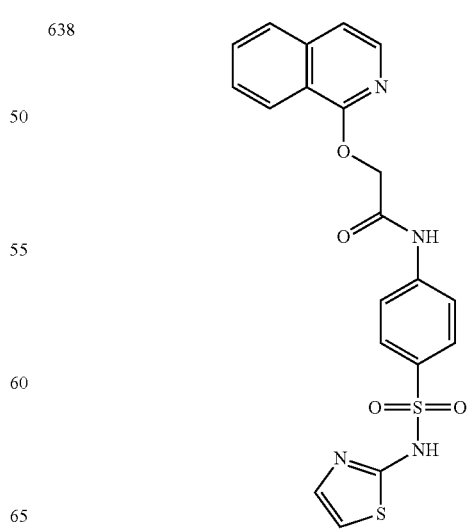 |

| # | Compound |
|---|---|
| 639 | 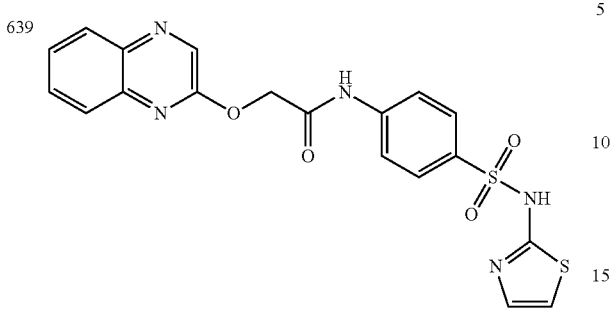 |
| 640 | 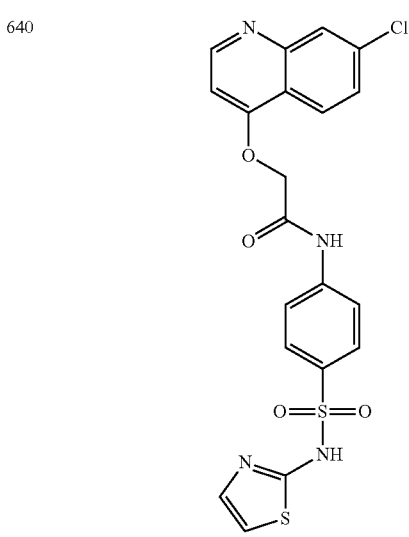 |
| 641 | 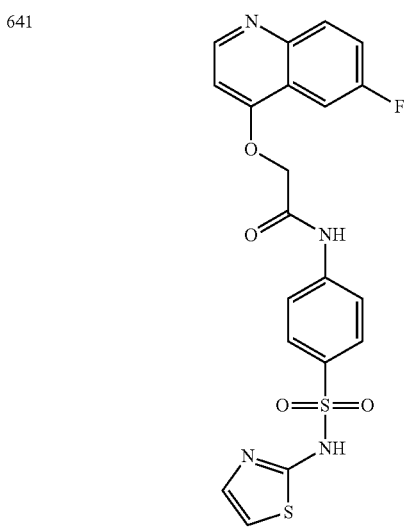 |
| # | Compound |
|---|---|
| 642 | 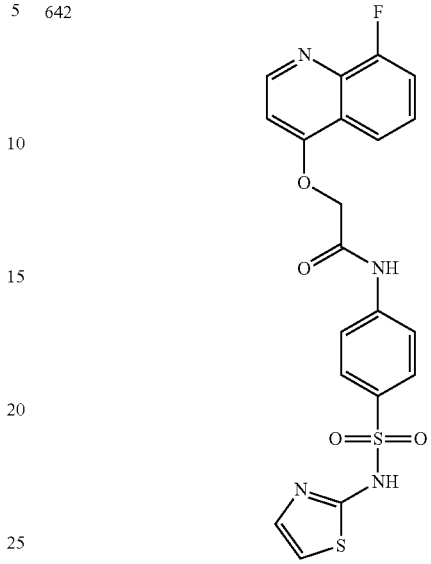 |
| 643 | 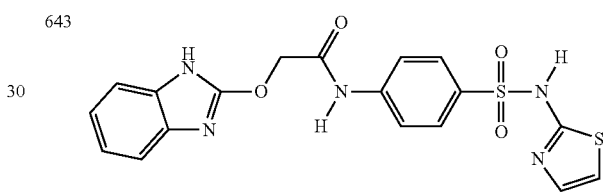 |
| 644 | 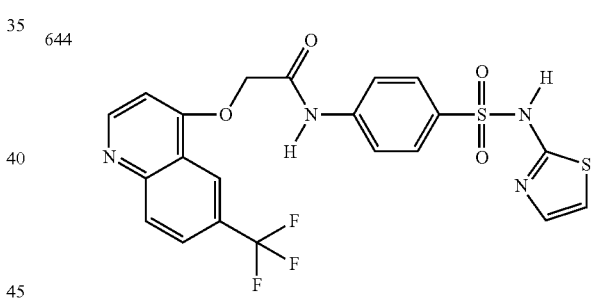 |
| 647 | 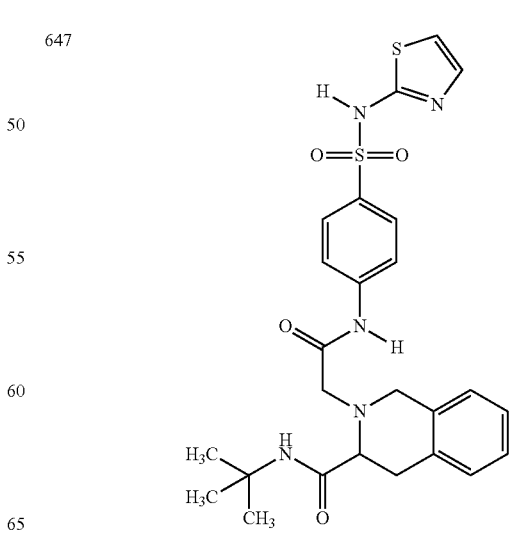 |

| # | Compound |
|---|---|
| 656 | 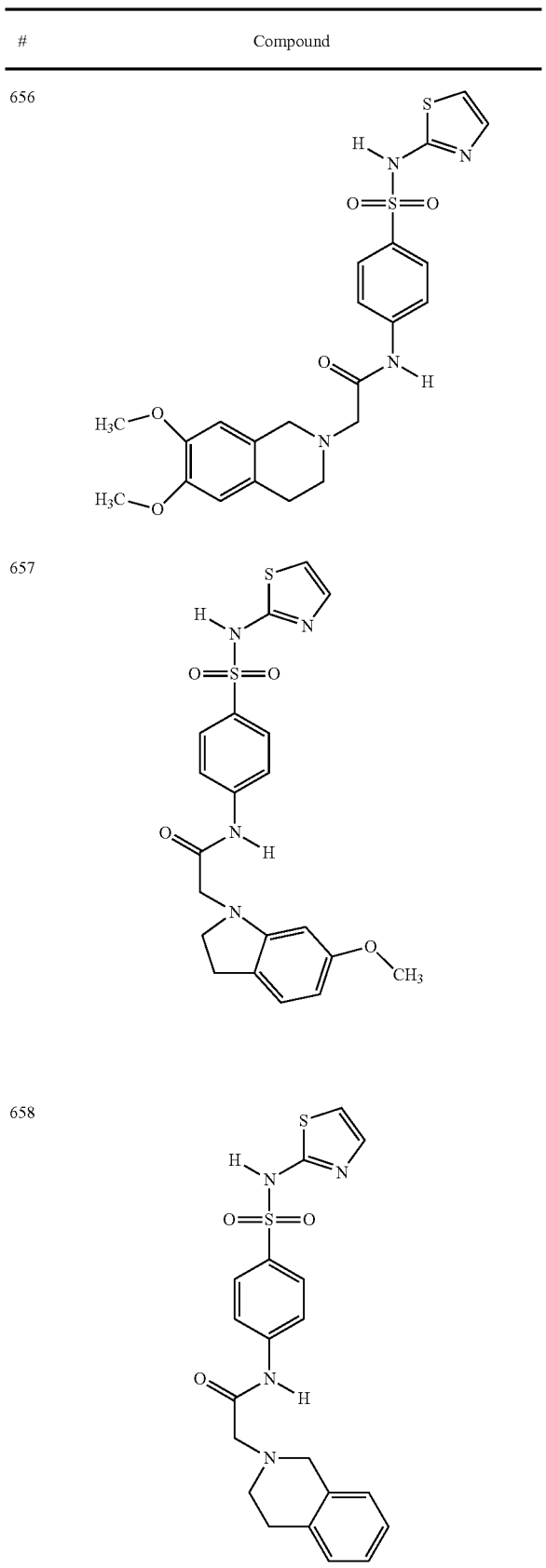 |
| 657 | |
| 658 | |
| # | Compound |
|---|---|
| 660 | 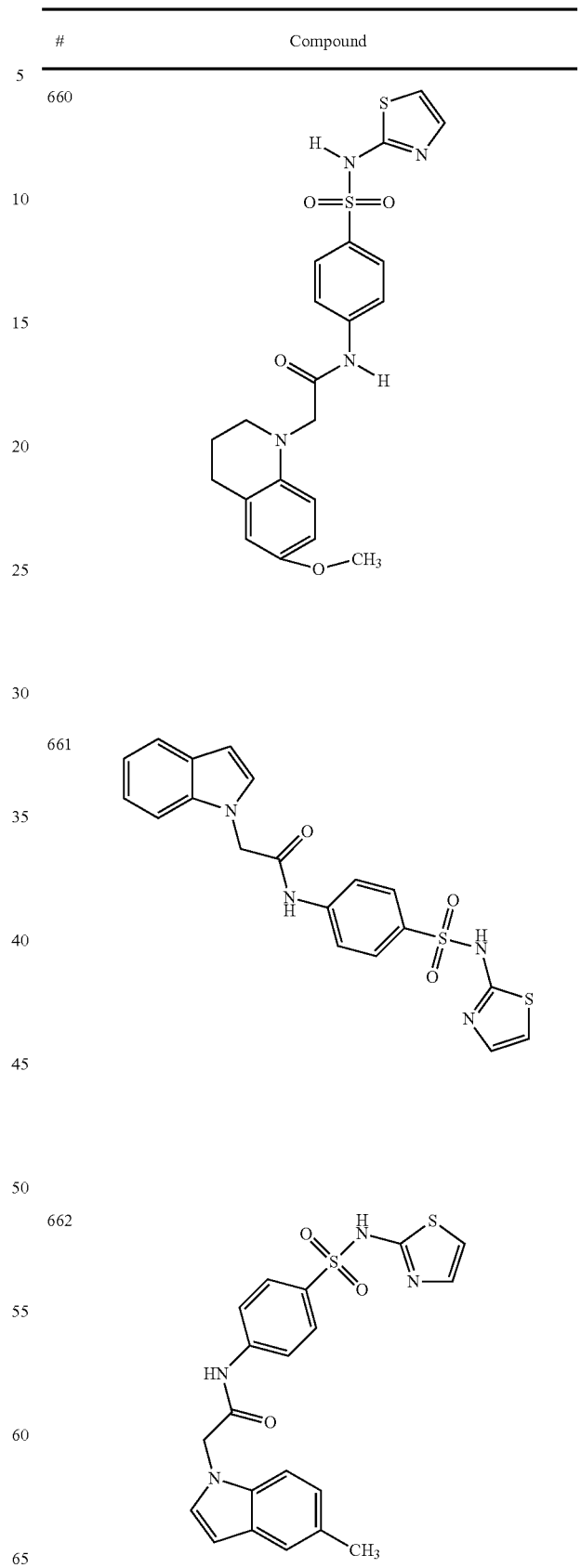 |
| 661 | |
| 662 | |

| # | Compound |
|---|---|
| 663 | 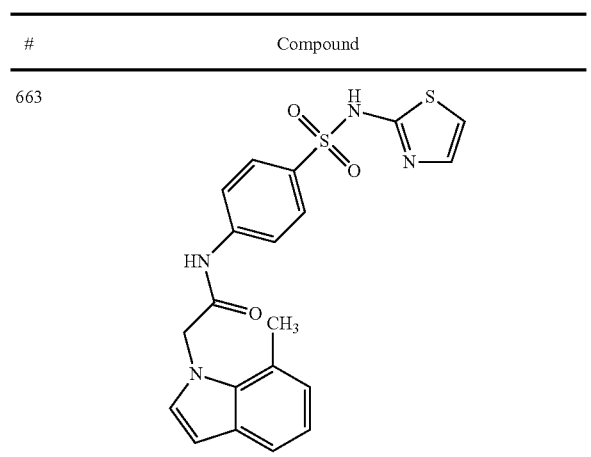 |
| 664 | 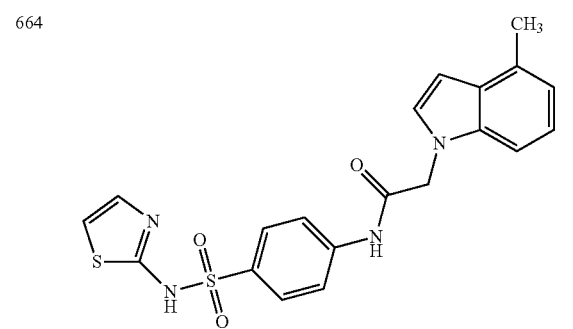 |
| 665 | 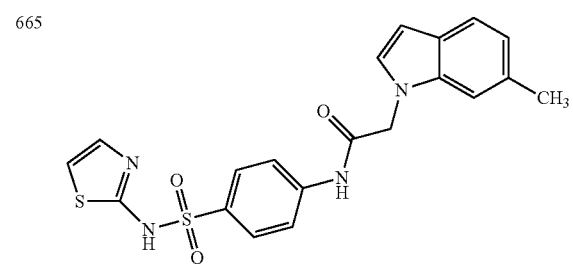 |
| 666 | 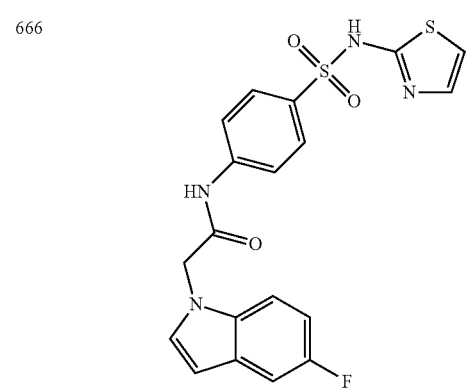 |
| # | Compound |
|---|---|
| 667 | 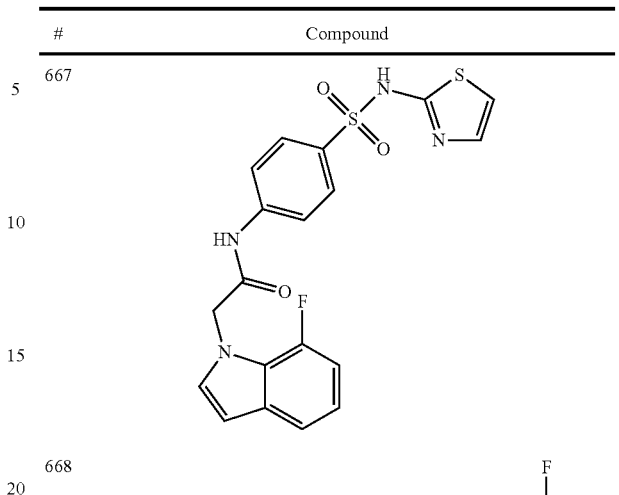 |
| 668 | 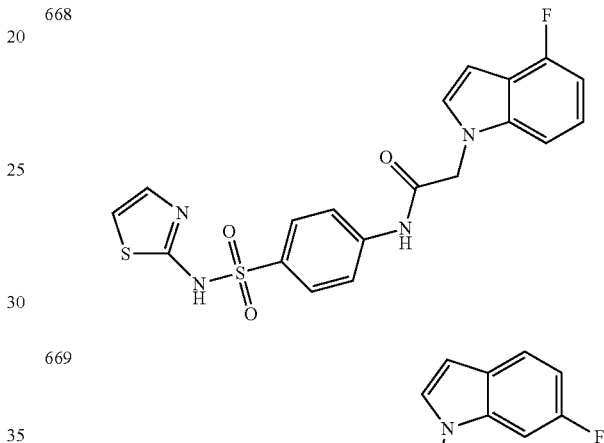 |
| 669 | |
| 670 | 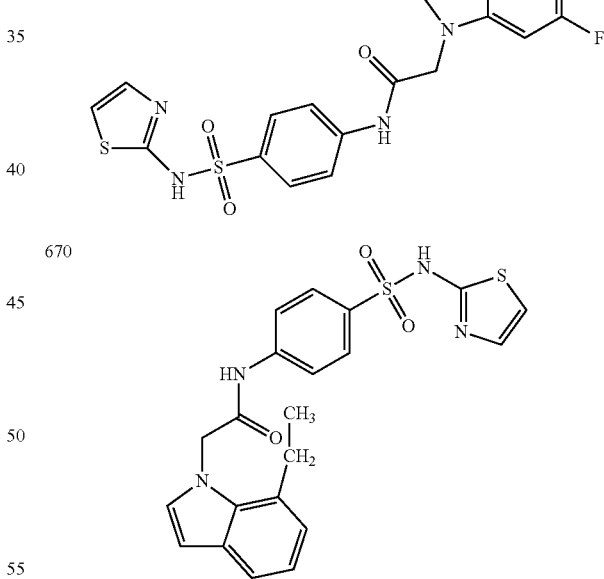 |
| 671 | 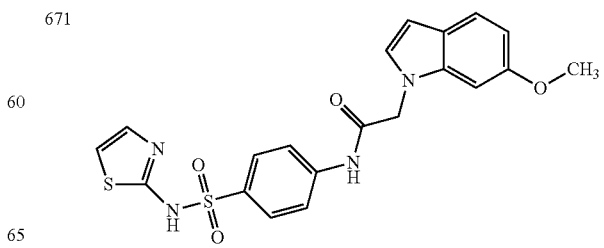 |

-continued

| # | Compound |
|---|---|
| 672 | |
| 673 | |
| 674 | |
| 675 | |
| 676 | |
| 677 | |
| 678 | |
| 679 | |

US 8,309,543 B2
153
-continued
| # | Compound |
|---|---|
| 680 | 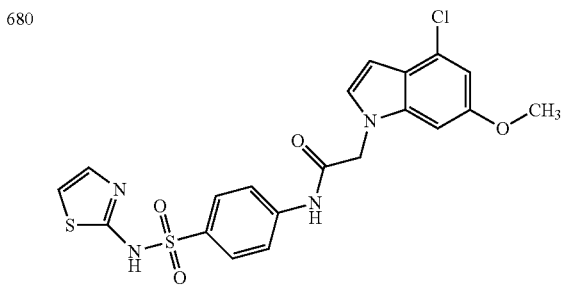 |
| 681 | 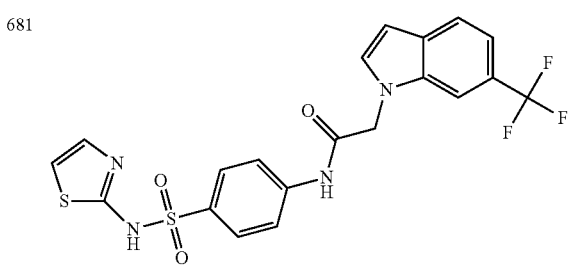 |
| 682 | 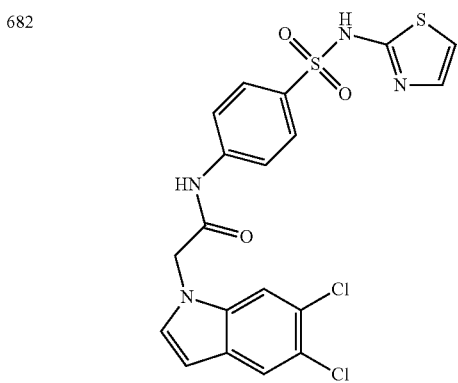 |
| 683 | 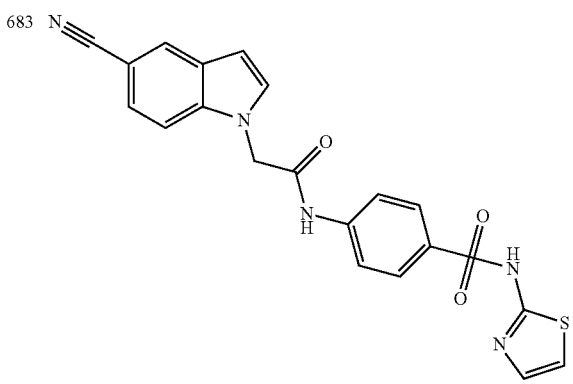 |
154
-continued
| # | Compound |
|---|---|
| 684 | 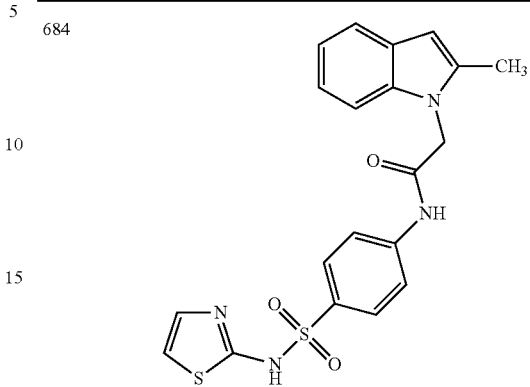 |
| 685 | 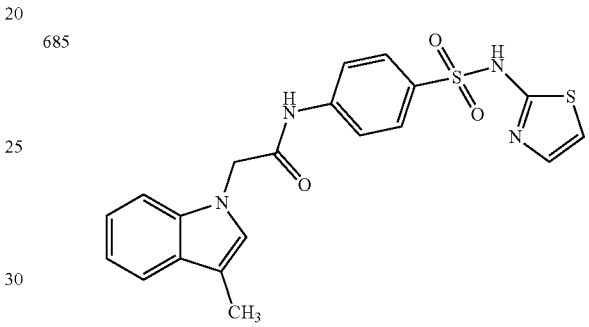 |
| 686 | 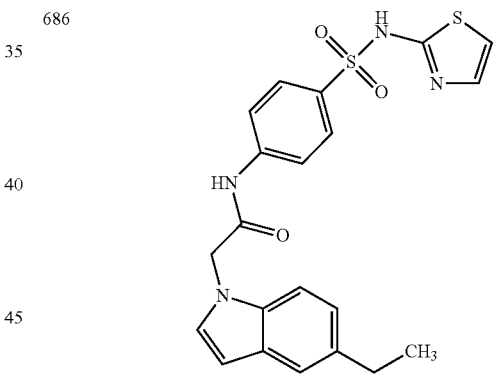 |
| 687 | 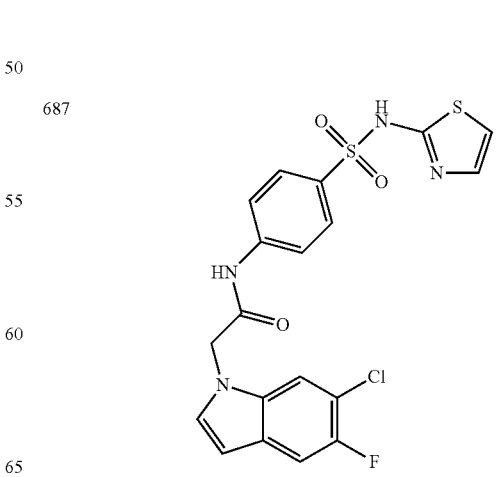 |

| # | Compound |
|---|---|
| 688 | (structure) |
| 689 | (structure) |
| 690 | (structure) |
| 691 | (structure) |
| 692 | (structure) |
| 693 | (structure) |
| 694 | (structure) |

| # | Compound |
|---|---|
| 695 | 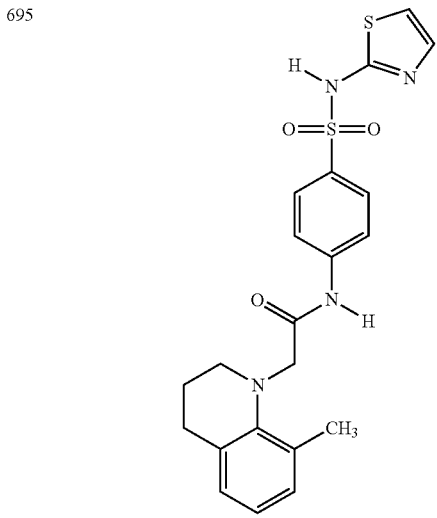 |
| 696 | 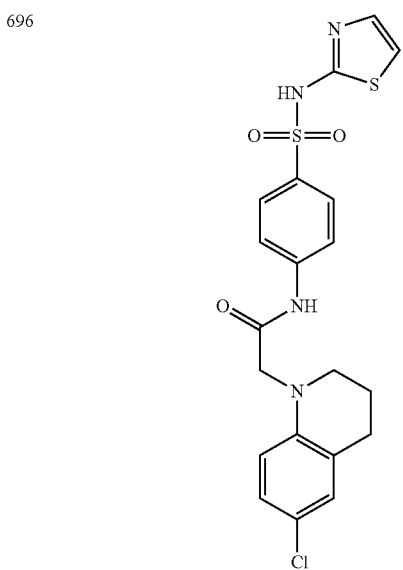 |
| 700 | 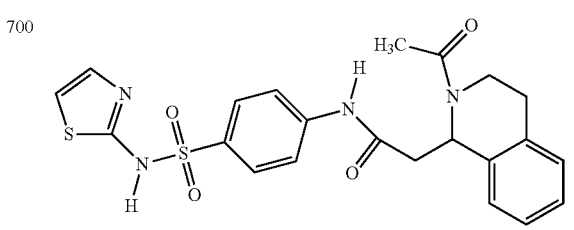 |
| # | Compound |
|---|---|
| 708 | 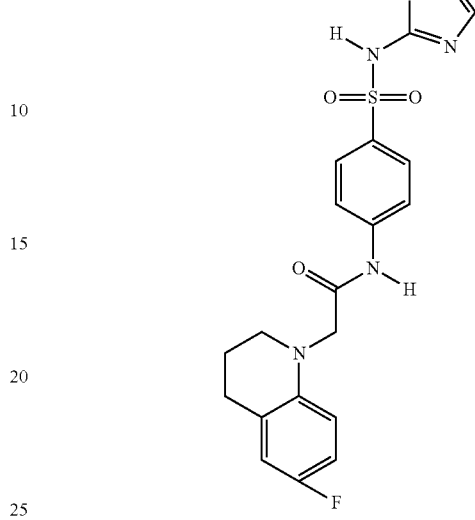 |
| 709 | 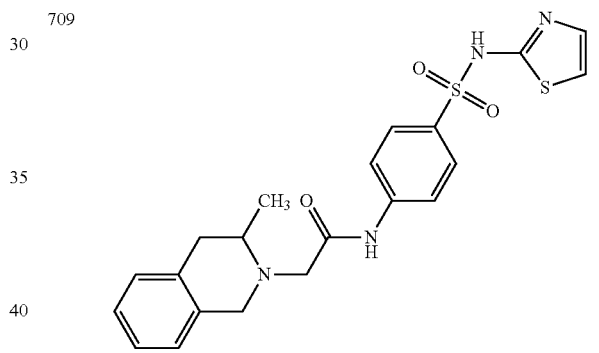 |
| 710 | 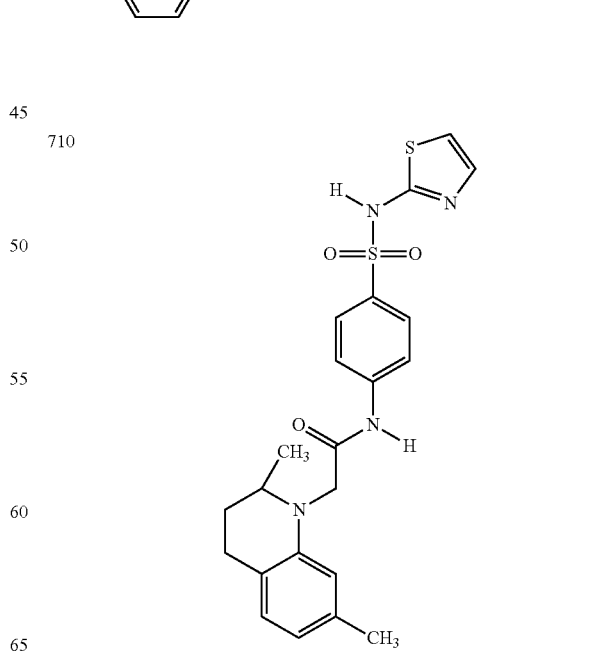 |

| # | Compound |
|---|---|
| 711 | 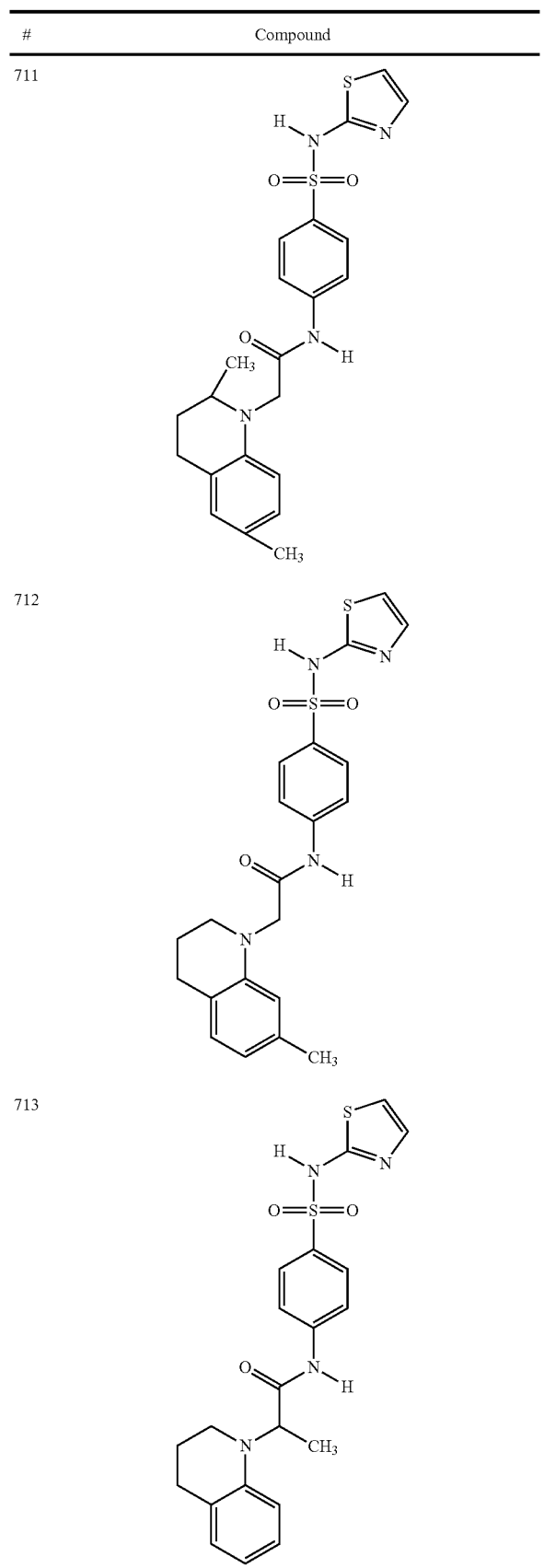 |
| 712 | |
| 713 | |
| # | Compound |
|---|---|
| 714 | 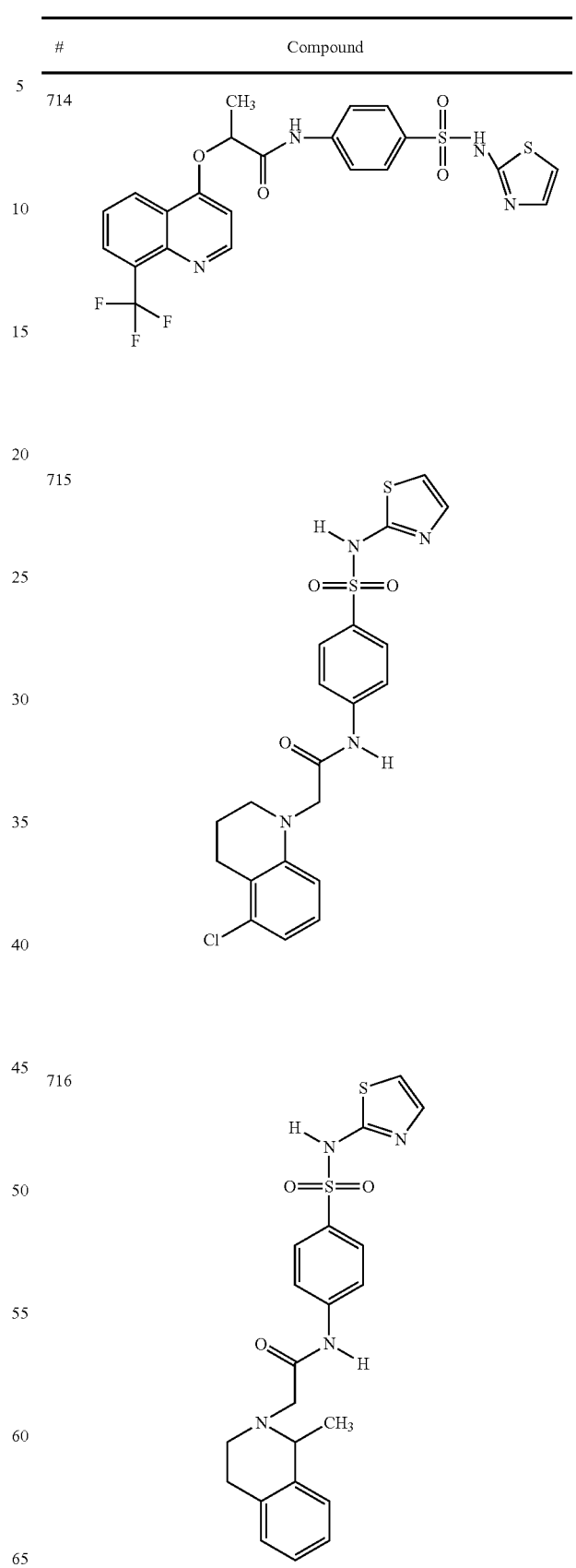 |
| 715 | |
| 716 | |

| # | Compound |
|---|---|
| 721 | (structure) |
| 722 | (structure) |
| 723 | (structure) |
| 724 | (structure) |
| 725 | (structure) |
| 726 | (structure) |

163
-continued
| # | Compound |
|---|---|
| 727 | 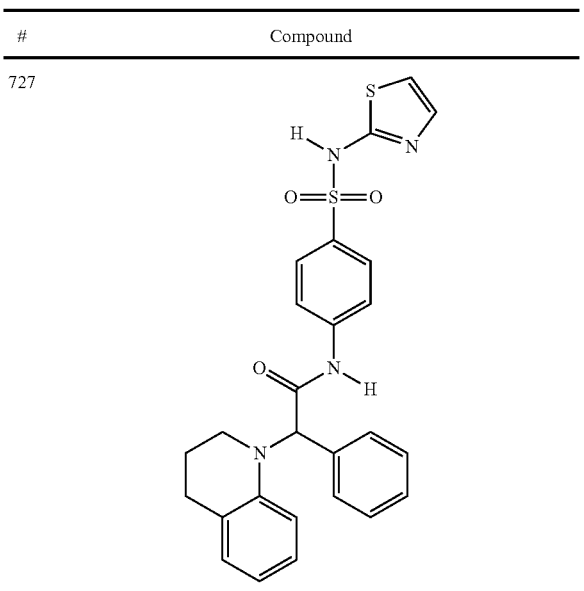 |
| 734 | 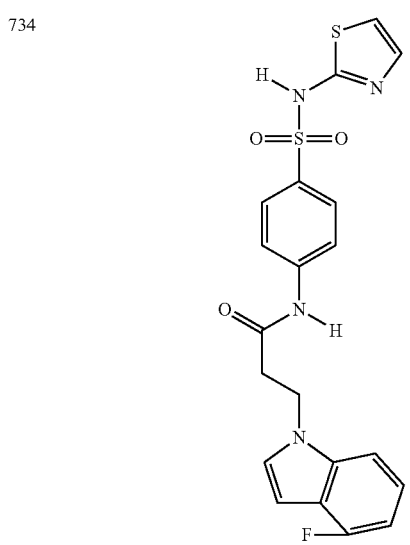 |
| 735 | 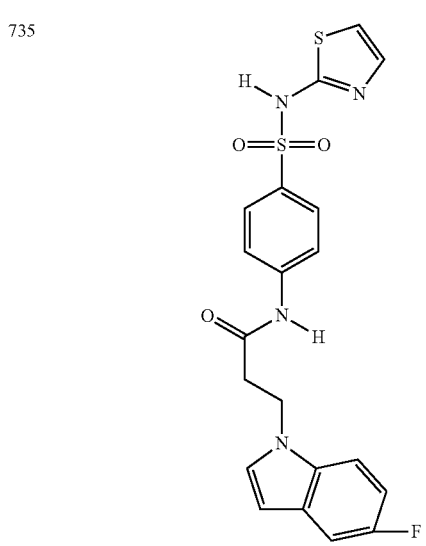 |
164
-continued
| # | Compound |
|---|---|
| 740 | 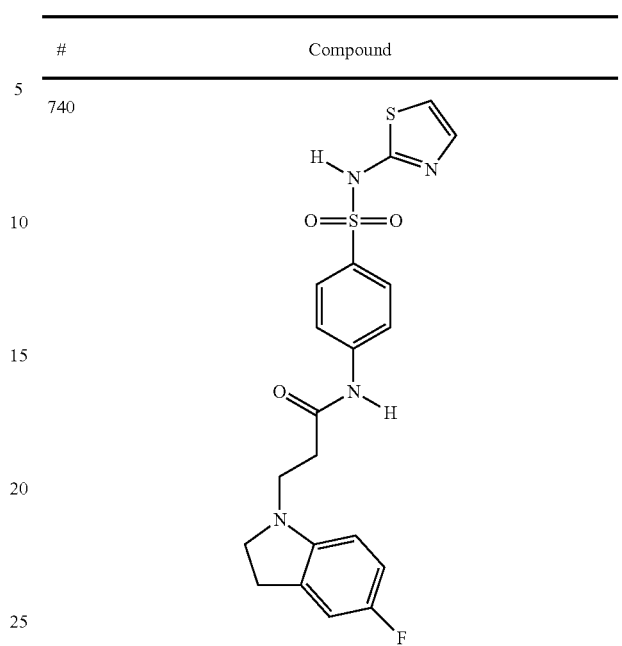 |
| 741 | 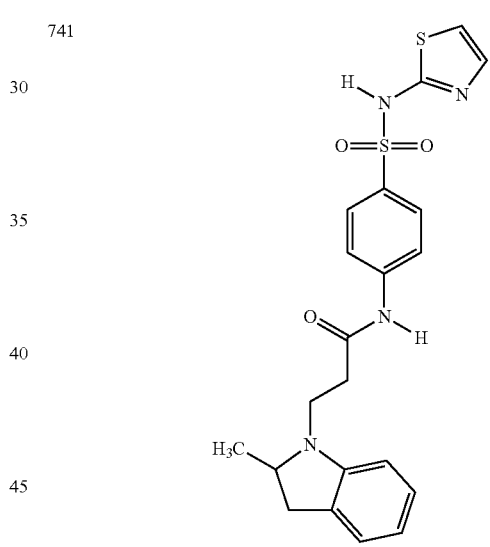 |
| 742 | 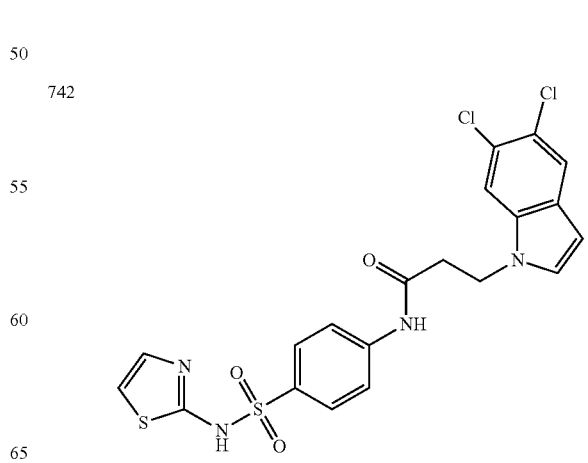 |

| # | Compound |
|---|---|
| 743 | (structure) |
| 744 | (structure) |
| 745 | (structure) |
| 746 | (structure) |

| # | Compound |
|---|---|
| 761 | (structure) |
| 762 | (structure) |
| 764 | (structure) |

167
-continued
| # | Compound |
|---|---|
| 765 | 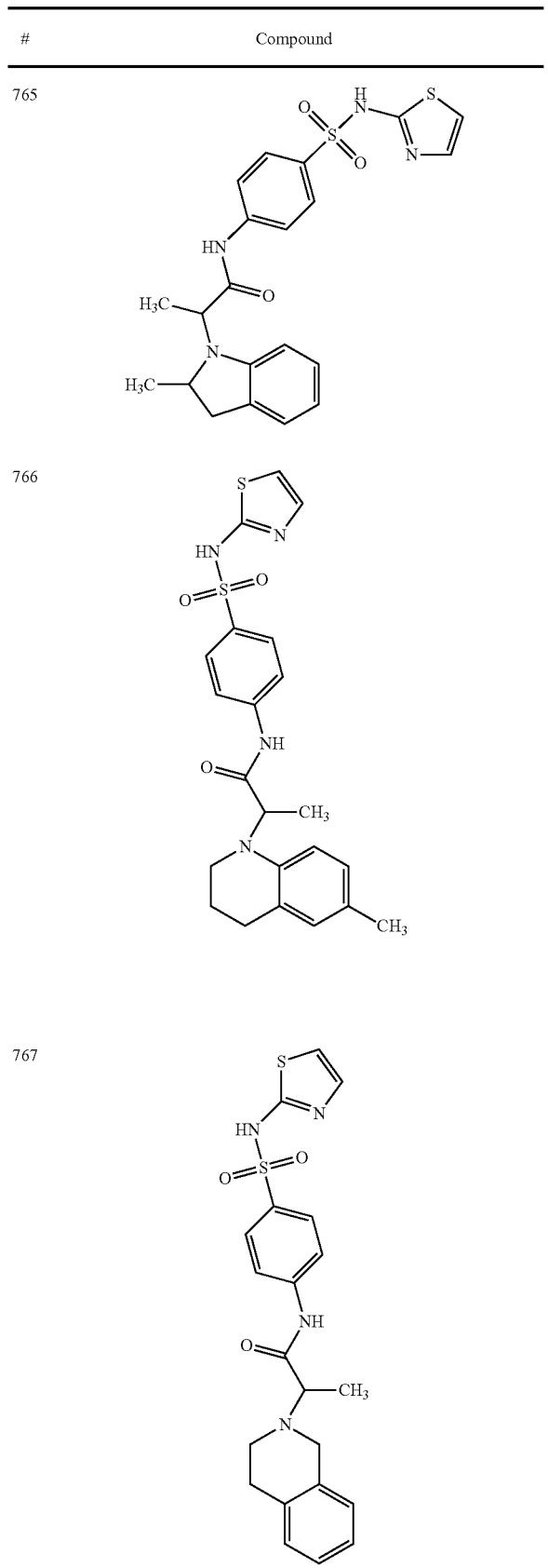 |
| 766 | |
| 767 | |
168
-continued
| # | Compound |
|---|---|
| 768 | 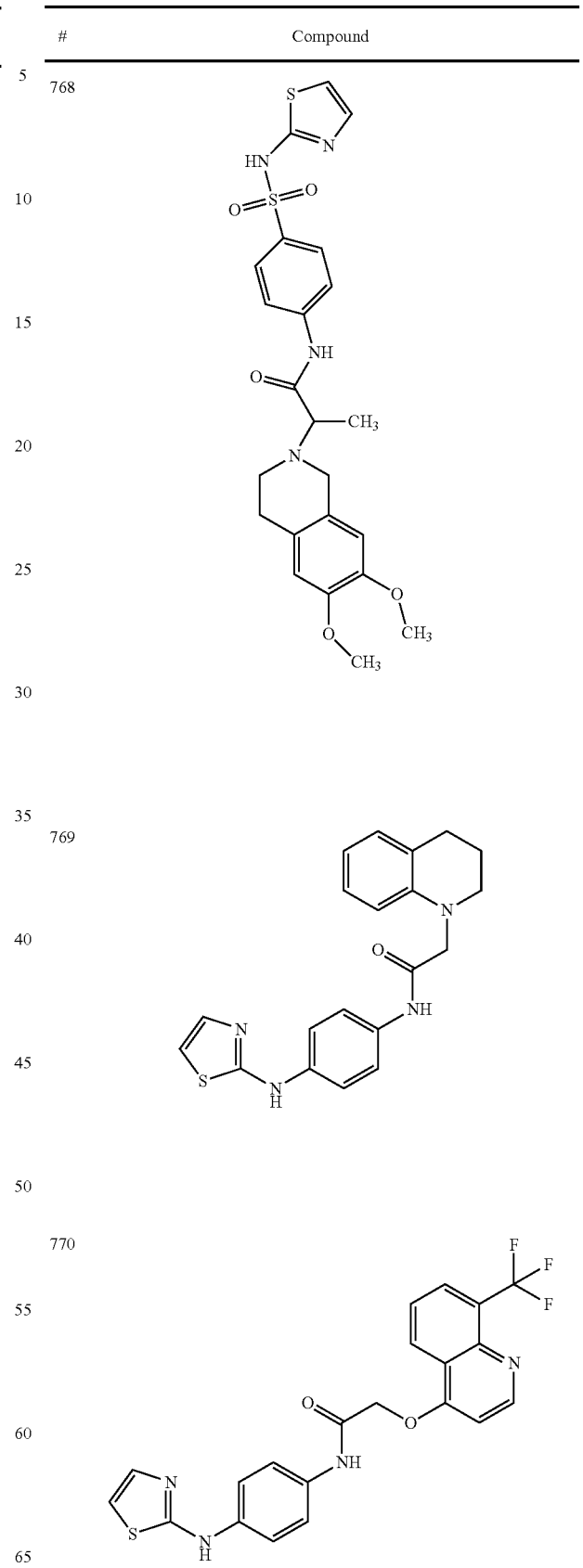 |
| 769 | |
| 770 | |

| # | Compound |
|---|---|
| 774 | 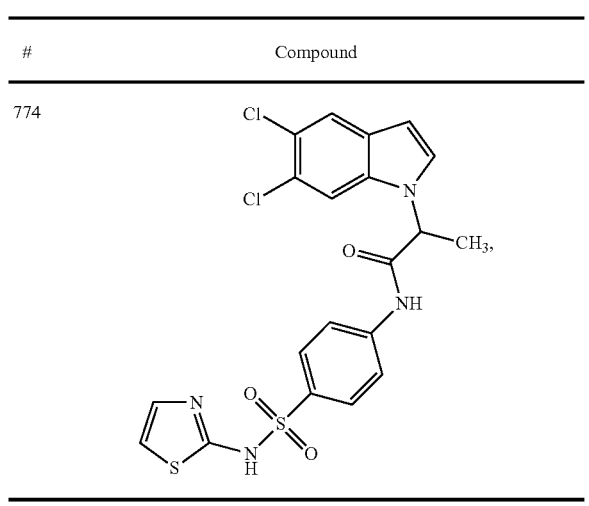 |

2. A method of treating or lessening the severity of a disease, disorder, or condition selected from acute, chronic, neuropathic, or inflammatory pain, migraine, cluster headaches, trigeminal neuralgia, epilepsy arrhythmia, visceral pain, osteoarthritis pain, postherpetic neuralgia, radicular pain, sciatica, back pain, head or neck pain, severe or intractable pain, nociceptive pain, breakthrough pain, postsurgical pain, or cancer pain, comprising the step of administering to said patient an effective amount of a compound selected from the following:

| # | Compound |
|---|---|
| 223 | |
| 385 | 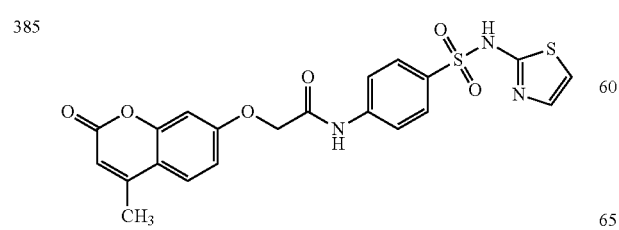 |

| # | Compound |
|---|---|
| 487 | |
| 494 | |
| 496 | |
| 499 | |

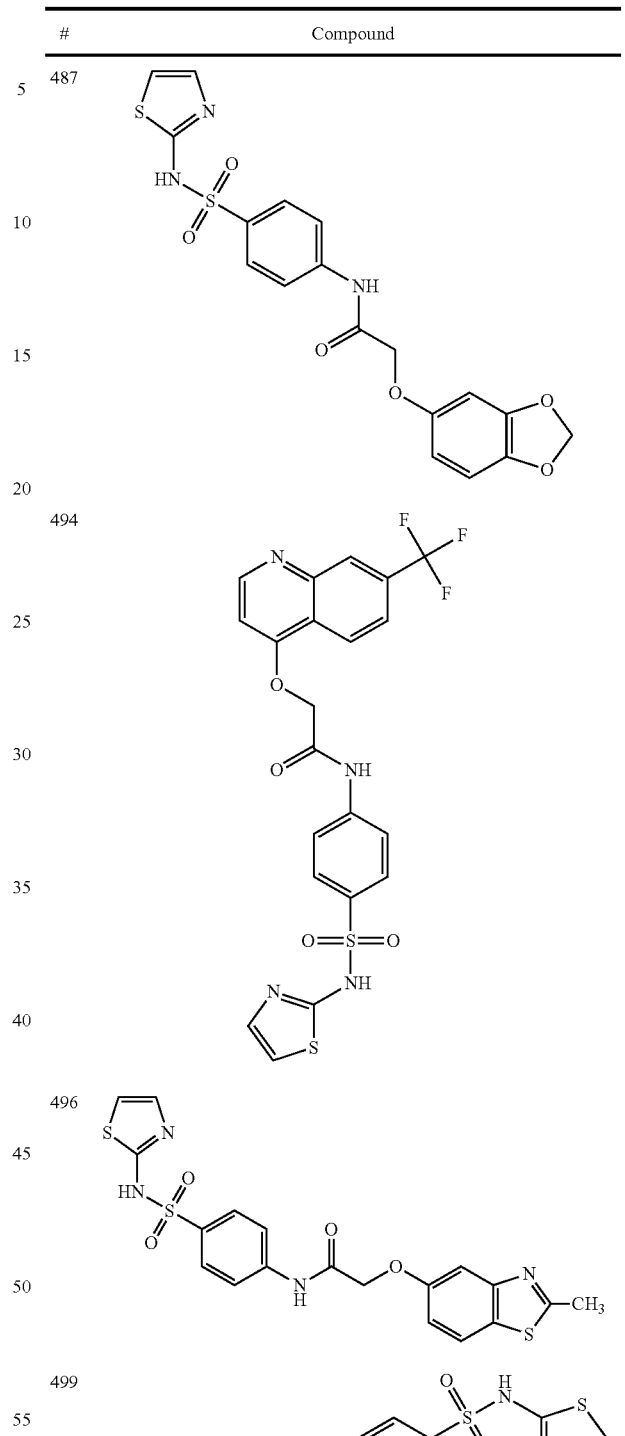

| # | Compound |
|---|---|
| 538 | 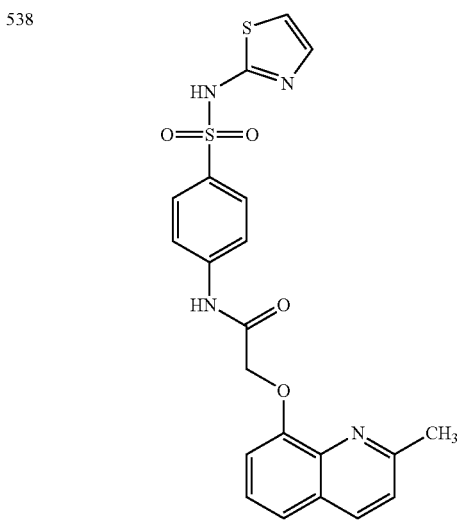 |
| 540 | 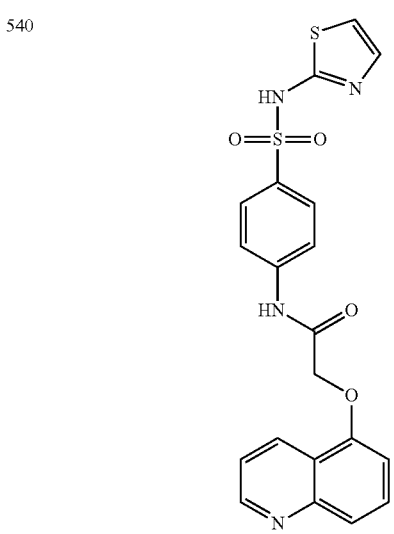 |
| # | Compound |
|---|---|
| 541 | 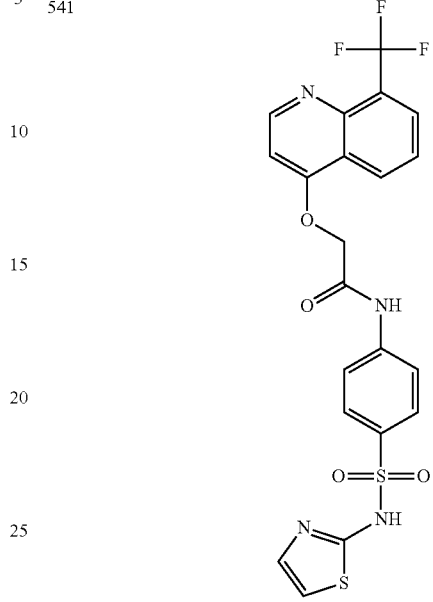 |
| 550 | |
| 557 | 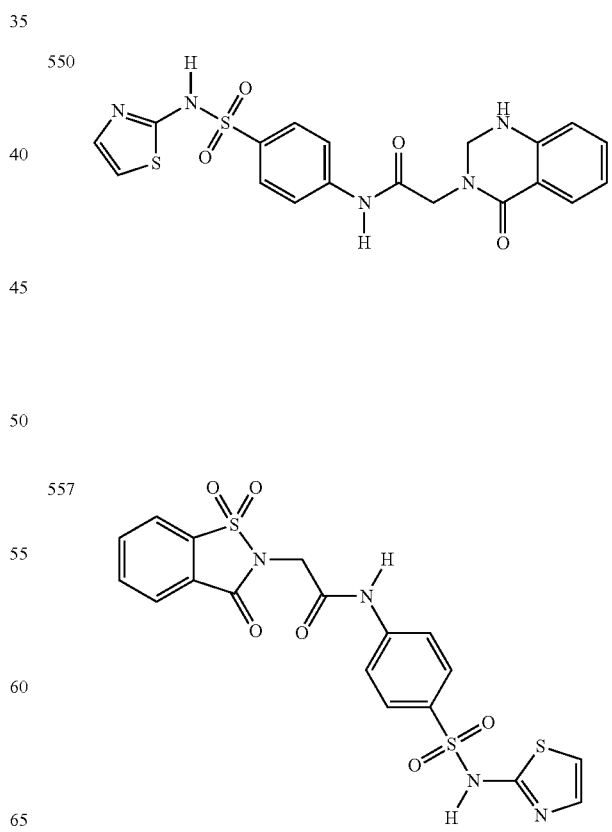 |

| # | Compound |
|---|---|
| 562 | 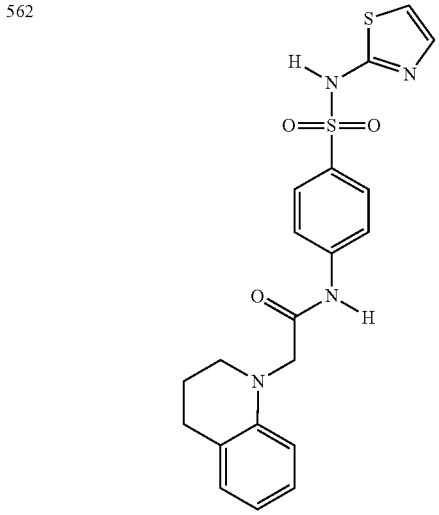 |
| 563 | 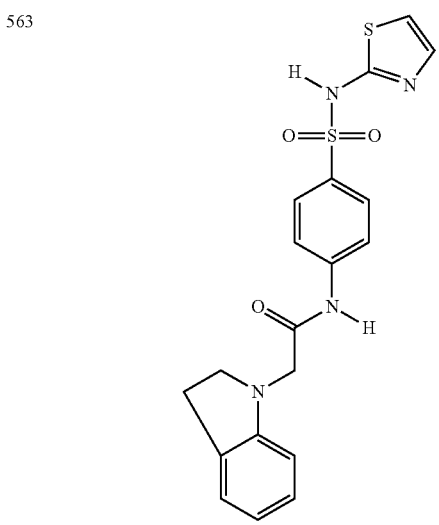 |
| 564 | 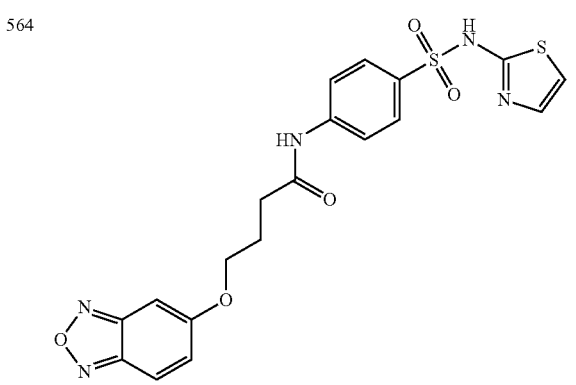 |
| # | Compound |
|---|---|
| 568 | 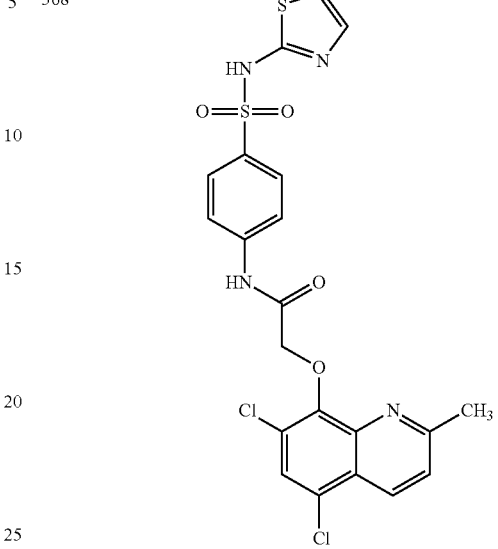 |
| 574 | 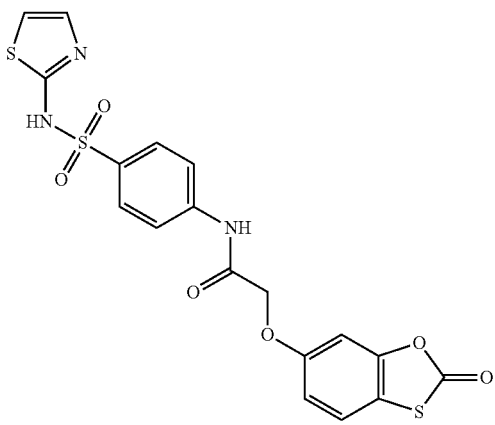 |
| 575 | 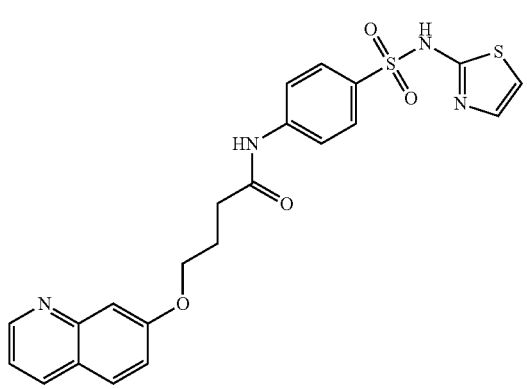 |

175
-continued
| # | Compound |
|---|---|
| 576 | 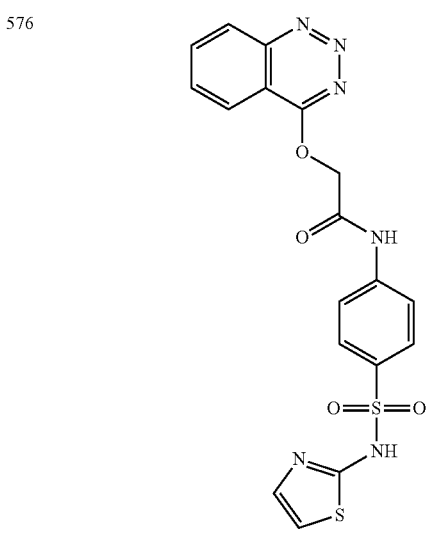 |
| 577 | 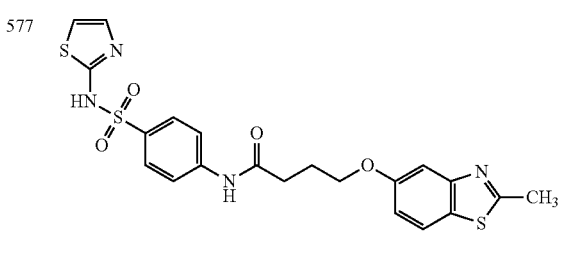 |
| 579 | 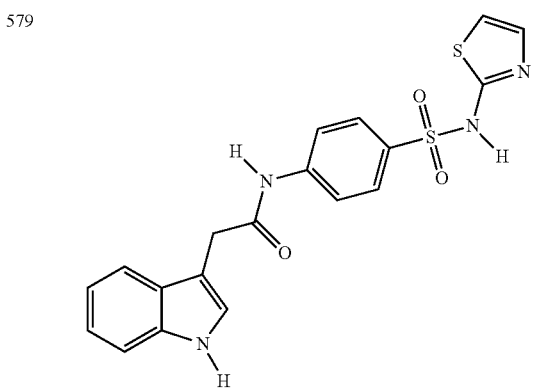 |
| 581 | 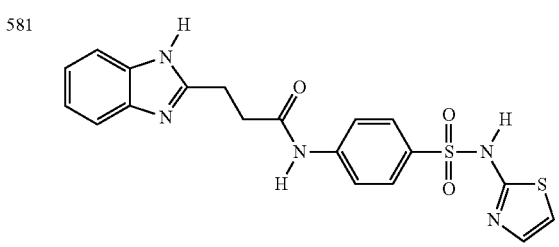 |
176
-continued
| # | Compound |
|---|---|
| 582 | 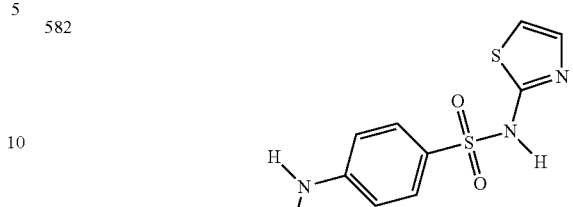 |
| 583 | 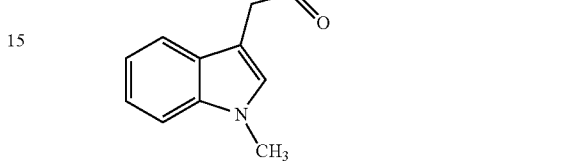 |
| 585 | 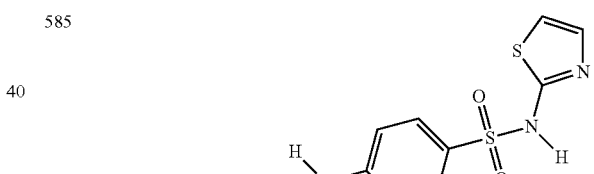 |
| 588 | 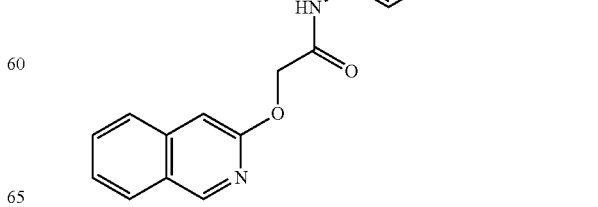 |

177
-continued
| # | Compound |
|---|---|
| 589 | 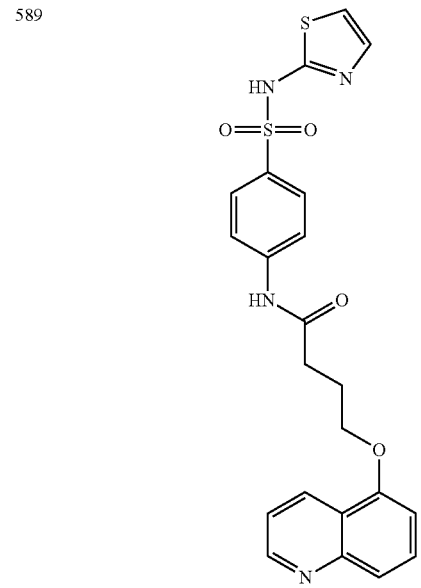 |
| 592 | 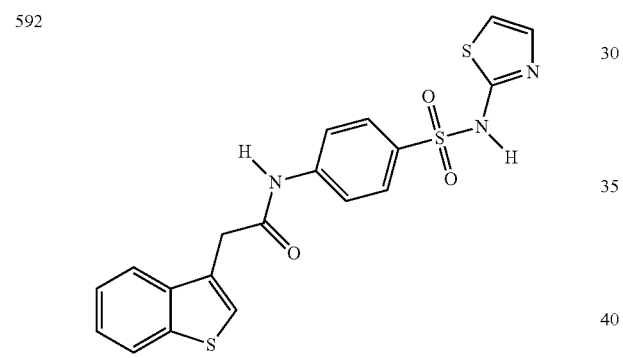 |
| 597 | 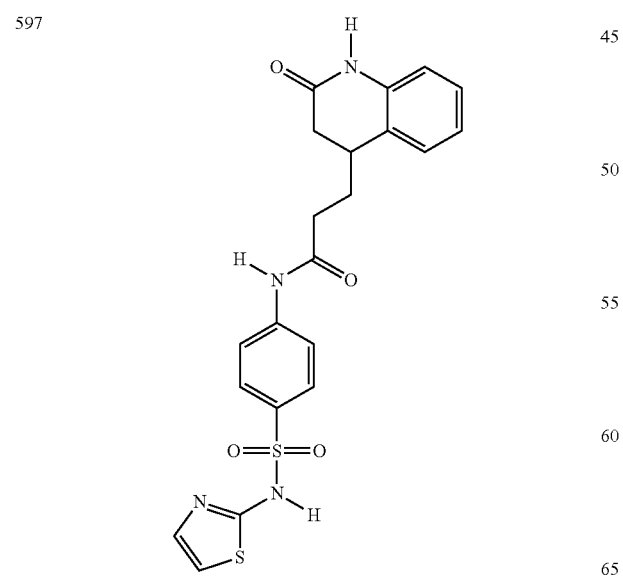 |
178
-continued
| # | Compound |
|---|---|
| 605 | 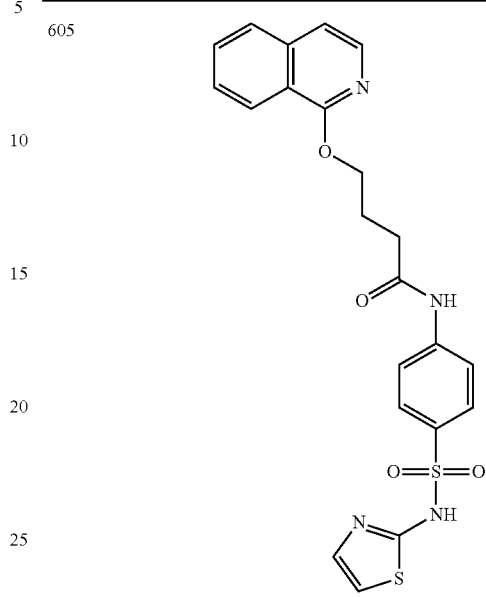 |
| 607 | 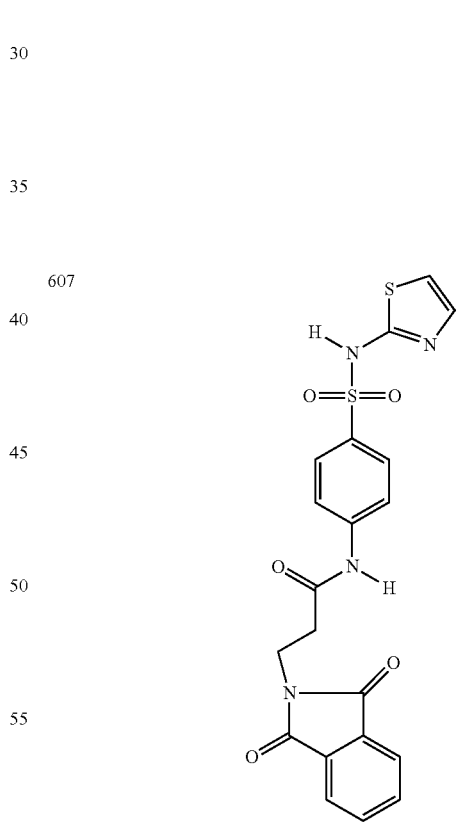 |

| # | Compound |
|---|---|
| 611 | 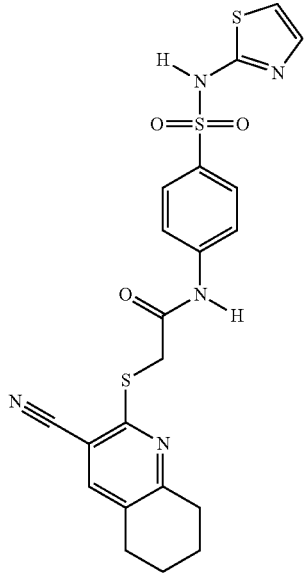 |
| 612 | 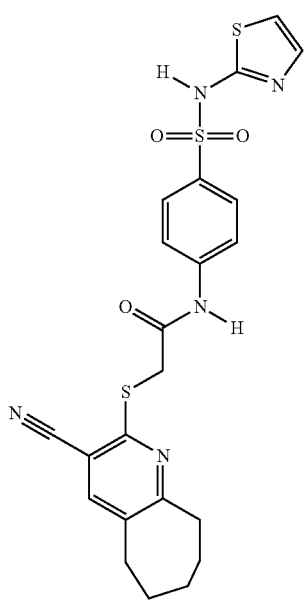 |
| # | Compound |
|---|---|
| 615 | 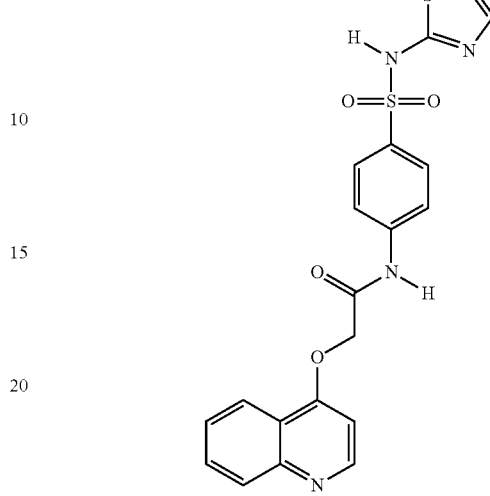 |
| 616 | 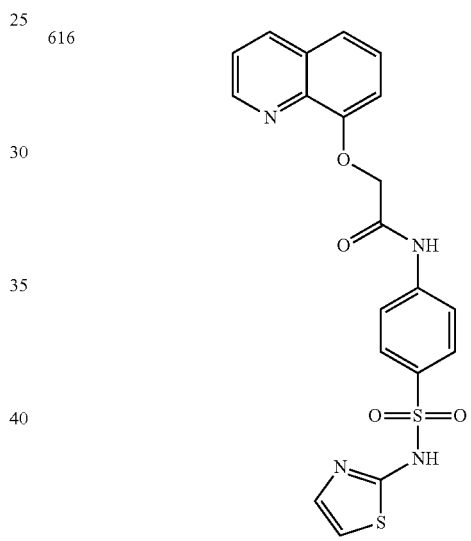 |
| 617 | 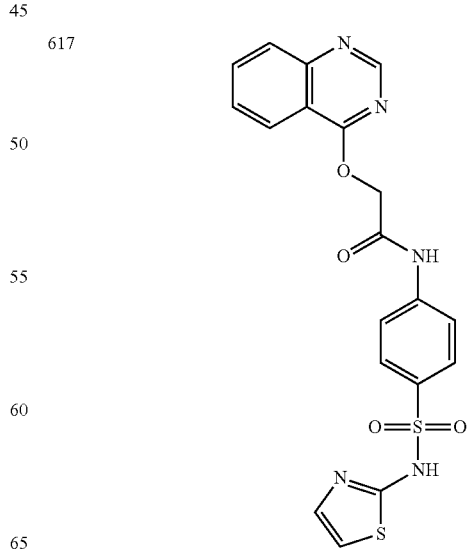 |

181
-continued
| # | Compound |
|---|----------|
| 618 | 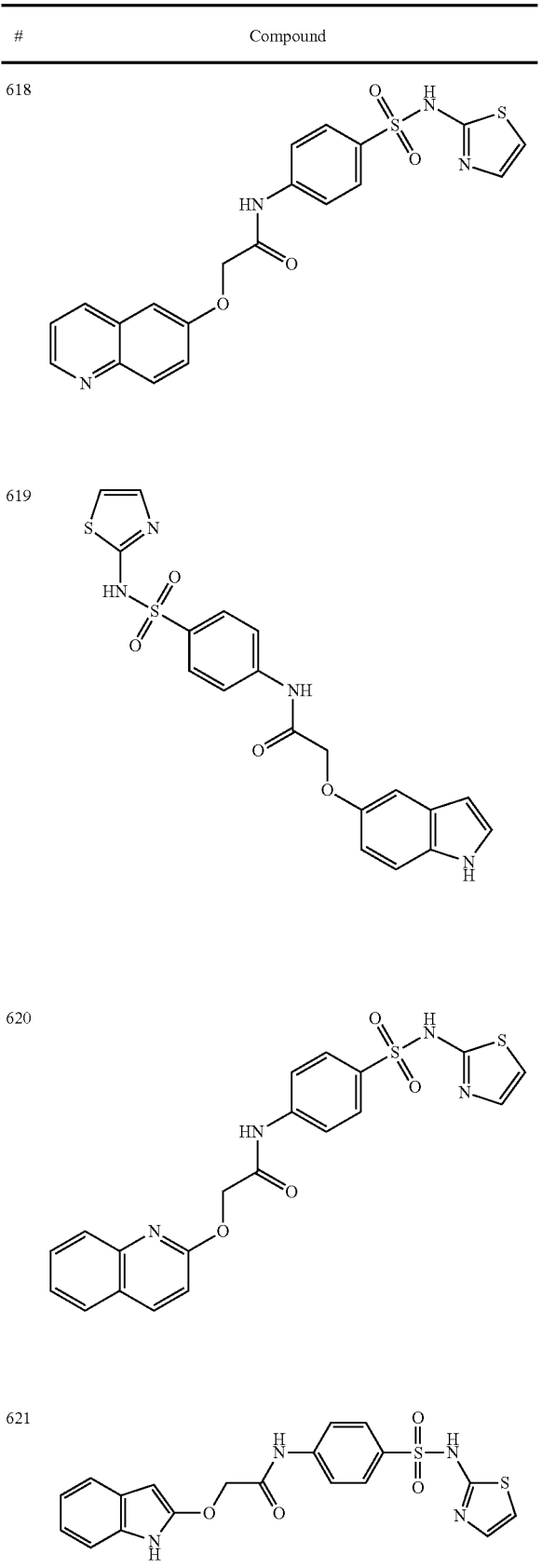 |
| 619 | |
| 620 | |
| 621 | |
182
-continued
| # | Compound |
|---|----------|
| 622 | 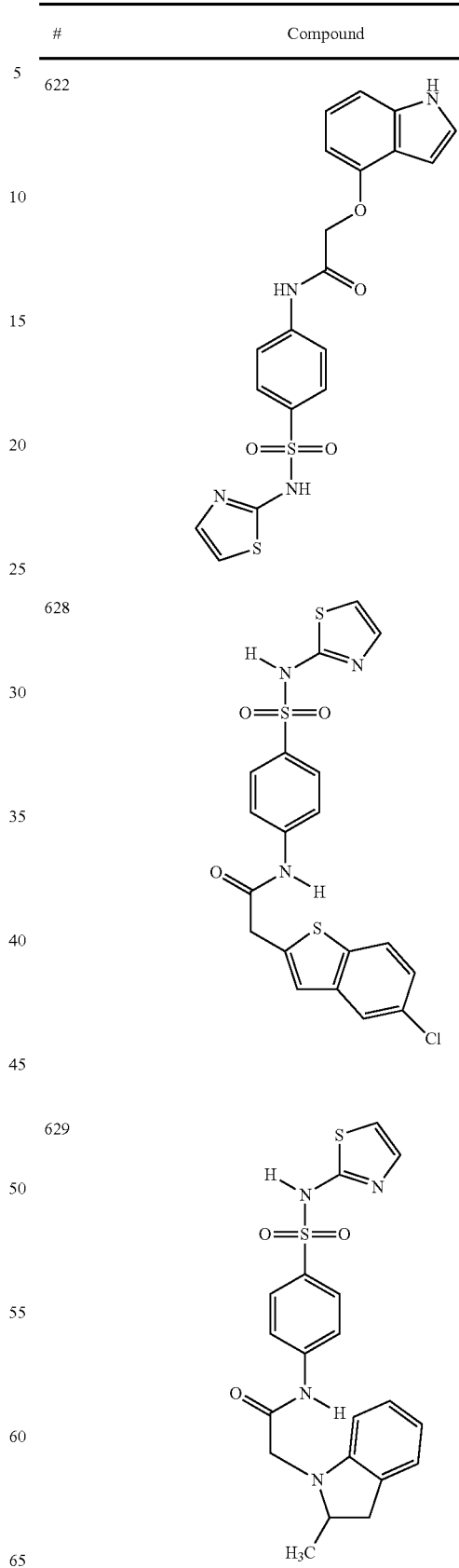 |
| 628 | |
| 629 | |

183
-continued
| # | Compound |
|---|---|
| 630 | 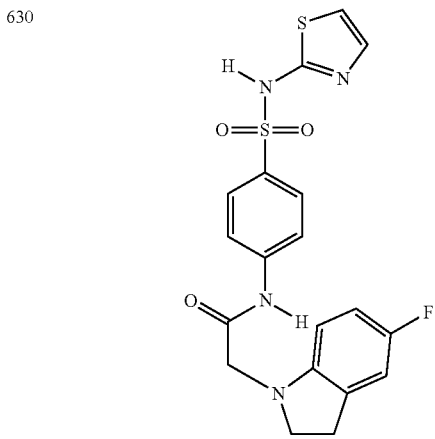 |
| 631 | 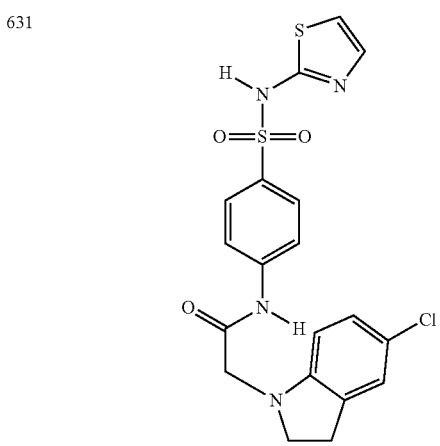 |
| 632 | 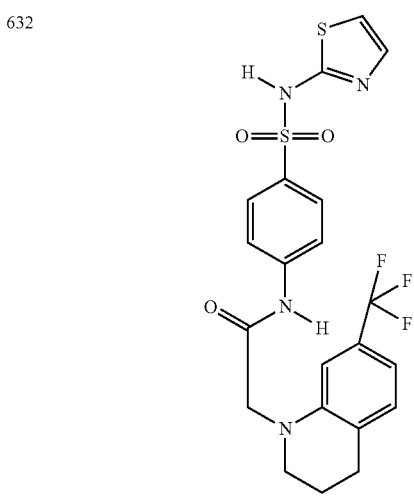 |
184
-continued
| # | Compound |
|---|---|
| 633 | 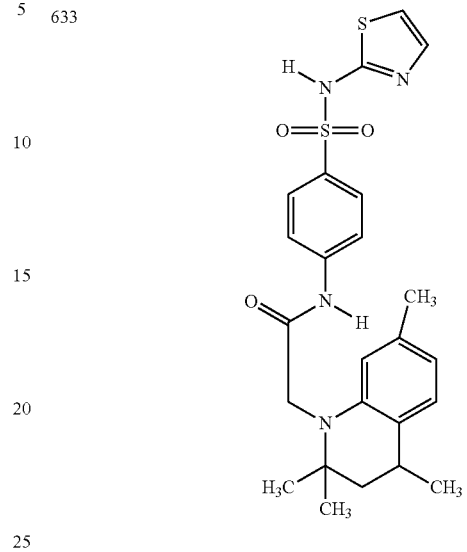 |
| 634 | 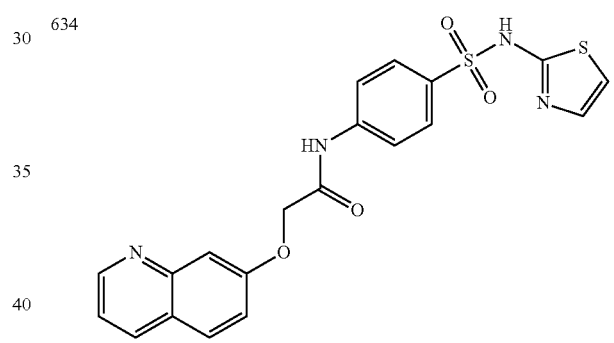 |
| 635 | 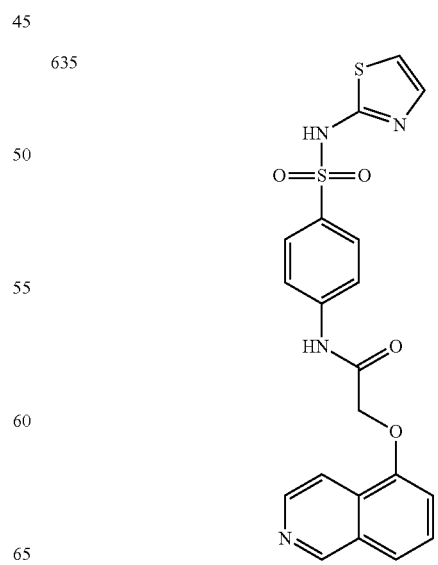 |

185
-continued
| # | Compound |
|---|---|
| 636 | 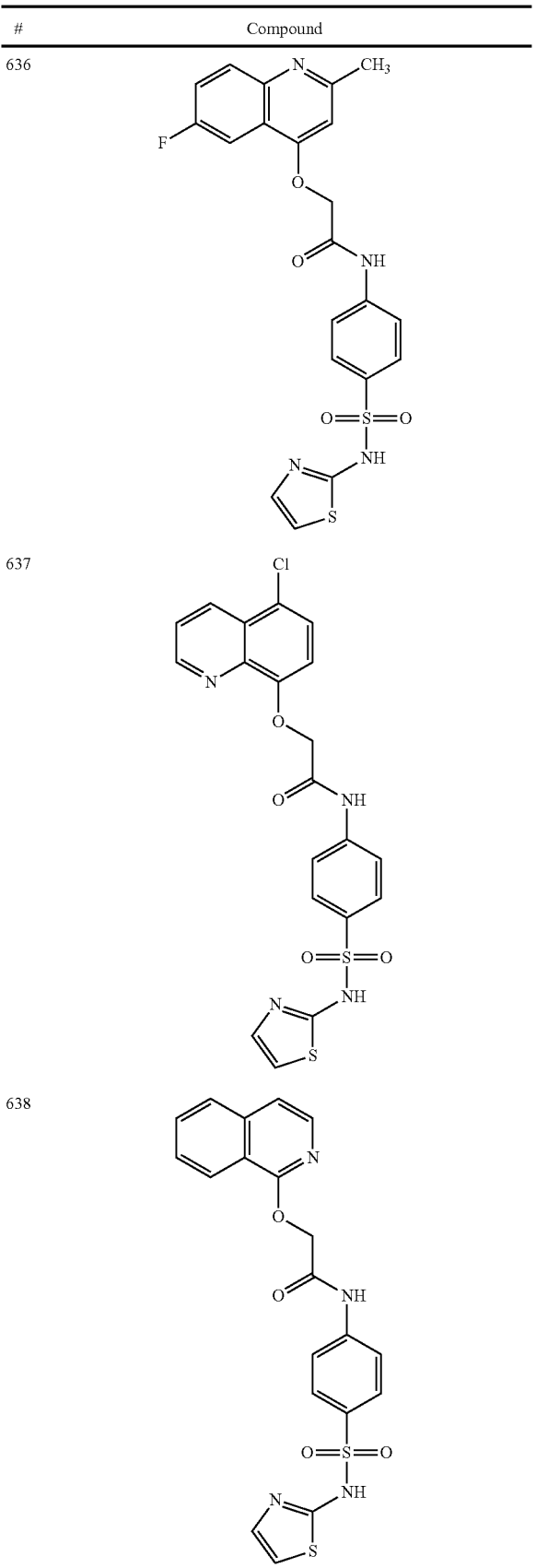 |
| 637 | |
| 638 | |
186
-continued
| # | Compound |
|---|---|
| 639 | 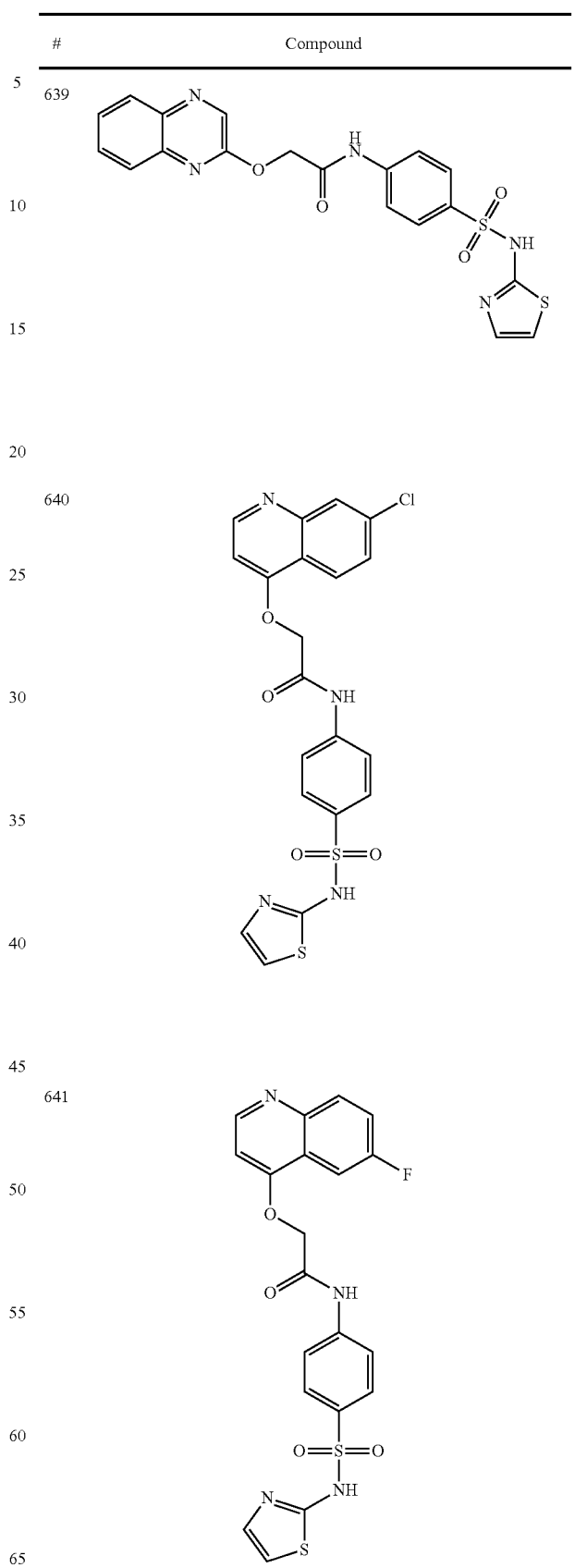 |
| 640 | |
| 641 | |

| # | Compound |
|---|---|
| 642 | 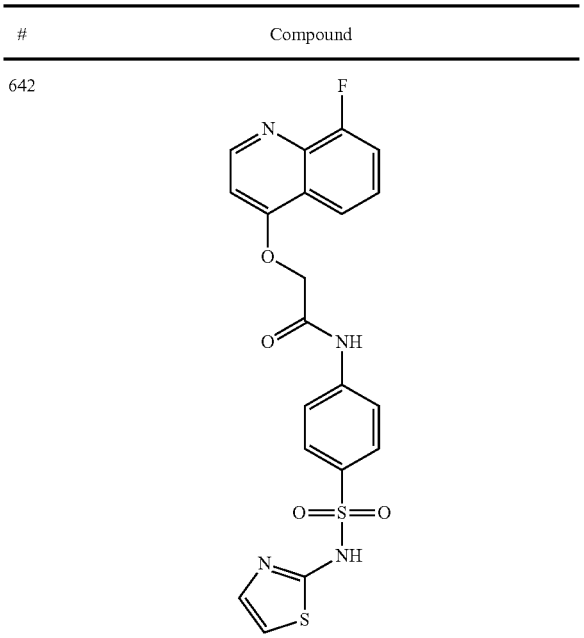 |
| 643 | 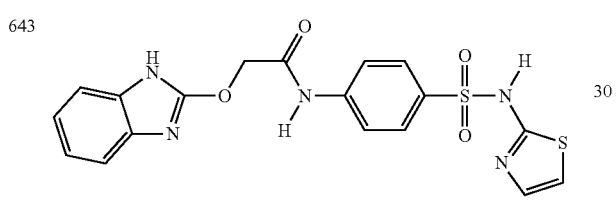 |
| 644 | 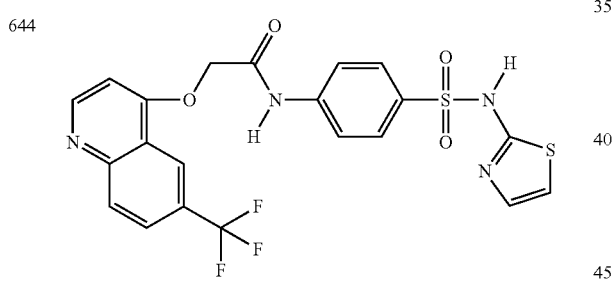 |
| 647 | 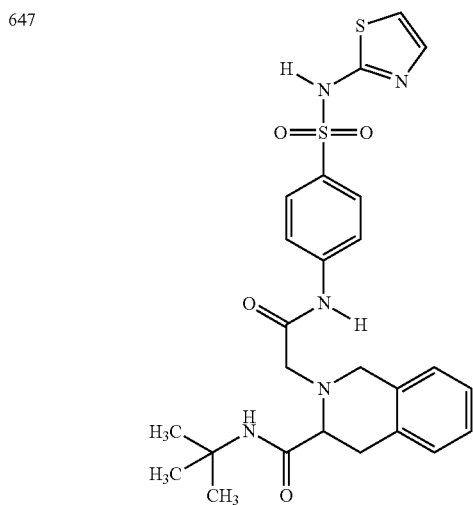 |
| # | Compound |
|---|---|
| 656 | 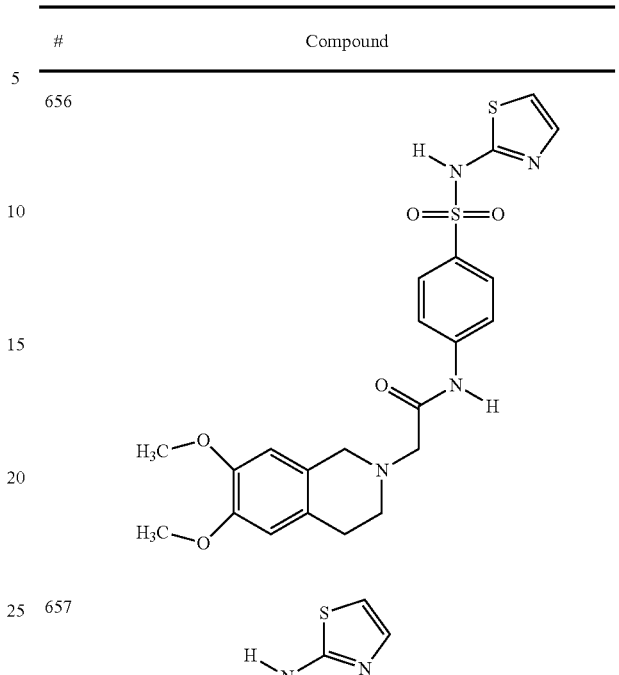 |
| 657 | 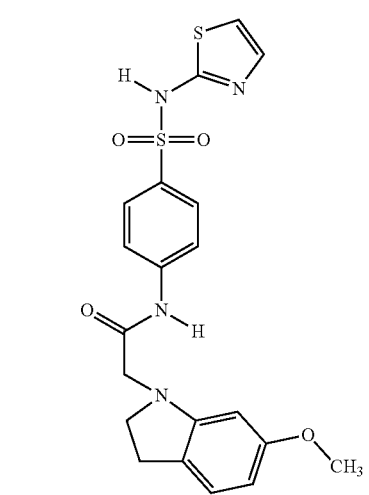 |
| 658 | 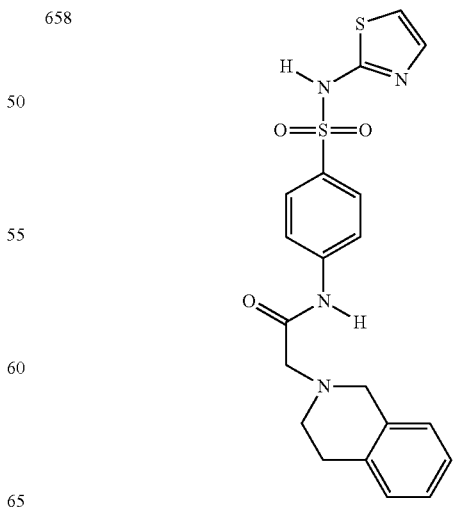 |

| # | Compound |
|---|---|
| 660 | 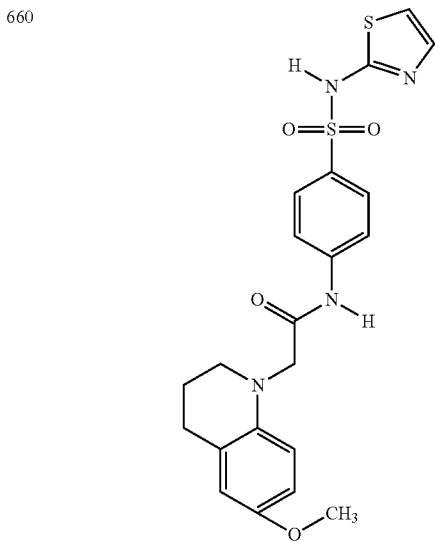 |
| 661 | 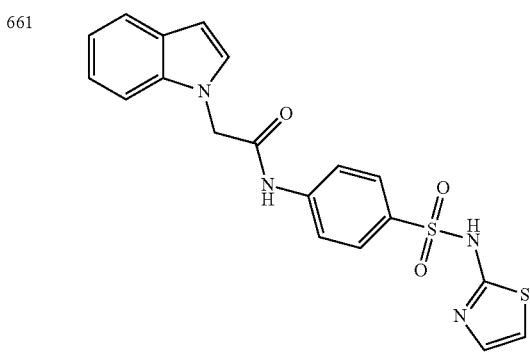 |
| 662 | 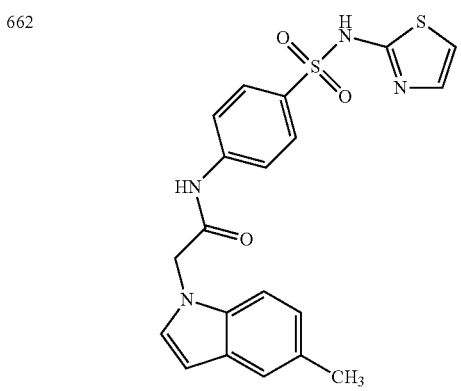 |
| # | Compound |
|---|---|
| 663 | 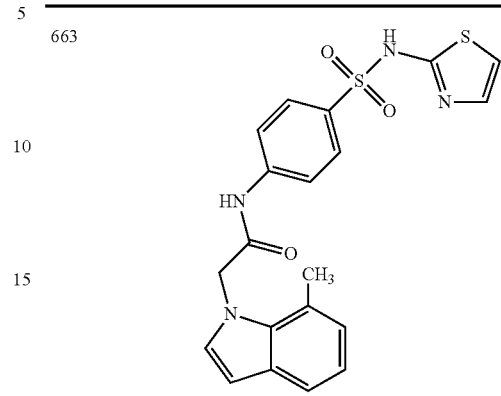 |
| 664 | 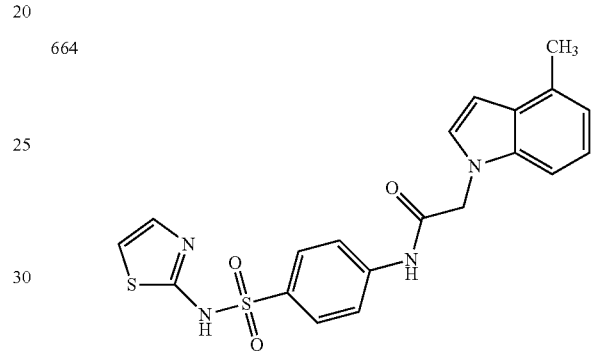 |
| 665 | 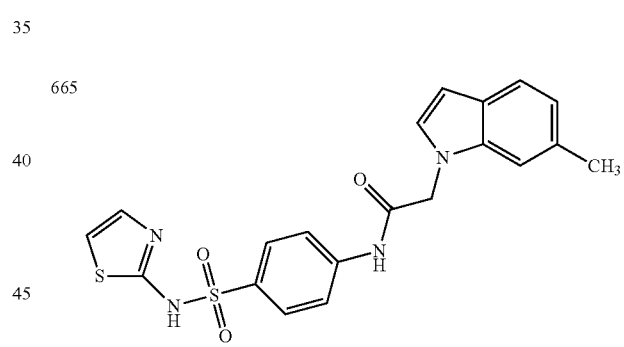 |
| 666 | 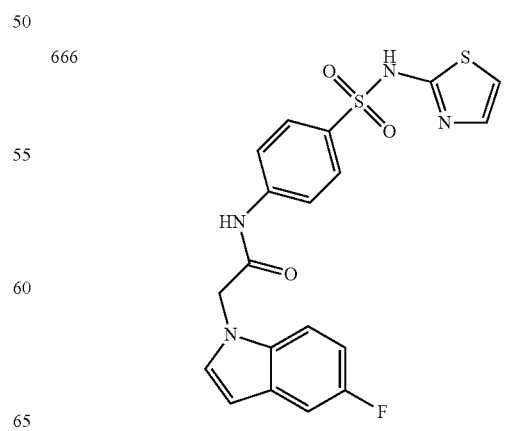 |

| # | Compound |
|---|---|
| 667 | 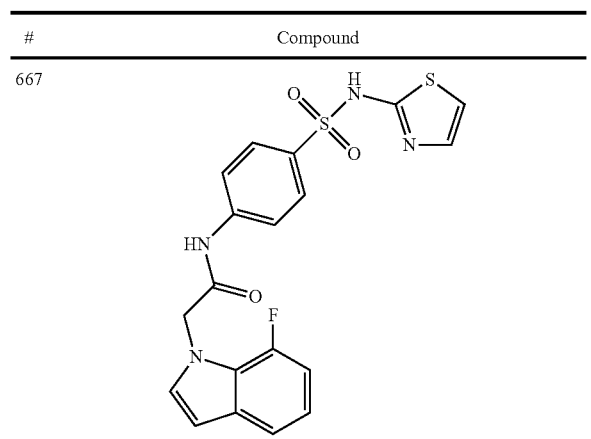 |
| 668 | 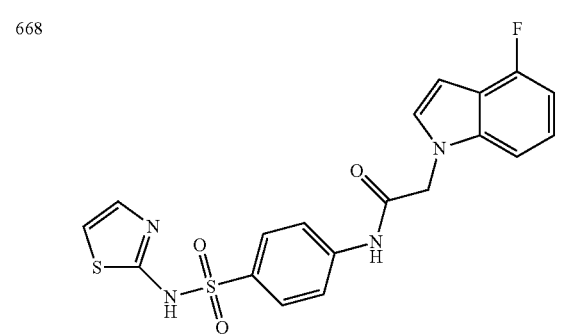 |
| 669 | 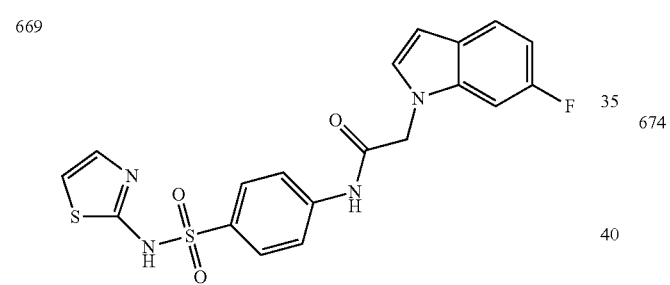 |
| 670 | 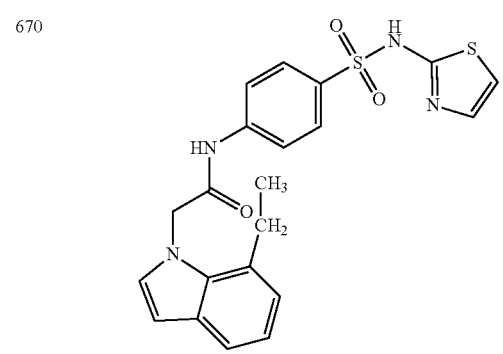 |
| 671 | 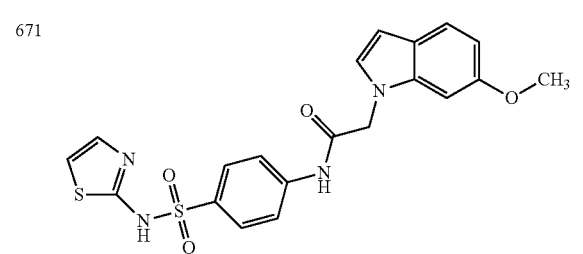 |
| # | Compound |
|---|---|
| 672 | 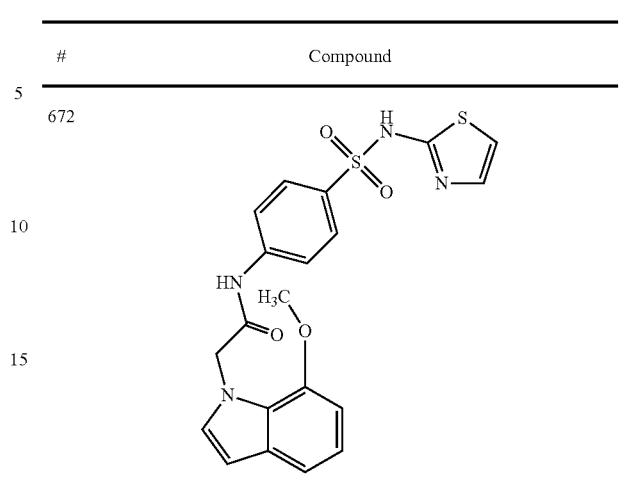 |
| 673 |  |
| 674 | 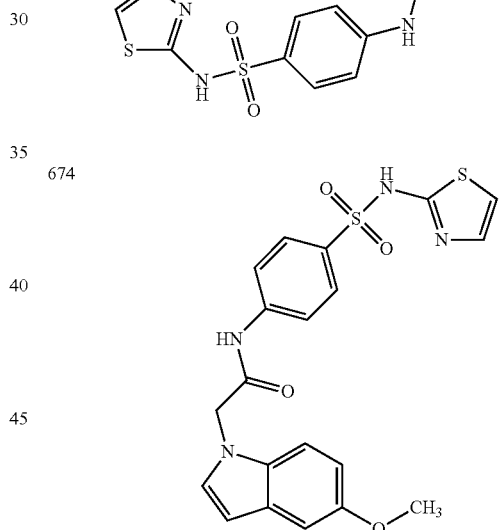 |
| 675 | 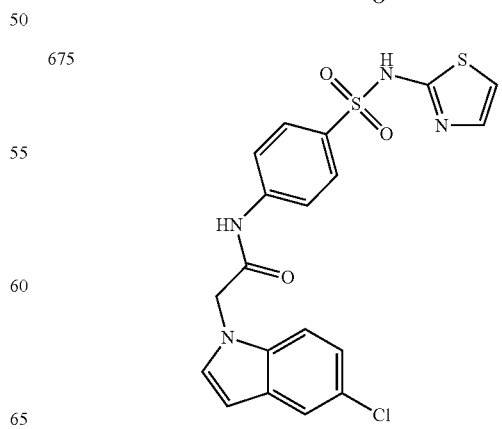 |

| # | Compound |
|---|---|
| 676 | 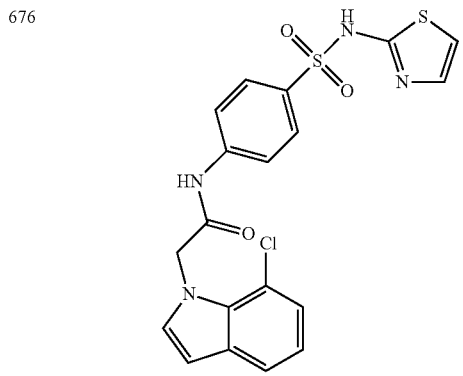 |
| 677 | 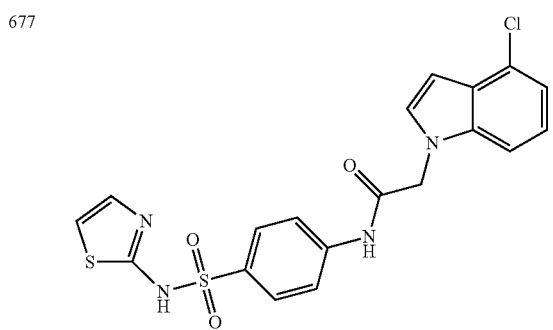 |
| 678 | 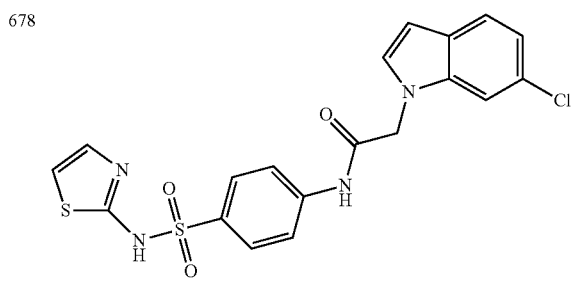 |
| 679 | 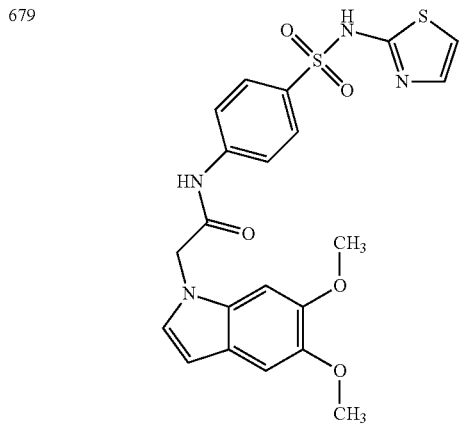 |
| # | Compound |
|---|---|
| 680 | 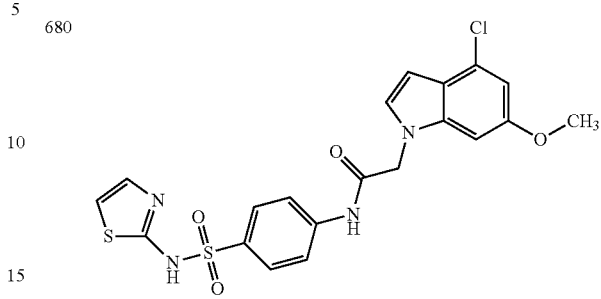 |
| 681 | 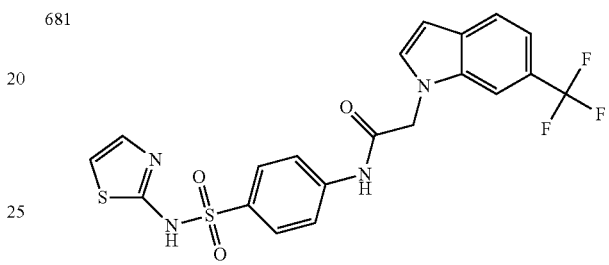 |
| 682 | 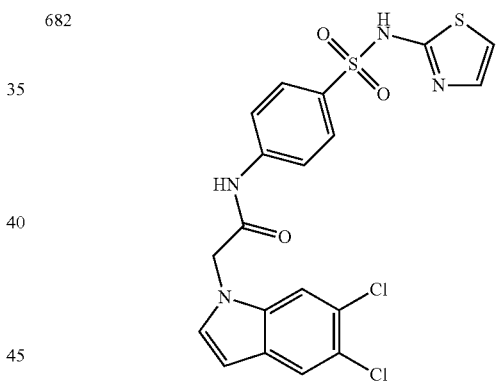 |
| 683 | 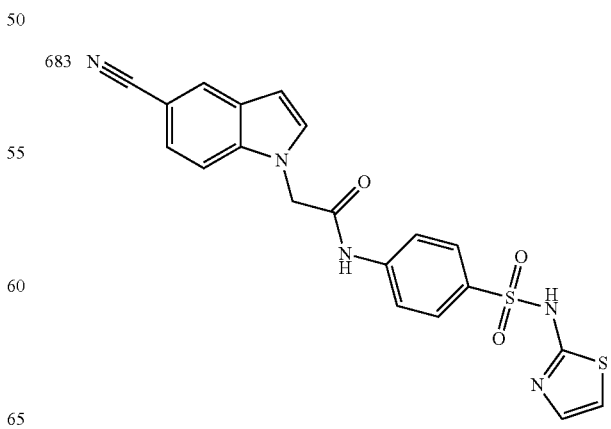 |

TABLE-continued
| # | Compound |
|---|---|
| 684 | 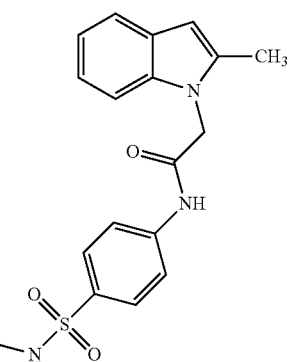 |
| 685 | 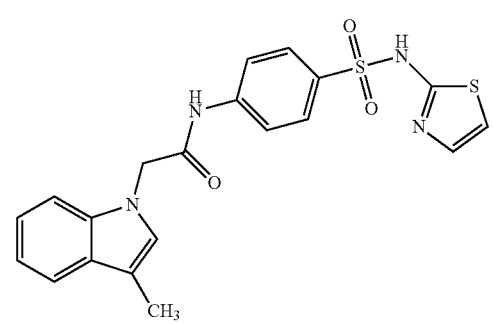 |
| 686 | 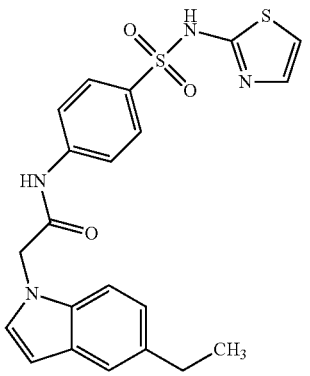 |
| 687 | 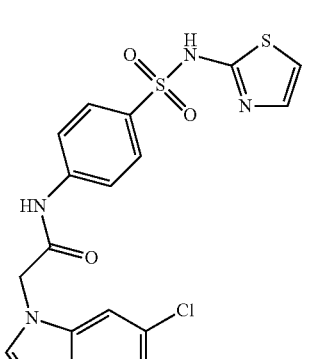 |
| 688 | 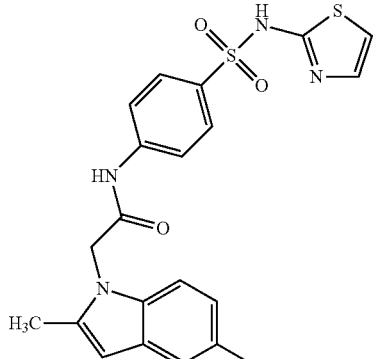 |
| 689 | 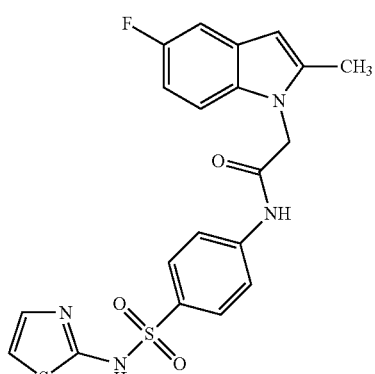 |
| 690 | 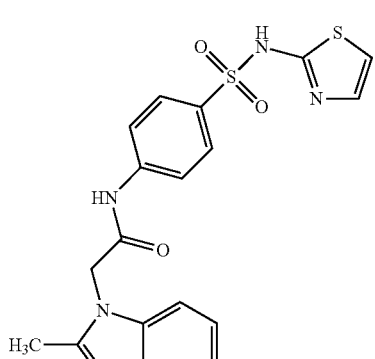 |
| 691 | 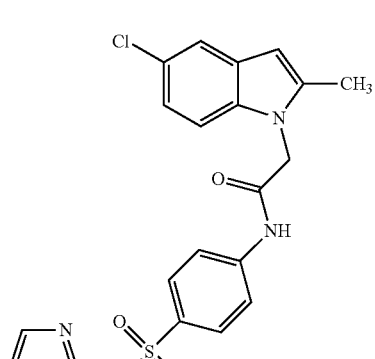 |

| # | Compound |
|---|---|
| 692 | 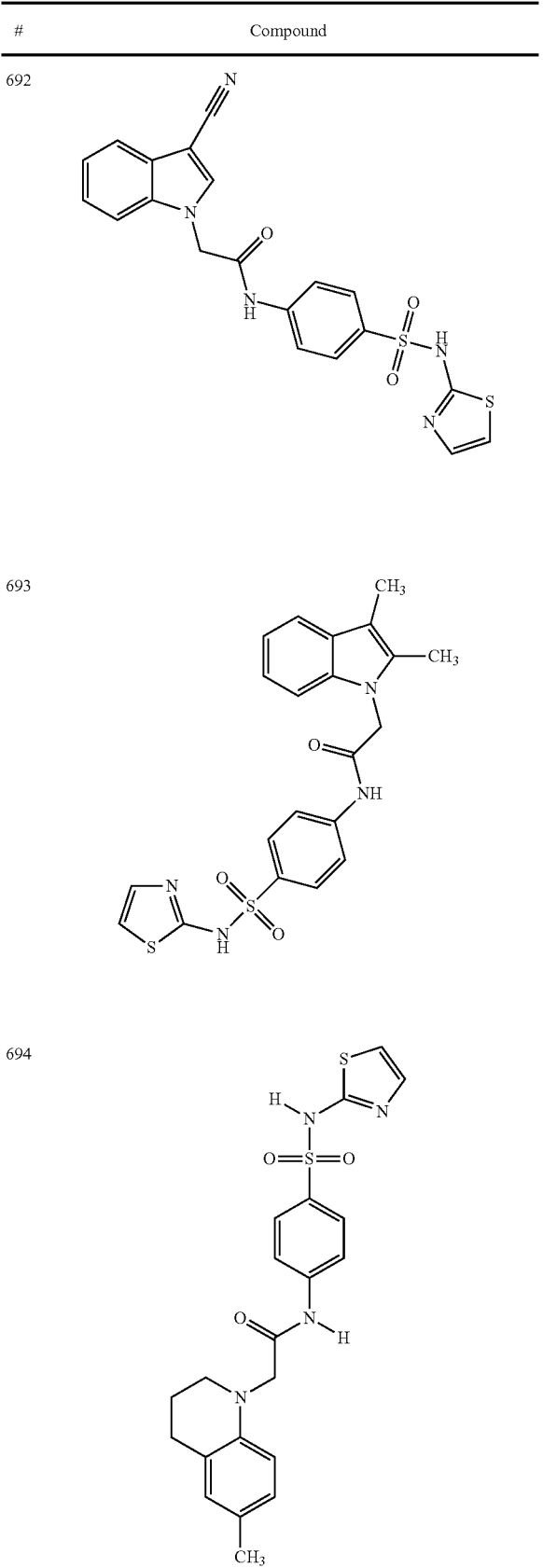 |
| 693 | |
| 694 | |
| # | Compound |
|---|---|
| 695 | 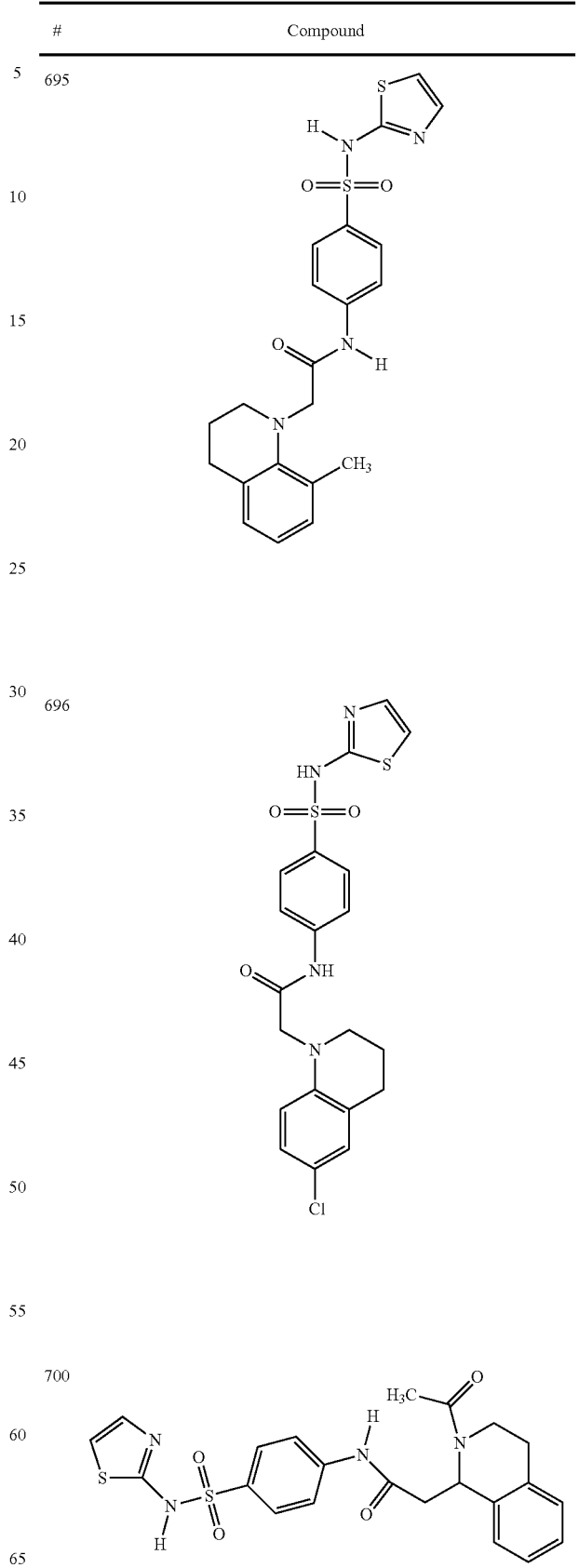 |
| 696 | |
| 700 | |

199
-continued
| # | Compound |
|---|---|
| 708 | 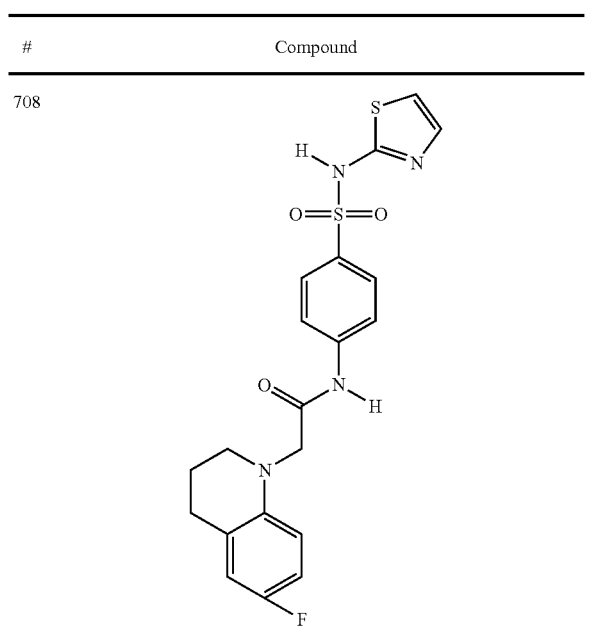 |
| 709 | |
| 710 | |
200
-continued
| # | Compound |
|---|---|
| 711 | 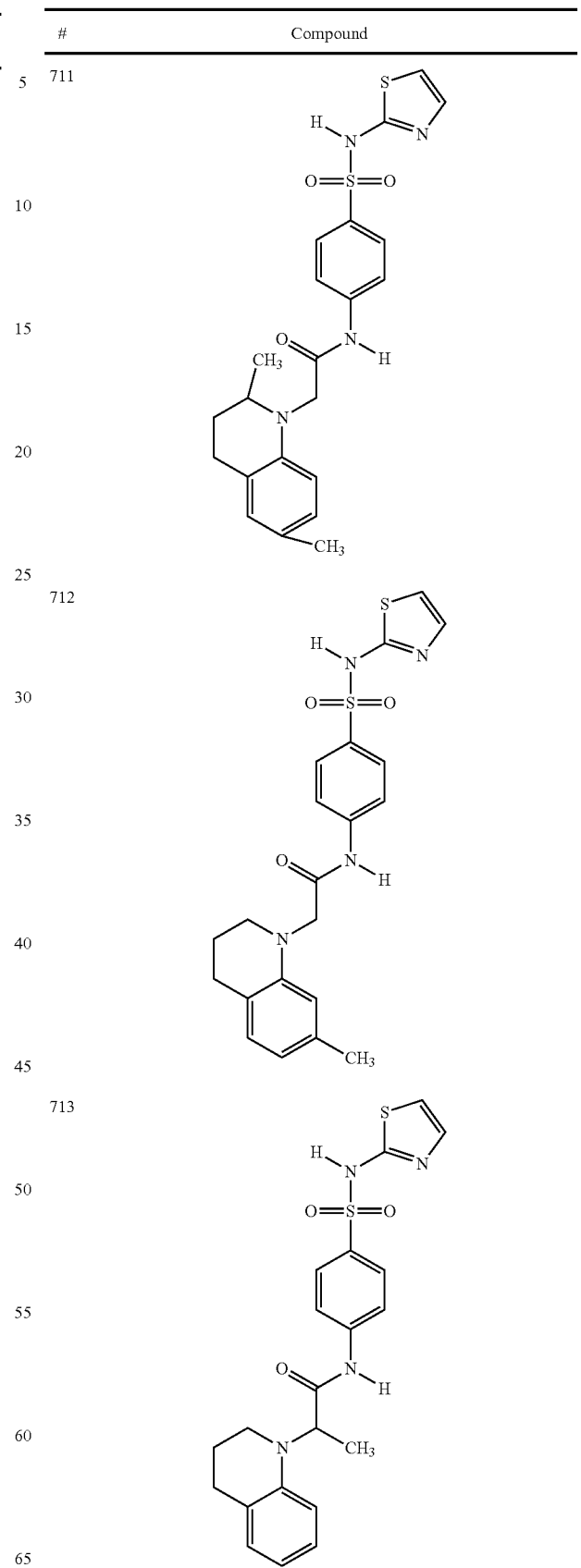 |
| 712 | |
| 713 | |

201
-continued

| # | Compound |
|---|---|
| 714 | |
| 715 | |
| 716 | |

202
-continued

| # | Compound |
|---|---|
| 721 | |
| 722 | |
| 723 | |

| # | Compound |
|---|---|
| 724 | 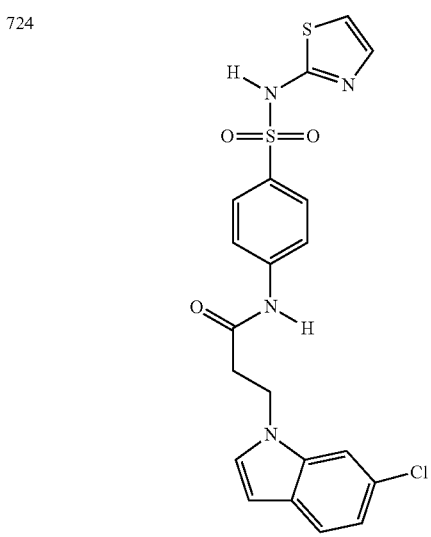 |
| 725 | 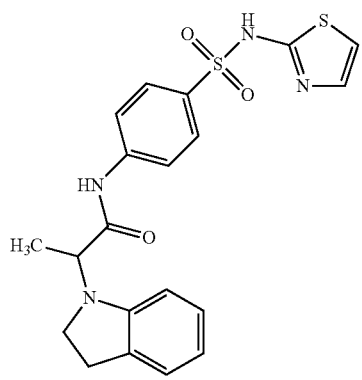 |
| 726 | 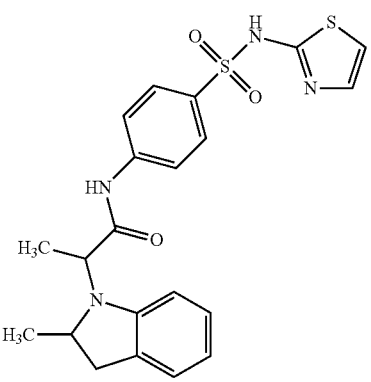 |
| # | Compound |
|---|---|
| 727 | 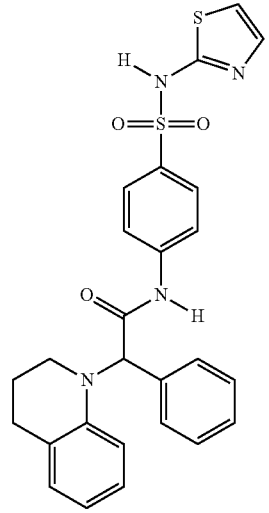 |
| 734 | 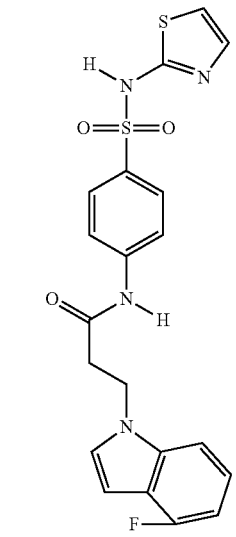 |
| 735 | 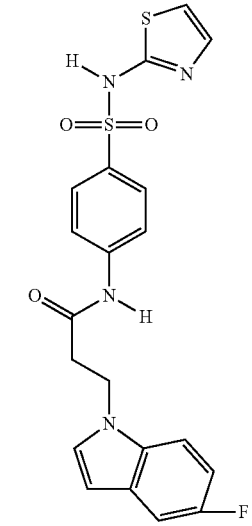 |

| # | Compound |
|---|---|
| 740 | 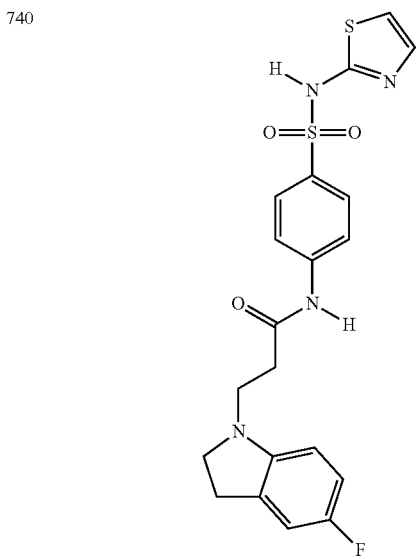 |
| 741 | 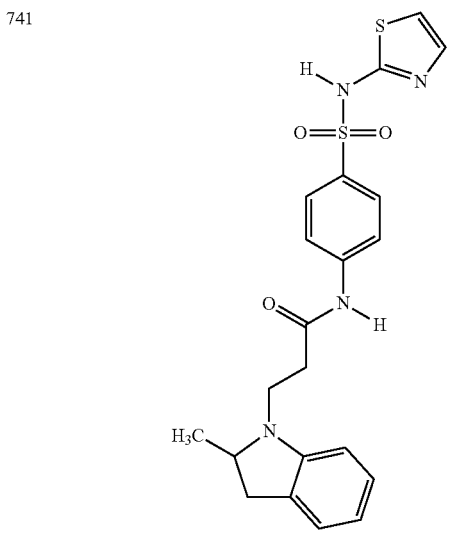 |
| 742 | 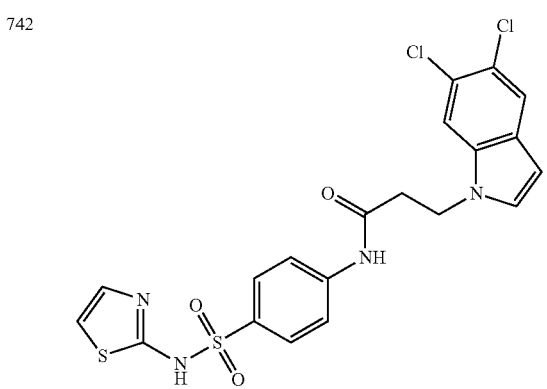 |
| # | Compound |
|---|---|
| 743 |  |
| 744 | 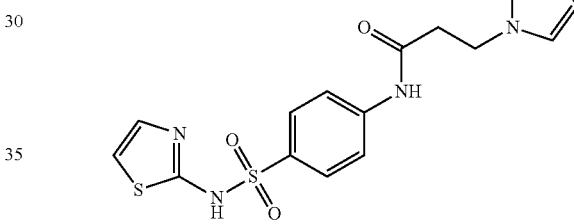 |
| 745 | 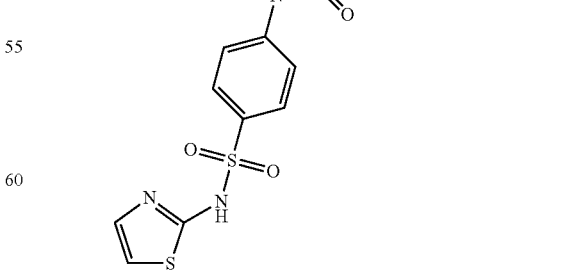 |

-continued
| # | Compound |
|---|---|
| 746 | 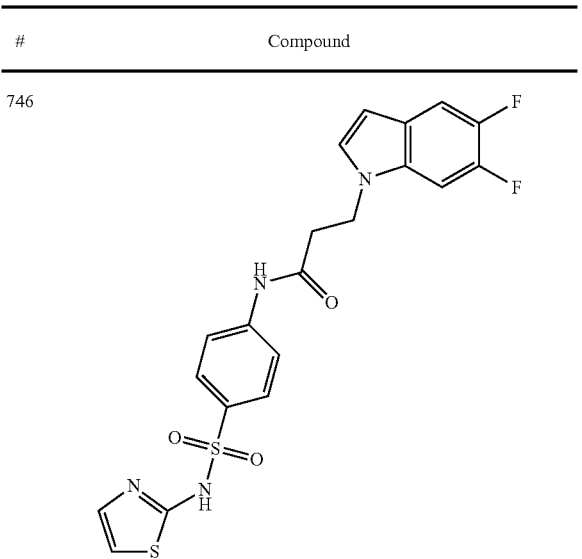 |
| 761 | 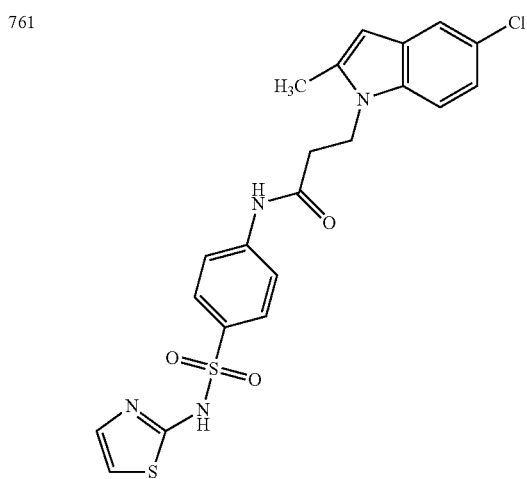 |
| 762 | 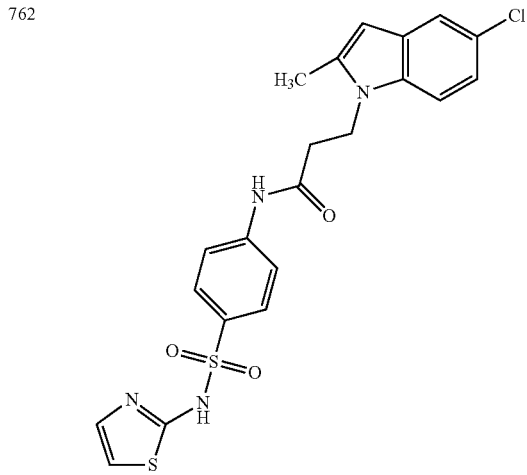 |
-continued
| # | Compound |
|---|---|
| 764 | 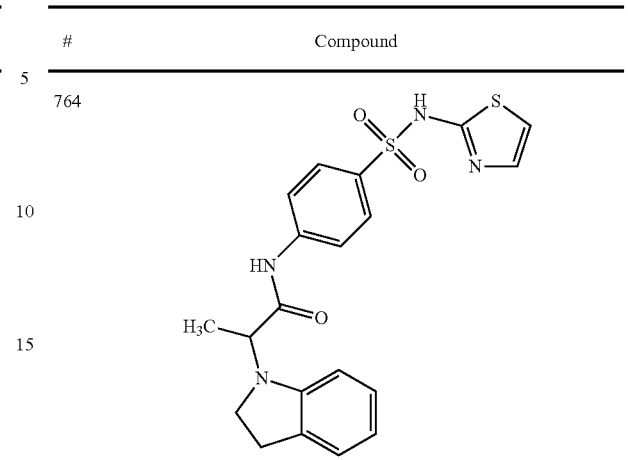 |
| 765 | 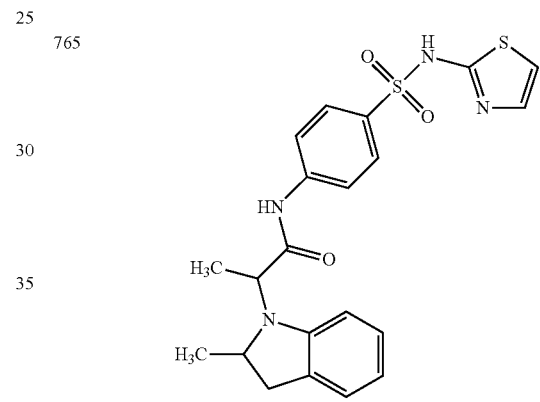 |
| 766 | 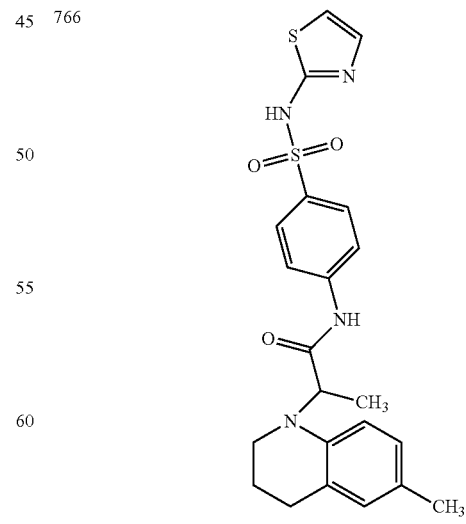 |

| # | Compound |
|---|---|
| 767 | 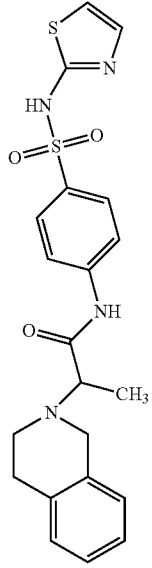 |
| 768 | 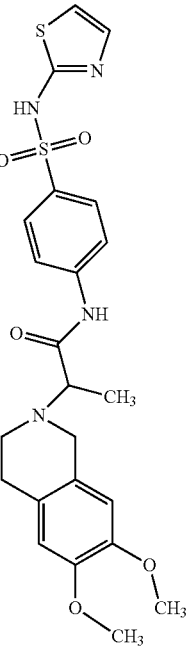 |
| 769 | 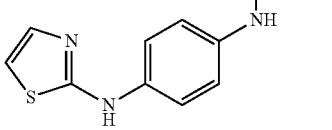 |
| 770 | 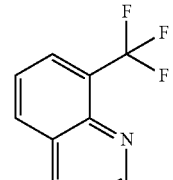 |
| | or |
| 774 | 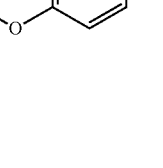 |

3. The method according to claim 2, wherein the disease, condition, or disorder is implicated in the activation or hyperactivity of voltage-gated sodium channels.

4. The method according to claim 2, wherein the disease, condition, or disorder is radicular pain, sciatica, back pain, head pain, neck pain.

5. The method according to claim 2, wherein the disease, condition, or disorder is severe or intractable pain, acute pain, postsurgical pain, back pain, or cancer pain.

6. The method according to claim 2, wherein the disease, condition, or disorder is implicated in the activation or hyperactivity of voltage-gated calcium channels.

7. The method according to claim 6, wherein the disease, condition, or disorder is acute, chronic, neuropathic, or inflammatory pain.

* * * * *